United States Patent
Sadelain et al.

(10) Patent No.: US 11,717,579 B2
(45) Date of Patent: Aug. 8, 2023

(54) GLOBIN GENE THERAPY FOR TREATING HEMOGLOBINOPATHIES

(71) Applicants: MEMORIAL SLOAN-KETTERING CANCER CENTER, New York, NY (US); UNIVERSITY OF WASHINGTON, Seattle, WA (US)

(72) Inventors: Michel Sadelain, New York, NY (US); Isabelle Riviere, New York, NY (US); Jorge Mansilla-Soto, New York, NY (US); Xiuyan Wang, New York, NY (US); George Stamatoyannopoulos, Seattle, WA (US); John Stamatoyannopoulos, Seattle, WA (US); Mingdong Liu, Seattle, WA (US)

(73) Assignees: MEMORIAL SLOAN-KETTERING CANCER CENTER, New York, NY (US); UNIVERSITY OF WASHINGTON, Seattle, WA (US)

( * ) Notice: Subject to any disclaimer, the term of this patent is extended or adjusted under 35 U.S.C. 154(b) by 277 days.

(21) Appl. No.: 15/449,416

(22) Filed: Mar. 3, 2017

(65) Prior Publication Data

US 2017/0173185 A1 Jun. 22, 2017

Related U.S. Application Data

(63) Continuation of application No. PCT/US2015/048698, filed on Sep. 4, 2015.

(60) Provisional application No. 62/045,997, filed on Sep. 4, 2014.

(51) Int. Cl.
| | |
|---|---|
| *C12N 15/86* | (2006.01) |
| *C12N 15/63* | (2006.01) |
| *A61K 48/00* | (2006.01) |
| *C12N 15/11* | (2006.01) |
| *C07K 14/805* | (2006.01) |
| *C12N 9/22* | (2006.01) |
| *C12N 15/85* | (2006.01) |

(52) U.S. Cl.
CPC ...... *A61K 48/0066* (2013.01); *A61K 48/0058* (2013.01); *C07K 14/805* (2013.01); *C12N 9/22* (2013.01); *C12N 15/85* (2013.01); *C12N 15/86* (2013.01); *C12N 2740/10043* (2013.01); *C12N 2740/15043* (2013.01); *C12N 2740/16043* (2013.01); *C12N 2830/008* (2013.01); *C12N 2830/15* (2013.01); *C12N 2830/30* (2013.01); *C12N 2830/40* (2013.01); *C12N 2830/46* (2013.01); *C12N 2830/48* (2013.01); *C12N 2830/50* (2013.01)

(58) Field of Classification Search
None
See application file for complete search history.

(56) References Cited

U.S. PATENT DOCUMENTS

| | | | |
|---|---|---|---|
| 2003/0022303 A1 | 1/2003 | Sadelain et al. | |
| 2008/0069805 A1* | 3/2008 | Williams | C12N 5/0647 424/93.21 |
| 2009/0156534 A1 | 6/2009 | Lisowski et al. | |
| 2010/0022006 A1 | 1/2010 | Kim et al. | |
| 2012/0115227 A1 | 5/2012 | Cohen-Haguenauer et al. | |
| 2015/0216903 A1* | 8/2015 | Heffner | C12N 15/86 424/93.21 |
| 2017/0145077 A1* | 5/2017 | Malik | C07K 14/805 |

FOREIGN PATENT DOCUMENTS

| | | |
|---|---|---|
| JP | 2002-536965 A | 11/2002 |
| WO | WO 2004/005458 A2 | 1/2004 |
| WO | WO 2010/046493 A2 | 4/2010 |
| WO | WO 2014/026110 A2 | 2/2014 |
| WO | WO 2014/043131 A1 | 3/2014 |
| WO | WO 2015/138852 A1 | 9/2015 |

OTHER PUBLICATIONS

Ong and Corces, CTCF: an architectural protein bridging genome topology and function, Nature, 2014, pp. 234-246.*
Plasschaert et al, CTCF binding site sequence differences are associated with unique regulatory and functional trends during embryonic stem cell differentiation, Nucleic Acids Research, 2014, vol. 42, No. 2, pp. 774-789.*
Chandrakasan and Malik, Gene Therapy for Hemoglobinopathies: The State of the Field and the Future, Hematol Oncol Clin North Am. Apr. 2014 ; 28(2): 199-216.*
Papapetrou et al., Genomic safe harbors permit high β-globin transgene expression in thalassemia induced pluripotent stem cellsNature, 2011, pp. 73-81.*
Database EMBL [Online] "Homo sapiens chromosome 1 clone RP11-550H2, complete sequence," retrieved from EBI accession No. EM STD:AC092813 Database accession No. AC092813 (Jul. 31, 2001).
Groth et al., "Identification and Characterization of Enhancer-Blocking Insulators to Reduce Retroviral Vector Genotoxicity," PLoS ONE 8(10):e76528 (2013).
Liu et al., "Genomic discovery of potent chromatin insulators for human gene therapy," Nature Biotechnology 33(2):498-203 (2015).
Adams et al., "Binding of Disparate Transcriptional Activators to Nucleosomal DNA Is Inherently Cooperative," Molecular and Cellular Biology 15(3):1405-1421 (1995).

(Continued)

*Primary Examiner* — Maria Marvich
(74) *Attorney, Agent, or Firm* — Baker Botts L.L.P.

(57) ABSTRACT

The presently disclosed subject matter provides for expression cassettes that allow for expression of a globin gene or a functional portion thereof, vectors comprising thereof, and cells transduced with such expression cassettes and vectors. The presently disclosed subject matter further provides methods for treating a hemoglobinopathy in a subject comprising administering an effective amount of such transduced cells to the subject.

61 Claims, 11 Drawing Sheets

Specification includes a Sequence Listing.

(56) References Cited

OTHER PUBLICATIONS

Aker et al., "Extended Core Sequences from the cHS4 Insulator Are Necessary for Protecting Retroviral Vectors from Silencing Position Effects," Hum Gene Ther 18:333-343 (2007).
Armstrong et al., "NF-E2 Disrupts Chromatin Structure at Human β-Globin Locus Control Region Hypersensitive Site 2 In Vitro," Mol. Cell. Biol. 16(10):5634-5644 (1996).
Arumugam et al., "Genotoxic Potential of Lineage-specific Lentivirus Vectors Carrying the β-Globin Locus Control Region," Mol Ther 17(11):1929-1937 (2009).
Arumugam et al., "Improved Human β-globin Expression from Self-inactivating Lentiviral Vectors Carrying the Chicken Hypersensitive Site-4 (cHS4) Insulator Element," Mol Ther 15(10):1863-1871 (2007).
Atweh et al., "Pharmacological Induction of Fetal Hemoglobin in Sickle Cell Disease and β-Thalassemia," Semin Hematol 38:367-373 (2001).
Bank et al., "A Phase I/II Clinical Trial of β-Globin Gene Therapy for β-Thalassemia," Ann N.Y. Acad. Sci. 1054:308-316 (2005).
Barski et al., "High-Resolution Profiling of Histone Methylations in the Human Genome," Cell 129:823-837 (2007).
Baum et al., "Mutagenesis and Oncogenesis by Chromosomal Insertion of Gene Transfer Vectors," Hum Gene Ther 17:253-263 (2006).
Bell et al., "The Protein CTCF Is Required for the Enhancer Blocking Activity of Vertebrate Insulators," Cell 98:387-396 (1999).
Borgna-Pignatti et al., "Survival and complications in patients with thalassemia major treated with transfusion and deferoxamine," Haematologica 89:1187-1193 (2004).
Boulad et al., "Bone Marrow Transplantation for Homozygous β-Thalassemia. The Memorial Sloan-Kettering Cancer Center Experience," Ann NY Acad Sci 850:498-502 (1998).
Braun et al., "Gene Therapy for Wiskott-Aldrich Syndrome-Long-Term Efficacy and Genotoxicity," Sci Transl Med 6:227ra33 (2014).
Brownell et al., "Special HATs for special occasions: linking histone acetylation to chromatin assembly and gene activation," Curr Opin Genet Dev 6:176-184 (1996).
Burgess-Beusse et al., "The insulation of genes from external enhancers and silencing chromatin," PNAS USA 99(Suppl 4):16433-16437 (2002).
Caterina et al., "Multiple elements in human β-globin locus control region 5' HS 2 are involved in enhancer activity and position-independent, transgene expression," Nucleic Acids Res. 22(6):1006-1011 (1994).
Cavazzana-Calvo et al., "Transfusion independence and HMGA2 activation after gene therapy of human β-thalassaemia," Nature 467:318-322 (2010).
Chang et al., "Epigenetic Modifications and Chromosome Conformations of the Beta Globin Locus throughout Development," Stem Cell Rev and Rep 9:397-407 (2013).
Chang et al., "Lentiviral siRNAs targeting multiple highly conserved RNA sequences of human immunodeficiency virus type 1," Gene Ther 12:1133-1144 (2005).
Chang et al., "The Genetic Engineering of Hematopoietic Stem Cells: the Rise of Lentiviral Vectors, the Conundrum of the LTR, and the Promise of Lineage-Restricted Vectors," Mol Ther 15(3):445-456 (2007).
Charache et al., "Hydroxyurea: Effects on Hemoglobin F Production in Patients With Sickle Cell Anemia," Blood 79(10):2555-2565 (1992).
Chung et al., "Characterization of the chicken β-globin insulator," PNAS USA 94:575-580 (1997).
Cooley, T.B. & Lee, P., "A Series of Cases of Splenomegaly in Children with Anemia and Peculiar Bone Changes," Trans. Am. Pediatr. Soc. 37:29 (1925).
Dickson et al., "VFZF 1 Elements Mediate Protection from DNA Methylation," PLoS Genet 6:e1000804 (2010).

Dorschner et al., "High-throughput localization of functional elements by quantitative chromatin profiling," Nat Methods 1(3):219-225 (2004).
Elgin, "DNAase I-Hypersensitive Sites of Chromatin," Cell 27:413-415 (1981).
Elgin, S.C., "Molecular Biology. Anatomy of hypersensitive sites," Nature 309:213-214 (1984).
Elnitski et al., "Conserved E Boxes Function as Part of the Enhancer in Hypersensitive Site 2 of the β-Globin Locus Control Region," The Journal of Biological Chemistry 272(1):369-378 (1997).
Emery et al., "A chromatin insulator protects retrovirus vectors from chromosomal position effects," PNAS USA 97(16):9150-9155 (2000).
Emery et al., "Development of a Condensed Locus Control Region Cassette and Testing in Retrovirus Vectors for Aγ-Globin," Blood Cells, Molecules, and Diseases 24(16):322-339 (1998).
Emery et al., "Development of virus vectors for gene therapy of β chain hemoglobinopathies: flanking with a chromatin insulator reduces γ-globin gene silencing in vivo," Blood 100:2012-2019 (2002).
Emery, "The Use of Chromatin Insulators to Improve the Expression and Safety of Integrating Gene Transfer Vectors," Hum Gene Ther 22:761-774 (2011).
Evans-Galea et al., "Suppression of Clonal Dominance in Cultured Human Lymphoid Cells by Addition of the cHS4 Insulator to a Lentiviral Vector," Mol Ther 15(4):801-809 (2007).
Farrell et al., "Conserved CTCF Insulator Elements Flank the Mouse and Human β-Globin Loci," Mol. Cell Biol. 22(11):3820-3831 (2002).
Felsenfeld et al., "Chromatin structure and gene expression," PNAS USA 93:9384-9388 (1996).
Felsenfeld et al., "Controlling the double helix," Nature 421:448-453 (2003).
Felsenfeld, "Chromatin as an essential part of the transcriptional mechanism," Nature 355:219-224 (1992).
Fraser et al., "Each hypersensitive site of the human β-globin locus control region confers a different developmental pattern of expression on the globin genes," Genes & Development 7:106-113 (1993).
Gaszner et al., "Insulators: exploiting transcriptional and epigenetic mechanisms," Nat Rev Genet 7:703-713 (2006).
Giardina et al., "Chelation Therapy in β-Thalassemia: An Optimistic Update," Semin Hematol 38:360-366 (2001).
Giardini et al., "Bone marrow transplantation in the treatment of thalassemia," Current Opinion in Hematology 1:170-176 (1994).
Giles et al., "Chromatin Boundaries, Insulators, and Long-Range Interactions in the Nucleus," Cold Spring Harbor Symposia on Quantitative Biology 75:79-85 (2010).
Gross et al., "Nuclease Hypersensitive Sites in Chromatin," Ann Rev Biochem 57:159-197 (1988).
Hanawa et al., "Optimized Lentiviral Vector Design Improves Titer and Transgene Expression of Vectors Containing the Chicken β-Globin Locus HS4 Insulator Element," Mol Ther 17(4):667-674 (2009).
Hardison et al., "Locus control regions of mammalian β-globin gene clusters: combining phylogenetic analyses and experimental results to gain functional insights," Gene 205:73-94 (1997).
Hino et al., "Sea urchin insulator protects lentiviral vector from silencing by maintaining active chromatin structure," Gene Ther 11:819-828 (2004).
Horak et al., "GATA-1 binding sites mapped in the P-globin locus by using mammalian chip-chip analysis," PNAS 99(5):2924-2929 (2002).
Jakobsson et al., "Dynamics of transgene expression in a neural stem cell line transduced with lentiviral vectors incorporating the cHS4 insulator," Experimental Cell Research 298:611-623 (2004).
Johnson et al., "Highly Restricted Localization of RNA Polymerase II within a Locus Control Region of a Tissue-Specific Chromatin Domain," Molecular and Cellular Biology 23(18):6484-6493 (2003).
Kadonaga, "Eukaryotic Transcription: An Interlaced Network of Transcription Factors and Chromatin-Modifying Machines," Cell 92:307-313 (1998).
Kim et al., "Analysis of the Vertebrate Insulator Protein CTCF-Binding Sites in the Human Genome," Cell 128:1231-1245 (2007).

(56) References Cited

OTHER PUBLICATIONS

Kingston et al., "ATP-dependent remodeling and acetylation as regulators of chromatin fluidity," Genes & Development 13:2339-2352 (1999).
Ladis et al., "Survival in a large cohort of Greek patients with transfusion-dependent beta thalassaemia and mortality ratios compared to the general population," European Journal of Haematology 86:332-338 (2011).
Leboulch et al., "Mutagenesis of retroviral vectors transducing human β-globin gene and β-globin locus control region derivatives results in stable transmission of an active transcriptional structure," EMBO J 13(13):3065-3076 (1994).
Levings et al., "Recruitment of transcription complexes to the β-globin locus control region and transcription of hypersensitive site 3 prior to erythroid differentiation of murine embryonic stem cells," The FEBS Journal 273:746-755 (2006).
Li et al., "Evidence that DNase I hypersensitive site 5 of the human β-globin locus control region functions as a chromosomal insulator in transgenic mice," Nucleic Acids Res 30(11):2484-2491 (2002).
Li et al., "Genomic and Functional Assays Demonstrate Reduced Gammaretroviral Vector Genotoxicity Associated With Use of the cHS4 Chromatin Insulator," Mol Ther 17(4):716-724 (2009).
Li et al., "Hypersensitive Site 5 of the Human β Locus Control Region Functions as a Chromatin Insulator," Blood 84(5):1399-1401 (1994).
Li et al., "The cHS4 chromatin insulator reduces gammaretroviral vector silencing by epigenetic modifications of integrated provirus," Gene Ther 15:49-53 (2008).
Lisowski et al., "Locus control region elements HS1 and HS4 enhance the therapeutic efficacy of globin gene transfer in β-thalassemic mice," Blood 110(13):4175-4178 (2007).
Lowrey et al., "Mechanism of DNase I hypersensitive site formation within the human globin locus control region," PNAS USA 89:1143-1147 (1992).
Lucarelli et al., "Bone Marrow Transplantation in Adult Thalassemic Patients," Blood 93(4):1164-1167 (1999).
Luzzatto et al., "Sickle cell anaemia. A simple disease with no cure," Nature 337:17-18 (1989).
Ma et al., "High-Level Sustained Transgene Expression in Human Embryonic Stem Cells Using Lentiviral Vectors," Stem Cells 21:111-117 (2003).
Mancuso et al., "A Prospective Study of Hepatocellular Carcinoma Incidence in Thalassemia," Hemoglobin 30(1):119-124 (2006).
Maurano et al., "Systematic Localization of Common Disease-Associated Variation in Regulatory DNA," Science 337:1190-1195 (2012).
May et al., "Successful treatment of murine β-thalassemia intermedia by transfer of the human β-globin gene," Blood 99:1902-1908 (2002).
May et al., "Therapeutic haemoglobin synthesis in β-thalassaemic mice expressing lentivirus-encoded human β-globin," Nature 406:82-86 (2000).
McArthur et al., "Quantification of DNaseI-sensitivity by Real-time PCR: Quantitative Analysis of DNaseI-hypersensitivity of the Mouse β-Globin LCR," J Mol Biol 313:27-34 (2001).
McGhee et al., "A 200 Base Pair Region at the 5' End of the Chicken Adult β-Globin Gene Is Accessible to Nuclease Digestion," Cell 27:45-55 (1981).
Miccio et al., "In vivo selection of genetically modified erythroblastic progenitors leads to long-term correction of β-thalassemia," PNAS USA 105(30):10547-10552 (2008).
Moi et al., "Synergistic enhancement of globin gene expression by activator protein-1-like proteins," PNAS USA 87:9000-9004 (1990).
Nagel et al., "Structural bases of the inhibitory effects of hemoglobin F and hemoglobin A2 on the polymerization of hemoglobin S," PNAS USA 76(2):670-672 (1979).
Navas et al., "Developmental specificity of the Interaction between the Locus Control Region and Embryonic or Fetal Globin Genes in Transgenic Mice with an HS3 Core Deletion," Molecular and Cellular Biology 18(7):4188-4196 (1998).

Neph et al., "An expansive human regulatory lexicon encoded in transcription factor footprints," Nature 489:83-90 (2012).
Neph et al., "Circuitry and Dynamics of Human Transcription Factor Regulatory Networks," Cell 150:1274-1286 (2012).
Ney et al., "Tandem AP-1-binding sites within the human β-globin dominant control region function as an inducible enhancer in erythroid cells," Genes Dev. 4:993-1006 (1990).
Nienhuis et al., "Genotoxicity of Retroviral Integration In Hematopoietic Cells," Mol Ther 13(6):1031-1049 (2006).
Nienhuis, "Development of gene therapy for blood disorders: an update," Blood 122(9):1556-1564 (2013).
Nishino et al. "Partial correction of murine β-thalassemia with a gammaretrovirus vector for human γ-globin," Blood Cells Mol Dis 37:1-7 (2006).
Ohlsson et al., "CTCF is a uniquely versatile transcription regulator linked to epigenetics and disease," TRENDS Genet. 17(9):520-527 (2001).
Papayannopoulou et al., "Hemopoietic lineage commitment decisions: in vivo evidence from a transgenic mouse model harboring μLCR-βpro-LacZ as a transgene," Blood 95:1274-1282 (2000).
Pauling et al., "Sickle Cell Anemia, a Molecular Disease," Science 110:543-546 (1949).
Pawliuk et al., "Correction of Sickle Cell Disease in Transgenic Mouse Models by Gene Therapy," Science 294:2368-2371 (2001).
Perrine et al., "Induction of Fetal Globin in β-Thalassemia: Cellular Obstacles and Molecular Progress," Ann NY Acad Sci 1054:257-265 (2005).
Persons et al., "Gene Therapy for the Hemoglobin Disorders," Semin Hematol 41:279-286 (2004).
Persons, "The challenge of obtaining therapeutic levels of genetically modified hematopoietic stem cells in β-thalassemia patients," Ann NY Acad Sci 1202:69-74 (2010).
Perumbeti et al., "Therapy for β-globinopathies: a brief review and determinants for successful and safe correction," Ann NY Acad Sci 1202:36-44 (2010).
Pestina et al., "Correction of Murine Sickle Cell Disease Using γ-Globin Lentiviral Vectors to Mediate High-Level Expression of Fetal Hemoglobin," Mol Ther 17(2):245-252 (2009).
Phillips et al., "CTCF: Master Weaver of the Genome," Cell 137:1194-1211 (2009).
Platt et al., "Hydroxyurea Enhances Fetal Hemoglobin Production in Sickle Cell Anemia," J. Clin. Invest. 74:652-656 (1984).
Pluta et al., "Tight control of transgene expression by lentivirus vectors containing second-generation tetracycline-responsive promoters," J Gene Med 7:803-817 (2005).
Puthenveetil et al., "Successful correction of the human β-thalassemia major phenotype using a lentiviral vector," Blood 104:3445-3453 (2004).
Ramezani et al., "Combinatorial Incorporation of Enhancer-Blocking Components of the Chicken β-Globin 5'HS4 and Human T-cell Receptor a/δ BEAD-1 Insulators in Self-Inactivating Retroviral Vectors Reduces Their Genotoxic Potential," Stem Cells 26:3257-3266 (2008).
Ramezani et al., "Performance- and safety-enhanced lentiviral vectors containing the human interferon-β scaffold attachment region and the chicken β-globin insulator," Blood 101:4717-4724 (2003).
Ramezani et al., "Stable Gammaretroviral Vector Expression during Embryonic Stem Cell-Derived In Vitro Hematopoietic Development," Mol Ther 14(2):245-254 (2006).
Recillas-Targa et al., "Position-effect protection and enhancer blocking by the chicken β-globin insulator are separable activities," PNAS USA 99(10):6883-6888 (2002).
Renda et al., "Critical DNA Binding Interactions Of The Insulator Protein CTCF: A Small Number of Zinc Fingers Mediate Strong Binding, and a Single Finger-DNA Interaction Controls Binding at Imprinted Loci," J Biol Chem 282(46):33336-33345 (2007).
Rivella et al., "A novel murine model of Cooley anemia and its rescue by lentiviral-mediated human β-globin gene transfer," Blood 101:2932-2939 (2003).
Rivella et al., "The cHS4 Insulator Increases the Probability of Retroviral Expression at Random Chromosomal Integration Sites," J Virol 74(10):4679-4687 (2000).

(56) References Cited

OTHER PUBLICATIONS

Ryu et al., "A chromatin insulator blocks interactions between globin regulatory elements and cellular promoters in erythroid cells," Blood Cells Mol Dis 39:221-228 (2007).
Ryu et al., "An experimental system for the evaluation of retroviral vector design to diminish the risk for proto-oncogene activation," Blood 111(4):1866-1875 (2008).
Sabo et al., "Discovery of functional noncoding elements by digital analysis of chromatin structure," PNAS USA 101(48): 16837-16842 (2004).
Sabo et al., "Genome-scale mapping of DNase I sensitivity in vivo using tiling DNA microarrays," Nat Methods 3(7):511-518 (2006).
Sabo et al., "Genome-wide identification of DNaseI hypersensitive sites using active chromatin sequence libraries," PNAS USA 101(13):4537-4542 (2004).
Sadelain et al., "Generation of a high-titer retroviral vector capable of expressing high levels of the human β-globin gene," PNAS USA 92:6728-6732 (1995).
Sadelain et al., "Stem Cell Engineering for the Treatment of Severe Hemoglobinopathies," Curr Mol Med 8:690-697 (2008).
Sadelain et al., "Therapeutic Options for Patients with Severe β-Thalassemia: The Need for Globin Gene Therapy," Hum Gene Ther 18:1-9 (2007).
Sadelain, "Genetic Treatment of the Haemoglobinopathies: Recombinations and New Combinations," Br J Haematol 98:247-253 (1997).
Sadelain, "Recent advances in globin gene transfer for the treatment of beta-thalassemia and sickle cell anemia," Current Opinion in Hematology 13:142-148 (2006).
Samakoglu et al., "A genetic strategy to treat sickle cell anemia by coregulating globin transgene expression and RNA interference," Nat. Biotechnol 24:89-94 (2006).
Schmidt et al., "Waves of Retrotransposon Expansion Remodel Genome Organization and CTCF Binding in Multiple Mammalian Lineages," Cell 148:335-348 (2012).
Shimotsuma et al., "DNase I Hypersensitivity and e-Globin Transcriptional Enhancement Are Separable in Locus Control Region (LCR) HS1 Mutant Human β-Globin YAC Transgenic Mice," Journal of Biological Chemistry 285(19): 14495-14503 (2010).
Shivdasani et al., "Transcription Factor NF-E2 is Required for Platelet Formation Independent of the Actions of Thrombopoietin/MGDF in Megakaryocyte Development," Cell 81:695-704 (1995).
Stamatoyannopoulos, "Prospects for developing a molecular cure for thalassemia," Hematology 10(Suppl 1):255-257 (2005).
Stamatoyannopoulos, G., Nienhuis, AW., Majerus, P. & Varmus, H. The Molecular Basis of Blood Diseases. WE Saunders, Philadelphia (1994).
Stergachis et al., "Developmental Fate and Cellular Maturity Encoded in Human Regulatory DNA Landscapes," Cell 154:888-903 (2013).
Stergachis et al., "Exonic Transcription Factor Binding Directs Codon Choice and Affects Protein Evolution," Science 342:1367-1372 (2013).
Struhl, "Histone acetylation and transcriptional regulatory mechanisms," Genes & Development 12:599-606 (1998).
Swank et al., "Fetal gene reactivation," Curr Opin Genet Dev 8:366-370 (1998).
Talbot et al., "The 5'HS2 of the globin locus control region enhances transcription through the interaction of a multimeric complex binding at two functionally distinct NF-E2 binding sites," EMBO J 10(6):1391-1398 (1991).
Telfer et al. "Improved survival in thalassemia major patients on switching from desferrioxamine to combined chelation therapy with desferrioxamine and deferiprone," Haematologica 94(12):1777-1778 (2009).
Thurman et al., "The accessible chromatin landscape of the human genome," Nature 489:75-82 (2012).
Tisdale et al., "Toward Gene Therapy for Disorders of Globin Synthesis," Semin Hematol 38(4):382-392 (2001).
Tsukiyama et al., "Chromatin remodeling and transcription," Curr Opin Genet Dev 7:182-191 (1997).
Vermylen et al., "Haematopoietic stem cell transplantation for sickle cell anaemia: the first 50 patients transplanted in Belgium," Bone Marrow Transplant 22:1-6 (1998).
Vieira et al., "Recruitment of Transcription Complexes to the β-Globin Gene Locus in Vivo and in Vitro," J Biol Chem 279(48):50350-50357 (2004).
Wallace et al., "We gather together: insulators and genome organization," Curr Opin Genet Dev 17:400-407 (2007).
Wang et al., "Widespread plasticity in CTCF occupancy linked to DNA methylation," Genome Research 22:1680-1688 (2012).
Weatherall et al., "The Thalassemia Syndromes," Texas Reports on Biology and Medicine 40:323-333 (1980-1981) Oxford (1981).
Weatherall, "Phenotype-Genotype Relationships In Monogenic Disease: Lessons From The Thalassaemias," Nature Reviews Genetics 2:245-255 (2001).
Wilber et al., "Transcriptional regulation of fetal to adult hemoglobin switching: new therapeutic opportunities," Blood 117(15):3945-3953 (2011).
Wolffe et al., "Activators and repressors: making use of chromatin to regulate transcription," Genes to Cells 2:291-302 (1997).
Wu, "The 5' ends of *Drosophila* heat shock genes in chromatin are hypersensitive to DNase I," Nature 286:854-860 (1980).
Yannaki et al., "Gene therapy for β-thalassaemia: the continuing challenge," Expert Reviews in Molecular Medicine 12:e31 (2010).
Yannaki et al., "Topological Constraints Governing the Use of the Chicken HS4 Chromatin Insulator in Oncoretrovirus Vectors," Mol Ther 5(5):589-598 (2002).
Yao et al., "Retrovirus silencer blocking by the cHS4 insulator is CTCF independent," Nucleic Acids Res 31(18):5317-5323 (2003).
Yusufzai et al., "The 5'-HS4 chicken β-globin insulator is a CTCF-dependent nuclear matrix-associated element," PNAS USA 101(23):18620-8624 (2004).

\* cited by examiner

- ALAS Intron 1:

SEQ ID NO: 13 • XhoI_PacI~ TCTCCCACGCCCTGGTCTCAGCTTGGGGAGTGGTCAGACCCCAATGGCGATAAACTCTGGCAACTTATCTGTGcaCTGCAGGCTCAGCCCCA
AcaGCTTTAGCTTTCACAAGCAGGCAGGGAAGGCAAACACATATCTCCAGATATGAGG—PacI (TTAAT/TAA)

- ALAS Intron 8:

SEQ ID NO: 14 • SdaI~ CTAAACCCCTCCCCACCCTAGCCCCCAAGCTTCATCTCTTAGCTCCACTCCTGACCCTATCCAGCTAAAGGTCCCCACCCAGCTCCTGCCTATCTAGTCAT
TGCATATGGCAAGACTTGAAAGTCCTATCTCAAAGCAGCAGAATTATCAGCTACGACT—SdaI (CCTGCA/GG)

- BLVRB:

SEQ ID NO: 15 • PaiI~ CCATCCCCACCACTCCCTGCCCCACAGCCCAGACTTGACCAACTCCCAGCTccGCCTGGGACTTCCAGATATGGGGCCCCACCCTTGCAGGCCTTGC
GGACGCTGAAGATATTGACTATCTGCGTGCCggAAAAGGGTG—PaiI (TTA|TAA)

- PPOX:

SEQ ID NO: 16 • AgeI_ AAAGGCTGGGGTGGGAGTAGGCGGATTTGAAGCACTTGTTGGCCTACAGAGGTGTGCAAGCAGAGCACCTCAGAACTCAGGGCTACTGCCCGCCCCC
GAGCCCTGCCAGGGCCGATAGCCAGGAGGGTGTGGCCCTTATCTGCACCCAGCAGCAGCGCCGCCGGGGGTACGGTC—AgeI (a/ccggt)

- Spectrin—alpha

SEQ ID NO: 17 • Xma_CAGTTGCCTCAGCTGAGTATGTCTTCTAAAGATAAGTCGATTGTGTATGCCTGATGGATTCTAGGACCAAGCAAGAGGTTTTTTTTCCCCACATACTTA
ACGTTTCTATATTTCTATTTGAATTGACTGGACAGTTCCATTTGAATTATTTCTCTCTCTCTCTGACACATTTATCTGCCA —Xma (c/ccggg) —XhoI

FIG. 8

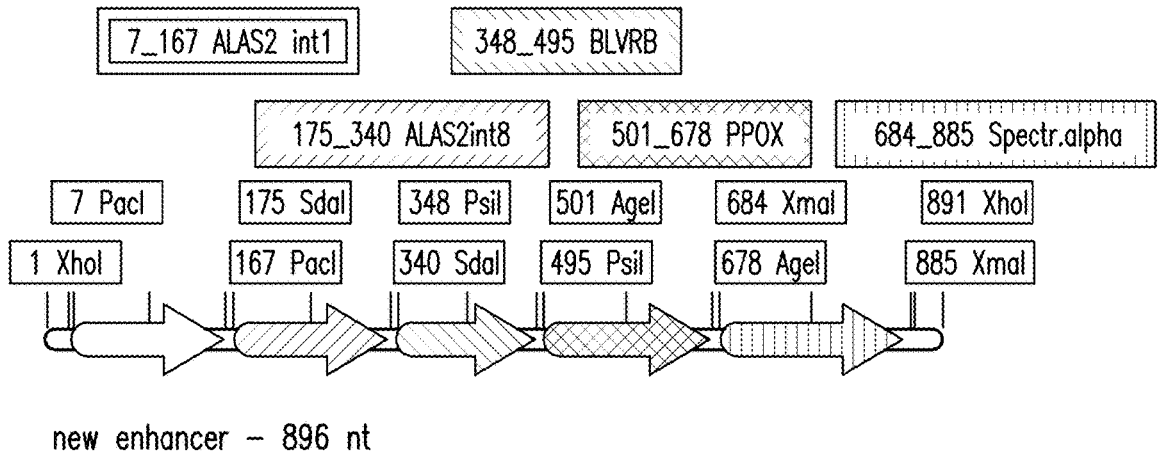

SEQ ID
NO: 26
• New-ENHANCER
• CTCGAGttaattaaTCTCCCACGCCCTGGTCTCAGCTTGGGGAGTGGTCAGACCCCAATGGCGATAA
ACTCTGGCAACTTTATCTGTGcaCTGCAGGCTCAGCCCCAAcaGCTTTAGCTTTCACAAGCAGGCAGGGG
AAGGGAAACACATATCTCCAGATATGAGGttaattaacctgcaggCTAAACCCCTCCCCCACCCTAGCCC
CAAGCTTCATCTTAGCTCCACTCCTGACCCTATCCAGCTAAAGGTCCCCACCCAGCTCCTGCCTATCTAG
TCATTGCATATGGCAAGACTTGAAAGTCCTATCTCAAAGCAGCAGAATTATCAGCTACGACTcctgcagg
ttataaCCATCCCCCAGCACTCCCTGCCCCCACAGCCCAGACTTGACCAACTCCCAGCTccGCCTGGGAC
TTCCAGATATGGGGCCCCACCCTTGCAGGCCTTGGGGACGCTGAAGATATTGACTATCTGCGTGCCggAA
AAGGGTGttataaaccggtAAAGGCTGGGGGTGGGAGTAGCGGATTTGAAGCACTTGTTGGCCTACAGAG
GTGTGGCAAGCAGAGCACCTCAGAACTCAGGCGTACTGCCCGCCGCCCGAGCCCTGCGAGGGCCGATAGC
GAGGGTGTGGCCCTTATCTGCACCCAGCAGAGCGCCGGCGGGGTACGGTCaccggtcccgggCAGTTGCC
TCAGCTGAGTATGTCTTCTAAAGATAATGTCGATTGTGTATGGCTGATGGGATTCTAGGACCAAGCAAGA
GGTTTTTTTTTTTCCCCCACATACTTAACGTTTCTATATTTCTATTTGAATTCGACTGGACAGTTCCATT
TGAATTATTTCTCTCTCTCTCTCTCTGACACATTTTATCTTGCCAcccgggCTCGAG

FIG. 9

GLOBIN GENE THERAPY FOR TREATING HEMOGLOBINOPATHIES

CROSS-REFERENCE TO RELATED APPLICATIONS

This application is a continuation of International Patent Application No. PCT/US15/48698 filed Sep. 4, 2015, which claims priority to U.S. Provisional Application No. 62/045,997 filed Sep. 4, 2014, the contents of which is hereby incorporated by reference in its entirety herein, and to each of which priority is claimed.

GRANT INFORMATION

This invention was made with government support under Grant No. HL053750 and HL057612 awarded by the National Institutes of Health. The government has certain rights in the invention.

SEQUENCE LISTING

The specification further incorporates by reference the Sequence Listing submitted via EFS on Mar. 3, 2017. Pursuant to 37 C.F.R. § 1.52(e)(5), the Sequence Listing text file, identified as 0727340477SL, is 126,316 bytes in size and was created on Mar. 3, 2017. The Sequence Listing, electronically filed on Mar. 3, 2017, does not extend beyond the scope of the specification and thus does not contain new matter.

INTRODUCTION

The presently disclosed subject matter provides expression cassettes and vectors comprising such expression cassettes that express a globin protein, e.g., a human β-globin protein. The presently disclosed subject matter further provides expression cassettes that comprise a globin gene or a functional portion thereof operably linked to a β-globin locus control region (LCR) comprising a plurality of Dnase I hypersensitive sites. The expression cassettes of the presently disclosed subject matter comprise one or more insulators that counteract the effect of enhancer elements. The insulators disclosed herein do not substantially adversely impact the titer of a vector that comprises the presently disclosed expression cassettes. The expression cassettes and vectors can be used for treating a hemoglobinopathy, e.g., β-thalassemia, and sickle cell anemia.

BACKGROUND

β-thalassemia and sickle cell anemia are severe congenital anemias that are caused by defective production of the β chain of hemoglobin. In β-thalassemia, the β chain deficit leads to the intracellular precipitation of excess α-globin chains, causing ineffective erythropoiesis and hemolytic anemia (Weatherall and Clegg (1981), Stamatoyannopoulos et al., (1994), Weatherall (2001), Steinberg (2001)). In the most severe forms found in homozygotes or compound heterozygotes, anemia is lethal within the first years of life in the absence of any treatment (Cooley and Lee (1925)). Lifelong transfusion therapy is needed to correct anemia, suppress ineffective erythropoiesis and inhibit gastrointestinal iron absorption (Weatherall and Clegg (1981), Stamatoyannopoulos et al. (1994), Weatherall (2001), Steinberg (2001)). However, transfusion therapy itself leads to iron overload, which is lethal if untreated. The prevention and treatment of iron overload are the major goals of current patient management (Giardina (2001)). The only current curative treatment to cure β-thalassemia is to provide erythroid precursors harboring normal globin genes through allogeneic bone marrow transplantation (BMT) (Giardini and Lucarelli (1994), Boulad et al. (1998), Lucarelli et al. (1999), Tisdale and Sadelain (2001)).

In sickle cell anemia, the hemoglobin β chain is mutated at amino acid position 6 (Glu→Val), leading to the synthesis of $β^S$ instead of the normal $β^A$ chain (Steinberg (2001), Pauling et al. (1949)). The resulting hemoglobin, HbS, causes accelerated red cell destruction, erythroid hyperplasia and painful vaso-occlusive 'crises' (Steinberg (2001)). Vaso-occlusion can damage organs, eventually causing long-term disabilities (e.g. following stroke or bone necrosis), and sometimes sudden death. While a very serious disorder, the course of sickle cell disease is typically unpredictable (Steinberg (2001)). By increasing production of fetal hemoglobin (Swank and Stamatoyannopoulos (1998)) and suppressing hematopoiesis, hydroxyurea can produce a measurable clinical benefit (Platt et al. (1984)), Charache et al. (1992), Atweh and Loukopoulos (2001)). Since hydroxyurea is a cytotoxic agent, there is a great need for alternative, less toxic drugs to induce γ-globin gene expression (Perrine et al. (2005), Stamatoyannopoulos (2005)). As for β-thalassemia, allogeneic bone marrow transplantation (BMT) is at present the only curative therapy for sickle cell disease (Tisdale and Sadelain (2001), Vermylen et al. (1998), Luzzatto and Goodfellow (1989)).

BMT, however, is not available as a therapeutic option to most patients suffering from β-thalassemia or sickle cell disease, due to the lack of an HLA-matched bone marrow donor for most individuals. Furthermore, although potentially curative, allogeneic BMT is not devoid of complications. Safe transplantation requires the identification of a histo-compatible donor to minimize the risks of graft rejection and graft-versus-host disease (Tisdale and Sadelain (2001), Vermylen et al. (1998), Luzzatto and Goodfellow (1989)). Because of the greater risks associated with matched-unrelated or mismatched transplants, most patients have to settle for life-long transfusion therapy, which does not correct ineffective erythropoiesis and exacerbates systemic iron accumulation. Moreover, despite the considerable improvement in life expectancy in the last decades (Borgna-Pignatti et al. (2004), Telfer et al. (2009), Ladis et al. (2011)), the risk of some serious complications arising over the long term from viral infections, iron toxicity and liver cirrhosis, remain (Mancuso et al. (2006)). These medical risks, together with the socio-economic cost of chronic β-thalassemia, underscore the need for safe, effective and curative therapies.

The only means to cure rather than treat severe β-thalassemia is to provide the patient with healthy hematopoietic stem cells (HSCs). HSCs normally give rise to all blood cell types, including 20 billion RBCs per day in adults. HSCs can be harvested from a donor with wild-type β-globin genes to yield long-lived red blood cells (RBCs) with a normal content in hemoglobin. Alternatively, one may genetically correct the patient's own HSCs, which at once resolves the search for a donor and eliminates the risks of graft-versus-host disease and graft rejection associated with allogeneic BMT (Sadelain (1997), Sadelain et al. (2007)). Globin gene transfer aims to restore the capacity of the β-thalassemic subject's own blood-forming stem cells to generate RBCs with a sufficient hemoglobin content Sadelain et al. (2007), Persons and Tisdale (2004), Sadelain (2006)). The goal in patients with sickle cell anemia is to prevent sickling, which can be achieved by diluting the endogenous HbS with a non-sickling Hb that incorporates the vector-encoded globin chain. The patient's own HSCs are the cells that have to be genetically modified to ensure long-lasting therapeutic benefits and achieve a curative stem cell-based therapy.

The implementation of globin gene transfer for the treatment of severe β-thalassemia and sickle cell anemia requires the efficient introduction of a regulated human β- or β-like globin gene in HSCs. The β-globin gene (or β-like variant) must be expressed in erythroid-specific fashion and at high level, especially for the treatment of transfusion-dependent beta-zero thalassemias.

The globin vectors developed to date present shortcomings that may limit or even preclude their safe use in thalassemia and sickle cell patients. Some of the β-globin locus control region (LCR) components contained in the vectors, in particular Dnase I hypersensitive site-2 (HS2), may have non-erythroid activity, exposing patients to the risk of insertional oncogenesis as seen with non-specific expression vectors. Further, the use of large LCR segments can be detrimental to the production of high titer vectors and the efficient transduction of patients HSCs. Accordingly, there is a need for novel globin expression cassettes that allow for therapeutic expression of a globin gene (e.g., human β-globin gene) in erythroid-specific and differentiation stage-specific fashion with minimal risk of insertional oncogenesis, and that enable high level transduction, thus improving their safety when used in treating thalassemia and sickle cell patients.

SUMMARY OF THE INVENTION

The presently disclosed subject matter generally provides enhancer blocking insulators, and certain insulators additionally possess barrier insulator activity. The presently disclosed subject matter also provides expression cassettes comprising one or more insulators and allows for expression of a globin gene (e.g., a human β globin gene). Also provided are vectors comprising such expression cassettes, cells transduced with such expression cassettes or such vectors, and uses of such expression cassettes for treating hemoglobinopathies (e.g., β-thalassemia and sickle cell anemia).

In certain non-limiting embodiments, the presently disclosed subject matter provides an insulator comprising the CTCF binding site sequence set forth in SEQ ID NO:18, for example, but not limited to, an insulator comprising SEQ ID NO: 24 or SEQ ID NO:25, such as an insulator having the nucleotide sequence set forth in SEQ ID NO:1 (and see infra). The presently disclosed subject matter also provides expression cassettes comprising at least one insulator comprising the CTCF binding site sequence set forth in SEQ ID NO:18, for example, but not limited to, an insulator comprising SEQ ID NO: 24 or SEQ ID NO:25, such as an insulator having the nucleotide sequence set forth in SEQ ID NO:1. In a non-limiting embodiment, an expression cassette comprises at least one insulator comprising the CTCF binding site sequence set forth in SEQ ID NO:18, for example, but not limited to, an insulator comprising SEQ ID NO: 24 or SEQ ID NO:25, such as an insulator having the nucleotide sequence set forth in SEQ ID NO:1, and a globin gene or a functional portion thereof operably linked to a β-globin locus control region (LCR). In certain embodiments, the β-globin LCR does not comprise a Dnase I hypersensitive site-2 (HS2) region. In certain embodiments, the β-globin LCR region does not comprise a core sequence of HS2. In one non-limiting embodiment, the core sequence of HS2 has the nucleotide sequence set forth in SEQ ID NO:20. In one non-limiting embodiment, the core sequence of HS2 has the nucleotide sequence set forth in SEQ ID NO:21. In certain embodiments, the β-globin LCR does not comprise a HS2 region that sustains the enhancer activity of HS2. In one non-limiting embodiment, the β-globin LCR comprises a Dnase I hypersensitive site-1 (HS1) region, a Dnase I hypersensitive site-3 (HS3) region, and a Dnase I hypersensitive site-4 (HS4) region. In certain embodiments, the HS3 region is positioned between the HS1 and the HS4 region.

In certain embodiments, the HS1 region is about 1.1 kb bp in length. In one non-limiting embodiment, the HS1 region is between about 500 bp and about 1000 bp in length. In one non-limiting embodiment, the HS1 region has the nucleotide sequence set forth in SEQ ID NO:2. In certain embodiments, the HS1 region is about 600 bp in length. In one non-limiting embodiment, the HS1 region is 602 bp in length. In certain embodiments, the HS1 region is between about 500 and about 600 bp in length. In one non-limiting embodiment, the HS1 region has the nucleotide sequence set forth in SEQ ID NO:3. In certain embodiments, the HS1 region is about 490 bp in length. In one non-limiting embodiment, the HS1 region is 489 bp in length. In one non-limiting embodiment, the HS1 region has the nucleotide sequence set forth in SEQ ID NO:4. In one non-limiting embodiment, the β-globin LCR comprises a HS1 region having a nucleotide sequence set forth in SEQ ID NO:2, a HS3 region having a nucleotide sequence set forth in SEQ ID NO:5, and a HS4 region having a nucleotide sequence set forth in SEQ ID NO:6, and the β-globin LCR region does not comprise a HS2 region. In one non-limiting embodiment, the β-globin LCR region comprises a HS1 region having a nucleotide sequence set forth in SEQ ID NO:3, a HS3 region having a nucleotide sequence set forth in SEQ ID NO:5, and a HS4 region having a nucleotide sequence set forth in SEQ ID NO:8, and the β-globin LCR does not comprise a HS2 region. In one non-limiting embodiment, the β-globin LCR comprises a HS1 region having a nucleotide sequence set forth in SEQ ID NO:4, a HS3 region having a nucleotide sequence set forth in SEQ ID NO:5, and a HS4 region having a nucleotide sequence set forth in SEQ ID NO:8, and the β-globin LCR does not comprise a HS2 region.

In certain embodiments, the β-globin LCR region does not comprise a HS1 region and/or does not comprise a HS2 region, and the β-globin LCR does not comprise a core sequence of HS2. In certain embodiments, the β-globin LCR does not comprise a core sequence of HS1. In one non-limiting embodiment, the core sequence of HS1 has the nucleotide sequence set forth in SEQ ID NO:22. In one non-limiting embodiment, the core sequence of HS1 has the nucleotide sequence set forth in SEQ ID NO:23. In certain embodiments, the β-globin LCR does not comprise a HS1 region that sustains the function of HS1. In certain embodiments, the β-globin LCR comprises a HS3 region and a HS4 region and does not comprise a core sequence of HS1. In certain embodiments, the HS3 region is positioned between a globin gene or functional portion thereof and the HS4 region. In certain embodiments, the HS3 region is between about 200 and about 1400 bp in length, e.g., between about 1300 and 1400 bp in length. In certain embodiments, the HS3 region is about 1300 bp in length. In one non-limiting embodiment, the HS3 region is 1301 bp in length. In one non-limiting embodiment, the HS3 region has the nucleotide sequence set forth in SEQ ID NO:5. In certain embodiments, the HS4 region is between about 200 and about 1200 bp in length, e.g., between about 400 and about 1100 bp in length. In certain embodiments, the HS4 region is about 1.1 kb in length. In one non-limiting embodiment, the HS4 region is 1065 bp in length. In one non-limiting embodiment, the HS4 region has the nucleotide sequence set forth in SEQ ID NO:6. In one non-limiting embodiment, the HS4 region has the nucleotide sequence set forth in SEQ ID NO:7. In certain embodiments, the HS4 region is about 450 bp in length. In one non-limiting embodiment, the HS4 region is 446 bp in length. In one non-limiting embodiment, the HS4 region has the nucleotide sequence set forth in SEQ ID NO:8. In one non-limiting embodiment, the β-globin LCR region comprises a HS3 region having the nucleotide sequence set forth in SEQ ID NO:5 and a HS4 region having a nucleotide sequence set forth in SEQ ID NO:6, and the β-globin LCR region does not comprise a HS1 region or a HS2 region.

Alternatively, the β-globin LCR region can comprise a HS2 region, a HS3 region, and a HS4 region. In certain embodiments, the HS2 region is between about 400 and about 1000 bp in length, e.g., between about 800 and 900 bp in length. In certain embodiments, the HS2 region is about 860 bp in length. In one non-limiting embodiment, the HS2 region has the nucleotide sequence set forth in SEQ ID NO:9. In certain embodiments, the HS3 region is about 1300 bp in length. In one non-limiting embodiment, the HS3 region is 1301 bp in length. In one non-limiting embodiment, the HS3 region has the nucleotide sequence set forth in SEQ ID NO:5. In certain embodiments, the HS4 region is about 1.1 kb in length. In one non-limiting embodiment, the HS4 region is 1065 bp in length. In one non-limiting embodiment, the HS4 region has the nucleotide sequence set forth in SEQ ID NO:7. In one non-limiting embodiment, the β-globin LCR region comprises a HS2 region having the nucleotide sequence set forth in SEQ ID NO:9, a HS3 region having the nucleotide sequence set forth in SEQ ID NO:5, and a HS4 region having the nucleotide sequence set forth in SEQ ID NO:7. Additionally, the β-globin LCR region can further comprise a HS1 region.

In certain embodiments, the globin gene is selected from the group consisting of β-globin gene, γ-globin gene, and δ-globin gene. In one non-limiting embodiment, the globin gene is human β-globin gene. In non-limiting embodiments, the human β-globin gene is selected from the group consisting of a wild-type human β-globin gene, a deleted human β-globin gene comprising one or more deletions of intron sequences, and a mutated human β-globin gene encoding at least one anti-sickling amino acid residue. In one non-limiting embodiment, the human β-globin gene is human $\beta^{A}$-globin gene encoding a threonine to glutamine mutation at codon 87 ($\beta^{A-T87Q}$).

In certain embodiments, the expression cassette comprises one insulator comprising the CTCF binding site sequence set forth in SEQ ID NO:18, for example, but not limited to, an insulator comprising SEQ ID NO: 24 or SEQ ID NO:25, such as an insulator having the nucleotide sequence set forth in SEQ ID NO:1. In certain embodiments, the expression cassette comprises two insulators, each comprising the CTCF binding site sequence set forth in SEQ ID NO:18, for example, but not limited to, where one or both insulators comprise SEQ ID NO: 24 or SEQ ID NO:25 and/or have the nucleotide sequence set forth in SEQ ID NO:1.

In certain embodiments, the expression cassette further comprises a β-globin promoter. In certain embodiments, the β-globin promoter is positioned between the globin gene or functional portion thereof and β-globin LCR region. In certain embodiments, the β-globin promoter is between about 200 and about 700 bp in length. In one non-limiting embodiment, the β-globin promoter is a human β-globin promoter that is about 613 bp in length. In one non-limiting embodiment, the human β-globin promoter has the nucleotide sequence set forth in SEQ ID NO:10. In another non-limiting embodiment, the β-globin promoter is a human β-globin promoter that is about 265 bp in length. In one non-limiting embodiment, the β human β-globin promoter has the nucleotide sequence set forth in SEQ ID NO:11.

In certain embodiments, the expression cassette further comprises a human β-globin 3' enhancer. In certain embodiments, the human β-globin 3' enhancer is positioned in the upstream of the globin gene or functional portion thereof. In certain embodiments, the β-globin 3' enhancer is between about 700 and about 900 bp in length, e.g., between about 800 and 900 bp in length. In one non-limiting embodiment, the human β-globin 3' enhancer is about 879 bp in length. In one non-limiting embodiment, the human β-globin 3' enhancer has the nucleotide sequence set forth in SEQ ID NO:12.

In certain embodiments, the expression cassette further comprises at least one erythroid-specific enhancer. In certain embodiments, the at least one erythroid-specific enhancer is positioned between the globin gene or functional portion thereof and the β-globin LCR region. In certain embodiments, the at least one erythroid-specific enhancer has a nucleotide sequence selected from the group consisting of SEQ ID NOS: 13, 14, 15, 16 and 17. In certain embodiments, the at least one erythroid-specific enhancer is between about 100 and about 200 bp in length. In certain embodiments, the expression cassette comprises one, two or three erythroid-specific enhancers.

In certain embodiments, the expression cassette allows for expression of the globin gene or functional portion thereof in a mammal. In one non-limiting embodiment, the expression cassette allows for expression of a human β-globin gene. In certain embodiments, the expression of the globin gene or functional portion thereof is restricted to erythroid tissue.

The presently disclosed subject matter also provides recombinant vectors comprising the above-described expression cassettes. In certain embodiments, the recombinant vector is a retroviral vector. In one non-limiting embodiment, the retroviral vector is a lentivirus vector. In certain embodiments, the expression cassette comprised in the recombinant vector comprises one insulator. In certain embodiments, the recombinant vector further comprises a Woodchuck hepatitis post-regulatory element (WPRE) in the 3' long terminal repeat (LTR) of the vector. In certain embodiments, the recombinant vector further comprises a bovine growth hormone polyadenylation signal in the 3' long terminal repeat (LTR) of the vector.

In addition, the presently disclosed subject matter provides non-naturally occurring or engineered nucleases comprising the above-described expression cassettes. In certain embodiments, the nuclease is selected from the group consisting of a non-naturally occurring or engineered zinc-finger nuclease (ZFN), a non-naturally occurring or engineered meganuclease, and a non-naturally occurring or engineered transcription activator-like effector nuclease (TALEN). In certain embodiments, the nuclease comprises a DNA binding domain and a nuclease cleavage domain. In certain embodiments, the nuclease binds to a genomic safe harbor site. In certain embodiments, the nuclease generates a double strand break (DSB) at the genomic safe harbor site. In certain embodiments, the expression cassette comprised in the nuclease comprises two of the insulator having the nucleotide sequence set forth in SEQ ID NO:1. In certain embodiments, the nuclease allows for targeted delivery of the expression cassette. The presently disclosed subject matter also provides polynucleotides encoding the above-described nucleases, and vectors comprising the polynucleotides. In one non-limiting embodiment, the vector is a lentiviral vector.

Furthermore, the presently disclosed subject matter provides non-naturally occurring or engineered CRISPR-Cas systems comprising the above-described expression cassettes. In certain embodiments, the CRISPR-Cas system comprises a CRISPR-Cas nuclease and single-guide RNA. In certain embodiments, the CRISPR-Cas system binds to a genomic safe harbor site. In certain embodiments, the CRISPR-Cas system generates a double strand break (DSB) at the genomic safe harbor site. In certain embodiments, the expression cassette comprised in the CRISPR-Cas system comprises two of the insulator having the nucleotide sequence set forth in SEQ ID NO:1. In certain embodiments, the CRISPR-Cas allows for targeted delivery of the expression cassette. The presently disclosed subject matter also provides polynucleotides encoding the above-described CRISPR-Cas systems, and vectors comprising the polynucleotides. In one non-limiting embodiment, the vector is a lentiviral vector.

In some embodiments, the genomic safe harbor site is an extragenic genomic safe harbor site. In certain embodiments, the genomic safe harbor site is located on chromosome 1. In some embodiments, the genomic safe harbor meets all of the following five criteria: (1) distance of at least 50 kb from the 5' end of any gene (e.g., from the 5' end of the gene), (ii) distance of at least 300 kb from any cancer-related gene, (iii) within an open/accessible chromatin structure (measured by DNA cleavage with natural or engineered nucleases), (iv) location outside a gene transcription unit and (v) location outside ultraconserved regions (UCRs), microRNA or long non-coding RNA of the human genome.

Additionally, the presently disclosed subject matter provides cells transduced with the above-described expression cassettes, cells transduced with the above-described recombinant vectors, cells transduced with the above-described nucleases, cells transduced with the above-described CRISPR-Cas systems. In addition, the presently disclosed subject matter provides cells transduced with the above-described vectors. In certain embodiments, the cell is selected from the group consisting of a hematopoietic stem cell, an embryonic stem cell, an induced pluripotent stem cell, and a hemogenic endothelium cell. In one non-limiting embodiment, the hematopoietic stem cell is a CD34+ hematopoietic stem cell. In certain embodiments, the cell is transduced ex vivo.

Also provided are pharmaceutical compositions comprising an effective amount of the above-described cells and a pharmaceutically acceptable carrier. The presently disclosed subject matter also provides pharmaceutical compositions for treating a hemoglobinopathy comprising an effective amount of the above-described cells and a pharmaceutically acceptable carrier.

Furthermore, the presently disclosed subject matter provides kits for treating a hemoglobinopathy comprising the above-described cells. In certain embodiments, the kits further comprise written instructions for using the cell for treating a subject having a hemoglobinopathy.

In addition, the presently disclosed subject matter provides methods of treating a hemoglobinopathy in a subject, comprising administering an effective amount of the above-described cells to the subject, thereby restoring the subject's ability to produce red blood cells containing normal hemoglobin. In certain embodiments, a therapeutically relevant level of hemoglobin is produced in the subject following administering the cell to the subject. In certain amendments, the method comprises administering an effective amount of the cell transduced with the above-described recombinant vector. In some embodiments, the vector copy number of the recombinant vector in the cell that provides for the therapeutically relevant level of hemoglobin in the subject is about 0.5-2 vector copy number per cell. In certain embodiments, the method corrects ineffective erythropoiesis in the subject. In certain embodiments, the method does not incur the risk of graft-versus-host disease in the subject. In certain embodiments, the method does not comprise administering an immunosuppressive agent. In certain embodiments, the cell is selected from the group consisting of a hematopoietic stem cell, an embryonic stem cell, an induced pluripotent stem cell, and a hemogenic endothelium cell. In one non-limiting embodiment, the subject is a human. In certain embodiments, the cell is from the subject. In one non-limiting embodiment, the cell is from bone marrow of the subject.

In accordance with the presently disclosed subject matter, the hemoglobinopathy can be selected from the group consisting of hemoglobin C disease, hemoglobin sickle cell disease (SCD), sickle cell anemia, hereditary anemia, thalassemia, β-thalassemia, thalassemia major, thalassemia intermedia, α-thalassemia, and hemoglobin H disease. In one non-limiting embodiment, the hemoglobinopathy is β-thalassemia. In another non-limiting embodiment, the hemoglobinopathy is sickle cell anemia.

BRIEF DESCRIPTION OF THE FIGURES

The following Detailed Description, given by way of example, but not intended to limit the invention to specific embodiments described, may be understood in conjunction with the accompanying drawings.

FIG. 8 represents the erythroid-specific enhancers in accordance with certain embodiments of the presently disclosed subject matter.

FIG. 9 represents the erythroid-specific enhancers in accordance with certain embodiments of the presently disclosed subject matter.

DETAILED DESCRIPTION OF THE INVENTION

Figure 1:
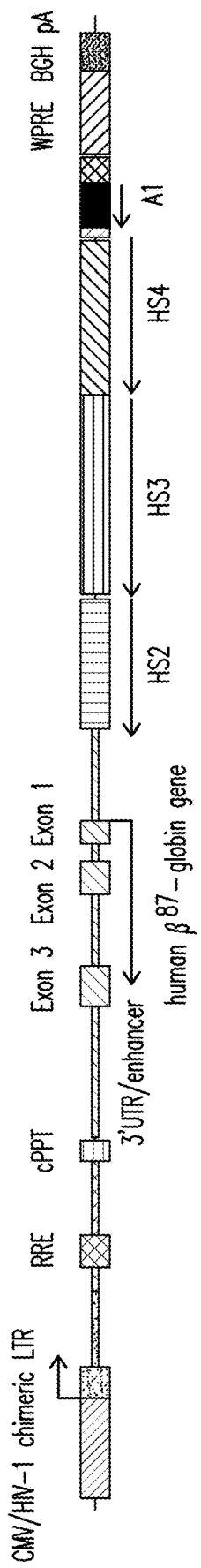
FIG. 1 depicts a recombinant vector comprising an expression cassette in accordance with one non-limiting embodiment of the presently disclosed subject matter.

The presently disclosed subject matter generally provides expression cassettes that allow for expression of a globin gene (e.g., human β-globin gene). In one non-limiting example, the expression cassette comprises at least one insulator comprising the CTCF binding site sequence set forth in SEQ ID NO:18, for example, but not limited to, an insulator comprising SEQ ID NO: 24 or SEQ ID NO:25, such as an insulator having the nucleotide sequence set forth in SEQ ID NO:1 and a globin gene or a functional portion thereof operably linked to a β-globin locus control region (LCR) region. The expression of the globin gene induced by the presently disclosed expression cassettes is erythroid-specific, differentiation stage-specific, high-level, and sustained. The presently disclosed subject matter also provides recombinant vectors, non-naturally occurring or engineered nucleases, and non-naturally occurring or engineered CRISPR-Cas systems comprising such expression cassettes, and cells transduced with such expression cassettes, recombinant vectors, nucleases and CRISPR-Cas systems. The presently disclosed expression cassettes and vectors comprising thereof provide for a safe gene transfer therapy as therapeutic transgene expression is achieved (e.g., a therapeutically relevant level of hemoglobin is produced) with a low vector copy number per cell (e.g., 0.5-2, 1-2, or even 0.5-1). In addition, the presently disclosed subject matter provides methods of using such transduced cells for treating a hemoglobinopathy (e.g., β-thalassemia and sickle cell anemia).

I. DEFINITIONS

Unless defined otherwise, all technical and scientific terms used herein have the meaning commonly understood by a person skilled in the art to which this invention belongs. The following references provide one of skill with a general definition of many of the terms used in this invention: Singleton et al., Dictionary of Microbiology and Molecular Biology (2nd ed. 1994); The Cambridge Dictionary of Science and Technology (Walker ed., 1988); The Glossary of Genetics, 5th Ed., R. Rieger et al. (eds.), Springer Verlag (1991); and Hale & Marham, The Harper Collins Dictionary of Biology (1991). As used herein, the following terms have the meanings ascribed to them below, unless specified otherwise.

As used herein, the term "expression cassette" refers to a nucleic acid construct, generated recombinantly or synthetically, with a series of specified nucleic acid elements, which permit transcription of a particular nucleic acid in a target cell. The expression cassette can be incorporated into a plasmid, chromosome, mitochondrial DNA, plastid DNA, virus or nucleic acid region. The expression cassette portion can include a gene to be transcribed and elements that control the expression of the gene (e.g., a promoter).

As used herein, the term "β-globin locus control region (LCR) region" refers to a polynucleotide composed of one or more Dnase I hypersensitive site (HS) regions, including a HS1 region, a HS2 region, a HS3 region, and a HS4 region. The structure of many LCRs of the β-globin genes have been published, e.g., human (Li et al., *J. Biol. Chem.* (1985); 260:14, 901; Li et al., *Proc. Natl. Acad. Sci.* (1990) 87:8207); mouse (Shehee et al., J. Mol. Biol. (1989); 205: 41); rabbit (Margot et al., J. Mol. Biol. (1989); 205:15); and goat (Li, Q., et al., *Genomics* (1991); 9:488), each of which are incorporated by reference herein. In certain embodiments, the β-globin LCR region comprises a HS2 region (e.g., a β-globin LCR region comprising a HS2 region, a HS3 region and a HS4 region; and a β-globin LCR region comprising a HS1 region, a HS2 region, a HS3 region and a HS4 region). In certain embodiments, the β-globin LCR region does not comprise a HS2 region (e.g., a β-globin LCR region comprising a HS1 region, a HS3 region, a HS4 region). In certain embodiments, the β-globin LCR region does not comprise a HS2 region or a HS1 region (e.g., a β-globin LCR region comprising a HS3 region and a HS4 region).

As used herein, the term "recombinant" includes reference to a cell or vector, that has been modified by the introduction of a heterologous nucleic acid or that the cell is derived from a cell so modified. Thus, for example, recombinant cells express genes that are not found in identical form within the native (non-recombinant) form of the cell or express native genes that are otherwise abnormally expressed, under expressed or not expressed at all as a result of deliberate human intervention or may have reduced or eliminated expression of a native gene.

As used herein, the term "globin" refers to a family of heme-containing proteins that are involved in the binding and transport of oxygen. Subunits of vertebrate and invertebrate hemoglobins, vertebrate and invertebrate myoglobins or mutants thereof are included by the term globin.

As used herein, the term "wild-type" refers to the normal gene, virus, or organism found in nature without any mutation or modification.

The terms "polynucleotide", "nucleotide", "nucleotide sequence", "nucleic acid" and "oligonucleotide" are used interchangeably. They refer to a polymeric form of nucleotides of any length, either deoxyribonucleotides or ribonucleotides, or analogs thereof. Polynucleotides may have any three dimensional structure, and may perform any function, known or unknown. The following are non limiting examples of polynucleotides: coding or non-coding regions of a gene or gene region, loci (locus) defined from linkage analysis, exons, introns, messenger RNA (mRNA), transfer RNA, ribosomal RNA, short interfering RNA (siRNA), short-hairpin RNA (shRNA), micro-RNA (miRNA), ribozymes, cDNA, recombinant polynucleotides, branched polynucleotides, plasmids, vectors, isolated DNA of any sequence, isolated RNA of any sequence, nucleic acid probes, and primers. A polynucleotide can comprise one or more modified nucleotides, such as methylated nucleotides and nucleotide analogs. In particular embodiments, the presently disclosed subject matter provides polynucleotides encoding one or more globin genes or functional portions thereof. If present, modifications to the nucleotide structure may be imparted before or after assembly of the polymer. The sequence of nucleotides may be interrupted by non nucleotide components. A polynucleotide may be further modified after polymerization, such as by conjugation with a labeling component. Such polynucleotides need not be 100% identical with an endogenous nucleic acid sequence, but will typically exhibit substantial identity. Polynucleotides having "substantial identity" to an endogenous sequence are typically capable of hybridizing with at least one strand of a double-stranded nucleic acid molecule. By "hybridize" is meant pair to form a double-stranded molecule between complementary polynucleotide sequences (e.g., a gene described herein), or portions thereof, under various conditions of stringency. (See, e.g., Wahl, G. M. and S. L. Berger (1987) Methods Enzymol. 152:399; Kimmel, A. R. (1987) Methods Enzymol. 152:507).

For example, stringent salt concentration will ordinarily be less than about 750 mM NaCl and 75 mM trisodium citrate, preferably less than about 500 mM NaCl and 50 mM trisodium citrate, and more preferably less than about 250 mM NaCl and 25 mM trisodium citrate. Low stringency hybridization can be obtained in the absence of organic solvent, e.g., formamide, while high stringency hybridization can be obtained in the presence of at least about 35% formamide, and more preferably at least about 50% formamide. Stringent temperature conditions will ordinarily include temperatures of at least about 30° C., more preferably of at least about 37° C., and most preferably of at least about 42° C. Varying additional parameters, such as hybridization time, the concentration of detergent, e.g., sodium dodecyl sulfate (SDS), and the inclusion or exclusion of carrier DNA, are well known to those skilled in the art. Various levels of stringency are accomplished by combining these various conditions as needed. In a preferred: embodiment, hybridization will occur at 30° C. in 750 mM NaCl, 75 mM trisodium citrate, and 1% SDS. In a more preferred embodiment, hybridization will occur at 37° C. in 500 mM NaCl, 50 mM trisodium citrate, 1% SDS, 35% formamide, and 100 µg/ml denatured salmon sperm DNA (ssDNA). In a most preferred embodiment, hybridization will occur at 42° C. in 250 mM NaCl, 25 mM trisodium citrate, 1% SDS, 50% formamide, and 200 µg/ml ssDNA. Useful variations on these conditions will be readily apparent to those skilled in the art.

For most applications, washing steps that follow hybridization will also vary in stringency. Wash stringency conditions can be defined by salt concentration and by temperature. As above, wash stringency can be increased by decreasing salt concentration or by increasing temperature. For example, stringent salt concentration for the wash steps will preferably be less than about 30 mM NaCl and 3 mM trisodium citrate, and most preferably less than about 15 mM NaCl and 1.5 mM trisodium citrate. Stringent temperature conditions for the wash steps will ordinarily include a temperature of at least about 25° C., more preferably of at least about 42° C., and even more preferably of at least about 68° C. In a preferred embodiment, wash steps will occur at 25° C. in 30 mM NaCl, 3 mM trisodium citrate, and 0.1% SDS. In a more preferred embodiment, wash steps will occur at 42° C. in 15 mM NaCl, 1.5 mM trisodium citrate, and 0.1% SDS. In a more preferred embodiment, wash steps will occur at 68° C. in 15 mM NaCl, 1.5 mM trisodium citrate, and 0.1% SDS. Additional variations on these conditions will be readily apparent to those skilled in the art. Hybridization techniques are well known to those skilled in the art and are described, for example, in Benton and Davis (Science 196:180, 1977); Grunstein and Rogness (Proc. Natl. Acad. Sci., USA 72:3961, 1975); Ausubel et al. (Current Protocols in Molecular Biology, Wiley Interscience, New York, 2001); Berger and Kimmel (Guide to Molecular Cloning Techniques, 1987, Academic Press, New York); and Sambrook et al., Molecular Cloning: A Laboratory Manual, Cold Spring Harbor Laboratory Press, New York.

As used herein, the terms "polypeptide" and "protein" are used interchangeably to refer to a polymer of amino acid residues and to variants and synthetic analogues of the same. Thus, these terms apply to amino acid polymers in which one or more amino acid residues are synthetic non-naturally occurring amino acids, such as a chemical analogue of a corresponding naturally occurring amino acid, as well as to naturally-occurring amino acid polymers. Particular embodiments of the presently disclosed subject matter also include polypeptide "variants." Polypeptide "variant" refers to polypeptides that are distinguished from a reference polypeptide by the addition, deletion, truncations, and/or substitution of at least one amino acid residue, and that retain a biological activity. In certain embodiments, a polypeptide variant is distinguished from a reference polypeptide by one or more substitutions, which may be conservative or non-conservative, as known in the art. In certain embodiments, a variant polypeptide includes an amino acid sequence having at least about 50%, 55%, 60%, 65%, 70%, 75%, 80%, 85%, 90%, 91%, 92%, 93%, 94%, 95%, 96%, 97%, 98%, 99% or more sequence identity or similarity to a corresponding sequence of a reference polypeptide. In certain embodiments, the amino acid additions or deletions occur at the C-terminal end and/or the N-terminal end of the reference polypeptide. In certain embodiments, the amino acid deletions include C-terminal truncations of about 1, about 2, about 3, about 4, about 5, about 6, about 7, about 8, about 9, about 10, about 15, about 20, about 25, about 30, about 35, about 40, about 45, 50, about 55, about 60, about 65, about 70, about 75, about 80, about 85, about 90, about 95, about 100, about 105, about 110, about 115, about 120, about 125, about 130, about 135, about 140, about 145, about 150, about 155, about 160, about 165, about 170, or about 175 or more amino acids, including all intervening numbers of amino acids, e.g., 25, 26, 27, 29, 30 . . . 100, 101, 102, 103, 104, 105 . . . 170, 171, 172, 173, 174, etc.

As noted above, polypeptides of the presently disclosed subject matter may be altered in various ways including amino acid substitutions, deletions, truncations, and insertions. Methods for such manipulations are generally known in the art. For example, amino acid sequence variants of a reference polypeptide can be prepared by mutations in the DNA. Methods for mutagenesis and nucleotide sequence alterations are well known in the art. See, for example, Kunkel (1985, Proc. Natl. Acad. Sci. USA. 82: 488-492), Kunkel et al., (1987, Methods in Enzymol, 154: 367-382), U.S. Pat. No. 4,873,192, Watson, J. D. et al., Molecular Biology of the Gene, Fourth Edition, Benjamin/Cummings, Menlo Park, Calif., 1987) and the references cited therein. Guidance as to appropriate amino acid substitutions that do not affect biological activity of the protein of interest may be found in the model of Dayhoff et al., (1978) Atlas of Protein Sequence and Structure (Natl. Biomed. Res. Found., Washington, D.C.).

As used herein, the term "substantially identical" refers to a polypeptide or a polynucleotide exhibiting at least 50% identity to a reference amino acid sequence (for example, any one of the amino acid sequences described herein) or a nucleic acid sequence (for example, any one of the nucleic acid sequences described herein). Preferably, such a sequence is at least 60%, more preferably 80% or 85%, and more preferably 90%, 95% or even 99% identical at the amino acid level or nucleic acid to the sequence used for comparison.

Sequence identity or homology is typically measured using sequence analysis software (for example, Sequence Analysis Software Package of the Genetics Computer Group, University of Wisconsin Biotechnology Center, 1710 University Avenue, Madison, Wis. 53705, BLAST, BEST-FIT, GAP, or PILEUP/PRETTYBOX programs). Such software matches identical or similar sequences by assigning degrees of homology to various substitutions, deletions, and/or other modifications. In an exemplary approach to determining the degree of identity or homology, a BLAST program may be used, with a probability score between e-3 and e-100 indicating a closely related sequence. The percentage of identity between two sequences can also be determined with programs such as DNAMAN (Lynnon Biosoft, version 3.2). Using this program two sequences can be. aligned using the optimal alignment algorithm (Smith and Waterman, 1981). After alignment of the two sequences the percentage identity can be calculated by dividing the number of identical nucleotides between the two sequences by the length of the aligned sequences minus the length of all gaps.

Terms that describe the orientation of polynucleotides include: 5' (normally the end of the polynucleotide having a free phosphate group) and 3' (normally the end of the polynucleotide having a free hydroxyl (OH) group). Polynucleotide sequences can be annotated in the 5' to 3' orientation or the 3' to 5' orientation.

As used herein, a "single guide RNA" or a "synthetic guide RNA" refers to the polynucleotide sequence comprising the guide sequence, the tracr sequence and the tracr mate sequence. The term "guide sequence" refers to the about 20 bp sequence within the guide RNA that specifies the target site and may be used interchangeably with the terms "guide" or "spacer". The term "tracr mate sequence" may also be used interchangeably with the term "direct repeat(s)".

The terms "non-naturally occurring" or "engineered" are used interchangeably and indicate the involvement of the hand of man. The terms, when referring to nucleic acid molecules or polypeptides mean that the nucleic acid molecule or the polypeptide is at least substantially free from at least one other component with which they are naturally associated in nature and as found in nature.

As used herein, the term "expression" refers to the process by which a polynucleotide is transcribed from a DNA template (such as into and mRNA or other RNA transcript) and/or the process by which a transcribed mRNA is subsequently translated into peptides, polypeptides, or proteins. Transcripts and encoded polypeptides may be collectively referred to as "gene product." If the polynucleotide is derived from genomic DNA, expression may include splicing of the mRNA in a eukaryotic cell.

As used herein, the term "treating" or "treatment" refers to clinical intervention in an attempt to alter the disease course of the individual or cell being treated, and can be performed either for prophylaxis or during the course of clinical pathology. Therapeutic effects of treatment include, without limitation, preventing occurrence or recurrence of disease, alleviation of symptoms, diminishment of any direct or indirect pathological consequences of the disease, preventing metastases, decreasing the rate of disease progression, amelioration or palliation of the disease state, and remission or improved prognosis. By preventing progression of a disease or disorder, a treatment can prevent deterioration due to a disorder in an affected or diagnosed subject or a subject suspected of having the disorder, but also a treatment may prevent the onset of the disorder or a symptom of the disorder in a subject at risk for the disorder or suspected of having the disorder.

As used herein, the term "subject" refers to any animal (e.g., a mammal), including, but not limited to, humans, non-human primates, rodents, and the like (e.g., which is to be the recipient of a particular treatment, or from whom cells are harvested).

As used herein, the term "isolated cell" refers to a cell that is separated from the molecular and/or cellular components that naturally accompany the cell. As used herein, the term "isolated" refers to material that is free, substantially free, or essentially free to varying degrees from components which normally accompany it as found in its native state. "Isolate" denotes a degree of separation from original source or surroundings.

As used herein, the term "cell population" refers to a group of at least two cells expressing similar or different phenotypes. In non-limiting examples, a cell population can include at least about 10, at least about 100, at least about 200, at least about 300, at least about 400, at least about 500, at least about 600, at least about 700, at least about 800, at least about 900, at least about $10^3$ cells, at least about $10^4$ cells, at least about $10^5$ cells, at least about $10^6$ cells, at least about $10^7$ cells, or at least about $10^8$ cells expressing similar or different phenotypes.

As used herein, the term "cleavage" refers to the breakage of the covalent backbone of a DNA molecule. Cleavage can be initiated by a variety of methods including, but not limited to, enzymatic or chemical hydrolysis of a phosphodiester bond. Both single-stranded cleavage and double-stranded cleavage are possible, and double-stranded cleavage can occur as a result of two distinct single-stranded cleavage events. DNA cleavage can result in the production of either blunt ends or staggered ends. In certain embodiments, fusion polypeptides are used for targeted double-stranded DNA cleavage.

As used herein, the term "cleavage half-domain" refers to a polypeptide sequence which, in conjunction with a second polypeptide (either identical or different) forms a complex having cleavage activity (preferably double-strand cleavage activity). The terms "first and second cleavage half-domains;" "+ and − cleavage half-domains" and "right and left cleavage half-domains" are used interchangeably to refer to pairs of cleavage half-domains that dimerize.

As used herein, the term "chromosome" refers to a chromatin complex comprising all or a portion of the genome of a cell. The genome of a cell is often characterized by its karyotype, which is the collection of all the chromosomes that comprise the genome of the cell. The genome of a cell can comprise one or more chromosomes.

As used herein, the term "gene" includes a DNA region encoding a gene product, as well as all DNA regions which regulate the production of the gene product, whether or not such regulatory sequences are adjacent to coding and/or transcribed sequences. Accordingly, a gene includes, but is not limited to, promoter sequences, terminators, translational regulatory sequences such as ribosome binding sites and internal ribosome entry sites, enhancers, silencers, insulators, boundary elements, replication origins, matrix attachment sites and locus control regions The terms "operative linkage" and "operatively linked" (or "operably linked") are used interchangeably with reference to a juxtaposition of two or more components (such as sequence elements), in which the components are arranged such that both components function normally and allow the possibility that at least one of the components can mediate a function that is exerted upon at least one of the other components. By way of illustration, a transcriptional regulatory sequence, such as a promoter, is operatively linked to a coding sequence if the transcriptional regulatory sequence controls the level of transcription of the coding sequence in response to the presence or absence of one or more transcriptional regulatory factors. A transcriptional regulatory sequence is generally operatively linked in cis with a coding sequence, but need not be directly adjacent to it. For example, an enhancer is a transcriptional regulatory sequence that is operatively linked to a coding sequence, even though they are not contiguous.

A "functional region" or "functional portion" of a protein, polypeptide or nucleic acid is a protein, polypeptide or nucleic acid whose sequence is not identical to the full-length protein, polypeptide or nucleic acid, yet retains the same function as the full-length protein, polypeptide or nucleic acid. A functional region can possess more, fewer, or the same number of residues as the corresponding native molecule, and/or can contain one or more amino acid or nucleotide substitutions. Methods for determining the function of a nucleic acid (e.g., coding function, ability to hybridize to another nucleic acid) are well-known in the art. Similarly, methods for determining protein function are well-known. For example, the DNA-binding function of a polypeptide can be determined, for example, by filter-binding, electrophoretic mobility-shift, or immunoprecipitation assays. DNA cleavage can be assayed by gel electrophoresis. The ability of a protein to interact with another protein can be determined, for example, by co-immunoprecipitation, two-hybrid assays or complementation, both genetic and biochemical.

As used herein, the term "promoter" refers to a recognition site of a polynucleotide (DNA or RNA) to which an RNA polymerase binds. The term "enhancer" refers to a segment of DNA which contains sequences capable of providing enhanced transcription and in some instances can function independent of their orientation relative to another control sequence. An enhancer can function cooperatively or additively with promoters and/or other enhancer elements.

As used herein, the term "vector" refers to any genetic element, such as a plasmid, phage, transposon, cosmid, chromosome, virus, virion, etc., which is capable of replication when associated with the proper control elements and which can transfer gene sequences into cells. Thus, the term includes cloning and expression vehicles, as well as viral vectors and plasmid vectors.

As used herein, the term "modulate" refers to altering positively or negatively. Exemplary modulations include an about 1%, about 2%, about 5%, about 10%, about 25%, about 50%, about 75%, or about 100% change.

As used herein, the term "increase" refers to alter positively by at least about 5%, including, but not limited to, alter positively by about 5%, by about 10%, by about 25%, by about 30%, by about 50%, by about 75%, or by about 100%.

As used herein, the term "reduce" refers to alter negatively by at least about 5% including, but not limited to, alter negatively by about 5%, by about 10%, by about 25%, by about 30%, by about 50%, by about 75%, or by about 100%.

As used herein, the term "about" or "approximately" means within an acceptable error range for the particular value as determined by one of ordinary skill in the art, which will depend in part on how the value is measured or determined, i.e., the limitations of the measurement system. For example, "about" can mean within 3 or more than 3 standard deviations, per the practice in the art. Alternatively, "about" can mean a range of up to 20%, preferably up to 10%, more preferably up to 5%, and more preferably still up to 1% of a given value. Alternatively, particularly with respect to biological systems or processes, the term can mean within an order of magnitude, preferably within 5-fold, and more preferably within 2-fold, of a value.

II. INSULATORS

Several cases of vector-related malignant transformation have been reported in clinical settings, associated with the activation of cellular oncogenes by vector-encoded enhancers (Baum et al. (2006), Nienhuis et al. (2006), Ramezani et al. (2006)) and various vector modifications have been performed or proposed to reduce vector genotoxicity (Baum et al. (2006), Nienhuis et al. (2006), Ramezani et al. (2006)). A class of DNA elements known as chromatin insulators has been recognized as one approach to improve vector safety and performance (Emery (2011)).

Insulators are naturally occurring DNA elements that help from the functional boundaries between adjacent chromatin domains. Insulators bind proteins that modify chromatin and alter regional gene expression. The placement of insulators in the vectors described herein offer various potential benefits including, but not limited to, 1) shielding of the vector from positional effect variegation of expression by flanking chromosomes (i.e., barrier activity, which may decrease position effects and vector silencing); and 2) shielding flanking chromosomes from insertional trans-activation of endogenous gene expression by the vector (enhancer blocking). There are two basic classes of chromatin insulators: (a) barrier insulators that block the encroachment of silencing heterochromatin into adjoining regions of open chromatin that are transcriptionally permissive, and (b) enhancer blocking insulators that prevent enhancer-mediated transcriptional activation of adjoining regions. The sequences that mediate these activities are physically separable and mechanistically distinct (Recillas-Targa et al. (2002)). Chromatin insulators do not exhibit inherent transcriptional enhancing or repressing activities on their own. As such, they make ideal elements for reducing the interaction between gene transfer vectors and the target cell genome. Insulators can help to preserve the independent function of genes or transcription units embedded in a genome or genetic context in which their expression may otherwise be influenced by regulatory signals within the genome or genetic context (see, e.g., Burgess-Beusse et al. (2002) *Proc. Nat'l Acad. Sci. USA*, 99: 16433; and Zhan et al. (2001) *Hum. Genet.*, 109: 471).

The problems created by insertional mutagenesis of viral vectors are widely known (Nienhuis (2013), Baum et al. (2006), Nienhuis et al. (2006)) as is the evidence that the risks of genotoxicity can be reduced by the use of chromatin insulators (Arumugam et al. (2007), Emery (2011), Evans-Galea et al. (2007), Rivella et al. (2000), Emery et al. (2000), Emery et al. (2002), Yannaki et al. (2002), Hino et al. (2004), Ramezani et al. (2003), Ramezani et al. (2008)). The presently disclosed subject matter provides novel insulators that are powerful enhancer blocking insulators, and certain insulators additionally possess barrier insulator activity. In vertebrates, the function of enhancer blocking insulators is mediated through the zinc-finger DNA-binding factor CTCF (Gaszner and Felsenfeld (2006), Wallace and Felsenfeld (2007)). In general, these elements are thought to function through physical loop structures, which are established by CTCF-mediated interactions between adjacent insulator elements or through CTCF-mediated tethering of the chromatin fiber to structural elements within the nucleus. The first characterized vertebrate chromatin insulator is located within the chicken β-globin locus control region. This element, which contains a DNase-I hypersensitive site-4 (cHS4), appears to constitute the 5' boundary of the chicken β-globin locus (Prioleau et al. (1999) EMBO J. 18: 4035-4048). A 1.2-kb region containing the cHS4 element displays classic insulator activities, including the ability to block the interaction of globin gene promoters and enhancers in cell lines (Chung et al. (1993) Cell, 74: 505-514), and the ability to protect expression cassettes in *Drosophila* (Id.), transformed cell lines (Pikaart et al. (1998) *Genes Dev.* 12: 2852-2862), and transgenic mammals (Wang et al. (1997) *Nat. Biotechnol.*, 15: 239-243; Taboit-Dameron et al. (1999) Transgenic Res., 8: 223-235) from position effects. Much of this activity is contained in a 250-bp region. Within this stretch is a 49-bp cHS4 element (Chung et al. (1997) *Proc. Natl. Acad. Sci., USA,* 94: 575-580) that interacts with the zinc finger DNA binding protein CTCF implicated in enhancer-blocking assays (Bell et al. (1999) *Cell,* 98: 387-396).

Insulators, such as cHS4, can block the interaction between enhancers and promoters when placed between these elements (Evans-Galea et al. (2007), Chung et al. (1997), Bell et al. (1999), Ryu et al. (2007), Ryu et al. (2008)). Several studies have demonstrated the ability of the cHS4 insulator to reduce position-effect silencing of gammaretroviral vectors (Evans-Galea et al. (2007), Rivella et al. (2000), Emery et al. (2000), Emery et al. (2002), Yannaki et al. (2002), Hino et al. (2004), Ramezani et al. (2006), Yao et al. (2003), Nishino et al. (2006), Aker et al. (2007), Li and Emery (2008)), and lentiviral vectors (Bank et al. (2005), Arumugam et al. (2007), Puthenveetil et al. (2004), Evans-Galea et al. (2007), Ramezani et al. (2003), Aker et al. (2007), Ma et al. (2003), Chang et al. (2005), Pluta et al. (2005)). Those appropriately designed studies demonstrated that inclusion of the 1.2 kb version of the cHS4 insulator increased the likelihood and/or consistency of vector transgene expression in at least some settings (Arumugam et al. (2007), Emery (2011), Evans-Galea et al. (2007), Emery et al. (2002), Yannaki et al. (2002), Hino et al. (2004), Ramezani et al. (2006), Aker et al. (2007), Li and Emery (2008), Pluta et al. (2005). Jakobsson et al. (2004)). Nevertheless, the degree of protection afforded by the cHS4 insulator is far from complete. In addition, the inclusion of the 1.2 Kb cHS4 can adversely affect vector titers while the smallest cHS4 core has been proven ineffective (Aker et al. (2007), Jakobsson et al. (2004)). By contrast, the insulators of the presently disclosed subject matter do not affect adversely the titers of viral vectors, and are more powerful and effective than the cHS4 insulator.

The presently disclosed insulators are identified through genomic approaches, e.g., using genomic approaches to identify insulators that are powerful enhancer blockers as well as barrier insulators of the human genome. The presently disclosed insulators enhance the safety of gene therapy (e.g., stem cell gene therapy, globin gene therapy). For gene therapy of the hemoglobinopathies, powerful enhancers are required to achieve therapeutic levels of globin gene expression. Powerful insulators therefore represent one means to protect the genomic environment from the powerful enhancers of the integrating vectors.

The presently disclosed insulators possess powerful enhancer blocking activity. For example, and not by way of limitation, an insulator of the present disclosure can reduce the activity of an enhancer element by at least about 10%, at least about 20%, at least about 30%, at least about 40%, at least about 50%, at least about 55%, at least about 60%, at least about 65%, at least about 70%, at least about 75%, at least about 80%, at least about 85%, at least about 90%, at least about 91%, at least about 92%, at least about 93%, at least about 94%, at least about 95%, at least about 96%, at least about 97%, at least about 98% or at least about 99%. In certain embodiments, the insulators possess barrier activity in addition to enhancer blocking activity. The presently disclosed insulators substantially decrease the risks of insertional mutagenesis and genotoxicity associated with viral vectors. Furthermore, when a presently disclosed insulator is incorporated into a vector, the insulator does not adversely effect vector titers of the vector. In certain embodiments, the insulators (e.g., insulator A1) increase the in vivo expression of the globin gene or functional portion thereof.

In certain embodiments, the insulator comprises a Transcriptional repressor CTCF binding site, which has the nucleotide sequence set forth in SEQ ID NO: 18, which is provided below:

[SEQ ID NO: 18]
CACCAGGTGGCGCT.

In one non-limiting embodiment, the insulator has the nucleotide sequence set forth in SEQ ID NO:1, which is provided below, or a sequence which is at least about 95 percent homologous, or at least about 98 percent identical (homologous), to SEQ ID NO:1. This insulator having the nucleotide sequence set forth in SEQ ID NO:1 is designated as insulator A1.

[SEQ ID NO: 1]
TCCTTCCTTTCTAAATGACGAGAGAGACAGAAGAATTCTTCAAGGTTAGT

GTGTCCAGCATGCAACCTTTCCTTCCTGGATGAGCATCCCTGGAGTAGGA

GAGCCAGCCTGCCTCCTGCGCTGGCACAGAGCCCGGTTCCCTAGACAACT

GCCTCTCCAAATCTGATGTCCAGCGCCACCTGGTGTCCACATCAAGCAGA

CACAATTAATAGTCAACCTGTTCAGGAAAACTGTGAGGGGGAAAAAAAAG

AAAGAGGATTTATGAAGGGAAAAGAAAGTTTAGAGGATATGCCACGATTG

GCTAG

In certain embodiments, the insulator comprises a nucleotide sequence as set forth in SEQ ID NO:24, or a sequence which is at least about 95 percent identical, or at least about 98 percent identical, to SEQ ID NO: 24.

[SEQ ID NO: 24]
CCAATC GTGGCATATC CTCTAAACTT TCTTTTCCCT TCATAAATCC

TCTTTCTTTT TTTTCCCCCT CACAGTTTTC CTGAACAGGT

TGACTATTAA TTGTGTCTGC TTGATGTGGA CACCAGGTGG

CGCTGGACAT CAGATTTGGA GAGGCAGTTG TCTAGGGAAC

CGGGCTCTGT GCCAGCGCAG GAGGCAGGCT GGCTCTCCTA

TTCCAGGGAT GCTCATCCAG GAAGGAAAGG TTGCATGCTG

GACACACTAA CCTTGAAGAA TTCTTCTGTC TCTCTCGTCA

TTTAGAAAGG AAGGA.

In certain embodiments, the insulator comprises a nucleotide sequence as set forth in SEQ ID NO:25 (which is the reverse complement of SEQ ID NO:1), or a sequence which is at least about 95 percent identical, or at least about 98 percent identical, to SEQ ID NO: 25.

[SEQ ID NO: 25]
CTAGCCAATCGTGGCATATCCTCTAAACTTTCTTTTCCCTTCATAAATCC

TCTTTCTTTTTTTTCCCCCTCACAGTTTTCCTGAACAGGTTGACTATTAA

TTGTGTCTGCTTGATGTGGACACCAGGTGGCGCTGGACATCAGATTTGGA

GAGGCAGTTGTCTAGGGAACCGGGCTCTGTGCCAGCGCAGGAGGCAGGCT

-continued

```
GGCTCTCCTACTCCAGGGATGCTCATCCAGGAAGGAAAGGTTGCATGCTG

GACACACTAACCTTGAAGAATTCTTCTGTCTCTCTCGTCATTTAGAAAGG

AAGGA
```

In certain embodiments, the insulator comprises a nucleotide sequence as set forth in hg18 coordinates 76229933 to 76230115 of chromosome 1.

In certain embodiments, the insulator comprises a nucleotide sequence between residues 68041 and 68160, or between residues and 68041 and 68210, or between residues 68041 and 68280, or between residues 68005 and 68305, of *Homo sapiens* chromosome 1 clone RP11-550H2, GenBank Accession No. AC092813.2, or a sequence at least 95 or 98 percent identical thereto.

III. EXPRESSION CASSETTES

The presently disclosed subject matter provides expression cassettes comprising one or more the above-disclosed insulators (e.g., insulator A1). In certain embodiments, an expression cassette comprises at least one insulator having the nucleotide sequence set forth in SEQ ID NO:1, and a globin gene or a functional portion thereof operably linked to a β-globin LCR region.

β-Globin LCR Region

The human β-globin gene cluster consists of five genes embedded within one of many olfactory receptor gene arrays (Bulger et al., *PNAS* (1999); 96:5129-5134). The cluster spans over 80 kb on chromosome 11p15.4, and includes the five expressed β-like genes and cis-acting regulatory elements that direct their stage-specific expression during ontogeny (Forget (2001), *Molecular Mechanism of Beta Thalassemia.* Steinberg M H et al., Eds. Disorders of Hemoglobin. Genetics, Pathophysiology and Clinical Management, Cambridge University Press, Cambridge). The genes are arranged in the order of their developmental expression (Stamatoyannopoulos et al., (2001) *Hemoglobin Switching.* In: Stamatoyannopoulos G, et al., Eds. Molecular Basis of Blood Disorders, W.B. Saunders, Philadelphia, Pa.), 5'-ε-$^G$γ-$^A$γ-ψη-δ-β-3'. The α-like globin gene cluster (5'-ξ2-ψξ1-ψα2-ψα1-α2-α1-θ-3') is located very close to the telomere of the short arm of chromosome 16 and spans about 40 kb. The expression of genes encoded within these two independent clusters is limited to erythroid cells and balanced so that the output of the β-globin-like chains matches that of the α-chains. This fine tuned balance is regulated at the transcriptional, posttranscriptional and posttranslational levels.

Developmental stage-specific expression is controlled by a number of proximal or distal cis-acting elements and the transcriptional factors that bind to them. In the case of the β-globin gene (HBB), the proximal regulatory elements comprise the β-globin promoter and two downstream enhancers, one located in the second intron of β-globin and the other approximately 800 bp downstream of the gene (Antoniou et al., *EMBO J.* (1988); 7:377-384; Trudel et al., *Genes Dev.* (1987); 1:954-961; Trudel et al., *Mol. Cell. Biol.* (1987); 7:4024-4029). The most prominent distal regulatory element is the β-globin LCR, located 50-60 kb upstream of the HBB and composed of several sub-regions with heightened sensitivity to DNaseI in erythroid cells (Forget (2001); Grosveld et al., *Cell* (1987); 51:975-985; Talbot et al., *Nature* (1989); 338:352). The most prominent property of the LCR is its strong, transcription-enhancing activity. An exemplary nucleotide sequence of the human β-globin region on chromosome 11 is set forth in SEQ ID NO:19 (GenBank Access No.: NG_000007.3), which is provided below:

[SEQ ID NO: 19]
```
ggatcctcacatgagttcagtatataattgtaacagaataaaaaatcaattatgtattcaagttgctagtgtcttaagaggttcac attttatctaactgattatcacaaaaatacttcgagttacttttcattataattcctgactacacatgaagagactgacacgtag gtgccttacttaggtaggttaagtaatttatccaaaaccacacaatgtagaacctaagctgattcggccatagaaacacaatatgt ggtataaatgagacagagggattt ctctccttcctatgctgtcagatgaatactgagatagaatatttagttcatctatcacacat taaacgggactttacatttctgtctgttgaagatttgggtgtgggga taactcaaggtatcatatccaagggatggatgaaggcag gtgactctaacagaaagggaaaggatgttggcaaggctatgttcatgaaagtatatgtaaaatccacattaagcttctttctgcat gcattggcaatgtttatgaataatgtgtatgtaaaagtgtgctgtatattcaaaagtgtttcatgtgcctaggggtgtcaaatact ttgagtttgtaagtatatacttctctgtaatgtgtctgaatatctctatttacttgattctcaataagtaggtatcatagtgaaca tctgacaaatgtttgaggaacaatttagtgtttacctattcaccaaaatttattaaatgcctaatctgtatcagatatacaattat ctggcgaaatctgtaattcctaatttaaacagctgtgtagcctaattagggataaaggcatgcaaacccataatttgtgtaggttg aaatgagctatagaaaaatgcagtatatttatcagaagtctttagggtcatgaaaaggaatggtcaactgacactgccagggactc atatgtaagagataactaatgtgaagtgactttaaaggagaaattagcagaagttttctttccatgtctcctcatcatgttacaat aacggaagagattaaaacaacaaatacatttagacagcaatgtttatcctggttagatgttttaatctaaatctatcttggagtgt taaaatgcatttgctcacctactttaaaatataaatgaaggtaggaacctgtagatacaaaaagttggagaaaaaaagacaataaa gatgacaaaaatctattaatccttgatagaaaatgagaagagataaaacactggtttacataaagaaaataagatggatagatagc agatccttataaaagtgataatttgagaaaaaaaatactccatattctgagtttcttcacataaaataatacaaatctgctgtggt aagttacaaagagatagatttttttatcattatataaaagatattttaaacagagttatacaacaaaggaacagactatgtcatata ttctcacttatcactataaacatctcagaaaaatctgcaaaatcatttcatagcattttaaatagttaggaataatgtagaaaact
```

```
gaaacagttctaagtttcccacaaacttagagtctcaaatgttgcattacctaacttacctgcaaatattttatacaaatttgcac
atgctactctagtcaaaaatatatgtacattatgggtattttctgtgtgtaacttggttctagttgcttcttcagaaatagcctc
tattttgatttacctgataaaatcacattcctctccaaagccttctaaatacttccagactaactacttttagtacatctaaga
agaaaagagttttgtctcttatccacctctgagtcaaaaagcagcatgtccatcaattggtacatagttcccacagcccacttag
ctctggattggagttctacttggcattgtttgcaactacatggacgtaaaatgcatggattctcttgaaaaaatgtttctgccatg
atgttctctgaaagagactaaccttccctcgctttgcagagaaagactcgtgtaatccttgacaatgtcatctcatctatttattc
ccatgtctacccatatgtgaccttcatgtctttgctctaagcccctacatcctcaatctacacactaggatagtataaaagtaata
gtaataatagtagtaatagtaataacaatacaatgattatggcttatactatacacaagacactgttgatatatttatttcatttag
tattcacagtaactctgtgcctcaagtactattgtaatacccttaagaggaggaaactgaggcacagggcctaaagtaatattc
caagatgaagtggctactaactgacagagggcataattcaactcatgatatttggctctagaatacatgctctgaatcattataca
ataataattcatgaggaaacattttttaaagcctaagttatttgctctgaaataagacataatttggggtgagaaagcttagattc
catgaagtattacagcatttggtagtcttttttgcactccaggtcttattttactgcttaaacataataaaacatatggttcagta
tgcctttgattttacaataatattcctgttatttttggaagcacagggtgtgggataatgctaattactagtgattagtattgaga
ggtgacagcgtgctggcagtcctcacagccctcgctcgctcttggcgcctcctctgcctgggctcccacattggtggcacttgagg
agcccttcagccggccgctgcactgtgggagccttttctgggctggccaaggccagagccggctccctcagcttgccaggaggtg
tggagggacagacgcgggcaggaaccgggctgtgcgccgtgcttgagggagttccgggtgggcatggctccgaggaccccgcact
cggagccgccagccggccccaccggccgcgggcagtgaggggcttagcacctgggccagcagctgctgtgctcaattcctcgccgg
gccttagctgccttcctgcggggcagggctcgggacctgcagcgcgccatgcctgagcctccccaccttcatgggctcctgtgcgg
cccgagcctcgccgacgagcgccgcccctgctccagggcacccagtcccatcgaccacccaagggctgaagagtgcgggcgcacg
gcaggggactggcaggcagctcccctgcagcccaggtgcgggatccactgggtgaagccggctaggctcctgagtttgctgggga
tgcgaagaacccttatgtctagataagggattgtaaatacaccaattggcactctgtatctagctcaaggtttgtaaacacaccaa
tcagcaccctgtgtctagctcagggtttgtgaatgcaccaatcaacactctatctagctactctggtggggccttggagaaccttt
atgtctagctcagggattgtaaatacaccaatcggcagtctgtatctagctcaaggtttgtaaacacaccaatcagcaccctgtgt
ctagctcagggtttgtgaatgcaccaatcaacactctgtatctagctactctggtggggacgtggagaacctttatgtctagctca
gggattgtaaatacaccactcggcagtctgtatctagctcaaggtttgtaaacacaccaatcagcaccctgtgtctagctcagggt
ttgtgaatgcaccaatcaacactctgtatctagctactctggtggggacttggagaacctttgtgtggacactctgtatctagcta
atctggtggggacgtggagaacctttgtgtctagctcatggattgtaaatgcaccaatcagtgccctgtcaaaacagaccactggg
ctctaccaatcagcaggatgtgggtggggccagataagagaataaaagcaggctgcccgagccagcagtggcaacccgctcgggtc
cccttccacactgtggaagctttgttcttcgctctttgcaataaatcttgctgctgctcactgtttgggtctacactgcctttat
gagctgtaacgctcaccgcgaaggtctgcagcttcactcttgaagccagcgagaccacgaacccaccgggaggaacgaacaactcc
agaggcgccgccttaagagctggaacgttcactgtgaaggtctgcagcttcactcctgagccagcgagaccacgaacccatcagaa
ggaagaaactccgaacacatccaaacatcagaacgaacaaactccacacacgcagcctttaagaactgtaacactcaccacgaggg
tccccggcttcattcttgaagtcagtgaaaccaagaacccaccaattccggacacagtatgtcagaaacaatatgagtcactaaat
caatatacttctcaacaatttccaacagcccttgcaattaacttggccatgtgactggttgtgactaaaataatgtggagataata
atgtgttactccctaaggcagagtgcccttctatcattctctttcccttcctctatgtggcagaaagtaaaagattctgaaatgat
aaagtcaatcacaggaaggcacctggactcctggcccactgcttggaggagagcactcaggaccatgaacatctgactgtgacgta
gcaataaagaaacccacgtttcatatgaaactgcttaaaattaatgcacaagtcatgttttgatgttgcacatttgtctttatt
tgtggcttgttttgcttccacatcaatccactcaaggcctacattctgctataatgcaatttcaagttctttacaggccgagaaaa
atgaatctgaattcctgacctccaaaagtgatcaagatatttttagttcaggctccaaaattttctcattttcataggttttcctc
gattgatcattattcatgatttgcaaggaatcattcaatgttttctaaatctattactgcatcctgacacatatgacattttaact
```

-continued

```
atgttccagattttttgaatgaagagtgtaaattttaaatgttttcaccacaaaaaataagtatgtgaagtggtggatttgttaatt
agccttatttaaccatttaatattgtacacgtacaccaaagcatcatgttgtacccatgaatacacacaattattatttgtcaat
ttaaaatgaaataataaaaaataacaaaggcattagcctctgcattgcctttaccggtcatcctcacggtgactaacgcaaaaac
gttctatttcatccttacaaacatccctatctttgatgcctcttgtctagatctctatcccctcctgttttctctacgttattta
tatgggtatcatcaccatcctggacaacatcaggacagatatccctcaccaagccaatgttcctctctatgttggctcaaatgtcc
ttgaacttcctttcaccaccctttccacagtcaaaaggatattgtagtttaatgcctcagagttcagcttttaagcttctgacaa
attattcttcctctttaggttctcctttatggaatcttctgtactgatggccatgtcctttaactactatgtagatatctgctact
acctgtattatgcctctacctttattagcagagttatctgtactgttggcatgacaatcatttgttaatatgacttgcctttcctt
tttctgctattcttgatcaaatggctcctctttcttgctcctctcatttctcctgccttcacttggacgtgcttcacgtagtctgt
gcttatgactggattaaaaattgatatggacttatcctaatgttgttcgtcataatatgggtttatggtccattattatttccta
tgcattgatctggagaaggcttcaatcctttttactctttgtggaaaatatctgtaaaccttctggttcactctgctatagcaattt
cagtttaggctagtaagcatgaggatgcctccttctctgattttttcccacagtctgttggtcacagaataacctgagtgattactg
atgaaagagtgagaatgttattgatagtcacaatgacaaaaaacaaacaactacagtcaaaatgtttctctttttattagtggatt
atatttcctgacctatatctggcaggactctttagagaggtagctgaagctgctgttatgaccactagagggaagaagatacctgt
ggagctaatggtccaagatggtggagcccaagcaaggaagttgttaaggagcccttttgattgaaggtgggtgcccccaccttac
agggacaggacatctggatactcctcccagtttctccagtttcccttttttcctaatatatctcctgataaaatgtctatactcact
tccccatttctaataataaagcaaaggctagttagtaagacatcaccttgcattttgaaaatgccatagactttcaaaattatttc
atacatcggtctttctttatttcaagagtccagaaatggcaacattacctttgattcaatgtaatggaaagagctctttcaagaga
cagagaaaagaataatttaatttctttccccacacctccttccctgtctcttaccctatcttccttccttctaccctcccatttc
tctctctcatttctcagaagtatattttgaaaggattcatagcagacagctaaggctggttttttctaagtgaagaagtgatattg
agaaggtagggttgcatgagcccttcagttttttagtttatatacatctgtattgttagaatgttttataatataaataaaatta
tttctcagttatatactagctatgtaacctgtggatatttccttaagtattacaagctatacttaactcacttggaaaactcaaat
aaatacctgcttcatagttattaataaggattaagtgagataatgcccataagattcctattaataacagataaatacatcacac
acacacacattgaaaggattcttactttgtgctaggaactataataagttcattgatgcattatatcattaagttctaatttcaac
actagaaggcaggtattatctaaatttcatactggatacctccaaactcataaagataattaaattgccttttgtcatatatttat
tcaaaagggtaaactcaaactatggcttgtctaatttttatatatcaccctactgaacatgaccctattgtgatattttataaaatt
attctcaagttattatgaggatgttgaaagacagagaggatggggtgctatgccccaaatcagcctcacaattaagctaagcagct
aagagtcttgcagggtagtgtagggaccacagggttaaggggcagtagaattatactcccactttagtttcatttcaaacaatcc
atacacacacagccctgagcacttacaaattatactacgctctatacttttttgtttaaatgtataaataagtggatgaaagaatag
atagatagatagacagatagatgatagataggaataaatgcttgccttcatagctgtctccctaccttgttcaaaatgttcctgtcc
agaccaaagtaccttgccttcacttaagtaatcaattcctaggttatattctgatgtcaaaggaagtcaaaagatgtgaaaacaa
tttctgacccacaactcatgctttgtagatgactagatcaaaaaatttcagccatatcttaacagtgagtgaacaggaaatctcct
cttttcctacatctgagatcccagcttctaagaccttcaattctcactcttgatgcaacagaccttggaagcatacaggagagct
gaacttggtcaacaaaggagaaaagtttgttggcctccaaaggcacagctcaaacttttcaagccttctctaatcttaaaggtaaa
caagggtctcatttctttgagaacttcagggaaaatagacaaggacttgcctggtgcttttggtaggggagcttgcactttccccc
tttctggaggaaatatttatccccaggtagttccctttttgcaccagtggttctttgaagagacttccacctgggaacagttaaac
agcaactacagggccttgaactgcacactttcagtccggtcctcacagttgaaaagacctaagcttgtgcctgatttaagccttt
tggtcataaaacattgaattctaatctccctctcaaccctacagtcacccatttggtatattaaagatgtgttgtctactgtctag
tatccctcaagtagtgtcaggaattagtcatttaaatagtctgcaagccaggagtggtggctcatgtctgtaattccagcacttga
gaggtagaagtgggaggactgcttgagctcaagagtttgatattatcctggacaacatagcaagacctcgtctctacttaaaaaaa
aaaaaaaaattagccaggcatgtgatgtacacctgtagtcccagctactcaggaggccgaaatgggaggatcccttgagctcagga
```

-continued

```
ggtcaaggctgcagtgagacatgatcttgccactgcactccagcctggacagcagagtgaaaccttgcctcacgaaacagaataca
aaaacaaacaaacaaaaaactgctccgcaatgcgcttccttgatgctctaccacataggtctgggtactttgtacacattatctca
ttgctgttcataattgttagattaattttgtaatattgatattattcctagaaagctgaggcctcaagatgataacttttattttc
tggacttgtaatagctttctcttgtattcaccatgttgtaactttcttagagtagtaacaatataaagttattgtgagttttgca
aacacagcaaacacaacgacccatatagacattgatgtgaaattgtctattgtcaatttatgggaaaacaagtatgtacttttttct
actaagccattgaaacaggaataacagaacaagattgaaagaatacattttccgaaattacttgagtattatacaaagacaagcac
gtggacctggaggagggttattgtccatgactggtgtgtggagacaaatgcaggtttataatagatgggatggcatctagcgcaa
tgactttgccatcacttttagagagctcttggggaccccagtacacaagaggggacgcagggtatatgtagacatctcattcttttt
tcttagtgtgagaataagaatagccatgacctgagtttatagacaatgagccctttctctctcccactcagcagctatgagatgg
cttgccctgcctctctactaggctgactcactccaaggcccagcaatgggcagggctctgtcagggctttgatagcactatctgca
gagccagggccgagaaggggtggactccagagactctccctcccattcccgagcagggtttgcttatttatgcatttaaatgatat
atttattttaaaagaaataacaggagactgcccagccctggctgtgacatggaaactatgtagaatattttgggttccattttttt
ttccttctttcagttagaggaaaaggggctcactgcacatacactagacagaaagtcaggagctttgaatccaagcctgatcattt
ccatgtcatactgagaaagtccccaccccttctctgagcctcagtttctctttttataagtaggagtctggagtaaatgatttccaa
tggctctcatttcaatacaaaatttccgtttattaaatgcatgagcttctgttactccaagactgagaaggaaattgaacctgaga
ctcattgactggcaagatgtcccagaggctctcattcagcaataaaattctcaccttcacccaggccactgagtgtcagatttg
catgcactagttcacgtgtgtaaaaaggaggatgcttctttcctttgtattctcacatacctttaggaaagaacttagcacccttc
ccacacagccatcccaataactcatttcagtgactcaaccccttgactttataaaagtcttgggcagtatagagcagagattaagag
tacagatgctggagccagaccacctgagtgattagtgactcagttctcttagtagttgtatgactcagtttcttcatctgtaaaa
tggagggttttttaattagtttgttttgagaaagggtctcactctgtcacccaaatgggagtgtagtggcaaaatctcggctcac
tgcaacttgcacttcccaggctcaagcggtcctcccacctcaacatcctgagtagctggaaccacaggtacacaccaccataccc
gctaatttttgtatttttggtagagatggggtttcacatgttacacaggatggtctcagactccggagctcaagcaatctgccca
cctcagccttccaaagtgctgggattataagcatgattacaggagttttaacaggctcataagattgttctgcagcccgagtgagt
taatacatgcaaagagtttaaagcagtgacttataaatgctaactactctagaaatgtttgctagtatttttgtttaactgcaat
cattcttgctgcaggtgaaaactagtgttctgtactttatgcccattcatctttaactgtaataataaaaataactgacatttatt
gaaggctatcagagactgtaattagtgctttgcataattaatcatatttaatactcttggattcttcaggtagatactattatta
tcccattttactacagttaaaaaaactacctctcaacttgctcaagcatacactctcacacacacaaacataaactactagcaaa
tagtagaattgagatttggtcctaattatgtctttgctcactatccaataaatatttattgacatgtacttcttggcagtctgtat
gctggatgctggggatacaaagatgtttaaatttaagctccagtctctgcttccaaaggcctcccaggccaagttatccattcaga
aagcattttttactctttgcattccactgttttcctaagtgactaaaaaattacactttattcgtctgtgtcctgctctgggatg
atagtctgacttcctaacctgagcctaacatccctgacatcaggaaagactacaccatgtggagaagggtggtggttttgattg
ctgctgtcttcagttagatggttaactttgtgaagttgaaaactgtggctctctggttgactgttagagttctggcacttgtcact
atgcctattatttaacaaatgcatgaatgcttcagaatatgggaatattatcttctggaatagggaatcaagttatattatgtaac
ccaggattagaagattcttctgtgtgtaagaatttcataaacattaagctgtctagcaaaagcaagggcttggaaaatctgtgagc
tcctcaccatatagaaagcttttaacccatcattgaataaatccctatagggatttctaccctgagcaaaaggctggtcttgatt
aattcccaaactcatatagctctgagaaagtctatgctgttaacgttttcttgtctgctaccccatcatatgcacaacaataaatg
caggcctaggcatgactgaaggctctctcataattcttggttgcatgaatcagattatcaacagaaatgttgagacaaactatggg
gaagcagggtatgaaagagctctgaatgaaatggaaaccgcaatgcttcctgcccattcagggctccagcatgtagaaatctgggg
ctttgtgaagactggcttaaaatcagaagcccccattggataagagtagggaagaacctagagcctacgctgagcaggtttccttca
tgtgacagggagcctcctgccccgaacttccagggatcctctcttaagtgtttcctgctggaatctcctcacttctatctggaaat
```

-continued

```
ggtttctccacagtccagcccctggctagttgaaagagttacccatgcagaggccctcctagcatccagagactagtgcttagatt
cctactttcagcgttggacaacctggatccacttgcccagtgttcttccttagttcctacccttcgaccttgatcctcctttatctt
cctgaaccctgctgagatgatctatgtggggagaatggcttctttgagaaacatcttcttcgttagtggcctgcccctcattccca
ctttaatatccagaatcactataagaagaatataataagaggaataactcttattataggtaagggaaaattaagaggcatacgtg
atgggatgagtaagagaggagagggaaggattaatggacgataaaatctactactatttgttgagacctttttatagtctaatcaat
tttgctattgttttccatcctcacgctaactccataaaaaaacactattattatctttattttgccatgacaagactgagctcaga
agagtcaagcatttgcctaaggtcggacatgtcagaggcagtgccagacctatgtgagactctgcagctactgctcatgggccctg
tgctgcactgatgaggaggatcagatggatggggcaatgaagcaaaggaatcattctgtggataaaggagacagccatgaagaagt
ctatgactgtaaatttgggagcaggagtctctaaggacttggatttcaaggaattttgactcagcaaacacaagaccctcacggtg
actttgcgagctggtgtgccagatgtgtctatcagaggttccagggagggtggggtggggtcagggctggccaccagctatcaggg
cccagatgggttataggctggcaggctcagataggtggttaggtcaggttggtggtgctgggtggagtccatgactcccaggagcc
aggagagatagaccatgagtagagggcagacatgggaaaggtgggggaggcacagcatagcagcatttttcattctactactacat
gggactgctcccctataccccagctaggggcaagtgccttgactcctatgttttcaggatcatcatctataaagtaagagtaata
attgtgtctatctcataggggttattatgaggatcaaaggagatgcacactctctggaccagtggcctaacagttcaggacagagct
atgggcttcctatgtatgggtcagtggtctcaatgtgcaggcaagttccagaagatagcatcaaccactgttagagatatactgc
cagtctcagagcctgatgttaatttagcaatgggctgggaccctcctccagtagaaccttctaaccagctgctgcagtcaaagtcg
aatgcagctggttagactttttttaatgaaagcttagctttcattaaagattaagctcctaagcagggcacagatgaaattgtcta
acagcaactttgccatctaaaaaaatctgacttcactggaaacatggaagcccaaggttctgaacatgagaaattttaggaatct
gcacaggagttgagagggaaacaagatggtgaagggactagaaaccacatgagagacacgaggaaatagtgtagatttaggctgga
ggtaaatgaaagagaagtgggaattaatacttactgaaatctttctatatgtcaggtgccattttatgatatttaataatctcatt
acatatggtaattctgtgagatatgtattattgaacatactataattaatactaatgataagtaacacctcttgagtacttagtat
atgctagaatcaaatttaagtttatcatatgaggccgggcacggtggctcatatatgggattacatgcctgtaatcccagcacttt
gggaggccaaggcaattggatcacctgaggtcaggagttccagaccagcctggccaacatggtgaaaccccttctctactaaaaaa
tacaaaaaatcagccaggtgtggtggcacgcgtctataatcccagctactcaggaggctgaggcaggagaatcacttgaacccagg
aggtggaggttgcagtgagctaagattgcaccactgcactccagcctaggcgacagagtgagactccatctcaaaaaaaaaaaaag
aagtttattatatgaattaacttagttttactcacaccaatactcagaagtagattattacctcatttattgatgaggagcccaat
gtacttgtagtgtagatcaactttattgaaagcacaagctaataagtagacaattagtaattagaagtcagatggtctgagctctcc
tactgtctacattacatgagctcttattaactggggactcgaaaatcaaagacatgaaataatttgtccaagcttacagaaccacc
aagtagtaaggctaggatgtagacccagttctgctacctctgaagacagtgttttttccacagcaaaacacaaactcagatattgt
ggatgcgagaaattagaagtagatattcctgccctgtggcccttgcttcttacttttacttcttgtcgattggaagttgtggtcca
agccacagttgcagaccatacttcctcaaccataattgcatttcttcaggaaagtttgagggagaaaaaggtaaagaaaaatttag
aaacaacttcagaataaagagattttctcttgggttacagagattgtcatatgacaaattataagcagacacttgagaaaactgaa
ggcccatgcctgcccaaattaccctttgacccccttggtcaagctgcaactttggttaaagggagtgtttatgtgttatagtgttca
tttactcttctggtctaacccattggctccgtcttcatcctgcagtgacctcagtgcctcagaaacatacatatgtttgtctagtt
taagtttgtgtgaaattctaactagcgtcaagaactgagggccctaaactatgctaggaatagtgctgtggtgctgtgataggtac
acaagaaatgagaagaaactgcagattctctgcatctccctttgccgggtctgacaacaaagtttccccaaattttaccaatgcaa
gccatttctccatatgctaactactttaaaatcatttggggcttcacattgtctttctcatctgtaaaaagaatggaagaactcat
tcctacagaactccctatgtcttccctgatgggctagagttcctcttttctcaaaaattagccattattgtatttccttctaagcca
aagctcagaggtcttgtattgcccagtgacatgcacactggtcaaaagtaggctaagtagaagggtactttcacaggaacagagag
caaaagaggtgggtgaatgagagggtaagtgagaaaagacaaatgagaagttacaacatgatggcttgttgtctaaatatctccta
gggaattattgtgagaggtctgaatagtgttgtaaaataagctgaatctgctgccaacattaacagtcaagaaatacctccgaata
```

-continued

```
actgtacctccaattattctttaaggtagcatgcaactgtaatagttgcatgtatatatttatcataatactgtaacagaaaacac ttactgaatatatactgtgtccctagttctttacacaataaactaatctcatcctcataattctattagctaatacatattatcat cctatatttcagagacttcaagaagttaagcaacttgctcaagatcatctaagaagtaggtggtatttctgggctcatttggcccc tcctaatctctcatggcaacatggctgcctaaagtgttgattgccttaattcatcagggatgggctcatactcactgcagacctta actggcatcctctttctcttatgtgatctgcctgaccctagtagacttatgaaatttctgatgagaaaggagagaggagaaaggcag agctgactgtgatgagtgatgaaggtgccttctcatctgggtaccagtgggcctctaagactaagtcactctgtctcactgtgtc ttagccagttccttacagcttgccctgatgggagatagagaatgggtatcctccaacaaaaaaataaattttcatttctcaaggtc caacttatgttttcttaattttttaaaaaaatcttgaccattctccactctctaaaataatccacagtgagagaaacattcttttcc cccatcccataaatacctctattaaatatggaaaatctgggcatggtgtctcacacctgtaatcccagcactttgggaggctgagg tgggtggactgcttggagctcaggagttcaagaccatcttggacaacatggtgatacccgcctctacaaaaagtacaaaaattag cctggcatggtggtgtgcacctgtaatcccagctattagggtggctgaggcaggagaattgcttgaacccgggaggcggaggttgc agtgagctgagatcgtgccactgcactccagcctgggggacagagcacattataattaactgttatttttacttggactcttgtg gggaataagatacatgttttattcttatttatgattcaagcactgaaaatagtgtttagcatccagcaggtgcttcaaaaccattt gctgaatgattactatactttttacaagctcagctccctctatcccttccagcatcctcatctctgattaaataagcttcagttttt tccttagttcctgttacatttctgtgtgtctccattagtgacctcccatagtccaagcatgagcagttctggccaggcccctgtcg gggtcagtgccccaccccgccttctggttctgtgtaaccttctaagcaaaccttctggctcaagcacagcaatgctgagtcatga tgagtcatgctgaggcttagggtgtgtgcccagatgttctcagcctagagtgatgactcctatctgggtccccagcaggatgctta cagggcagatggcaaaaaaaggagaagctgaccacctgactaaaactccacctcaaacggcatcataaagaaaatggatgcctga gacagaatgtgacatattctagaatatattatttcctgaatatatatatatatacacatatacgtatatatatatatatata tatttgttgttatcaattgccatagaatgattagttattgtgaatcaaatatttatcttgcaggtggcctctatacctagaagcgg cagaatcaggctttattaatacatgtgtatagattttttaggatctatacacatgtattaatatgaaacaaggatatggaagaggaa ggcatgaaaacaggaaaagaaaacaaaccttgtttgccattttaaggcaccctggacagctaggtggcaaaaggcctgtgctgtt agaggacacatgctcacatacggggtcagatctgacttgggtgctactgggaagctctcatcttaaggatacatctcaggccagt cttggtgcattaggaagatgtaggcaactctgatcctgagaggaaagaaacattcctccaggagagctaaaagggttcacctgtgt gggtaactgtgaaggactacaagaggatgaaaaacaatgacagacagacataatgcttgtgggagaaaaaacaggaggtcaagggg atagagaaggcttccagaagaatggctttgaagctggcttctgtaggagttcacagtggcaaagatgtttcagaaatgtgacatga cttaaggaactatacaaaaaggaacaaatttaaggagaggcagataaattagttcaacagacatgcaaggaattttcagatgaatg ttatgtctccactgagcttcttgaggttagcagctgtgagggttttgcaggcccaggacccattacaggacctcacgtatacttga cactgttttttgtattcatttgtgaatgaatgacctcttgtcagtctactcggtttcgctgtgaatgaatgatgtcttgtcagcct acttggtttcgctaagagcacagagagaagatttagtgatgctatgtaaaaacttccttttttggttcaagtgtatgtttgtgatag aaatgaagacaggctacatgatgcatatctaacataaacacaaacattaagaaaggaaatcaacctgaagagtatttatacagata acaaaatacagagagtgagttaaatgtgtaataactgtggcacaggctggaatatgagccatttaaatcacaaattaattagaaaa aaaacagtggggaaaaaattccatggatgggtctagaaagactagcattgttttaggttgagtggcagtgtttaaagggtgatatc agactaaacttgaaatatgtggctaaataactagaatactctttatttttttcgtatcatgaatagcagatatagcttgatggcccc atgcttggtttaacatccttgctgttcctgacatgaaatccttaattttttgacaaaggggctattcattttcattttatattgggc ctagaaattatgtgatggtcctgaggaaaagtttatagcttgtctatttctctctctaacatagttgtcagcacaatgcctaggc tataggaagtactcaaagcttgttaaattgaattctatccttcttattcaattctacacatggaggaaaaactcatcagggatgga ggcacgcctctaaggaaggcaggtgtggctctgcagtgtgattgggtacttgcaggacgaagggtggggtgggagtggctaaccctt ccattcctagtgcagaggtcacagcctaaacatcaaattccttgaggtgcggtggctcactcctgtaatcacagcagtttgggacg ccaaggtgggcagatcacttgaggtcaggagttggacaccagcccagccaacatagtgaaacctggtctctgcttaaaaatataaa
```

-continued

```
aattagctggacgtggtgacgggagcctgtaatccaactacttgggaggctgaggcaggagaatcgcttgaaccggggaggtggag
tttgcactgagcagagatcatgccattgcactccagcctccagagcgagactctgtctaaagaaaaacgaaaacaaacaaacaaac
aaacaaacaaaacccatcaaattccctgaccgaacagaattctgtctgattgttctctgacttatctaccattttccctccttaaa
gaaactgtgaacttccttcagctagaggggcctggctcagaagcctctggtcagcatccaagaaatacttgatgtcactttggcta
aaggtatgatgtgtagacaagctccagagatggtttctcatttccatatccacccacccagctttccaattttaaagccaattctg
aggtagagactgtgatgaacaaacaccttgacaaaattcaacccaaagactcactttgcctagcttcaaaatccttactctgacat
atactcacagccagaaattagcatgcactagagtgtgcatgagtgcaacacacacacacaccaattccatattctctgtcagaaaa
tcctgttggttttcgtgaaaggatgttttcagaggctgaccccttgccttcacctccaatgctaccactctggtctaagtcactg
tcaccaccacctaaattatagctgttgactcataacaatcttcctgcttctaccactgccccactacaatttcttcccaatatact
atccaaattagtcttttcaaaatgtaagtcatatatggtcacctctttgttcaaagtcttctgatagtttcctatatcatttataa
taaaaccaaatccttacaattctctacaatagttgttcatgcatatattatgtttattacagatacatatatatagctctcatata
aataaatatatatatttatgtgtatgtgtgtagagtgttttttcttacaactctatgatgtaggtattattagtgtcccaaatttt
ataatttaggacttctatgatctcatcttttattctcccccttcaccgaatctcatcctacattggccttattgatattccttgaaa
attctaagcatcttacatctttagggtatttacatttgccattccctatgccctaaatatttaatcatagtttcatataaatgggt
tcctcatcatctatgggtactctctcaggtgttaactttatagtgaggacttcctgccatactacttaaagtagcgatacccttt
caccctgtcctaatcacactctggccttcatttcagtttttttttttctccatagcacctaatctcattggtatataacatgttt
catttgcttatttaatgtcaagctcttccactatcaagtccatgaaaacaggaactttattcctctattctgtttttgtgctgta
ttcttagcaattttacaattttgaatgaatgaatgagcagtcaaacacatatacaactataattaaaaggatgtatgctgacacat
ccactgctatgcacacacaaagaaatcagtggagtagagctggaagtgctaagcctgcatagagctagttagccctccgcaggcag
agccttgatgggattactgagttctagaattggactcatttgttttgtaggctgagatttgctcttgaaaacttgttctgaccaaa
ataaaaggctcaaaagatgaatatcgaaaccagggtgttttttacactggaatttataactagagcactcatgtttatgtaagcaa
ttaattgtttcatcagtcaggtaaaagtaaagaaaaactgtgccaaggcaggtagcctaatgcaatatgccactaaagtaaacatt
atttcataggtgtcagatatggcttattcatccatcttcatgggaaggatggccttggcctggacatcagtgttatgtgaggttca
aaacacctctaggctataaggcaacagagctccttttttttttttctgtgctttcctggctgtccaaatctctaatgataagcata
cttctattcaatgagaatattctgtaagattatagttaagaattgtgggagccattccgtctcttatagttaaatttgagcttctt
ttatgatcactgttttttttaatatgctttaagttctggggtacatgtgccatggtggtttgctgcacccatcaacccgtcatctac
attaggtatttctcctaatgctatccttcccctagcccccaccccaacaggcccagtgtgtgatgttcccctccctgtgtcca
tggatcactggtttttttttgttttttttttttttttaaagtctcagttaaattttggaatgtaatttattttcctggtatccta
ggacttgcaagttatctggtcactttagccctcacgttttgatgataatcacatatttgtaaacacaacacacacacacacacaca
cacacatatatatatataaaacatatatatacataaacacacataacatatttatcgggcatttctgagcaactaatcatgcag
gactctcaaacactaacctatagccttttctatgtatctacttgtgtagaaaccaagcgtggggactgagaaggcaatagcaggag
cattctgactctcactgcctttagctaggcccctccctcatcacagctcagcatagtcctgagctcttatctatatccacacacag
tttctgacgctgcccagctatcaccatcccaagtctaaagaaaaaaataatgggtttgcccatctctgttgattagaaaacaaac
aaaataaaataagcccctaagctcccagaaaacatgactaaaccagcaagaagaagaaaatacaataggtatatgaggagactggt
gacactagtgtctgaatgaggcttgagtacagaaagaggctctagcagcatagtggtttagaggagatgtttctttccttcacag
atgccttagcctcaataagcttgcggttgtggaagtttactttcagaacaaactcctgtggggctagaattattgatggctaaaag
aagcccggggagggaaaaatcattcagcatcctcacccttagtgacacaaaacagagggggcctggttttccatatttcctcatg
atggatgatctcgttaatgaaggtggtctgacgagatcattgcttcttccatttaagccttgctcacttgccaatcctcagtttta
accttctccagagaaatacacattttttattcaggaaacatactatgttatagtttcaatactaaataatcaaagtactgaagata
gcatgcataggcaagaaaaagtccttagctttatgttgctgttgtttcagaatttaaaaaagatcaccaagtcaaggacttctcag
ttctagcactagaggtggaatcttagcatataatcagaggttttcaaaatttctagacataagattcaaagccctgcacttaaaa
```

-continued

```
tagtctcatttgaattaactctttatataaattgaaagcacattctgaactacttcagagtattgttttatttctatgttcttagt
tcataaatacattaggcaatgcaatttaattaaaaaaacccaagaatttcttagaattttaatcatgaaaataaatgaaggcatct
ttacttactcaaggtcccaaaaggtcaaagaaaccaggaaagtaaagctatatttcagcggaaaatgggatatttatgagttttct
aagttgacagactcaagttttaaccttcagtgcccatcatgtaggaaagtgtggcataactggctgattctggctttctactcctt
tttcccattaaagatccctcctgcttaattaacattcacaagtaactctggttgtactttaggcacagtggctcccgaggtcagtc
acacaataggatgtctgtgctccaagttgccagagagagagattactcttgagaatgagcctcagccctggctcaaactcacctgc
aaacttcgtgagagatgaggcagaggtacactacgaaagcaacagttagaagctaaatgatgagaacacatggactcatagaggga
aacaacgcatactgggcctatcagagggtggagggtgagagaaggagaggatcaggaaaaatcactaatggatgctaagcgtaat
acctgagtgatgagatcatctatacaacaaaccccccttgacattcatttatctatgtaacaaacctgcacatcctgtacatgtacc
cctgaacttaaaataaaagttgaaaacaagaaagcaacagtttgaacacttgttatggtctattctctcattctttacaattacac
tagaaaatagccacaggcttcctgcaaggcagccacagaatttatgacttgtgatatccaagtcattcctggataatgcaaaatct
aacacaaaatctagtagaatcatttgcttacatctattttgttctgagaatatagatttagatacataatggaagcagaataatt
taaaatctggctaatttagaatcctaagcagctcttttcctatcagtggtttacaagccttgtttatattttcctattttaaaaa
taaaaataaagtaagttatttgtggtaaagaatattcattaaagtatttatttcttagataataccatgaaaaacattcagtgaag
tgaagggcctactttacttaacaagaatctaatttatataatttttcatactaatagcatctaagaacagtacaatatttgactct
tcaggttaaacatatgtcataaattagccagaaagatttaagaaaatattggatgtttccttgtttaaattaggcatcttacagtt
tttagaatcctgcatagaacttaagaaattacaaatgctaaagcaaacccaaacaggcaggaattaatcttcatcgaatttgggtg
tttctttctaaaagtcctttatacttaaatgtcttaagacatacatagattttattttactaattttaattatatagacaataaat
gaatattcttactgattacttttctgactgtctaatctttctgatctatcctggatggccataacacttatctctctgaactttg
ggcttttaatataggaaagaaaagcaataatccattttttcatggtatctcatatgataaacaaataaaatgcttaaaaatgagcag
gtgaagcaatttatcttgaaccaacaagcatcgaagcaataatgagactgcccgcagcctacctgacttctgagtcaggatttata
agccttgttactgagacacaaacctgggcctttcaatgctataacctttcttgaagctcctccctaccacctttagccataaggaa
acatggaatgggtcagatccctggatgcaagccaggtctggaaccataggcagtaaggagagaagaaaatgtgggctctgcaactg
gctccgagggagcaggagaggatcaacccccatactctgaatctaagagaagactggtgtccatactctgaatgggaagaatgatgg
gattacccatagggcttgttttagggagaaacctgttctccaaactcttggccttgagatacctggtccttattccttggactttg
gcaatgtctgaccctcacattcaagttctgaggaagggccactgccttcatactgtggatctgtagcaaattcccctgaaaaccc
agagctgtatcttaattggttaaaaaaaattatattatctcaacgactgttcttctctgagtagccaagctcagcttggttcaagc
tacaagcagctgagctgcttttttgtctagtcattgttcttttatttcagtggatcaaatacgttcttccaaacctaggatcttgt
cttcctaggctatatattttgtcccaggaagtcttaatctggggtccacagaacactaggggctggtgaagtttatagaaaaaaa
atctgtatttttacttacatgtaactgaaatttagcatttcttctactttgaatgcaaaggacaaactagaatgacatcatcagt
acctattgcatagttataaagagaaaccacagatattttcatactacaccataggtattgcagatcttttgttttttgttttgtt
tgagatggagtttcgctcttattgcccaggctggagtgcagtggcatgatttcggctcactgcaacctccccttcctgcattcaag
caattctcctgccttggcctcctgagtagctgggattacaggcacctgccaccatgccagtctaatttttgtatttttagtagag
atggggtttcgccatgttggccaggctggtcttgaactcctgacctcagatgatctgcccgccttggcctcctgaagtgctgggat
tataggtgtgagccaccacgcctggcccattgcagatattttttaattcacatttatctgcatcactacttggatcttaaggtagct
gtagacccaatcctagatctaatgctttcataaagaagcaaatataataaatactataccacaaatgtaatgtttgatgtctgata
atgatatttcagtgtaattaaacttagcactcctatgtatattatttgatgcaataaaaacatattttttagcacttacagtctg
ccaaactggcctgtgacacaaaaaaagtttaggaattcctggttttgtctgtgttagccaatggttagaatatatgctcagaaaga
taccattggttaatagctaaaagaaaatggagtagaaattcagtggcctggaataataacaatttgggcagtcattaagtcaggtg
aagacttctggaatcatgggagaaaagcaagggagacattcttacttgccacaagtgttttttttttttttttttttttatcacaaa
```

-continued

```
cataagaaaatataataaataacaaagtcaggttatagaagagagaaacgctcttagtaaacttggaatatggaatccccaaaggc acttgacttgggagacaggagccatactgctaagtgaaaaagacgaagaacctctagggcctgaacatacaggaaattgtaggaac agaaattcctagatctggtggggcaaggggagccataggagaaagaaatggtagaaatggatggagacggaggcagaggtgggcag atcatgaggtcaagagatcgagaccatcctggcaaacatggtgaaatcccgtctctactaaaaataaaaaaattagctgggcatgg tggcatgcgcctgtagtcccagctgctcgggaggctgaggcaggagaatcgtttgaacccaggaggcgaaggttgcagtgagctga gatagtgccattgcactccagtctggcaacagagtgagactccgtctcaaaaaaaaaaaaaaagaaagaaagaaaagaaaaagaa aaaagaaaaaataaatggatgtagaacaagccagaaggaggaactgggctggggcaatgagattatggtgatgtaagggacttttta tagaattaacaatgctggaatttgtggaactctgcttctattattcccccaatcattacttctgtcacattgatagttaaataatt tctgtgaatttattccttgattctaaaatatgaggataatgacaatggtattataagggcagattaagtgatatagcatgagcaat attcttcaggcacatggatcgaattgaatacactgtaaatcccaacttccagtttcagctctaccaagtaaagagctagcaagtca tcaaaatggggacatacagaaaaaaaaaaggacactagaggaataatatacctgactcctagcctgattaatatatcgattcact tttttctctgtttgatgacaaattctggctttaaataattttaggattttaggcttctcagctcccttcccagtgagaagtataag caggacagacaggcaagcaagaagagagcccaggcaatactcacaaagtagccaatgtccctgtggtcatagagaaatgaaaag agagaggattctctggaagcactggatgtaatcttttctgtctgtcctctctagggaatcaccccaaggtactgtactttgggatt aaggctttagtcccactgtggactacttgctattctgttcagttctagaaggaactatgtacggttttgtctccctagagaaac taaggtacagaagttttgtttacaatgcactccttaagagagctagaactgggtgagattctgttttaacagctttattttctttt ccttggccctgttttgtcactgtcaccacctttaaggcaaatgttaaatgcgctttggctgaaacttttttttcctatttttgagat ttgctcctttatatgaggctttcttggaaaaggagaatgggagagatggatatcattttggaagatgatgaagagggtaaaaaagg ggacaaatggaaatttgtgttgcagatagatgaggagccaacaaaaaagagcctcaggatccagcacacattatcacaaacttagt gtccatccatcactgctgaccctctccggacctgactccaccctgagggacacaggtcagccttgaccaatgacttttaagtacc atggagaacaggggccagaacttcggcagtaaagaataaaaggccagacagagaggcagcagcacatatctgcttccgacacagc tgcaatcactagcaagctctcaggcctggcatcatggtgcattttactgctgaggagaaggctgccgtcactagcctgtggagcaa gatgaatgtggaagaggctggaggtgaagccttgggcaggtaagcattggttctcaatgcatgggaatgaagggtgaatattaccc tagcaagttgattgggaaagtcctcaagatttttgcatctctaattttgtatctgatatggtgtcatttcatagactcctcgttg tttacccctggacccagagattttttgacagctttggaaacctgtcgtctccctctgccatcctgggcaaccccaaggtcaaggcc catggcaagaaggtgctgacttcctttggagatgctattaaaaacatggacaacctcaagcccgcctttgctaagctgagtgagct gcactgtgacaagctgcatgtggatcctgagaacttcaaggtgagttcaggtgctggtgatgtgattttttggctttatattttga cattaattgaagctcataatcttattggaaagaccaacaaagatctcagaaatcatgggtcgagcttgatgttagaacagcagact tctagtgagcataaccaaaacttacatgattcagaactagtgacagtaaaggactactaacagcctgaattggcttaacttttcag gaaatcttgccagaacttgatgtgtttatcccagagaattgtattatagaattgtagacttgtgaaagaagaatgaaatttggctt ttggtagatgaaagtccatttcaaggaaatagaaatgccttatttttatgtgggtcatgataattgaggtttagaaagagattttttg caaaaaaataaaagatttgctcaaagaaaaataagacacattttctaaaatatgttaaatttcccatcagtattgtgaccaagtg aaggcttgtttccgaatttgttgggggattttaaactcccgctgagaactcttgcagcactcacattctacatttacaaaaattaga caattgcttaaagaaaaacagggagagagggaacccaataatactggtaaaatggggaaggggtgagggtgtaggtaggtagaat gttgaatgtagggctcatagaataaaattgaacctaagctcatctgaatttttgggtgggcacaaaccttggaacagtttgaggt cagggttgtctaggaatgtaggtataaagccgttttgtttgttttgttttttcatcaagttgttttcggaaacttctactca acatgcctgtgtgttattttgtcttttgcctaacagctcctgggtaacgtgatggtgattattctggctactcactttggcaagga gttcaccctgaagtgcaggctgcctggcagaagctggtgtctgctgtcgccattgccctggcccataagtaccactgagttctct tccagtttgcaggtgttcctgtgaccctgacaccctccttctgcacatggggactgggcttggccttgagagaaagccttctgttt aataaagtacattttcttcagtaatcaaaaattgcaattttatcttctccatctttttactcttgtgttaaaaggaaaaagtgttca tgggctgagggatggagagaaacataggaagaaccaagagcttccttaagaaatgtatggggggcttgtaaaattaatgtggatgtt
```

-continued

```
atgggagaattccaggattccaaggaggatgatatgatggagaaaaatctttatcggggtgggaaaatggttaattaagtggacag agactcctaggcagttttttactgcaccggggaaagaaggagctgttagtggtacctgagaaagcagatttgtggtacatgtcactt ttcattaaaaacaaaaacaaaacaaaacaaaacttcatagatatccaagatataggctagaattactattttaatttactcttatt tacattttgaagtagctagcttgtcacatgttttatgaaattgatttggagataagatgagtgtgtatcaacaatagcctgctctt tccatgaaggattccattatttcatgggttagctgaagctaagacacatgatatcattgtgcattatcttctgatagaatgtaaca tgcactaaaataaagttagagttaggacctgagtgggaaagttttggagagtgtgatgaagacttccgtgggagatagaatact aataaaggcttaaattctaaaaccagcaagctagggcttcgtgacttgcatgaaactggctctctggaagtagaagggagagtaag acatacgtagaggactaggaaagaccagatagtacagggcctggctacaaaaatacaagcttttactatgctattgcaatactaaa cgataagcattaggatgttaagtgactcaggaaataagattttgggaaaaagtaatctgcttatgtgcacaaaatggattcaagtt tgcagataaaataaaatatggatgatgattcaaggggacagatacaatggttcaaacccaagaggagcagtgagtctgtggaattt gaaggatggacaaggtggggtgagaaagacatagtattcgactgactgtgggagatgagaaggaagaaggaggtgataaatgact gaaagctcccagactggtgaagataacaggaggaaaccatgcactgacctggtgactctcatgtgtgaagggtagagggatattaa cagatttacttttaggaagtgctagattggtcagggagttttgaccttcaggtcttgtgtctttcatatcaaggaacctttgcat tttccaagttagagtgccatattttggcaaatataacttattagtaattttatagtgctctcacattgatcagacttttttcctgt gaattacttttgaatttggctgtatatatccagaatatgggagagagacaaataattattgtagttgcaggctatcaacaatactg gtctctctgagcccttataaccctttcaatatgcccataaacagagtaaacagggattattcatggcactaaatattttcacctagtc agtcaacaaatgggagcaatgtgcattttttgatacatattttatatatttatgggtacatgtgatacttacatgcctagaaca tgtgatgattaagtctagatatttaggatatccattgctttgagcatttatcatttctatgtattgagaaaatttcaaatcctcat ttctagccattttgaaatatataataaatagtaattaactatagtcaccctactcaaatatcaaacattatggcttaatccttcta tccaactgtgtttgtacctattaaccaacatctcttaaatccctcccatacacactcacacttttttccagcctctgataactatc attctactctctaccaccatgagacccacttttttagctcccacagatgaataaaaacatgtgatatttgactttctgtatctggc ttattttattatctatctctttggcataccaagagtttgttttgttctgcttcagggctttcaattaacataatgacctctggtt ccatccatgttgctacaaatgacaagatttcattcttttttcatggcaaaatagtactgtgcaaaaatacaatttttttaatccgttc atctgttgatagacacttaggttgatcccaaaccttaactattgtgaatagtgcttcaataaacatgagtgtaatgtgtccattgg atatactgatttcctttcttttggataaataaccactagtgagattgctggattgtatgatagttctgttttttagtttactgagaa atcttcatactgttttccataatggttgtactattttacattcccaccaacagtgtgtaagaaagagttcccttttctccatatcc tcacaaggatctgttattttttgtcttttttgttaatagccgttttaactagagtaagtagatatctcattgtagttttgatttgc atttccctgatcattagtgatgttgagaatttttcatatgtttgttggtcatttgtatatctttttctgagaattgtctgttcat gtccttagcctacttttattgggattgtttgttattttcttgataatctatttgtgttcatttagagcctggatattattcttt tgtcagatgtatagattgtgaagattttctcccactctgtgggttgtctgtttattctgcagactcttccttttgccatgcaaaag ctcttagtttaattagtcccagatattttctttgtttttatgtatttgcatttgtgttcttggtcatgaaatcctttcctaagc caatgtgtagaagggttttccgatgttattttctagaattgttacagtttcagggcttagatttaagtccttgatccatcttgag ttgattttgtataaggtgagagatgaagatccagtttcattctcctacatgtagcttgccagctatccccgcaccatttgttgaa tagggtgccctttccccactttatgttttttgtttgctttgtcaaagatcagttggatgtaagtatttgagtttatttctgggttct ctattctgttccattggtcgatgtgcctatttgtacaccagcatcatgctgttttggtgactatggccttattgtatagtttgaaa tgaggtaatgtaatgccttcagatttgttctttttttagacttgcttgtttattgggctcttttttggttccataagaattttag gattgttttttctagttctgtgaagactaatggtggtattttgatgggaattgcaatgaatttgtaggttgcttctggcattatgg ccattttcacaatattgattctacccatctatgagaatggcatgtgtttccatttgtttgtgtcttatatgattactttcagccgt gttttgtagttttccttgtagatgtctttcacctccttggtaggtatatattcctaagttttttgttttgttttgttttgttttttt gcagctattgtaaaggggttgagttcttgatttttattctcagcttggtcattgctggtatgtaagaaagcaactcattggtgtac
```

-continued

```
gttaattttgtatccagaaactttgctgaattattttatcagttctaggggttttggaggagtctttagagttttctacatacac
aatcatatcatcagcaaacagtgacagtttgactttctctttaacaatttggatgtgctttacttgtttctcttgtctgattgctc
ttgctaggacttccagtaatatgttaaagagaagtggtgagagtgggtatccttgtctcattccagttttcagacagaatgctttt
aacttttccccattcaatataatgttggctgtgtgtttaccatagctggcttttattacattgaggtatgtcctttgtaaaccgat
tttgctgagttttagtcataaagtgatgttgaattttgttgaatgcagtttctgtggctattgagataatcacatgattttgtttc
caattctctttatgttgtgtatcacacttattgacttgcgtatgttaaaccatccgtgcatccctcgcatgaaacccacttgatc
atgggttttgatatgctgtcggatgctattagctagtattttgtcaaggatgttggcatctatgttcatcagggatattgatctgt
agtgttttttttttttggttatgttcttcccagttttggtattaaggtgatactggcttcatagaatgatttagggaggattctc
tctttctctatcttgtagaatactgtcaataggattggtatcaattcttcctttgaatgtctggtagaattcagctgtgaatctatc
tggtcctggactttttttgttgttggtaaattttttattatcatttcagtcttgctgcttattactggtctgttcagggtatctaatt
cttcctgacttaagctagagccctgtatctttccaggaattcgaacgtctcctttaggttttctagtttatgcatgtaaaggtgtt
catagtagccttgaataatcttttgtatttctgtggtatcagtaatagtatctcctgttttgtttctaattgagtttatttgcact
tctctcctcttttcttggtaatcttgctaatggtctatcagtttttatttatcttttcaaagaaccagctttttatttcatttagc
ttttgtatttttttgcagttgttttaatttcatttagttctcctcttatcttagttattcccttcttttgctgggttttggttct
gtttgttttgtttctctagtttcttgtggtgtgaccttatattgtctgtctgtcctcttcagactctttgacatcgacatttag
ggctgtgaactttccttttagcaccatctttgctgtatcctagaggttttgataggttgtgtcactattgtcggtcagttcaagta
attttgttgttcttattatactttaagttctgggatacatgtgcagaatgtgcaggtttgttacataggtatagatgtgccatggt
ggtttgctgcacccatcaacctgtcatctacattaggtatttcttttaatgttatccctctcctaacccctcaccccccgacagg
ccctggtgtgtgatgttcccctccctgtgtccatgtgttctcattgttcaactcccacttatgagtgagaacgtgtggtgtttggt
ttctctgttcctgtgttagtttgctcagaatgatggtttccaccttcatccatgtccctgcaaagacatgaactcatcattttat
ggctgcatagtattccatggtgtatatgtgccacattttctttatccattatatcgctgatggccatttgggttggttccaagtct
ttgctattgtgaatagtgccacaataaacatacgtgtgcacgtgtctttatagtagaatgatttctaattctttgggtatataccc
agtaatgggattgctgggtcaaacagtatttctggttctagatccttgaggaatcgccacactgtcttccacaatggttgaactaa
tttacacacccatcaacagtgtaaaattttttcctattcttccacatcctctccagcacctttttgtttcctgacttttaataattg
ccattctaactggcatgagatggtatctcattgtggttttgatttgcatttctctaatgaccagtgatgatgagcttcttttcatg
tgtttcttggccacataaatgacttctttagagaagcatctgttcatatcctttgtccacttttttgatggggtcgttaggttttttt
cttgtaaatttgttgaagttctttgtagattttggatgttagccctttgtcagatggatagattgcaaaaattttctcccattctg
taggttgcctgttcactctgatgatagtcttttgctgtgcagaagctctttagtttaattagatcccatatgtcaattttggcctt
tgttgtcattgcttttgatgttttagtcgtgaattttttgcccatgcctatgtcctgaatggtattgcctaggttatcttctaggat
ttttatggttttaggttgcacatttaagtctttaatccaccttgagttaattttttgtataaggtgtaaggaaggggtacagtttca
gttttatgcatattgctagccagttttttccagcaccatttattaaatagggaattctttctccattgcttttgtgatgtttgtcaa
agatcagatggtcgtagatgtgtggcattatttctgaggcttctgttctgttccactggtctatatatctgttttggtaccagtac
catgctgttttttgttactgtagccttgtagtatagtttgaagtcaggtagcatcatgcctccagctttgttcttttttgtttaggat
tgtcttggctatatgggctcttttttgattccatatgacatttaaagtagttttttctaattctttgaaaaaagtcagtggtagct
tgatggggatagcattgaatctataaattactttgggcagtatggccattttaaagatattgattctttctatctatgagcatgga
atgttttttccatttgtttgtgtcctctcttatttccttgagcagtgagtggtttgtagctctccttgaagaggttcttcacatccc
ttagaagttgtatttctaggtattttattttattctctttgcagcaattgtgaatgggagttcacccatgatttggctctctgctt
gtctattattggtgtataggaacgcttgtgatttctgcacactgattttgtatcttgagactttgctgaagctgtttatcagctta
agatttgggctgagatgacagggtcttctaaatatacaatcatgtcatctgcaaacagagacaatttgacttcctctcttcctat
ttgaatatgcttatttctttctcttgcctgattgtcctggcgagaacttccaatactatgttgagtaagagtggcgagagggcat
ccttgtcttgtgccggttttcaaagcaaatgattttttaaatttccatcttgatttcattgttgacccaatgatcattcaggagcag
```

-continued

```
gttatttaatttccctgtatttgcatggttttgaaggttccttttgtagttgatttccaatttattctactgtggtctgagagag tgcttgatataatttcaattttaaaaatttattgaggcttgttttgtggcatatcatatggcctatcttggagaaagttccatgt gctgatgaatagaatgtgtattctgcagttgttgggtagaatgtcctgtaaatatctgttaagtccatttgttctttaaatccatt gtttctttgtagactgtcttgatgacctgcctagtgcagtcagtggagtattgaagtcccccactattattatgttgctgtctagt ctagtagtaattgttttataaatttgggatctccagtattagatgcatatatattaagaattgtaatattctcccattggacaagg gcttttatcattatatgatgtccctctttgtctttttttaactgctgtttctttaaagtttgttttgtctgacataagaatagctgc tttggctcgcttttggtgtccatttgtgtggaatgtcattttccacccctttaccttaagtttatgtgagtccttatgtgttaggt gagtctcctgaaggcggcagataactggttggtgaattcttattcattctgcaattctgtatcttttaagtggagcatttagtcca tttacattcaacatcagtattgaggtgtgaggtactattccattcttcgtggtatttgttgcctgtgtatcttttatctgtattt ttgttgtatatgtcctatgggatttatgctttaaagaggttctgttttgatgtgcttccagggtttatttcaagatttagagctcc ttttatcagttcttgtagtgttggcttggtagtgccgaattctctcagcatttgttttttctgaaaaacactgtgtattttcttcat ttgtgaagcttagtttcactggatataaaattcttggctgataattgttttgtttaagaaggctgaagatagggccatattcactt ctagcttttacggtttctgctgagaaatctgctgttaatctgataggttttctttcataggttacctggtagtttcacctcacagc tcttaagattctctttgtctttagataaactttggatactctgatgacaatgtacctaggcaatgatattttttgcaatgaatttccc aggtgtttattgagcttcttgtatttggatatctaggtctctagcaaggtggggaagttttccttgattatttccctggataagt tttccaaacttttagatttctcttctttctcaggaatgctgattattcttaggtttgattgtttaacataatcccagatttcttgg aggctttgttcatattttcttattctttttctttgtctttgttggattgggttaattcaaaaactttgtcttcaagctctgaatt tcttctgcttggattctattgctgagactttctagagcatttttgcatttctataagtgcatccattcatccattgtttcctgaagt tttgaatgttttttatttatgctatctctttaactgaagatttctcccctcatttcttgtatcatattttggtttttttaaaatt ggacttcaccttcctcggatgcctccttgattagcttaataactgaccttctgaattattttttcaggtaaatcagggatttcttct tggtttggatgcattgctggtgagctagtatgattttttgggggggtgttaaagaaccttgtttttcatattaccagagttagtttt ctggttccttctcacttgggtaggctctgtcagagggaaagtctaggcctcaaggctgagacttttgtcccatgaggtgttccctt gatgtagcacagtccccctttcctaggcgtggggcttcctgagagccgaactgtagtgattgttatctctcttctggatctagcc acccatcaggtctaccagactccaggctggtactgggtttgtctgcacagagtcttgtgacgtgaaccatctgtgggtctctcag ccatagatacaaccacctgctccaatggaggtggcagaggatgaaatggactctgtgagggtccttacttttggttgttcaatgca ctattttgtgctggttggcctcctgccaggaggtggcacttctagaaagcatcagcagaggcagtcaggtggtggtggctgggg gggctggggcaccctagaactcccaagaatatatgccctttgtcttcagctaccagggtgagtaaggaaggaccatcaggtgggg caggactagtcgtgtctgagctcagagtctccttgggcaggtctttctgtggctactgtgggaggatgggggtgtagtttccaggt caatggatttatgttcctaggacaattatggctgcctctgctgtgtcatgcaggtcatcaggaaagtgggggaaagcaagcagtca cgtgacttgcccagctccatgcaactcaaaaggttggtctcacttccagcgtgcaccctccccgcaacagcaccgaatctgttt ccatgcagtcagtgagcaaggctgagaacttgccccaggctaccagctgcgaaaccaagtagggctgtcctacttccctgccagtg gagtctgcacaccaaattcatgtccccccaccaaccccccactgcccagcccctagatctggccaggtggagattttcttttcc tgtcatcttttcccagttcctctggcagccctcccaaatgacccctgtgaggcaaggcagaaatggcttcctaggggacccagaga gcccacagggcttttcccgctgcttcctctaccccctgtattttgcttggccctctaaattgactcagctccaggtaaggtcagaat cttctcctgtggtctagatcttcaggttccccagtgaggatgtgtgtttgggggtagacggtcccccttttccacttccacagttt gggcactcacaatatttggggtgtttcccgggtcctgcaggagcaatctgcttctttcagagggtgtgtcgttctctcagctttc ttgatttatttctgcaggtggttctgcaaaaaaaattcctgatgggagacttcacatgctgctctgtgcatccgagtgggagctgc aatgtacttctgctgcctcccatctgccatcaccctctaatttgtcggtaatatgcattttttaatcaatctttttttctctctctc tcttttcttctcccccaaaactatactgcccctttgatatcaaggaatcaaggacgtgatgttgaggggtgggcagtggatacact ctttaccccttagggagctatatctagatttagatattgccaattcaagataacttaattgaaagcaaattcataatgaatacaca
```

-continued

```
cacacacacacacatctgcatgacaagattttttaatagttgaaagaataactaataattgtccacaggcaataagggcttttttaag
caaaacagttgtgataaacaggtcattcttagaatagtaatccagccaatagtacaggttgcttagagattatgtcattaccagag
ttaaaattctataatggcttctcactccctaccactgaggacaagtttatgtccttaggtttatgcttccctgaaacaataccacc
tgctattctccactttacatatcaacggcactggttctttatctaactctctggcacagcaggagtttgttttcttctgcttcaga
gctttgaatttactatttcagcttctaaactttatttggcaatgccttcccatggcagattccttctgtcattttgcctctgttcg
aatactttctccttaatttcattcttagttaataatatctgaaattattttgttgtttaacttaattattaattttatgtatgttc
tacctagattataatcttcagaggaaagttttattctctgacttatttaacttaaatgcccactactttaaaaattatgacattta
tttaacagatatttgctgaacaaatgtttgaaaatacatgggaaagaatgcttgaaaacacttgaaattgcttgtgtaaagaaaca
gttttatcagttaggatttaatcaatgtcagaagcaatgatataggaaaaatcgaggaataagacagttatggataaggagaaatc
aacaaactcttaaaagatattgcctcaaaagcataagaggaaataagggtttatacatgacttttagaacactgccttggttttttg
gataaatggggaagttgtttgaaaacaggagggatcctagatattccttagtctgaggaggagcaattaagattcacttgtttaga
ggctgggagtggtggctcacgcctgtaatcccagaattttgggaggccaaggcaggcagatcacctgaggtcaagagttcaagacc
aacctggccaacatggtgaaatcccatctctacaaaaatacaaaaattagacaggcatgatggcaagtgcctgtaatcccagctac
ttgggaggctgaggaaggagaattgcttgaacctggaaggcaggagttgcagtgagccgagatcataccactgcactccagcctgg
gtgacagaacaagactctgtctcaaaaaaaaaaagagagattcaaaagattcacttgtttaggccttagcgggcttagacaccag
tctctgacacattcttaaaggtcaggctctacaaatggaacccaaccagactctcagatatggccaaagatctatacacacccatc
tcacagatcccctatcttaaagagaccctaatttgggttcacctcagtctctataatctgtaccagcataccaataaaaatctttc
tcacccatccttagattgagagaagtcacttattattatgtgagtaactggaagatactgataagttgacaaatctttttctttcc
tttcttattcaacttttattttaacttccaaagaacaagtgcaatatgtgcagcttttgttgcgcaggtcaacatgtatctttctgg
tcttttagccgcctaacactttgagcagatataagccttacacaggattatgaagtctgaaaggattccaccaatattattataat
tcctatcaacctgataggttaggggaaggtagagctctcctccaataagccagatttccagagtttctgacgtcataatctaccaa
ggtcatggatcgagttcagagaaaaaacaaagcaaaaccaaacctaccaaaaaataaaaatcccaaagaaaaaataaagaaaaaa
acagcatgaatacttcctgccatgttaagtggccaatatgtcagaaacagcactgagttacagataaagatgtctaaactacagtg
acatcccagctgtcacagtgtgtggactattagtcaataaaacagtccctgcctcttaagagttgttttccatgcaaatacatgtc
ttatgtcttagaataagattccctaagaagtgaacctagcatttatacaagataattaattctaatccatagtatctggtaaagag
cattctaccatcatctttaccgagcatagaagagctacaccaaaaccctgggtcatcagccagcacatacacttatccagtgataa
atacacatcatcgggtgcctacatacatacctgaatataaaaaaaaatactttttgctgagatgaaacaggcgtgatttatttcaaat
aggtacggataagtagatattgaagtaaggattcagtcttatattatattacataacattaatctattcctgcactgaaactgttg
ctttataggattttttcactacactaatgagaacttaagagataatggcctaaaaccacagagagtatattcaaagataagtatagc
acttcttatttggaaaccaatgcttactaaatgagactaagacgtgtcccatcaaaaatcctggacctatgcctaaaacacatttc
acaatccctgaacttttcaaaaattggtacatgctttaacttttaaactacaggcctcactggagctacagacaagaaggtgaaaaa
cggctgacaaaagaagtcctggtatcttctatggtgggagaagaaaactagctaaagggaagaataaattagagaaaaattggaat
gactgaatcggaacaaggcaaaggctataaaaaaaattaagcagcagtatcctcttgggggcccttccccacactatctcaatgc
aaatatctgtctgaaacggtccctggctaaactccacccatggggttggccagccttgccttgaccaatagccttgacaaggcaaac
ttgaccaatagtcttagagtatccagtgaggccaggggccggcggctggctagggatgaagaataaaaggaagcacccttcagcag
ttccacacactcgcttctggaacgtctgaggttatcaataagctcctagtccagacgccatggtcatttcacagaggaggacaag
gctactatcacaagcctgtggggcaaggtgaatgtggaagatgctggaggagaaacccctgggaaggtaggctctggtgaccaggac
aagggagggaaggaaggaccctgtgcctggcaaaagtccaggtcgcttctcaggatttgtggcaccttctgactgtcaaactgttc
ttgtcaatctcacaggctcctggttgtctacccatggacccagaggttctttgacagctttggcaacctgtcctctgcctctgcca
tcatgggcaaccccaaagtcaaggcacatggcaagaaggtgctgacttccttgggagatgccataaagcacctggatgatctcaag
ggcacctttgcccagctgagtgaactgcactgtgacaagctgcatgtggatcctgagaacttcaaggtgagtccaggagatgtttc
```

-continued

```
agcactgttgcctttagtctcgaggcaacttagacaactgagtattgatctgagcacagcagggtgtgagctgtttgaagatactg gggttgggagtgaagaaactgcagaggactaactgggctgagacccagtggcaatgttttagggcctaaggagtgcctctgaaaat ctagatggacaactttgactttgagaaagagaggtggaaatgaggaaaatgacttttctttattagatttcggtagaaagaactt tcacctttcccctattttgttattcgttttaaaacatctatctggaggcaggacaagtatggtcattaaaaagatgcaggcagaa ggcatatattggctcagtcaaagtggggaactttggtggccaaacatacattgctaaggctattcctatatcagctggacacatat aaaatgctgctaatgcttcattacaaacttatatcctttaattccagatgggggcaaagtatgtccaggggtgaggaacaattgaa acatttgggctggagtagattttgaaagtcagctctgtgtgtgtgtgtgtgtgcgcgcgtgtgtttgtgtgtgtgagagc gtgtgtttcttttaacgttttcagcctacagcatacagggttcatggtggcaagaagataacaagatttaaattatggccagtgac tagtgctgcaagaagaacaactacctgcatttaatgggaaagcaaaatctcaggctttgagggaagttaacataggcttgattctg ggtggaagcttggtgtgtagttatctggaggccaggctggagctctcagctcactatgggttcatctttattgtctcctttcatct caacagctcctgggaaatgtgctggtgaccgttttggcaatccatttcggcaaagaattcacccctgaggtgcaggcttcctggca gaagatggtgactggagtggccagtgccctgtcctccagataccactgagctcactgcccatgatgcagagctttcaaggataggc tttattctgcaagcaatcaaataataaatctattctgctaagagatcacacatggttgtcttcagttcttttttatgtcttttta aatatatgagccacaaagggttttatgttgagggatgtgtttatgtgtatttatacatggctatgtgtgtttgtgtcatgtgcaca ctccacactttttttgtttacgttagatgtgggttttgatgagcaaataaaagaactaggcaataaagaaacttgtacatgggagtt ctgcaagtgggagtaaaaggtgcaggagaaatctggttgaagaaagacctctataggacaggactcctcagaaacagatgttttg gaagagatggggaaaggttcagtgaagggggctgaaccccttccctggattgcagcacagcagcgaggaagggctcaacgaaga aaaagtgttccaagctttaggaagtcaaggtttaggcagggatagccattctattttattaggggcaatactatttccaacggcat ctggcttttctcagcccttgtgaggctctacagggaggttgaggtgttagagatcagagcaggaaacaggttttctttccacggt aactacaatgaagtgatccttactttactaaggaacttttcattttaagtgttgacgcatgcctaaagaggtgaaattaatcccat acccttaagtctacagactggtcacagcatttcaaggaggagacctcattgtaagcttctagggaggtggggacttaggtgaagga aatgagccagcagaagctcacaagtcagcatcagcgtgtcatgtctcagcagcagaacagcacggtcagatgaaaatatagtgtga agaatttgtataacattaattgagaaggcagattcactggagttcttatataattgaaagttaatgcacgttaataagcaagagtt tagtttaatgtgatggtgttatgaacttaacgcttgtgtctccagaaaattcacatgctgaatcccaactcccaattggctccat ttgtggggggaggctttggaaaagtaatcaggtttagaggagctcatgagagcagatccccatcatagaattattttcctcatcaga agcagagagattagccatttctcttccttctggtgaggacacagtgggaagtcagccacctgcaacccaggaagagagccctgacc aggaaccagcagaaaagtgagaaaaaatcctgttgttgaagtcacccagtctatgctattttgttatagcaccttgcactaagtaa ggcagatgaagaaagagaaaaaaataagcttcggtgttcagtggattagaaaccatgtttatctcaggtttacaaatctccacttg tcctctgtgtttcagaataaaataccaactctactactctcatctgtaagatgcaaatagtaagcctgagcccttctgtctaactt tgaattctattttttcttcaacgtactttaggcttgtaatgtgtttatatacagtgaaatgtcaagttctttctttatatttcttt cttcttttttttcctcagcctcagagttttccacatgcccttcctactttcaggaacttctttctccaaacgtcttctgcctggc tccatcaaatcataaaggacccacttcaaatgccatcactcactaccatttcacaattcgcactttctttctttgtcctttttttt tttagtaaaacaagtttataaaaaattgaaggaataaatgaatggctacttcataggcagagtagacgcaagggctactggttgcc gatttttattgttattttttcaatagtatgctaaacaaggggtagattatttatgctgcccattttttagaccataaaagataacttc ctgatgttgccatggcattttttttcctttaattttatttcattttcattttaatttcgaaggtacatgtgcaggatgtgcaggctt gttacatgggtaaatgtgtgtctttctggcctttagccatctgtatcaatgagcagatataagctttacacaggatcatgaagga tgaaagaatttcaccaatattataataatttcaatcaacctgatagcttaggggataaactaatttgaagatacagcttgcctccg ataagccagaattccagagcttctggcattataatctagcaaggttagagatcatggatcactttcagagaaaaacaaaacaaac taaccaaaagcaaaacagaaccaaaaaaccaccataaatacttcctaccctgttaatggtccaatatgtcagaaacagcactgtgt tagaaataaagctgtctaaagtacactaatattcgagttataatagtgtgtggactattagtcaataaaaacaacccttgcctctt
```

-continued

```
tagagttgttttccatgtacacgcacatcttatgtcttagagtaagattccctgagaagtgaacctagcatttatacaagataatt aattctaatccacagtacctgccaaagaacattctaccatcatctttactgagcatagaagagctacgccaaaaccctgggtcatc agccagcacacacacttatccagtggtaaatacacatcatctggtgtatacatacatacctgaatatggaatcaaatattttcta agatgaaacagtcatgatttatttcaaataggtacggataagtagatattgaggtaagcattaggtcttatattatgtaacactaa tctattactgcgctgaaactgtggctttatagaaattgttttcactgcactattgagaaattaagagataatggcaaaagtcacaa agagtatattcaaaaagaagtatagcacttttttccttagaaaccactgctaactgaaagagactaagatttgtcccgtcaaaaatc ctggacctatgcctaaaacacatttcacaatccctgaacttttcaaaaattggtacatgctttagctttaaactacaggcctcact ggagctagagacaagaaggtaaaaaacggctgacaaaagaagtcctggtatcctctatgatgggagaaggaaactagctaaaggga agaataaattagagaaaaactggaatgactgaatcggaacaaggcaaaggctataaaaaaaattagcagtatcctcttgggggccc cttcccacactatctcaatgcaaatatctgtctgaaacggtccctggctaaactccacccatgggttggccagccttgccttgac caatagccttgacaaggcaaacttgaccaatagtcttagagtatccagtgaggccaggggccggcggctggctagggatgaagaat aaaaggaagcacccttcagcagttccacacactcgcttctggaacgtctgaggttatcaataagctcctagtccagacgccatggg tcatttcacagaggaggacaaggctactatcacaagcctgtggggcaaggtgaatgtggaagatgctggaggagaaaccctgggaa ggtaggctctggtgaccaggacaagggagggaaggaaggaccctgtgcctggcaaaagtccaggtcgcttctcaggatttgtggca ccttctgactgtcaaactgttcttgtcaatctcacaggctcctggttgtctacccatggacccagaggttctttgacagctttggc aacctgtcctctgcctctgccatcatgggcaaccccaaagtcaaggcacatggcaagaaggtgctgacttccttgggagatgccac aaagcacctggatgatctcaagggcacctttgcccagctgagtgaactgcactgtgacaagctgcatgtggatcctgagaacttca aggtgagtccaggagatgtttcagccctgttgcctttagtctcgaggcaacttagacaacggagtattgatctgagcacagcaggg tgtgagctgtttgaagatactggggttgggggtgaagaaactgcagaggactaactgggctgagacccagtggtaatgttttaggg cctaaggagtgcctctaaaaatctagatggacaattttgactttgagaaaagagaggtggaaatgaggaaaatgacttttctttat tagattccagtagaaagaactttcatctttccctcatttttgttgttttaaaacatctatctggaggcaggacaagtatggtcgtt aaaaagatgcaggcagaaggcatatattggctcagtcaaagtggggaactttggtggccaaacatacattgctaaggctattccta tatcagctggacacatataaaatgctgctaatgcttcattacaaacttatatcctttaattccagatgggggcaaagtatgtccag gggtgaggaacaattgaaacatttgggctggagtagattttgaaagtcagctctgtgtgtgtgtgtgtgtgcgcgcgcgcgtgt gtgtgtgtgtcagcgtgtgtttcttttaacgtcttcagcctacaacatacaggttcatggtggcaagaagatagcaagattta aattatggccagtgactagtgcttgaaggggaacaactacctgcatttaatgggaaggcaaaatctcaggctttgagggaagttaa cataggcttgattctgggtggaagcttggtgtgtagttatctggaggccaggctggagctctcagctcactatgggttcatcttta ttgtctcctttcatctcaacagctcctgggaaatgtgctggtgaccgttttggcaatccatttcggcaaagaattcacccctgagg tgcaggcttcctggcagaagatggtgactgcagtggccagtgccctgtcctccagataccactgagctcactgcccatgattcaga gctttcaaggataggctttattctgcaagcaatacaaataataaatctattctgctgagagatcacacatgattttcttcagctct ttttttacatcttttaaatatatgagccacaaaggggtttatattgagggaagtgtgtatgtgtatttctgcatgcctgtttgtg tttgtggtgtgtgcatgctcctcatttattttatatgagatgtgcattttgatgagcaaataaaagcagtaaagacacttgtaca cgggagttctgcaagtgggagtaaatggtgtaggagaaatccggtgggaagaaagacctctataggacaggacttctcagaaacag atgtttggaagagatgggaaaaggttcagtgaagacctgggggctggattgattgcagctgagtagcaaggatggttcttaagga agggaaagtgttccaagctttaggaattcaaggtttagtcaggtgtagcaattctattttattaggaggaatactatttctaatgg cacttagcttttcacagcccttgtggatgcctaagaaagtgaaattaatcccatgccctcaagtgtgcagattggtcacagcattt caagggagagacctcattgtaagactctgggggaggtggggacttaggtgtaagaaatgaatcagcagaggctcacaagtcagcat gagcatgttatgtctgagaaacagaccagcactgtgagatcaaaatgtagtgggaagaatttgtacaacattaattggaaggctta cttaatggaattttttgtatagttggatgttagtgcatctctataagtaagagtttaatatgatggtgttacggacctaatgtttgt gtctcctcaaaattcacatgctgaatccccaactcccaactgaccttatctgtggggaggcttttgaaaagtaattaggtttaga tgagctcataagagcagatccccatcataaaattattttccttatcagaagcagagagacaagccatttctctttcctcccggtga
```

-continued

```
ggacacagtgagaagtccgccatctgcaatccaggaagagaaccctgaccacgagtcagccttcagaaatgtgagaaaaaactctg ttgttgaagccacccagtcttttgtattttgttatagcaccttgcactgagtaaggcagatgaagaaggagaaaaaaataagcttg ggttttgagtggactacagaccatgtttatctcaggtttgcaaagctcccctcgtccctatgtttcagtataaaatacctactct actactctcatctataagacccaaataataagcctgcgcccttctctctaactttgatttctcctattttttacttcaacatgcttt actctagccttgtaatgtcttacatacagtgaaatgtaaagttctttattcttttttcttcttcttttttctcctcagcctc agaatttggcacatgccttccttctttcaggaacttctccaacatctctgcctggctccatcatatcataaaggtcccacttcaa atgcagtcactaccgtttcagaatatgcactttcttcttttttgttttttgttttttttaagtcaaagcaaatttcttgagagag taaagaaataaacgaatgactactgcataggcagagcagccccgagggccgctggttgttccttttatggttatttcttgatgata tgttaaacaagttttggattatttatgccttctcttttaggccatatagggtaacttctgacattgccatggcattttctttt aatttaatttactgttaccttaaattcaggggtacacgtacaggatatgcaggtttgttttataggtaaaagtgtgccatggtttt aatgggttttttttttcttgtaaagttgtttaagtttcttgtttactctggatattaggcctttgtcagaagaatagattggaaaa tcttttcccattctgtagattgtctttcgctctgatggtagtttcttttgctgagcaggagctctttagtttaattagattccat tggtcaattttgcttttgctgcaattgcttttcacgctttcatcatgaaatctgtgcccgtgtttatatcatgaatagtattgcc ttgattttttctaggcttttatagtttgggtttttcatttaagtctctaatccatctggagttaattttggataaggtataag gaaggagtccagtttcattttcagcatatggctagccagttctcccccatcatttattaaattgaaaatcctttcccccatgctt gcttttgtcaggtttctaaaagaccagatggttgtaggtacaatatgcagtttcttcaagtcatataataccatctgaaatctctt attaattcatttcttttagtatgtatgctggtctcctctgctcactatagtgagggcaccattagccagagaatctgtctgtctag ttcatgtaagattctcagaattaagaaaaatggatggcatatgaatgaaacttcatggatgacatatggaatctaatatgtatttg ttgaattaatgcataagatgcaacagagagaagttgacaactgcaatgataacctggtattgatgatataagagtctatagatcac agtagaagcaataatcatggaaaacaattggaaatggggaacagccacaaacaagaaagaatcaatacttccaggaaagtgactgc aggtcacttttcctggagcgggtgagagaaaagtggaagttagcagtaactgctgaattcctggttggctgatgaaagatgggc agctgttcactggtacgcagggttttagatgtatgtacctaaggatatgaggtatggcaatgaacagaaattcttttgggaatgag ttttagggccattaaaggacatgacctgaagtttcctctgaggccagtccccacaactcaatataaatgtgtttcctgcatatagt caaagttgccacttctttttcttcatatcatcgatctctgctcttaaagataatcttggttttgcctcaaactgtttgtcactaca aactttccccatgttcctaagtaaaacaggtaactgcctctcaactatatcaagtagactaaaatattgtgtctctaatatcagaa attcagctttaatatattgggtttaactctttgaaatttagagtctccttgaaatacacatgggggtgatttcctaaactttattt cttgtaaggatttatctcagggggtaacacacaaaccagcatcctgaacctctaagtatgaggacagtaagccttaagaatataaaa taaactgttcttctctctgccggtggaagtgtgccctgtctattcctgaaattgcttgtttgagacgcatgagacgtgcagcacat gagacacgtgcagcagcctgtggaatattgtcagtgaagaatgtcttgcctgattagatataaagacaagttaaacacagcatta gactatagatcaagcctgtgccagacacaaatgacctaatgcccagcacgggccacggaatctcctatcctcttgcttgaacagag cagcacacttctcccccaacactattagatgttctggcataattttgtagatatgtaggatttgacatggactattgttcaatgat tcagaggaaatctcctttgttcagataagtacactgactactaaatggattaaaaaacacagtaataaaacccagttttccccta cttccctagtttgtttcttattctgctttcttccaagttgatgctggatagaggtgtttatttctattctaaaaagtgatgaaatt ggccgggcgcggtggctcacacctgtaatcccagcactttgggaggctgaggtgggcggatcacgaggtcaggagatcaagaccat cctggctaacatggtgaaaccccatctctactaaaaatacaaaaaattagccagagacagtggcgggtgcctgtagtcccagctac tcgggaggctgaggcaggagaatggcgtgaacctgggaggcagagcttgcggtgagcagagatcgcgccactgcacactccagcct gggtgacaaagcgagactccatctcaaaaaaaaaaaaaaaaagaaaagaaagaaagaaagaaaaaaaaactgatgaaattgt gtattcaatgtagtctcaagagaattgaaaaccaagaaaggctgtggcttcttccacataaagcctggatgaataacaggataaca cgttgttacattgtcacaactcctgatccaggaattgatggctaagatattcgtaattcttatccttttcagttgtaacttattcc tatttgtcagcattcaggttattagcggctgctggcgaagtccttgagaaataaactgcacactggatggtgggggtagtgtagga
```

-continued

```
aaatggaggggaaggaagtaaagtttcaaattaagcctgaacagcaaagttcccctgagaaggccacctggattctatcagaaact
cgaatgtccatcttgcaaaacttccttgcccaaaccccaccccctggagtcacaacccaccccttgaccaatagattcattttactga
gggaggcaaagggctggtcaatagattcatttcactgggagaggcaaagggctggggccagagaggagaagtaaaaagccacaca
tgaagcagcaatgcaggcatgcttctggctcatctgtgatcaccaggaaactcccagatctgacactgtagtgcatttcactgctg
acaagaaggctgctgccaccagcctgtgaagcaaggttaaggtgagaaggctggaggtgagattctgggcaggtaggtactggaag
ccgggacaaggtgcagaaaggcagaaagtgtttctgaaagagggattagcccgttgtcttacatagtctgactttgcacctgctct
gtgattatgactatcccacagtctcctggttgtctacccatggacctagaggtactttgaaagttttggatatctgggctctgact
gtgcaataatgggcaacccaaagtcaaggcacatggcaagaaggtgctgatctccttcggaaaagctgttatgctcacggatgac
ctcaaaggcacctttgctacactgagtgacctgcactgtaacaagctgcacgtggaccctgagaacttcctggtgagtagtaagta
cactcacgctttcttctttaccccttagatatttgcactatgggtacttttgaaagcagaggtggctttctcttgtgttatgagtca
gctatgggatatgatatttcagcagtgggattttgagagttatgttgctgtaaataacataactaaaatttggtagagcaaggact
atgaataatggaaggccacttaccatttgatagctctgaaaaacacatcttataaaaaattctggccaaatcaaactgagtgttt
ttggatgagggaacagaagttgagatagagaaaataacatctttcctttggtcagcgaaattttctataaaaattaatagtcactt
ttctgcatagtcctggaggttagaaaaagatcaactgaacaaagtagtgggaagctgttaaaaagaggattgtttccctccgaatg
atgatggtatacttttgtacgcatggtacaggattctttgttatgagtgtttgggaaaattgtatgtatgtatgtatgtatgtatg
tgatgactggggacttatcctatccattactgttccttgaagtactattatcctacttttttaaaaggacgaagtctctaaaaaaaa
aatgaaacaatcacaatatgttggggtagtgagttggcatagcaagtaagagaaggataggacacaatgggaggtgcagggctgcc
agtcatattgaagctgatatctagcccataatggtgagagttgctcaaactctggtgaaaaaggatgtaagtgttatatctattta
ctgcaagtccagcttgaggccttctattcactatgtaccattttctttttttatcttcactcccctcccagctcttaggcaacgtga
tattgattgttttggcaacccacttcagcgaggattttaccctacagatacaggcttcttggcagtaactaacaaatgctgtggtt
aatgctgtagcccacaagaccactgagttccctgtccactatgtttgtacctatggtccactatgtttgtacctatgtcccaaaat
ctcatctcctttagatgggggaggttggggagaagagcagtatcctgcctgctgattcagttcctgcatgataaaaatagaataaa
gaaatatgctctctaagaaatatcattgtactcttttttctgtctttatattttaccctgattcagccaaaaggacgcactatttct
gatggaaatgagaatgttggagaatgggagtttaaggacagagaagatactttcttgcaatcctgcaagaaaagagagaactcgtg
ggtggatttagtgggtagttactcctaggaaggggaaatcgtctctagaataagacaatgttttacagaaagggaggtcaatgg
aggtactcttggaggtgtaagaggattgttggtagtgtgtagaggtatgttaggactcaaattagaagttctgtataggctatta
tttgtatgaaactcaggatatagctcatttggtgactgcagttcacttctacttattttaaacaacatattttttattatttataa
tgaagtggggatggggcttcctagagaccaatcaagggccaaaccttgaactttctcttaacgtcttcaatggtattaatagagaa
ttatctctaaggcatgtgaactggctgtcttggttttcatctgtacttcatctgctacctctgtgacctgaaacatatttataatt
ccattaagctgtgcatatgatagatttatcatatgtattttccttaaaggattttgtaagaactaattgaattgatacctgtaaa
gtctttatcacactacccaataaataaatctctttgttcagctctctgtttctataaatatgtacaagttttattgttttttag
tggtagtgattttattctcttctatatatatacacacacatgtgtgcattcataaatatatacaatttttatgaataaaaaatta
ttagcaatcaatattgaaaaccactgattttttgtttatgtgagcaaacagcagattaaaaggctgagatttaggaaacagcacgtt
aagtcaagttgatagaggagaatatggacatttaaaagaggcaggatgatataaaattagggaaactggatgcagagaccagatga
agtaagaaaaatagctatcgtttttgagcaaaaatcactgaagtttcttgcatatgagagtgacataataaatagggaaacgtagaa
aattgattcacatgtatatatatatagaactgattagacaaagtctaacttgggtatagtcagaggagcttgctgtaattatat
tgaggtgatggataaagaactgaagttgatggaaacaatgaagttaagaaaaaaatcgagtaagagaccattgtggcagtgattg
cacagaactggaaaacattgtgaaacagagagtcagagatgacagctaaaatccctgtctgtgaatgaaagaaggaaatttattg
acagaacagcaaatgcctacaagcccctgtttggatctggcaatgaacgtagccattctgtggcaatcacttcaaactcctgtac
ccaagacccttaggaagtatgtagcaccctcaaacctaaaacctcaaagaaagaggttttagaagatataatacccctttcttctcc
agtttcattaatcccaaaacctctttctcaaagtatttcctctatgtgtccaccccaaagagctcacctcaccatatctcttgagt
```

-continued

```
gggagcacatagataggcggtgctaccatctaacagcttctgaaattcctttgtcatattttttgagtccccactaataacccacaa
agcagaataaataccagttgctcatgtacaataatcactcaactgctgtcttgtagcatacattaattaagcacattctttgaata
attactgtgtccaaacaatcacactttaaaatctcacacttgtgctatcccttgccttctgaatgtcactctgtattttaaatga
agagatgagggttgaatttcctgtgttacttattgttcatttctcgatgaggagttttcacattcacctttagtggaaaacacata
agtacacatcttacaggaaaaatataccaaactgacatgtagcatgaatgcttgtgcatgtagtcatataaaatcttgtagcaatg
taaacattctctgatatacacatacagatgtgtctatatgtctacacaatttcttatgctccatgaacaaacattccatgcacaca
taagaacacacactgttacagatgcatacttgagtgcattgacaaaattacccccagtcaatctagagaatttggatttctgcattt
gactctgttagcttttgtacatgctgttcatttactctgggtgatgtcttttccctcatttttgccttgtctatcttgtactcatactt
taagtcctaacttatatgttatctcaactaagaagctatttttttttaattttaactgggcttaaagccctgtctataaactctgc
tacaattatgggctctttcttataatatttagtgttttttcctactaatgtacttaatctgctcattgtatattcctaccactaaat
tttaacctcttttatggtagagacattgtcttgtaaactcttatttccctagtatttggagatgaaaaaaaagattaaattatcca
aaattagatctctcttttctacattatgagtattacactatccatagagaagtttgtttgagacctaaactgaggaacctttggtt
ctaaaatgactatgtgatatcttagtatttataggtcatgaggttccttcctctgcctctgctatagtttgattagtcaacaagca
tgtgtcatgcatttattcacatcagaatttcatacactaataagacatagtatcagaagtcagtttattagttatatcagttaggg
tccatcaaggaaaggacaaaccattatcagttactcaacctagaattaaatacagctcttaatagttaattatccttgtattggaa
gagctaaaatatcaaataaaggacagtgcagaaatctagatgttagtaacatcagaaaacctcttccgccattaggcctagaaggg
cagaaggagaaaatgtttataccaccagagtccagaaccagagcccataaccagaggtccactggattcagtgagctagtgggtgc
tccttggagagagccagaactgtctaatgggggcatcaaagtatcagccataaaaaaccataaaaaagactgtctgctgtaggaga
tccgttcagagagagagagagaccagaaataatcttgcttatgctttccctcagccagtgtttaccattgcagaatgtacatgcga
ctgaaagggtgaggaaacctgggaaatgtcagttcctcaaatacagagaacactgagggaaggatgagaaataaatgtgaaagcag
acatgaatggtaattgacagaaggaaactaggatgtgtccagtaaatgaataattacagtgtgcagtgattattgcaatgattaat
gtattgataagataatatgaaaacacagaattcaaacagcagtgaactgagattagaattgtggagagcactggcatttaagaatg
tcacacttagaatgtgtctctaggcattgttctgtgcatatatcatctcaatattcattatctgaaaattatgaattaggtacaaa
gctcaaataatttattttttcaggttagcaagaacttttttttttttttctgagatagagcattgctatggttgcccaggctgga
gtgcaatggcatgatccaggctcactgcaacatctgcctcccaggttcaagcgattctcctgcctcagcctcccaagtagctggca
ctacaggcatgtgccaccaccatgcctggctaattttctatttttagtagatagggggtttcaccatgttggtcaggctgatctcg
aactcctaacatcaggtgatccaccctcctcggcctctgaaagtgctgggatcacaggcgtgagccaccacacccagccaagaatg
tgaattttgtagaaggatataacccatatttctctgaccctagagtccttagtatacctcccataccatgtggctcatcctcctta
catacatttcccatctttcaccctaccttttccttttttgtttcagcttttcactgtgtcaaaatctagaaccttatctcctacctg
ctctgaaaccaacagcaagttgacttccattctaacccacattggcattacactaattaaaatcgatactgagttctaaaatcatc
ggggatttggggactatgtcttacttcatacttccttgagatttcacattaaatgttggtgttcattaaaggtccttcatttaac
tttgtattcatcacactcttggattcacagttatatctaaactcttaaatacagcctgtataatcccaattcccaactctgatttc
taacctctgacctccaacctcagtgccaaacccatatatcaaacaatgtactgggcttatttatatagatgtcctataggcacctc
agactcagcatgggtatttcacttgttatactaaaactgtttctcttccagtgttttccattttagtcattagatagctacttgcc
cattcaccaaggtcacagattaaaatcatttccctacctctaatcaacagttcgattctgcttcaatttgtccctatctattaatc
accactcttactgcccagtcaggtcctcattgtttcctgaacaagagtagatgctattctttccacttttagaccttatcctggct
ggatgcggtggctcaggcttgtaaacccagcactttgggaggccaaggcaggcagatcacttgaggtcaggagttcaagaccagcc
tgaccaacatggtgaaaccccatctctactaaaaatacaaaatcagccgggcgtgtggtgcatgcctgcagtcccagctattcagg
tggctgaggcaggagaattgcttgaacccaggaggcagaggttgcggtgagcctagattgcaccattgcactctagcttgggcaat
agggatgaaactccatctcagaagagaaaagaaaaaaagaccttattctgttatacaaatcctctcaatgcaatccatatagaata
```

-continued

```
aacatgtaaccagatctcccaatgtgtaaaatcatttcaggtagaacagaattaaagtgaaaagccaagtctttggaattaacaga caaagatcaaataacagtcctcatggccttaagaatttacctaacattttttttagaatcaatttttcttatatatgaattggaaac ataattcctccctcacaaacacattctaagattttaaggagatattgatgaagtacatcatctgtcatttttaacaggtagtggta gtgattcacacagcacattgatctgttcttgtatgttctgttccattctgtattcttgacctggttgtattctttctgagctcc agatccacatatctaagtacatcttttgcattttacaagagtgcatacaatacaatgtatccaagactgtatttctgattttatc gtaccactaaactcacaaatgtggccctattcttgtgttcacgactgacatcaccgtcatggtccaagtctgataatagaaatggc attgtcactttcttccctactgcaacagaagcccagctatttgtctcccattttctctacttctaaaatacatttcttcactaagt gagaataatcttttaaagacacaaatcaaaccatgccaccacctttcttgaattattcaatatctttcgttggcttccaggttaca gaaaaataacttgtaacaaagtttaaaggtcattcatggctcctctctacccttatttttataacatttcccttgtgatcagaatct caggcacatcatccatctttctatatacaaataaagtcatatagtttgaactcacctctggttacttttaatcaaccaaatgctgt aaaatgcatttgtatcgctacgtgttaagcagtagttgattcttttcatttctgtgtaatattctattctttgactataccgtaat ttatcaattctactgttggtaagcatttaagtggctaccggtttgaggtttttatgattattgctgtcataagcatttctatacat gtctttggatacacacatgcatgtgtttctgaatatctaaaaatgtaattgctaggtaatagacttatcaagcatccagcatttgt ggatactattaaaggttttccaaggggttatactattgtacagtgtcaccaacagagtttgagtttctattgatccatatcacca ccaaaatttgaactgtcagtcttatctcttctcttgtctctttttcctctttttttcttcccttcccctctcttcgtttcttt tctctcctcttctcttcttcctctcttcccttccctttctctttctcttccctatcccttctcctctcctctccctcctttttt ctcctctcctctccattatttattttccttcttctcctccatccctccatcctctctcttcccctcttccttccttcctttctc catttcttcctcctctttccttcaatccttccttttggatatgctcatgggtgtgtatttgtctgccattgtggcattatttgaat tcagaaaagagtgaaaaactactgggatcttcattcctgggtctaattccacattttttttaagaacacatctgtaaaaatgttc tgtactagcatattcccaggaacttcgttaaatttaatctggctgaatatggtaaatctacttttcactttgcattctttctttag tcataccataattttaaacattcaaaatatttgtatataatatttgattttatctgtcattaaaatgttaaccttaaaattcatgt ttccagaacctatttcaataactggtaaataaacactattcatttttaaatattcttttaatggatatttatttcaatataataa aaaattagagttttattataggaagaatttaccaaaagaaggaggaagcaagcaagtttaaactgcagcaatagatttgtccattc caacctctcaaaattcccttggagacaaaaatctctagaggcaaagaagaactttatattgagtcaacttgttaaaacatctgctt ttagataagttttcttagtataaagtgacagaaacaaataagttaaactctaagatacattccactatattagcctaaaacacttc tgcaaaaatgaaactaggaggatattttagaaacaactgctgaaagagatgcggtggggagatatgtagaggagaacagggtttc tgagtcaagacacacatgacagaacagccaatctcagggcaagttaagggaatagtggaatgaaggttcattttcattctcacaa actaatgaaaccctgcttatcttaaaccaacctgctcactggagcagggaggacaggaccagcataaaaggcagggcagagtcgac tgttgcttacactttcttctgacataacagtgttcactagcaacctcaaacagacaccatggtgcatctgactcctgaggagaaga ctgctgtcaatgccctgtggggcaaagtgaacgtggatgcagttggtggtgaggccctgggcaggttggtatcaaggttataagag aggctcaaggaggcaaatggaaactgggcatgtgtagacagagaagactcttgggtttctgataggcactgactctctgtcccttg ggctgttttcctaccctcagattactggtggtctaccccttggacccagaggttctttgagtcctttggggatctgtcctctcctga tgctgttatgggcaaccctaaggtgaaggctcatggcaagaaggtgctaggtgcctttagtgatggcctggctcacctggacaacc tcaagggcacttttctcagctgagtgagctgcactgtgacaagctgcacgtggatcctgagaacttcagggtgagtccaggagat gcttcacttttctcttttactttctaatcttacattttggttcttttacctacctgctcttctcccacattttttgtcatttact atattttatcatttaatgcttctaaaattttgttaattttttatttaaatattctgcattttttccttcctcacaatcttgctatt ttaaattatttaatatcctgtctttctctcccaaccccctcccttcattttccttctctaacaacaactcaaattatgcatacca gctctcacctgctaattctgcacttagaataatccttttgtctctccacatgggtatgggagaggctccaactcaaagatgagagg catagaatactgttttagaggctataaatcattttacaataaggaataattggaattttataaattctgtagtaaatggaatggaa aggaaagtgaatatttgattatgaaagactaggcagttacactggaggtggggcagaagtcgttgctaggagacagcccatcatca cactgattaatcaattaatttgtatctattaatctgtttatagtaattaatttgtatatgctatatacacatacaaaattaaaact
```

-continued

```
aatttggaattaatttgtatatagtattatacagcatatatagcatatatgtacatatatagactacatgctagttaagtacatag aggatgtgtgtgtatagatatatgttatatgtatgcattcatatatgtacttatttatgctgatgggaataacctggggatcagtt ttgtctaagatttgggcagaaaaaaatgggtgttggctcagtttctcagaagccagtctttatttctctgttaaccatatgcatgt atctgcctacctcttctccgcagctcttgggcaatgtgctggtgtgtgtgctggcccgcaactttggcaaggaattcaccccacaa atgcaggctgcctatcagaaggtggtggctggtgtggctaatgccctggctcacaagtaccattgagatcctggactgtttcctga taaccataagaagaccctatttccctagattctattttctgaacttgggaacacaatgcctacttcaagggtatggcttctgccta ataaagaatgttcagctcaacttcctgattaatttcacttatttcattttttgtccaggtgtgtaagaaggttcctgaggctcta cagatagggagcacttgtttattttacaaagagtacatgggaaagagaaaagcaagggaaccgtacaaggcattaatgggtgaca cttctacctccaaagagcagaaattatcaagaactcttgatacaaagataatactggcactgcagaggttctagggaagacctcaa ccctaagacatagcctcaagggtaatgctacgattaaactccaacaattactgagaaaataatgtgctcaattaaaggcataatga ttactcaagacaatgttatgttgtctttcttcctccttcctttgctgcacattgtagcccataatactatacccatcaagtgtt cctgctccaagaaatagcttcctcctcttacttgccccagaacatctctgtaaagaatttcctcttatcttcccatatttcagtca agattcattgctcacgtattacttgtgacctctcttgaccccagccacaataaacttctctatactacccaaaaaatctttccaaa ccctcccccacaccattttttatattttatattttctttatttatttcatgcacacacacacactccgtgcttataagcaattc tgcctattctctaccttcttacatgcctactgtgcctcatattaaattcatcaatgggcagaaagaaaatatttattcaagaaaac agtgaatgaatgaacgaatgagtaaatgagtaaatgaaggaatgattattccttgctttagaacttctggaattagaggacaatat taataataccatcgcacagtgtttctttgttgttaatgctacaacatacaaagaggaagcatgcagtaaacaaccgaacagttatt tcctttctgatcataggagtaatattttttccttgagcaccattttgccataggtaaaattagaaggattttagaactttctc agttgtatacattttaaaaatctgtattatatgcatgttgattaattttaaacttacttgaatacctaaacagaatctgttgttt ccttgtgtttgaaagtgctttcacagtaactctgtctgtactgccagaatatactgacaatgtgttatagttaactgttttgatca caacattttgaattgactggcagcagaagctcttttatatccatgtgttttccttaagtcattatacatagtaggcactgagaact ctttatatctgaataagatatttaggaaccactggtttacatatcagaagcagagctactcagggcattttggggaagatcacttt cacattcctgagcatagggaagttctcataagagtaagatattaaaaggagatacttgtgtggtattcgaaagacagtaagagaga ttgtagaccttatgatcttgatagggaaaacaaactacattcctttctccaaaagtcaaaaaaaaagagcaaatatagcttactat accttctattcctacaccattagaagtagtcagtgagtctaggcaagatgttggccctaaaaatccaaataccagagaattcatga gaacatcacctggatgggacatgtgccgagcacacacaattactatatgctaggcattgctatcttcatattgaagatgaggaggt caagagatgaaaaaagacttggcaccttgttgttatattaaaattatttgttagagtagagcttttgtaagagtctaggagtgtgg gagctaaatgatgatacacatggacacaaaaaatagatcaacagacacccaggcctacttgagggttgagggtgggaagagggaga cgatgaaaaagaacctattgggtattaagttcatcactgagtgatgaaataatctgtacatcaagacccagtgatatgcaatttac ctatataacttgtacatgtaccccaaatttaaaatgaaagttaaaacaaagtataggaatggaattaattcctcaagatttggct ttaattttatttgataatttatcaaatggttgttttcttttctcactatggcgttgctttataaactatgttcagtatgtctgaa tgaaagggtgtgtgtgtgtgaaagagagggagagaggaagggaagagaggacgtaataatgtgaatttgagttcatgaaaattt ttcaataaaataatttaatgtcaggagaattaagcctaatagtctcctaaatcatccatctcttgagcttcagagcagtcctctga attaatgcctacatgtttgtaaagggtgttcagactgaagccaagattctacctctaaagagatgcaatctcaaatttatctgaag actgtacctctgctctccataaattgacaccatggcccacttaatgaggttaaaaaaaagctaattctgaatgaaaatctgagccc agtggaggaaatattaatgaacaaggtgcagactgaaatataaattttctgtaataattatgcatatactttagcaaagttctgt ctatgttgactttattgcttttggtaagaaatacaacttttaaagtgaactaaactatcctatttccaaactattttgtgtgtg tgcggtttgtttctatgggttctggttttcttggagcattttatttcattttaattaattaattctgagagctgctgagttgtgt ttactgagagattgtgtatctgcgagagaagtctgtagcaagtagctagactgtgcttgacctaggaacatatacagtagattgct aaaatgtctcacttggggaattttagactaaacagtagagcatgtataaaaatactctagtcaagtgctgcttttgaaacaaatga
```

-continued

```
taaaaccacactcccatagatgagtgtcatgattttcatggaggaagttaatattcatcctctaagtatacccagactagggccat
tctgatataaaacattaggacttaagaaagattaatagactggagtaaaggaaatggacctctgtctctctcgctgtctctttttt
gaggacttgtgtgtgtgtgtgtgtgtgtgtgtgtgtgtgttgtggtcagtggggctggaataaaagtagaatagacctgcacct
gctgtggcatccattcacagagtagaagcaagctcacaatagtgaagatgtcagtaagcttgaatagttttcaggaacttttgaat
gctgatttagatttgaaactgaggctctgaccataaccaaatttgcactatttattgcttcttgaaacttatttgcctggtatgcc
tgggcttttgatggtcttagtatagcttgcagccttgtcctgcagggtattatgggtaatagaaagaaagtctgcgttacactc
tagtcacactaagtaactaccattggaaaagcaaccctgccttgaagccaggatgatggtatctgcagcagttgccaacacaaga
gaaggatccatagttcatcatttaaaaaagaaaacaaaatagaaaaaggaaaactatttctgagcataagaagttgtagggtaagt
ctttaagaaggtgacaatttctgccaatcaggatttcaaagctcttgctttgacaattttggtctttcagaatactataaatataa
cctatattataatttcataaagtctgtgcattttctttgacccaggatatttgcaaaagacatattcaaacttccgcagaacactt
tatttcacatatacatgcctcttatatcagggatgtgaaacagggtcttgaaaactgtctaaatctaaaacaatgctaatgcaggt
ttaaatttaataaaataaaatccaaaatctaacagccaagtcaaatctgcatgttttaacatttaaaatattttaaagacgtcttt
tcccaggattcaacatgtgaaatcttttctcagggatacacgtgtgcctagatcctcattgctttagttttttacagaggaatgaa
tataaaaagaaaatacttaaattttatccctcttacctctataatcatacataggcataatttttttaacctaggctccagatagcc
atagaagaaccaaacactttctgcgtgtgtgagaataatcagagtgagatttttcacaagtacctgatgagggttgagacaggta
gaaaaagtgagagatctctatttatttagcaataatagagaaagcatttaagagaataaagcaatggaaataagaaatttgtaaat
ttccttctgataactagaaatagaggatccagtttcttttggttaacctaaattttatttcatttttattgtttatttttattttat
tttattttattttgtgtaatcgtagtttcagagtgttagagctgaaaggaagaagtaggagaaacatgcaaagtaaaagtataaca
cttttccttactaaaccgacatgggtttccaggtaggggcaggattcaggatgactgacagggcccttagggaacactgagaccct
cgctgacctcataaatgcttgctacctttgctgttttaattacatcttttaatagcaggaagcagaactctgcacttcaaaagttt
ttcctcacctgaggagttaatttagtacaaggggaaaaagtacaggggatgggagaaaggcgatcacgttgggaagctatagaga
aagaagagtaaattttagtaaaggaggtttaaacaaacaaaatataaagagaaataggaacttgaatcaaggaaatgattttaaaa
cgcagtattcttagtggactagaggaaaaaaataatctgagccaagtagaagacctttcccctcctacccctactttctaagtca
cagaggcttttgttccccagacacttgcagattagtccaggcagaaacagttagatgtccccagttaacctcctatttgaca
ccactgattaccccattgatagtcacactttgggttgtaagtgacttttatttatttgtattttgactgcattaagaggtctct
agttttttatctcttgtttcccaaaacctaataagtaactaatgcacagagcacattgatttgtatttattctatttttagacata
atttattagcatgcatgagcaaattaagaaaaacaacaacaaatgaatgcatatatatgtatatgtatgtgtatatatacacac
atatatatatattttttcttttcttaccagaaggttttaatccaaataaggagaagatatgcttagaaccgaggtagagttttc
atccattctgtcctgtaagtattttgcatattctggagacgcaggaagagatccatctacatatcccaaagctgaattatggtaga
caaaactcttccacttttagtgcatcaacttcttatttgtgtaataagaaaattgggaaaacgatcttcaatatgcttaccaagct
gtgattccaaatattacgtaaatacacttgcaaaggaggatgttttagtagcaatttgtactgatggtatgggccaagagatat
atcttagagggagggctgagggtttgaagtccaactcctaagccagtgccagaagagccaaggacaggtacggctgtcatcactta
gacctcaccctgtggagccacaccctagggttggccaatctactcccaggagcagggagggcaggagccagggctgggcataaaag
tcagggcagagccatctattgcttacatttgcttctgacacaactgtgttcactagcaacctcaaacagacaccatggtgcatctg
actcctgaggagaagtctgccgttactgccctgtggggcaaggtgaacgtggatgaagttggtggtgaggccctgggcaggttggt
atcaaggttacaagacaggtttaaggagaccaatagaaactgggcatgtggagacagagaagactcttgggtttctgataggcact
gactctctctgcctattggtctattttcccacccttaggctgctggtggtctaccttggacccagaggttctttgagtcctttgg
ggatctgtccactcctgatgctgttatgggcaaccctaaggtgaaggctcatggcaagaaagtgctcggtgcctttagtgatggcc
tggctcacctggacaacctcaagggcacctttgccacactgagtgagctgcactgtgacaagctgcacgtggatcctgagaacttc
agggtgagtctatgggacgcttgatgttttcttttccccttcttttctatggttaagttcatgtcataggaaggggataagtaacag
ggtacagtttagaatgggaaacagacgaatgattgcatcagtgtggaagtctcaggatcgttttagtttcttttatttgctgttca
```

```
taacaattgttttcttttgtttaattcttgctttcttttttttcttctccgcaattttta ctattatacttaatgccttaacatt
gtgtataacaaaaggaaatatctctgagatacattaagtaacttaaaaaaaaacttta cacagtctgcctagtacattactatttg
gaatatatgtgtgcttatttgcatattcataatctccctactttattttcttttatttt aattgatacataatcattatacatat
ttatgggttaaagtgtaatgttttaatatgtgtacacatattgaccaaatcagggtaa ttttgcatttgtaattttaaaaaatgct
ttcttcttttaatatacttttttgtttatcttatttctaatactttccctaatctctttctttcagggcaataatgatacaatgta
tcatgcctctttgcaccattctaaagaataacagtgataatttctgggttaaggcaat agcaatatctctgcatataaatatttct
gcatataaattgtaactgatgtaagaggtttcatattgctaatagcagctacaatcca gctaccattctgcttttattttatggtt
gggataaggctggattattctgagtccaagctaggcccttttgctaatcatgttcata cctcttatcttcctcccacagctcctgg
gcaacgtgctggtctgtgtgctggcccatcactttggcaaagaattcacccaccagt gcaggctgcctatcagaaagtggtggct
ggtgtggctaatgccctggcccacaagtatcactaagctcgctttcttgctgtccaa tttctattaaaggttcctttgttccctaa
gtccaactactaaactgggggatattatgaagggccttgagcatctggattctgcct aataaaaaacatttattttcattgcaatg
atgtatttaaattatttctgaatattttactaaaaagggaatgtgggaggtcagtgcatttaaaacataaagaaatgaagagctag
ttcaaaccttgggaaaatacactatatcttaaactccatgaaagaaggtgaggctgc aaacagctaatgcacattggcaacagccc
ctgatgcatatgccttattcatccctcagaaaaggattcaagtagaggcttgatttg gaggttaaagttttgctatgctgtatttt
acattacttattgttttagctgtcctcatgaatgtcttttcactacccatttgcttat cctgcatctctcagccttgactccactc
agttctcttgcttagagataccacctttccctgaagtgttccttccatgttttacgg cgagatggtttctcctcgcctggccact
cagccttagttgtctctgttgtcttatagaggtctacttgaagaaggaaaaacagggg tcatggtttgactgtcctgtgagcccctt
cttccctgcctcccccactcacagtgacccggaatctgcagtgctagtctcccggaa ctatcactctttcacagtctgctttggaa
ggactgggcttagtatgaaaagttaggactgagaagaatttgaaaggcggcttttgt agcttgatattcactactgtcttattac
cctgtcataggcccaccccaaatggaagtcccattcttcctcaggatgtttaagatt agcattcaggaagagatcagaggtctgct
ggctcccttatcatgtcccttatggtgcttctggctctgcagttattagcatagtgtt accatcaaccaccttaacttcattttc
ttattcaatacctaggtaggtagatgctagattctggaaataaaatatgagtctcaa gtggtccttgtcctctctcccagtcaaat
tctgaatctagttggcaagattctgaaatcaaggcatataatcagtaataagtgatg atagaagggtatatagaagaattttatta
tatgagagggtgaaaccctcaaaatgaaatgaaatcagacccttgtcttacaccata aacaaaaataaatttgaatgggttaaaga
attaaactaagacctaaaaccataaaaattttttaaagaaatcaaaagaagaaaatt ctaatattcacgttgcagccgttttttgaa
tttgatatgagaagcaaaggcaacaaaaggaaaaataaagaagtgaggctacatcaa actaaaaaatttccacacaaaaaacaaaa
caatgaacaaatgaaaggtgaaccatgaaatggcatatttgcaaaccaaatatttct taaatattttggttaatatccaaaatata
taagaaacacagatgattcaataacaaacaaaaaattaaaaataggaaaataaaaaa atttaaaaagaagaaaatcctgccatttat
ggcagaattgatgaacctggaggatgtaaaactaagaaaaataagcctgacacaaaa agacaaatactacacaaccttgctcatat
gtgaaacataaaaaagtcactctcatggaaacagacagtagaggtatggtttccagg ggttggggtgggagaatcaggaaactat
tactcaaagggtataaaatttcagttatgtgggatgaataaattctagatatctaat gtacagcatcgtgactgtagttaattgta
ctgtaagtatatttaaaatttgcaaagagagtagatttttttttttttttagatggagttttgctcttgttgtccaggctggagtg
caatggcaagatcttggctcactgcaacctccgcctcctgggttcaagcaaatctcc tgcctcagcctcccgagtagctgggatta
caggcatgcgacaccatgcccagctaattttgtatttttagtagagacggggtttct ccatgttggtcaggctgatccgcctgcct
cggccacccaaagggctgggattacaggcgtgagccaccgggcctggccgagagta gatcttaaaagcatttaccacaagaaaag
gtaactatgtgagataatgggtatgttaattagcttgattgtggtaatcatttcaca aggtatacatatattaaaacatcatgttg
tacacccttaaatatacaattttttatttgtgaatgatacctcaataaagttgaaga ataataaaaaagaatagacatcacatgaa
ttaaaaaactaaaaaaataaaaaaaatgcatcttgatgattagaattgcattcttga ttttcagatacaaatatccatttgactgtt
tactcttttccaaaacaatacaataaattttagcactttatcttcattttccccttc caatctataattatatatatatatatttt
tagatattttgtatagttttactccctagattttctagtgttattattaaatagtgaa gaaatgtttacacttatgtacaaaatgt
```

-continued

```
tttgcatgcttttcttcatttctaacattctctctaagtttattctattttttctgattatccttaatattatctctttctgctg
gaaatacattgttacttttggtttatctaaaaatggcttcattttcttcattctaaaatcatgttaaattaataccactcatgtgt
aagtaagatagtggaataaatagaaatccaaaaactaaatctcactaaaatataataatgtgatatataaaaatatagcttttaaa
tttagcttggaaataaaaaacaaacagtaattgaacaactatacttttgaaaagagtaaagtgaaatgcttaactgcatatacca
caatcgattacacaattaggtgtgaaggtaaaattcagtcacgaaaaaactagaataaaaatatgggaagacatgtatataatctt
agagataacactgttatttaattatcaacccaaagtagaaactatcaagggagaaataaattcagtcaacaataaaagcatttaag
aagttattctaggctgggagcggtggctcacacctgcaattgcagcactttgggaggcctagacaggcggatcacgacgtcaggag
ttcaagatcagcctggccaacatagtgaaacctcatcgctactaaaaatataaaaacttagcctggcgtggtggcaggcatgtgta
atcccagcaatttgggaggctgaggcaggagaatcgcttgatcctgggaggcagaggttgcagtgagccaagattgtgccactgca
ttccagcccaggtgacagcatgagactccgtcacaaaaaaaaagaaaaaaaaaggggggggggagcggtggagccaagatgacc
gaataggaacagctccagtctatagctcccatcgtgagtgacgcagaagacgggtgatttctgcatttccaactgaggtaccaggt
tcatctcacagggaagtgccaggcagtgggtgcaggacagtaggtgcagtgcactgtgcatgagccaaagcagggcgaggcatcac
ctcacccgggaagcacaaggggtcagggaattccctttcctagtcaaagaaaagggtgacagatggcacctggaaaatcgggtcac
tcccgccctaatactgcgctcttccaacaagcttaacaaatggcacaccaggagattatatcccatgcctggctcagagggtccta
cgcccatggagcctcgctcattgctagcacagcagtctgaggtcaaactgcaaggtggcagtgaggctggggaggggtgcccacc
attgtccaggcttgagcaggtaaacaaagccgcctggaagctcgaactgggtggagcccaccacagctcaaggaggcctgcctgcc
tctgtaggctccacctctaggggcagggcacagacaaacaaaagacaacaagaacctctgcagacttaaatgtccctgtctgacag
ctttgaagagagtagtggttctcccagcacatagcttcagatctgagaacaggcagactgcctcctcaagtgggtccctgaccccc
gagtagcctaactggaggcatcccccagtagggcagactgacacctcacatggctggtactcctctaagacaaaacttccagag
gaatgatcaggcagcagcatttgcggttcaccaatatccactgttctgcagccaccgctgttgatacccaggaaaacagcttctgg
agtggacctccagtaaactccaacagacctgcagctgagggtcctgactgttagaaggaaaactaacaaacagaaaggacatccac
accaaaaacccatctgtacatcgccatcatcaaagaccaaaggtagataaaaccataaagatggggaaaaagcagagcagaaaaac
tggacactctaaaaatgagagtgcctctcctcctccaaagtaacgcagctcctcaccagcaatggaacaaagctgggcagagaatg
actttgacgagttgagagaggaaggcttcagaagatcaaactactccaagctaaaggaggaagttcgaacaaacggcaaagaagta
aaaaactttgaaaaaaaaattagatgaatggataactagaataaccaatgcacagaagtccttaaaggacctgatggagctgaaaac
caaggcaggagaactacgtgacaaatacacaagcctcagtaaccgatgagatcaactggaagaaagggtatcaatgacgaaagatg
aaatgaatgaaatgaagcatgaagagaagtttagagaaaaaagaataaaaagaaacgaacaaagcctccaagaaatatgggactat
gtgaaaagaccaaatctacatctaattggtgtagctgaaagtgatggggagaatggaaccaagttggaaaacactctgcaggatat
tatccaggagaacttccccaatctagcaaggcaagcccaaattcacattcaggaaatacagagaacgccacaaagatactcctaga
gaaaagcaactccaagacacataactgtcagattcaccaaagttgaaatgaaggaaaaaatgttaagggcagccagagagaaaggt
cgggttacccacaaagggaagcccatcagactaacagctgatctatcggcagaaactctacaagccagaagaagtgggggccaat
attcaacattgttaaagaaaagaattttcaacccagaatttcatatccagccaaactaagcttcataagtgaaggagaaataaat
cctttacagacaagcaaatgctgagagattttgtcaccaccaggcctgccctacaagagctcctgaaggaagcactaaacatggaa
aggaacaactagtatcagccactgcaaaaacatgccaaattgtaaagaccatcaaggctaggaagaaactgcatcaacgagcaaaa
taaccagctaacatcataatgacaggatcaaattcatacataacaatactcaccttaaatgtaaataggctaaatgctccaattaa
aagacacagactggcaaattggataaggagtcaagacccatctgtgttctgtattcaggaaacccatctcacgtgcagagacacac
ataggctcgaaataaaggatggaggaatatctaccaagcaaatggaaaacaaaaaaggcaggggttgcaatcctagtctctgat
aaaacagattttaaaccaacaaagatcaaaagagacaaagaaggccattacataatggcaaagggatctattcaagaagaagaact
aactatactaaatatatatgcacccaatacaggagcacccagattcataaaacaagtcctgagtgacctacaaagagacttagatg
cccacacaataataatgggagactttaacacccccactgtcaacattagacagatcaacgagacagaaagttaacaaggatatccag
gaattggactcagctctgcaccaagcagacctaatagacatctacagaactctccaccccaaatcaacagaatatacattctttc
```

-continued

```
agcaccacaccacacctattccaaaactgaccacatagttggaagtaaagctctcctcagcaaatgtaaaagaacagaaactataa caaactgtctctcagaccacagtgcaatcaaactagaactcaggattaagaaactcactcaaaaccactcagctacatggaaactg aacagcctgctcctgaatgactactgggtacataacaaaatgaaggcagaaataaagatgttctttgaaaccaacgagaacaaaga cacaacacaccagaatctctgagacacattcaaagcagtgtgtagagggaaatttatagcactaaatgcccacaaggaaagcagg aaagatctaaaattgacaccctaacatcacaattaaaaaactagagaagcaggagcaaacacattcaaaagctaacagaagacaag aaataactaagatcagagcagaagtgaaggacatagagacacaaaaaaccctcaaaaaaatcaatgaatccagaagctgttttt ttgaaaagatcaacaaaattgatagactgctagcaagactaataaagaagaaagagagaagaatcaaatagacgcaataaaaaat gacacggggtatcaccactgatcccacagaaatacaaactaccgtcagagaatactataaacacctctacgcaaataaactagaaa atctagaagaaatggataaattcctcgacacatacactctgccaagactaaaccaggaagaagttgtatctctgaatagaccaata acaggctctgaaattgaggcaataattaatagcttatcaaccaaaaaagtccgggaccagtaggattcatagccgaattctacca gaggtacaaggaggagctggtaccattccttctgaaactattccaatcaatagaaaaagagggaatcctccctaactcattttatg aggccagcatcatcctgataccaaagcctgacagagacacaacaaaaaaagagaatgttacaccaatatccttgatgaacattgat gcaaaaatcctcaataaaatactggcaaactgatccaccatgatcaagtgggcttcatccctgccatgcaaggctggttcaacata cgaaaatcaataaacataatccagcatataaacagaaccaaagcacaaaccatatgattatctcaatagatgcagaaaaggcctt tgacaaaattcaacaacgcttcatgctaaaaactctcaataaattaggtattgatgggacatatctcaaaataataagagctatct atgacaaacccacagccaatatcatactgagtggacaaaaactggaagcattcccttgaaaactggcacaaggcagggatgccct ctctcaccactcctattcaacatagtgttgtaagttctggccagggcaatcaggcaggagaaggaaataaagggcattcaattagg aaaagaggaagtgaaattgtccctgtttgcagatgacatgattgtatatctagaaaaccccattgtctcagcccaaaatctcctta agctgataagcaacttcagcaaagtctcaggatataaaatcagtgtgcaaaaatcacaagtattcctatgcaccaataacagacaa acagagagccaaatcatgagtgaactcccattcacaattgcttcaaagagaataaaatacctaggaatccaacttacaagggatgt gaaggacctcttcaaggagaactacaaaccactgctcaatgaaataaaagaggatacaaacaaatggaagaacattccatgctcat gggtaggaagaatcaatatcgtgaaaatggtcatactgcccaaggtaatttatagattcaatgccatccccatcaagctaccaatg actttcttcacagaactggaaaaaactactttaaagttcatatggaaccaaaaaagagcccacatcaccaaggcaatcctaagcca aaagaacaaagctggaggcatcacgctacctgacttcaaactatactacaatgctacggtaaccaaaacagcatggtactggtacc aaaacagagatctagaccaatggaacagaacagagccctcagaaataatgccgcatatctacaactatctgatctttgacaaacct gagagaaacaagcaatggggaaaggattccctatttaataaatggtgctgggaaaactggctagccatatgtagaaagctgaaact ggatcccttccttacaccttatacaaaaattaattcaagatggattaaagacttacatgttagacctaaaaccataaaaaccctag aaaaaaacctaggcaataccattcaggacataggcatgggcaaggacttcatgtctaaaacaccaaaagcaatggcaacaaaagac aaaatggacaaacgggatctaattaaactaaagagcttctgcacagctaaagaaactaccatcagagtgaacaggcaacctacaaa atgggagaaaattttgcaatctactcatctgacaaagggctaatatccagaatctacaatgaactcaaacaaatttacaagaaaa aacaaacaacccatcaaaaagtgggcaaaggatatgaacagacacttcgcaaagaagacatttatgtaatcaaaaaacacatga aaaaatgctcatcatcactagccatcagagaaatgcaaatcaaaccacaatgagataccatctcacaccagttagaatggcgatc attaaaaagtcaggaaacaacaggtgctgagaggatgtggagaaacaggaacaacttttacactgttggtgggactgtaaactag ttcaaccattgcggaagtcagtgtggcaattcctcaggaatctagaactagaaataccatttgacccagccatcccattactgggt acatacccaaaggattataaatcatgctgctataaagacacatgcacacgtatgtttattgcagcactattcacaatagcaaagac ttggaaccaacccaaatgtccaacaacgatagactggattaagaaaatgtggcacatatacaccatggaatactatgcagccataa aaaatgatgagttcatgtcctttgtagggacatggatgaagctggaaactatcattctcagcaaactatcacaaggagaataaacc aaacaccgcatgttctcactcataggtgggaattgaacaatgagaacacatggacacatgaagaggaacatcacactctggggact gttatgggtgggggcaggggcagggatagcactaggagatatacctaatgctaaatgacgagttaatgggtgcagcacaccaac
```

-continued
```
atggcacatgtatacatatataacaaacctgcatgttgtgcacatgtaccctaaaacttgaagtataataataaaaaaaagttatc ctattaaaactgatctcacacatccgtagagccattatcaagtctttctctttgaaatagacagaaatttagtgttttctcagtca gttaac
```

Five 5' hypersensitive site (HS) sites (HS1-HS5) and one 3' HS site have been identified in the human β-globin LCR (Stamatoyannopoulos et al., (2001)). The 5' HSs 1-4 are Dnase I hypersensitive sites. The HS2 and HS3 elements are the most powerful single elements within the LCR (Ellis et al., *EMBO J.* (1996), 15:562-568; Collis et al., *EMBO J.* (1990) 9:233-240), as corroborated by many groups. Deleting HS2 in the context of βYAC in transgenic mice severely affects HS site formation as well as expression of all of the human β-globin genes at every developmental stage (Bungert et al., *Mol. Cell Biol.* (1999); 19:3062-3072). It was reported that deletion of HS2 minimally reduced the expression of the embryonic εy and βhi globin genes in yolk sac-derived erythrocytes (Ley et al., Ann. N.Y. Acad. Sci. (1998); 850:45-53; Hug et al., *Mol. Cell Biol.* (1996); 26:2906-2912). HS2 functions primarily as an enhancer.

In certain embodiments, the β-globin LCR region comprises a HS2 region. In non-limiting example, the β-globin LCR region comprises a HS2 region, a HS3 region, and a HS4 region. In certain embodiments, the HS2 region, HS3 region and HS4 region within the β-globin LCR region are contiguous. In one non-limiting embodiment, the β-globin LCR region consisting essentially of a HS2 region, a HS3 region and a HS4 region. In another embodiment, the β-globin LCR region comprises two introduced GATA-1 binding sites at the junction between the HS3 region and the HS4 region. The HS3 region can lie between the HS2 region and the HS4 region. The length and the sequence of the HS2 region can vary. The HS2 region can have a length of from about 400 bp to about 1000 bp, e.g., from about 400 bp to about 500 bp, from about 500 bp to about 600 bp, from about 600 bp to about 700 bp, from about 700 bp to about 800 bp, from about 800 bp to about 900 bp, or from about 900 bp to about 1000 bp. In one non-limiting embodiment, the HS2 region has a length of 860 bp. In one non-limiting example, the HS2 region has the nucleotide sequence set forth in SEQ ID NO:9, which is provided below:

```
[SEQ ID NO: 9]
GTATATGTGTATATATATATATATATATTCAGGAAATAATATATTCTAGA

ATATGTCACATTCTGTCTCAGGCATCCATTTTCTTTATGATGCCGTTTGA

GGTGGAGTTTTAGTCAGGTGGTCAGCTTCTCCttttttttGCCATCTGCC

CTGTAAGCATCCTGCTGGGGACCCAGATAGGAGTCATCACTCTAGGCTGA

GAACATCTGGGCACACACCCTAAGCCTCAGCATGACTCATCATGACTCAG

CATTGCTGTGCTTGAGCCAGAAGGTTTGCTTAGAAGGTTACACAGAACCA

GAAGGCGGGGTGGGGCACTGACCCCGACAGGGGCCTGGCCAGAACTGCT

CATGCTTGGACTATGGGAGGTCACTAATGGAGACACACAGAAATGTAACA

GGAACTAAGGAAAAACTGAAGCTTATTTAATCAGAGATGAGATGCTGGAA

GGGATAGAGGGAGCTGAGCTTGTAAAAAGTATAGTAATCATTCAGCAAAT

GGTTTTGAAGCACCTGCTGGATGCTAAACACTATTTTCAGTGCTTGAATC

ATAAATAAGAATAAAACATGTATCTTATTCCCCACAAGAGTCCAAGTAAA
```

```
-continued
AAATAACAGTTAATTATAATGTGCTCTGTCCCCCAGGCTGGAGTGCAGTG

GCACGATCTCAGCTCACTGCAACCTCCGCCTCCCGGGTTCAAGCAATTCT

CCTGCCTCAGCCACCCTAATAGCTGGGATTACAGGTGCACACCACCATGC

CAGGCTAATTTTTGTACTTTTTGTAGAGGCAGGGTATCACCATGTTGTCC

AAGATGGTCTTGAACTCCTGAGCTCCAAGCAGTCCACCCACCTCAGCCTC

CCAAAGTGCT
```

In certain embodiments, the HS2 region has a length of about 840 bp. In certain embodiments, the HS2 region has a length of about 650 bp (e.g., 646 bp). In certain embodiments, the HS2 region has a length of about 420 bp (e.g., 423 bp).

The length and the sequence of the HS3 region can vary. The HS3 region can have a length of from about 200 bp to about 1400 bp, e.g., from about 200 bp to about 300 bp, from about 300 bp to about 400 bp, from about 400 bp to about 500 bp, from about 500 bp to about 600 bp, from about 600 bp to about 700 bp, from about 700 bp to about 800 bp, from about 800 bp to about 900 bp, from about 900 bp to about 1000 bp, from about 1000 bp to about 1100 bp, from about 1100 bp to about 1200 bp, from about 1200 bp to about 1300 bp, or from about 1300 bp to about 1400 bp. In certain embodiments, the HS3 region has a length of about 1300 bp. In one non-limiting embodiment, the HS3 region has a length of 1308 bp. In one non-limiting embodiment, the HS3 region has a length of 1301 bp. In one non-limiting example, the HS3 region has the nucleotide sequence set forth in SEQ ID NO:5, which is provided below:

```
[SEQ ID NO: 5]
AAGCTTTCATTAAAAAAAGTCTAACCAGCTGCATTCGACTTTGACTGCAG

CAGCTGGTTAGAAGGTTCTACTGGAGGAGGGTCCCAGCCCATTGCTAAAT

TAACATCAGGCTCTGAGACTGGCAGTATATCTCTAACAGTGGTTGATGCT

ATCTTCTGGAACTTGCCTGCTACATTGAGACCACTGACCCATACATAGGA

AGCCCATAGCTCTGTCCTGAACTGTTAGGCCACTGGTCCAGAGAGTGTGC

ATCTCCTTTGATCCTCATAATAACCCTATGAGATAGACACAATTATTACT

CTTACTTTATAGATGATGATCCTGAAAACATAGGAGTCAAGGCACTTGCC

CCTAGCTGGGGTATAGGGGAGCAGTCCCATGTAGTAGTAGAATGAAAAA

TGCTGCTATGCTGTGCCTCCCCCACCTTTCCCATGTCTGCCCTCTACTCA

TGGTCTATCTCTCCTGGCTCCTGGGAGTCATGGACTCCACCCAGCACCAC

CAACCTGACCTAACCACCTATCTGAGCCTGCCAGCCTATAACCCATCTGG

GCCCTGATAGCTGGTGGCCAGCCCTGACCCCACCCCACCCTCCCTGGAAC

CTCTGATAGACACATCTGGCACACCAGCTCGCAAAGTCACCGTGAGGGTC

TTGTGTTTGCTGAGTCAAAATTCCTTGAAATCCAAGTCCTTAGAGACTCC

TGCTCCCAAATTTACAGTCATAGACTTCTTCATGGCTGTCTCCTTTATCC

ACAGAATGATTCCTTTGCTTCATTGCCCCATCCATCTGATCCTCCTCATC
```

-continued

AGTGCAGCACAGGGCCCATGAGCAGTAGCTGCAGAGTCTCACATAGGTCT

GGCACTGCCTCTGACATGTCCGACCTTAGGCAAATGCTTGACTCTTCTGA

GCTCAGTCTTGTCATGGCAAAATAAAGATAATAATAGTGTTTTTTTATGG

AGTTAGCGTGAGGATGGAAAACAATAGCAAAATTGATTAGACTATAAAAG

GTCTCAACAAATAGTAGTAGATTTTATCATCCATTAATCCTTCCCTCTCC

TCTCTTACTCATCCCATCACGTATGCCTCTTAATTTTCCCTTACCTATAA

TAAGAGTTATTCCTCTTATTATATTCTTCTTATAGTGATTCTGGATATTA

AAGTGGGAATGAGGGGCAGGCCACTAACGAAGAAGATGTTTCTCAAAGAA

GCCATTCTCCCCACATAGATCATCTCAGCAGGGTTCAGGAAGATAAAGGA

GGATCAAGGTCGAAGGTAGGAACTAAGGAAGAACACTGGGCAAGTGGATC

C

In certain embodiments, the HS3 region has a length of about 850 bp (e.g., 845 bp). In certain embodiments, the HS3 region has a length of from about 280 bp to about 290 bp (e.g., 280 bp and 287 bp).

Similarly, the length and the sequence of the HS4 region can vary. The HS4 region can have a length of from about 200 bp to about 1200 bp, e.g., from about 200 bp to about 300 bp, from about 300 bp to about 400 bp, from about 400 bp to about 500 bp, from about 500 bp to about 600 bp, from about 600 bp to about 700 bp, from about 700 bp to about 800 bp, from about 800 bp to about 900 bp, from about 900 bp to about 1000 bp, from about 1000 bp to about 1100 bp, or from about 1100 bp to about 1200 bp.

In certain embodiments, the HS4 region has a length of about 1.0 kb or more. In certain embodiments, the HS4 region has a length of about 1.1 kb. In certain embodiments, the HS4 region has a length of about 1150 bp (e.g., 1153 bp). In one non-limiting embodiment, the HS4 region has a length of 1065 bp. In one non-limiting example, the HS4 region has the nucleotide sequence set forth in SEQ ID NO:6, which is provided below:

[SEQ ID NO: 6]
TGAGCCCCTTTTCCTCTAACTGAAAGAAGGAAAAAAAAAATGGAACCCAA

AATATTCTACATAGTTTCCATGTCACAGCCAGGGCTGGGCAGTCTCCTGT

TATTTCTTTTAAAATAAATATATCATTTAAATGCATAAATAAGCAAACCC

TGCTCGGGAATGGGAGGGAGAGTCTCTGGAGTCCACCCCTTCTCGGCCCT

GGCTCTGCAGATAGTGCTATCAAAGCCCTGACAGAGCCCTGCCCATTGCT

GGGCCTTGGAGTGAGTCAGCCTAGTAGAGAGGCAGGGCAAGCCATCTCAT

AGCTGCTGAGTGGGAGAGAGAAAAGGGCTCATTGTCTATAAACTCAGGTC

ATGGCTATTCTTATTCTCACACTAAGAAAAAGAATGAGATGTCTACATAT

ACCCTGCGTCCCTCTTGTGTACTGGGGCCCCAAGAGCTCTCTAAAAGT

GATGGCAAAGTCATTGCGCTAGATGCCATCCCATCTATTATAAACCTGCA

TTTGTCTCCACACACCAGTCATGGACAATAACCCTCCTCCCAGGTCCACG

TGCTTGTCTTTGTATAATACTCAAGTAATTTCGGAAAATGTATTCTTTCA

ATCTTGTTCTGTTATTCCTGTTTCAATGGCTTAGTAGAAAAAGTACATAC

TTGTTTTCCCATAAATTGACAATAGACAATTTCACATCAATGTCTATATG

GGTCGTTGTGTTTGCTGTGTTTGCAAAAACTCACAATAACTTTATATTGT

TACTACTCTAAGAAAGTTACAACATGGTGAATACAAGAGAAAGCTATTAC

AAGTCCAGAAAATAAAAGTTATCATCTTGAGGCCTCAGCTTTCTAGGAAT

AATATCAATATTACAAAATTTAATCTAACAATTATGAACAGCAATGAGAT

AATATGTACAAAGTACCCAGACCTATGTGGTAGAGCATCAAGGAAGCGCA

TTGCGGAGCAGTTTTTGTTTGTTTGTTTTTGTATTCTGTTTCGTGAGGC

AAGGTTTCACTCTGCTGTCCAGGCTGGAGTGCAGTGGCAAGATCATGTCT

CACTGCAGCCTTGAC

In one non-limiting example, the HS4 region has the nucleotide sequence set forth in SEQ ID NO:7, which is provided below:

[SEQ ID NO: 7]
TGAGCCCCTTTTCCTCTAACTGAAAGAAGGAAAAAAAAAATGGAACCCAA

AATATTCTACATAGTTTCCATGTCACAGCCAGGGCTGGGCAGTCTCCTGT

TATTTCTTTTAAAATAAATATATCATTAAATGCATAAATAAGCAAACCCT

GCTCGGGAATGGGAGGGAGAGTCTCTGGAGTCCACCCCTTCTCGGCCCTG

GCTCTGCAGATAGTGCTATCAAAGCCCTGACAGAGCCCTGCCCATTGCTG

GGCCTTGGAGTGAGTCAGCCTAGTAGAGAGGCAGGGCAAGCCATCTCATA

GCTGCTGAGTGGGAGAGAGAAAAGGGCTCATTGTCTATAAACTCAGGTCA

TGGCTATTCTTATTCTCACACTAAGAAAAAGAATGAGATGTCTACATATA

CCCTGCGTCCCTCTTGTGTACTGGGGCCCCAAGAGCTCTCTAAAAGTG

ATGGCAAAGTCATTGCGCTAGATGCCATCCCATCTATTATAAACCTGCAT

TTGTCTCCACACACCAGTCATGGACAATAACCCTCCTCCCAGGTCCACGT

GCTTGTCTTTGTATAATACTCAAGTAATTTCGGAAAATGTATTCTTTCAA

TCTTGTTCTGTTATTCCTGTTTCAATGGCTTAGTAGAAAAAGTACATACT

TGTTTTCCCATAAATTGACAATAGACAATTTCACATCAATGTCTATATGG

GTCGTTGTGTTTGCTGTGTTTGCAAAAACTCACAATAACTTTATATTGTT

ACTACTCTAAGAAAGTTACAACATGGTGAATACAAGAGAAAGCTATTACA

AGTCCAGAAAATAAAAGTTATCATCTTGAGGCCTCAGCTTTCTAGGaATA

ATATCAATATTACAAAATTAATCTAACAATTATGAACAGCAATGAGATAA

TATGTACAAAGTACCCAGACCTATGTGGTAGAGCATCAAGGAAGCGCATT

GCGGAGCAGTTTTTGTTTGTTTGTTTTTGTATTCTGTTTCGTGAGGCAA

GGTTTCACTCTGCTGTCCAGGCTGGAGTGCAGTGGCAAGATCATGTCTCA

CTGCAGCCTTGACAC

In certain embodiments, the HS4 region has a length of less than about 1.0 kb, e.g., less than about 900 bp, less than about 700 bp, less than about 600 bp, or less than about 500 bp. In certain embodiments, the HS4 region has a length of less than about 500 bp. In certain embodiments, the HS4 region has a length of about 450 bp. In one non-limiting embodiment, the HS4 region has a length of about 446 bp. In one non-limiting example, the HS4 region has the nucleotide sequence set forth in SEQ ID NO:8, which is provided below:

[SEQ ID NO: 8]
TGGAACCCAAAATATTCTACATAGTTTCCATGTCACAGCCAGGGCTGGGC

AGTCTCCTGTTATTTCTTTTAAAATAAATATATCATTTAAATGCATAAAT

AAGCAAACCCTGCTCGGGAATGGGAGGGAGAGTCTCTGGAGTCCACCCCT

TCTCGGCCCTGGCTCTGCAGATAGTGCTATCAAAGCCCTGACAGAGCCCT

GCCCATTGCTGGGCCTTGGAGTGAGTCAGCCTAGTAGAGAGGCAGGGCAA

GCCATCTCATAGCTGCTGAGTGGGAGAGAGAAAAGGGCTCATTGTCTATA

AACTCAGGTCATGGCTATTCTTATTCTCACACTAAGAAAAAGAATGAGAT

GTCTACATATACCCTGCGTCCCCTCTTGTGTACTGGGGTCCCCAAGAGCT

CTCTAAAAGTGATGGCAAAGTCATTGCGCTAGATGCCATCCCATCT

In certain embodiments, the HS4 region has a length of about 280 bp (e.g., 283 bp). In certain embodiments, the HS4 region has a length of about 240 bp (e.g., 243 bp).

In certain non-limiting embodiments, the β-globin LCR region comprises a HS2 region having the nucleotide sequence set forth in SEQ ID NO:9, SEQ ID NO:20 or SEQ ID NO:21, a HS3 region having the nucleotide sequence set forth in SEQ ID NO:5, and a HS4 region having the nucleotide sequence set forth in SEQ ID NO:6, SEQ ID NO:7 or SEQ ID NO:8.

In one non-limiting embodiment, the β-globin LCR region comprises a HS2 region having the nucleotide sequence set forth in SEQ ID NO:9, a HS3 region having the nucleotide sequence set forth in SEQ ID NO:5, and a HS4 region having the nucleotide sequence set forth in SEQ ID NO:7, as shown in FIG. 1.

In another non-limiting embodiment, the β-globin LCR region further comprises a HS1 region, i.e., a β-globin LCR region comprising a HS1 region, a HS2 region, a HS3 region, and a HS4 region. In certain embodiments, the HS1 region, HS2 region, HS3 region and HS4 region within the β-globin LCR region are contiguous. In one non-limiting embodiment, the β-globin LCR region consisting essentially of a HS1 region, a HS2 region, a HS3 region and a HS4 region. In another embodiment, the β-globin LCR region comprises two introduced GATA-1 binding sites at the junction between the HS3 region and the HS4 region.

The length and the sequence of the HS1 region can vary. In certain embodiments, the HS1 region is from about 300 bp to about 1500 bp in length, e.g., from about 300 bp to about 1100 bp in length. In certain embodiments, the HS1 region has a length of about 1.0 kb or more, e.g., about 1.1 kb, about 1.2 kb, about 1.3 kb, about 1.4 kb, or about 1.5 kb. In certain embodiments, the HS1 region has a length of about 1.1 kb. In one non-limiting example, the HS1 region has a length of 1074 bp. In one non-limiting example, the HS1 region has the nucleotide sequence set forth in SEQ ID NO:2, which is provided below:

[SEQ ID NO: 2]
AAGTAAACTTCCACAACCGCAAGCTTATTGAGGCTAAGGCATCTGTGAAG

GAAAGAAACATCTCCTCTAAACCACTATGCTGCTAGAGCCTCTTTTCTGT

ACTCAAGCCTCATTCAGACACTAGTGTCACCAGTCTCCTCATATACCTAT

TGTATTTTCTTCTTCTTGCTGGTTTAGTCATGTTTTCTGGGAGCTTAGGG

GCTTATTTTATTTTGTTTTGTTTTCTAATCAACAGAGATGGGCAAACCCA

TTATTTTTTTCTTTAGACTTGGGATGGTGATAGCTGGGCAGCGTCAGAAA

CTGTGTGTGGATATAGATAAGAGCTCGGACTATGCTGAGCTGTGATGAGG

GAGGGACCTAGCCAAAGGCAGTGAGAGTCAGAATGCTCCTGCTATTGCCT

TCTCAGTCCCCACGCTTGGTTTCTACACAAGTAGATACATAGAAAAGGCT

ATAGGTTAGTGTTTGAGAGTCCTGCATGAGTTAGTTGCTCAGAAATGCCC

GATAAATATGTTATGTGTGTTTATGTATATATATGTTTTATATATATATA

TGTGTGTGTGTGTGTGTGTGTGTTGTGTTTACAAATATGTGATTATCA

TCAAAACGTGAGGGCTAAAGTGACCAGATAACTTGCAGGTCCTAGGATAC

CAGGAAAATAAATTACATTCCAAAAATTTAACTGAGACTTTAAAAAAAAA

AAAAAAAAAAAAAAAAAAACCAGTGATCCATGGACACAGGGAGGGAACA

TCACACACTGGGGCCTGTTGGGGGTGGGGGCTAGGGGAAGGATAGCATT

AGGAGAAATACCTAATGTAGATGACGGGTTGATGGGTGCAGCAAACCACC

ATGGCACATGTACCCCAGAACTTAAAGCATATTAAAAAAACAGTGATCAT

AAAAGAAGCTCAAATTTAACTATAAGAGACGGAATGGCTCCCACAATTCT

TAACTATAATCTTACAGAATATTCTCATTGAATAGAAGTATGCTTATCAT

TAGAGATTTGGACAGCCAGGAAAGCACAGAAAAAAAAAAAGGAGCTCTG

TTGCCTTATAGCCTAGAGGTGTTT

In certain embodiments, the HS1 region has a length of less than about 1.0 kb, e.g., from about 400 bp to about 700 bp, from about 400 bp to about 500 bp, from about 500 bp to about 600 bp, from about 600 bp to about 700 bp, from about 700 bp to about 800 bp, from about 800 bp to about 900 bp, or from about 900 bp to about 1.0 kb. In certain embodiments, the HS1 region has a length of less than about 700 bp. In certain embodiments, the HS1 region has a length of about 600 bp. In one non-limiting embodiment, the HS1 region has a length of 602 bp. In one non-limiting example, the HS1 region has the nucleotide sequence set forth in SEQ ID NO:3, which is provided below:

[SEQ ID NO: 3]
GGCATCTGTGAAGGAAAGAAACATCTCCTCTAAACCACTATGCTGCTAGA

GCCTCTTTTCTGTACTCAAGCCTCATTCAGACACTAGTGTCACCAGTCTC

CTCATATACCTATTGTATTTTCTTCTTCTTGCTGGTTTAGTCATGTTTTC

TGGGAGCTTAGGGGCTTATTTTATTTTGTTTTGTTTTCTAATCAACAGAG

ATGGGCAAACCCATTATTTTTTCTTTAGACTTGGGATGGTGATAGCTGG

GCAGCGTCAGAAACTGTGTGTGGATATAGATAAGAGCTCGGACTATGCTG

AGCTGTGATGAGGGAGGGACCTAGCCAAAGGCAGTGAGAGTCAGAATGCT

CCTGCTATTGCCTTCTCAGTCCCCACGCTTGGTTTCTACACAAGTAGATA

CATAGAAAAGGCTATAGGTTAGTGTTTGAGAGTCCTGCATGAGTTAGTTG

CTCAGAAATGCCCGATAAATATGTTATGTGTGTTTATGTATATATATGTT

TTATATATATATATGTGTGTGTGTGTGTGTGTGTGTTGTGTTTACAAA

TATGTGATTATCATCAAAACGTGAGGGCTAAAGTGACCAGATAACTTGCA

GG

In certain embodiments, the HS1 region has a length of less than about 500 bp. In certain embodiments, the HS1 region has a length of about 490 bp. In one non-limiting embodiment, the HS1 region has a length of 489 bp. In one non-limiting example, the HS1 region has the nucleotide sequence set forth in SEQ ID NO:4, which is provided below:

[SEQ ID NO: 4]
GGCATCTGTGAAGGAAAGAAACATCTCCTCTAAACCACTATGCTGCTAGA

GCCTCTTTTCTGTACTCAAGCCTCATTCAGACACTAGTGTCACCAGTCTC

CTCATATACCTATTGTATTTTCTTCTTCTTGCTGGTTTAGTCATGTTTTC

TGGGAGCTTAGGGGCTTATTTTATTTTGTTTTGTTTTCTAATCAACAGAG

ATGGGCAAACCCATTATTTTTTTCTTTAGACTTGGGATGGTGATAGCTGG

GCAGCGTCAGAAACTGTGTGTGGATATAGATAAGAGCTCGGACTATGCTG

AGCTGTGATGAGGGAGGGACCTAGCCAAAGGCAGTGAGAGTCAGAATGCT

CCTGCTATTGCCTTCTCAGTCCCCACGCTTGGTTTCTACACAAGTAGATA

CATAGAAAAGGCTATAGGTTAGTGTTTGAGAGTCCTGCATGAGTTAGTTG

CTCAGAAATGCCCGATAAATATGTTATGTGTGTTTATGT

Recent studies have shown that HS2 is not erythroid-specific, but is expressed in other cell lines and lineages (See Example 3 and FIG. 7) and is also present in undifferentiated human embryonic stem cells (Chang et al., *Stem cell reviews* (2013); 9:397-407). Due to the non-erythroid activity of HS2, HS2-containing globin vectors may pose a risk for their safe use in clinical treatment, e.g., for treating thalassemia and sickle cell patients. In certain embodiments, the β-globin LCR region does not comprise a HS2 region. In certain embodiments, the β-globin LCR region does not comprise a core sequence of HS2. A core sequence of HS2 provides position independent, high level expression. In addition, a core sequence of HS2 sustains the enhancer activity of HS2. For example, the core sequence of HS2 enhances the transcription of a globin gene (e.g., human β-globin gene). Additionally, a core sequence of HS2 comprises one or more binding sites or binding motifs for ubiquitous as well as tissue-specific (e.g., erythroid-specific) proteins (e.g., transcription factors), including, but not limited to, members of AP1 family of proteins (e.g., NF-E2), GATA-1 (also known as "NF-E1" or "NFE1"), Krüppel-like Zn finger proteins (e.g., ubiquitous proteins Sp1 and YY1, and erythroid-restricted factor erythroid Krüppel-like factor (EKLF)), and basic helix-loop-helix (bHLH) proteins (E boxes) (e.g., USF and TAL1). AP1 binding sites are required for enhancement and induction (Moi and Kan (1990); Ney et al., (1990); Talbot and Grosveld (1991)). Furthermore, binding of NF-E2 can cause disruption of in vitro reconstituted chromatin at HS2 (Armstrong and Emerson (1996)). Mutations in the GATA-1 binding sites can cause a reduction in enhancer activity of HS2 in transgenic mice (Caterina et al., (1994)). Although both AP1 (e.g., AP1/NF-E2) and GATA1 binding sites are important for core function, mice lacking these factors do not show impaired globin gene expression (Weiss et al., 1994).

In certain embodiments, the β-globin LCR region does not comprise the full length of a core sequence of HS2. In certain embodiments, the core sequence of a HS2 region is a core sequence of human HS2. In one non-limiting embodiment, the core sequence of human HS2 comprises a tandem pair of binding sites for members of AP1 family of proteins (e.g., NF-E2) (referred to as "AP1/NF-E2" binding sites) (e.g., GCTGAGTCA, and GATGAGTCA), one binding site for Kruppel-like Zn finger proteins (e.g., AGGGTGTGT), one GATA-1 binding site (e.g., CTATCT), and three E boxes (CANNTG, e.g., CAGATG, and CACCTG). In one non-limiting embodiment, the β-globin LCR region does not comprise the full length of a 388 bp core sequence of human HS2, which has the nucleotide sequence set forth in SEQ ID NO:20 provided below:

[SEQ ID NO: 20]
TAAGCTTCAGTTTTTCCTTAGTTCCTGTTACATTTCTGTGTGTCTCCATT

AGTGACCTCCCATAGTCCAAGCATGAGCAGTTCTGGCCAGGCCCCTGTCG

GGGTCAGTGCCCCACCCCCGCCTTCTGGTTCTGTGTAACCTTCTAAGCAA

ACCTTCTGGCTCAAGCACAGCAATGCTGAGTCATGATGAGTCATGCTGAG

GCTTAGGGTGTGTGCCCAGATGTTCTCAGCCTAGAGTGATGACTCCTATC

TGGGTCCCCAGCAGGATGCTTACAGGGCAGATGGCAAAAAAAAGGAGAAG

CTGACCACCTGACTAAAACTCCACCTCAAACGGCATCATAAAGAAAATGG

ATGCCTGAGACAGAATGTGACATATTCTAGAATATATT

The nucleotide sequence set forth in SEQ ID NO:20 corresponds to nucleotides position 16671 to position 17058 of SEQ ID NO:19 (GenBank Access No.: NG 000007.3). In SEQ ID NO:20, one AP1/NF-E2 binding site having the nucleotide sequence of GCTGAGTCA is located at position 175 to position 183, one AP1/NF-E2 binding site having the nucleotide sequence of GATGAGTCA is located at position 185 to position 193, one binding site for Kruppel-like Zn finger proteins having the nucleotide sequence of AGGGTGTGT is located as position 205 to position 213, two E boxes, each of which have the nucleotide sequence of CAGATG, is located at position 217 to position 222, and position 278 to position 283, one GATA-1 binding site having the nucleotide sequence of CTATCT is located at position 246 to position 251, one E box having the nucleotide sequence of CACCTG is located at position 306 to position 311.

In one non-limiting embodiment, the β-globin LCR region does not comprise the full length of a 387 bp core sequence of human HS2, which has the nucleotide sequence set forth in SEQ ID NO:21 provided below:

[SEQ ID NO: 21]
TAAGCTTCAGTTTTTCCTTAGTTCCTGTTACATTTCTGTGTGTCTCCATT

AGTGACCTCCCATAGTCCAAGCATGAGCAGTTCTGGCCAGGCCCCTGTCG

GGGTCAGTGCCCCACCCCCGCCTTCTGGTTCTGTGTAACCTTCTAAGCAA

ACCTTCTGGCTCAAGCACAGCAATGCTGAGTCATGATGAGTCATGCTGAG

GCTAGGGTGTGTGCCCAGATGTTCTCAGCCTAGAGTGATGACTCCTATCT

GGGTCCCCAGCAGGATGCTTACAGGGCAGATGGCAAAAAAAAGGAGAAGC

TGACCACCTGACTAAAACTCCACCTCAAACGGCATCATAAAGAAAATGGA

TGCCTGAGACAGAATGTGACATATTCTAGAATATATT

In SEQ ID NO:21, one AP1/NF-E2 binding site having the nucleotide sequence of GCTGAGTCA is located at position 175 to position 183, one AP1/NF-E2 binding site having the nucleotide sequence of GATGAGTCA is located at position 185 to position 193, one binding site for Kruppel-like Zn finger proteins having the nucleotide sequence of AGGGTGTGT is located as position 204 to position 212, two E boxes, each of which have the nucleotide sequence of CAGATG, is located at position 216 to position 221, and position 277 to position 282, one GATA-1 binding site having the nucleotide sequence of CTATCT is located at position 245 to position 250, one E box having the nucleotide sequence of CACCTG is located at position 305 to position 310.

In certain embodiments, the β-globin LCR region does not comprise a HS2 region that comprises a core sequence of HS2. A HS2 region that comprises a core sequence of HS2 can vary in length and sequence. In non-limiting examples, a HS2 region that comprises a core sequence of HS2 is from about 400 bp to about 1000 bp, e.g., from about 400 bp to about 500 bp, from about 500 bp to about 600 bp, from about 600 bp to about 700 bp, from about 700 bp to about 800 bp, from about 800 bp to about 900 bp, or from about 900 bp to about 1000 bp, in length. In one non-limiting embodiment, the β-globin LCR region does not comprise a 840 bp HS2 region (e.g., the HS2 region comprised in the globin vector TNS9 disclosed in U.S. Pat. No. 7,541,179). In one non-limiting embodiment, the β-globin LCR region does not comprise a 860 bp HS2 region. In one non-limiting embodiment, the β-globin LCR region does not comprise an about 650 bp HS2 region. In one non-limiting example, the β-globin LCR region does not comprise a 646 bp HS2 region (e.g., the HS2 region comprised in the globin vector Lenti-Globin™, also known as "β$^{87}$"). In one non-limiting embodiment, the β-globin LCR region does not comprise an about 420 bp HS2 region. In one non-limiting example, the β-globin LCR region does not comprise a 423 bp HS2 region (e.g., the HS2 region comprised in the globin vector disclosed in Sadelain et al., *Proc. Nat'l Acad. Sci.* (USA) (1995); 92:6728-6732).

In certain embodiments, the β-globin LCR region does not comprise a HS2 region that sustains the enhancer activity of HS2. In certain embodiments, the β-globin LCR region does not comprise a HS2 region that is capable of enhancing the transcription of a globin gene (e.g., human β-globin gene). In non-limiting examples, the β-globin LCR region does not comprise a HS2 region whose ability to enhance the transcription of a globin gene (e.g., human β-globin gene) is no less than 60%, no less than 70%, no less than 80%, no less than 90%, or no less than 95% in comparison to a native HS2 region.

In certain embodiments, the β-globin LCR region does not comprise a HS2 region that comprises one, two, three, four, five, six or seven of the following binding sites: two (a tandem pair of) AP1/NF-E2 binding sites (e.g., GCTGAGTCA, and GATGAGTCA), one binding site for Kruppel-like Zn finger proteins (e.g., AGGGTGTGT), one GATA-1 binding site (e.g., CTATCT), and three E boxes (CANNTG, e.g., CAGATG, and CACCTG). In certain embodiments, the β-globin LCR region does not comprise a HS2 region that comprises six of the above-described binding sites. For example, in certain embodiments, the β-globin LCR region does not comprise a HS2 region that comprises two AP1/NF-E2 binding sites, one binding site for Kruppel-like Zn finger proteins, one GATA-1 binding site, and two not three E boxes. In certain embodiments, the β-globin LCR region does not comprise a HS2 region that comprises one not two AP1/NF-E2 binding site, one binding site for Kruppel-like Zn finger proteins, one GATA-1 binding site, and three E boxes. In certain embodiments, the β-globin LCR region does not comprise a HS2 region that comprises two AP1/NF-E2 binding sites, one GATA-1 binding site, and three E boxes and does not comprise one binding site for Kruppel-like Zn finger proteins. In certain embodiments, the β-globin LCR region does not comprise a HS2 region that comprises two AP1/NF-E2 binding sites, one binding site for Kruppel-like Zn finger proteins, and three E boxes, and does not comprise one GATA-1 binding site.

In certain embodiments, the β-globin LCR region comprises a HS1 region, a HS3 region, and a HS4 region, and does not comprise a HS2 region. In certain embodiments, the HS1 region, HS3 region and HS4 region within the β-globin LCR region are contiguous. In one non-limiting embodiment, the β-globin LCR region consisting essentially of a HS1 region, a HS3 region and a HS4 region. In another embodiment, the β-globin LCR region comprises two introduced GATA-1 binding sites at the junction between the HS3 region and the HS4 region. The HS3 region can lie between the HS1 region and the HS4 region.

In certain non-limiting embodiments, the β-globin LCR region comprises a HS1 region having the nucleotide sequence set forth in SEQ ID NO:2, SEQ ID NO:3, SEQ ID NO:4, SEQ ID NO:22 or SEQ ID NO:23, a HS3 region having the nucleotide sequence set forth in SEQ ID NO:5, and a HS4 region having the nucleotide sequence set forth in SEQ ID NO:6, SEQ ID NO:7 or SEQ ID NO:8, and the β-globin LCR region does not comprise a HS2 region.

Figure 2:
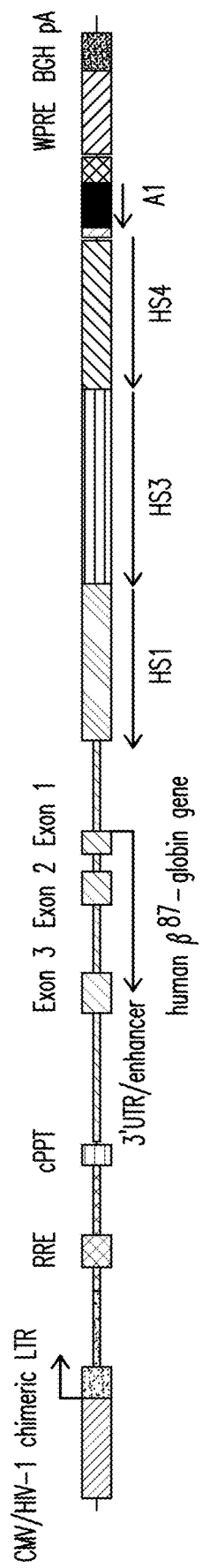
FIG. 2 depicts a recombinant vector an expression cassette in accordance with one non-limiting embodiment of the presently disclosed subject matter.

In one non-limiting embodiment, the β-globin LCR region comprises a HS1 region having the nucleotide sequence set forth in SEQ ID NO:2, a HS3 region having the nucleotide sequence set forth in SEQ ID NO:5, and a HS4 region having the nucleotide sequence set forth in SEQ ID NO:6, and the β-globin LCR region does not comprise a HS2 region, as shown in FIG. 2.

Figure 3:
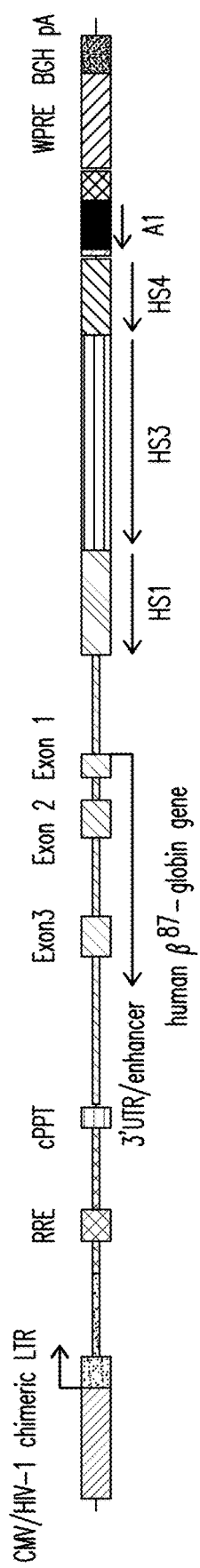
FIG. 3 depicts a recombinant vector an expression cassette in accordance with one non-limiting embodiment of the presently disclosed subject matter.

In one non-limiting embodiment, the β-globin LCR region comprises a HS1 region having the nucleotide sequence set forth in SEQ ID NO:3, a HS3 region having the nucleotide sequence set forth in SEQ ID NO:5, and a HS4 region having the nucleotide sequence set forth in SEQ ID NO:8, and the β-globin LCR region does not comprise a HS2 region, as shown in FIG. 3.

In one non-limiting embodiment, the β-globin LCR region comprises a HS1 region having the nucleotide sequence set forth in SEQ ID NO:4, a HS3 region having the nucleotide sequence set forth in SEQ ID NO:5, and a HS4 region having the nucleotide sequence set forth in SEQ ID NO:8, and the β-globin LCR region does not comprise a HS2 region.

In certain embodiments, the β-globin LCR region does not comprise a HS1 region or a HS2 region. In certain embodiments, the β-globin LCR region does not comprise a core sequence of HS1. A core sequence of HS1 sustains the activity of HS1, e.g., enhancer activity, or functioning as a facilitator or regulatory element to tether the enhancer activity of other HS regions, e.g., HS2-4. In addition, a core sequence of HS1 comprises one or more binding sites or binding motifs for ubiquitous as well as tissue-specific (e.g., erythroid-specific) proteins (e.g., transcription factors), including, but not limited to, GATA-1, and Kruppel-like Zn finger proteins (e.g., erythroid-restricted factor EKLF).

In certain embodiments, the β-globin LCR region does not comprise the full length of a core sequence of HS1. In certain embodiments, the core sequence of a HS1 region is a core sequence of human HS1. In one non-limiting embodiment, the core sequence of human HS1 comprises two GATA-1 binding sites (e.g., TTATCT, and CTATCA), and one binding site for EKLF (e.g., CCACACACA). In certain embodiments, the β-globin LCR region does not comprise the full length of a 286 bp core sequence of human HS1. In one non-limiting embodiment, the 286 bp core sequence of human HS1 has the nucleotide sequence set forth in SEQ ID NO:22 provided below:

[SEQ ID NO: 22]
```
CTGAGCAACTAACTCATGCAGGACTCTCAAACACTAACCTATAGCCTTTT

CTATGTATCTACTTGTGTAGAAACCAAGCGTGGGGACTGAGAAGGCAATA

GCAGGAGCATTCTGACTCTCACTGCCTTTGGCTAGGTCCCTCCCTCATCA

CAGCTCAGCATAGTCCGAGCTCTTATCTATATCCACACACAGTTTCTGAC

GCTGCCCAGCTATCACCATCCCAAGTCTAAAGAAAAAAATAATGGGTTTG

CCCATCTCTGTTGATTAGAAAACAAAACAAAATAAA
```

In SEQ ID NO:22, one GATA-1 binding site having the nucleotide sequence of TTATCT is located at position 173 to position 178, one GATA-1 binding site having the nucleotide sequence of CTATCA located at position 210 to position 215, and one binding site for EKLF having the nucleotide sequence of CCACACACA is located at position 183 to position 191.

In another non-limiting embodiment, the 286 bp core sequence of human HS1 has the nucleotide sequence set forth in SEQ ID NO:23 provided below:

[SEQ ID NO: 23]
```
CTGAGCAACTAATCATGCAGGACTCTCAAACACTAACCTATAGCCTTTTC

TATGTATCTACTTGTGTAGAAACCAAGCGTGGGGACTGAGAAGGCAATAG

CAGGAGCATTCTGACTCTCACTGCCTTTAGCTAGGCCCCTCCCTCATCAC

AGCTCAGCATAGTCCTGAGCTCTTATCTATATCCACACACAGTTTCTGAC

GCTGCCCAGCTATCACCATCCCAAGTCTAAAGAAAAAAATAATGGGTTTG

CCCATCTCTGTTGATTAGAAAACAAAACAAAATAAA
```

The nucleotide sequence set forth in SEQ ID NO:23 corresponds to nucleotides position 21481 to position 21766 of SEQ ID NO:19 (GenBank Access No.: NG_000007.3). In SEQ ID NO:23, one GATA-1 binding site having the nucleotide sequence of TTATCT is located at position 173 to position 178, one GATA-1 binding site having the nucleotide sequence of CTATCA located at position 210 to position 215, and one binding site for EKLF having the nucleotide sequence of CCACACACA is located at position 183 to position 191.

In certain embodiments, the β-globin LCR region does not comprise a HS1 region that comprises a core sequence of HS1. A HS1 region that comprises a core sequence of HS1 can vary in length and sequence. In non-limiting examples, a HS1 region that comprises a core sequence of HS1 is from about 300 bp to about 1200 bp, e.g., from about 300 bp to about 400 bp, from about 400 bp to about 500 bp, from about 500 bp to about 600 bp, from about 600 bp to about 700 bp, from about 700 bp to about 800 bp, from about 800 bp to about 900 bp, from about 900 bp to about 1000 bp, from about 1000 bp to about 1100 bp, or from about 1100 bp to about 1200 bp, in length. In one non-limiting embodiment, the β-globin LCR region does not comprise an about 1.0 kb bp HS1 region. In one non-limiting embodiment, the β-globin LCR region does not comprise an about 1.1 kb HS1 region.

In certain embodiments, the β-globin LCR region does not comprise a HS1 region that sustains the activity of HS1, e.g., enhancer activity, or functioning as a facilitator or regulatory element to tether the enhancer activity of other HS regions, e.g., HS2-4. In certain embodiments, the β-globin LCR region does not comprise a HS1 region that is capable of enhancing the transcription of a globin gene (e.g., human β-globin gene). In non-limiting examples, the β-globin LCR region does not comprise a HS1 region whose ability to enhance the transcription of a globin gene (e.g., human β-globin gene) is no less than 60%, no less than 70%, no less than 80%, no less than 90%, or no less than 95% in comparison to a native HS1 region. In non-limiting examples, the β-globin LCR region does not comprise a HS1 region whose ability to tether the enhancer activity of one or more of HS2-HS4 is no less than 60%, no less than 70%, no less than 80%, no less than 90%, or no less than 95% in comparison to a native HS1 region.

In certain embodiments, the β-globin LCR region does not comprise a HS1 region that comprises one, two, or three of the following binding sites: two GATA-1 binding sites (e.g., TTATCT, and CTATCA), and one binding site for EKLF (e.g., CCACACACA). In certain embodiments, the β-globin LCR region does not comprise a HS1 region that comprises two of the above-described binding sites. For example, in certain embodiments, the β-globin LCR region does not comprise a HS1 region that comprises two GATA-1 binding sites and does not comprise one binding site for EKLF. In certain embodiments, the β-globin LCR region does not comprise a HS1 region that comprises one not two AP1/NF-E2 binding site and one binding site for EKLF.

In certain embodiments, the β-globin LCR region comprises a HS3 region and a HS4 region, and the β-globin LCR region does not comprise a HS1 region or a HS2 region. In certain embodiments, the HS3 region and HS4 region within the β-globin LCR region are contiguous. In one non-limiting embodiment, the β-globin LCR region consisting essentially of a HS3 region and a HS4 region. In another embodiment, the β-globin LCR region comprises two introduced GATA-1 binding sites at the junction between the HS3 region and the HS4 region. The HS3 region can lie between the globin gene or functional portion thereof and the HS4 region.

In certain embodiments, the β-globin LCR region comprises a HS3 region having the nucleotide sequence set forth in SEQ ID NO:5 and a HS4 region having the nucleotide sequence set forth in SEQ ID NO:6, SEQ ID NO:7 or SEQ ID NO:8, and the β-globin LCR region does not comprise a HS1 region or a HS2 region.

Figure 4:
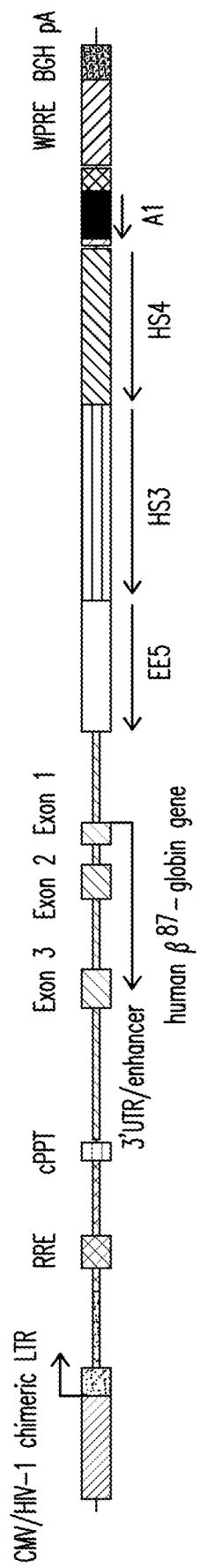
FIG. 4 depicts a recombinant vector an expression cassette in accordance with one non-limiting embodiment of the presently disclosed subject matter.

In one non-limiting embodiment, the β-globin LCR region comprises a HS3 region having the nucleotide sequence set forth in SEQ ID NO:5 and a HS4 region having the nucleotide sequence set forth in SEQ ID NO:6, and the β-globin LCR region does not comprise a HS1 region or a HS2 region, as shown in FIG. 4.

Globin Gene

In accordance with the presently disclosed subject matter, the expression cassette comprises a globin gene or a functional portion thereof. The globin gene can be a β-globin gene, a γ-globin gene, or a δ-globin gene. In certain embodiments, the expression cassette comprises a human β-globin gene. In accordance with the presently disclosed subject matter, the human β-globin gene can be a wild-type human β-globin gene, a deleted human β-globin gene comprising one or more deletions of intron sequences, or a mutated human β-globin gene encoding at least one anti-sickling amino acid residue. In one non-limiting embodiment, a presently disclosed expression cassette comprises a wild-type human β-globin gene. In another embodiment, the a presently disclosed expression cassette comprises a human $β^A$-globin gene encoding a threonine to glutamine mutation at codon 87 ($β^{A-T87Q}$). The glutamine residue at position 87 in the gamma-globin chain augments the anti-sickling activity of the gamma chain relative to the beta chain, while preserving adult oxygen-binding characteristics of the beta chain (Nagel et al., Proc. Natl. Acad. Sci. U.S.A. (1979); 76:670-672). In certain embodiments, a functional portion of a globin gene has at least 80%, at least 90%, at least 95%, or at least 99% identity to a corresponding wild-type reference polynucleotide sequence.

Promoters and Enhancers

In accordance with the presently disclosed subject matter, the expression cassette can further comprise a β-globin promoter. In certain embodiments, the β-globin promoter is positioned between the globin gene or functional portion thereof and the β-globin LCR region. The length and the sequence of the β-globin promoter can vary. In certain embodiments, the β-globin promoter is from about 100 bp to about 1600 bp in length, e.g., from about 200 bp to about 700 bp, from about 100 bp to about 200 bp, from about 200 bp to about 300 bp, from about 300 bp to about 400 bp, from about 400 bp to about 500 bp, from about 500 bp to about 600 bp, from about 600 bp to about 700 bp, from about 700 bp to about 800 bp, from about 800 bp to about 900 bp, from about 900 bp to about 1000 bp, from about 1000 bp to about 1100 bp, from about 1100 bp to about 1200 bp, from about 1200 bp to about 1300 bp, from about 1300 bp to about 1400 bp, from about 1400 bp to about 1500 bp, or from about 1500 bp to about 1600 bp in length. In certain embodiments, the β-globin promoter a human β-globin promoter that is about 130 bp, about 613 bp, about 265 bp, or about 1555 bp, in length. In one embodiment, the β-globin promoter is a human β-globin promoter that is about 613 bp in length. In one non-limiting example, the human β-globin promoter has the nucleotide sequence set forth in SEQ ID NO:10, which is provided below:

[SEQ ID NO: 10]
AAGCAATAGATGGCTCTGCCCTGACTTTTATGCCCAGCCCTGGCTCCTGC

CCTCCCTGCTCCTGGGAGTAGATTGGCCAACCCTAGGGTGTGGCTCCACA

GGGTGAGGTCTAAGTGATGACAGCCGTACCTGTCCTTGGCTCTTCTGGCA

CTGGCTTAGGAGTTGGACTTCAAACCCTCAGCCCTCCCTCTAAGATATAT

CTCTTGGCCCCATACCATCAGTACAAATTGCTACTAAAAACATCCTCCTT

TGCAAGTGTATTTACGTAATATTTGGAATCACAGCTTGGTAAGCATATTG

AAGATCGTTTTCCCAATTTTCTTATTACACAAATAAGAAATTGATGCACT

AAAAGTGGAAGAGTTTTGTCTACCATAATTCAGCTTTGGGATATGTAGAT

GGATCTCTTCCTGCGTCTCCAGAATATGCAAAATACTTACAGGACAGAAT

GGATGAAAACTCTACCTCAGTTCTAAGCATATCTTCTCCTTATTTGGATT

AAAACCTTCTGGTAAGAAAAGAAAAAAAATATATATATATATGTGTATAT

ATACACACATACATATACATATATATGCATTCATTTGTTGTTGTTTTCT

TAATTTGCTCATG

In one embodiment, the β-globin promoter is a human β-globin promoter that is about 265 bp in length. In one non-limiting example, the human β-globin promoter has the nucleotide sequence set forth in SEQ ID NO:11.

[SEQ ID NO: 11]
AAGCAATAGATGGCTCTGCCCTGACTTTTATGCCCAGCCCTGGCTCCTGC

CCTCCCTGCTCCTGGGAGTAGATTGGCCAACCCTAGGGTGTGGCTCCACA

GGGTGAGGTCTAAGTGATGACAGCCGTACCTGTCCTTGGCTCTTCTGGCA

-continued
CTGGCTTAGGAGTTGGACTTCAAACCCTCAGCCCTCCCTCTAAGATATAT

CTCTTGGCCCCATACCATCAGTACAAATTGCTACTAAAAACATCCTCCTT

TGCAAGTGTATTTAC

Additionally or alternatively, a presently disclosed expression cassette can further comprise a human β-globin 3' enhancer. In certain embodiments, the human β-globin 3' enhancer is positioned in the upstream of the globin gene or functional portion thereof. In certain embodiments, the β-globin 3' enhancer is from about 500 bp to about 1000 bp in length, e.g., from about 500 bp to about 600 bp, from about 600 bp to about 700 bp, from about 700 bp to about 800 bp, or from about 800 bp to about 900 bp in length. In one embodiment, the human β-globin 3' enhancer is about 879 bp in length. In one example, the human β-globin 3' enhancer has the nucleotide sequence set forth in SEQ ID NO:12.

[SEQ ID NO: 12]
TAGGTATTGAATAAGAAAAATGAAGTTAAGGTGGTTGATGGTAACACTAT

GCTAATAACTGCAGAGCCAGAAGCACCATAAGGGACATGATAAGGGAGCC

AGCAGACCTCTGATCTCTTCCTGAATGCTAATCTTAAACATCCTGAGGAA

GAATGGGACTTCCATTTGGGGTGGGCCTATGATAGGGTAATAAGACAGTA

GTGAATATCAAGCTACAAAAAGCCCCCTTTCAAATTCTTCTCAGTCCTAA

CTTTTCATACTAAGCCCAGTCCTTCCAAAGCAGACTGTGAAAGAGTGATA

GTTCCGGGAGACTAGCACTGCAGATTCCGGGTCACTGTGAGTGGGGGAGG

CAGGGAAGAAGGGCTCACAGGACAGTCAAACCATGCCCCCTGTTTTCCT

TCTTCAAGTAGACCTCTATAAGACAACAGAGACAACTAAGGCTGAGTGGC

CAGGCGAGGAGAAACCATCTCGCCGTAAAACATGGAAGGAACACTTCAGG

GGAAAGGTGGTATCTCTAAGCAAGAGAACTGAGTGGAGTCAAGGCTGAGA

GATGCAGGATAAGCAAATGGGTAGTGAAAAGACATTCATGAGGACAGCTA

AAACAATAAGTAATGTAAAATACAGCATAGCAAAACTTTAACCTCCAAAT

CAAGCCTCTACTTGAATCCTTTTCTGAGGGATGAATAAGGCATAGGCATC

AGGGGCTGTTGCCAATGTGCATTAGCTGTTTGCAGCCTCACCTTCTTTCA

TGGAGTTTAAGATATAGTGTATTTTCCCAAGGTTTGAACTAGCTCTTCAT

TTCTTTATGTTTTAAATGCACTGACCTCCCACATTCCCTTTTTAGTAAAA

TATTCAGAAATAATTTAAATACATCATTG

Furthermore, a presently disclosed expression cassette can further comprise at least one erythroid-specific enhancer. The presently disclosed expression cassette allows for expression of a globin gene (e.g., human β-globin gene) in erythroid-specific fashion. The erythroid-specific enhancer can enhance the expression of the globin gene in erythroid-specific fashion. For example, the erythroid-specific enhancer lack enhancer activity in non-erythroid tissues. In particularly, for the β-globin LCR region that lacks a HS2 region, which primarily functions as an expression enhancer, the addition of one or more erythroid-specific enhancers can compensate the enhancing activity of a HS2 region. Furthermore, the presently disclosed erythroid-specific enhancers do not decrease or reduce the titer of a vector comprising the expression cassette. The length of the erythroid-specific enhancer can vary, e.g., from about 100 bp to about 200 bp, from about 100 bp to about 120 bp, from about 120 bp to about 140 bp, from about 140 bp to about 200 (e.g., from about 140 bp to about 150 bp, from about 150 bp to about 160 bp, from about 160 bp to about 170 bp, from about 170 bp to about 180 bp, from about 180 bp to about 190 bp, or from about 190 bp to about 200 bp). In certain embodiments, the erythroid-specific enhancer has a length of from about 140 bp to about 200 bp. In one non-limiting embodiment, the erythroid-specific enhancer has a length of 152 bp, which has the nucleotide sequence set forth in SEQ ID NO:13, which is provided below:

[SEQ ID NO: 13]
TCTCCCACGCCCTGGTCTCAGCTTGGGGAGTGGTCAGACCCCAATGGCGA

TAAACTCTGGCAACTTTATCTGTGcaCTGCAGGCTCAGCCCCAAcaGCTT

TAGCTTTCACAAGCAGGCAGGGGAAGGGAAACACATATCTCCAGATATGA

GG

In one non-limiting embodiment, the erythroid-specific enhancer has a length of 157 bp, which has the nucleotide sequence set forth in SEQ ID NO:14, which is provided below:

[SEQ ID NO: 14]
CTAAACCCCTCCCCCACCCTAGCCCCAAGCTTCATCTTAGCTCCACTCCT

GACCCTATCCAGCTAAAGGTCCCCACCCAGCTCCTGCCTATCTAGTCATT

GCATATGGCAAGACTTGAAAGTCCTATCTCAAAGCAGCAGAATTATCAGC

TACGACT

In one non-limiting embodiment, the erythroid-specific enhancer has a length of 141 bp, which has the nucleotide sequence set forth in SEQ ID NO:15, which is provided below:

[SEQ ID NO: 15]
CCATCCCCAGCACTCCCTGCCCCCACAGCCCAGACTTGACCAACTCCCA

GCTCcGCCTGGGACTTCCAGATATGGGGCCCCACCCTTGCAGGCCTTGGG

GACGCTGAAGATATTGACTATCTGCGTGCCggAAAAGGGTG

In one non-limiting embodiment, the erythroid-specific enhancer has a length of 171 bp, which has the nucleotide sequence set forth in SEQ ID NO:16, which is provided below:

[SEQ ID NO: 16]
AAAGGCTGGGGGTGGGAGTAGCGGATTTGAAGCACTTGTTGGCCTACAGA

GGTGTGGCAAGCAGAGCACCTCAGAACTCAGGCGTACTGCCCGCCGCCCG

AGCCCTGCGAGGGCCGATAGCGAGGGTGTGGCCCTTATCTGCACCCAGCA

GAGCGCCGGCGGGGTACGGTC

In one non-limiting embodiment, the erythroid-specific enhancer has a length of 195 bp, which has the nucleotide effluence set forth in SRO TD NO. 17 which is provided below:

[SEQ ID NO: 17]
CAGTTGCCTCAGCTGAGTATGTCTTCTAAAGATAATGTCGATTGTGTATG

GCTGATGGGATTCTAGGACCAAGCAAGAGGTTTTTTTTTTCCCCCACAT

ACTTAACGTTTCTATATTTCTATTTGAATTCGACTGGACAGTTCCATTTG

AATTATTTCTCTCTCTCTCTCTCTGACACATTTTATCTTGCCA

Erythroid-specific enhancers can be identified and determined by any suitable methods known in the art. The erythroid-specific enhancers can be positioned at the 3' LTR (downstream) or the 5' LTR (downstream) of the β-globin LCR region. In one embodiment, the at least one erythroid-specific enhancer is positioned in the 5' LTR of the β-globin LCR region, e.g., the upstream of the HS3 region. The expression cassette can comprise one, two, three, four, or five erythroid-specific enhancers. In one embodiment, the expression cassette comprises one erythroid-specific enhancer. In another embodiment, the expression cassette comprises two erythroid-specific enhancers. In yet another embodiment, the expression cassette comprises three erythroid-specific enhancers. In certain embodiments, the expression cassette comprises four erythroid-specific enhancers. In a non-limiting embodiment, the expression cassette comprises five erythroid-specific enhancers.

Insulators

In accordance with the presently disclosed subject matter, the expression cassette comprises at least one of the above-described insulators. In certain embodiments, a presently disclosed expression cassette comprises at least one insulator comprising the CTCF binding site sequence set forth in SEQ ID NO:18, for example, but not limited to, an insulator comprising SEQ ID NO: 24 or SEQ ID NO:25, such as an insulator having the nucleotide sequence set forth in SEQ ID NO:1 (i.e., insulator A1). In various non-limiting embodiments, the insulator can be incorporated or inserted into one or both LTRs or elsewhere in the region of a presently disclosed expression cassette that integrates into the cellular genome. In one embodiment, the insulator is positioned at the 3' end of the expression cassette. In one embodiment, the insulator is positioned at the 5' end of the expression cassette. In one embodiment, the expression cassette comprises two of the insulator having the nucleotide sequence set forth in SEQ ID NO:1, where one insulator is positioned at the 3' end and the other insulator is positioned at the 5' end of the expression cassette.

The presently disclosed insulators possess powerful enhancer blocking activity. In certain embodiments, the insulators possess barrier activity in addition to enhancer blocking activity. The presently disclosed insulators substantially decrease the risks of insertional mutagenesis and genotoxicity associated with viral vectors. Furthermore, when a presently disclosed insulator is incorporated into a vector, the insulator does not adversely effect vector titers of the vector. In certain embodiments, the insulators (e.g., insulator A1) increase the in vivo expression of the globin gene or functional portion thereof. For the purpose of illustration and not limitation, FIGS. 1-4 show recombinant vectors comprising exemplary expression cassettes in accordance with certain embodiments of the presently disclosed subject matter. FIG. 1 shows a recombinant vector comprising a presently disclosed expression cassette that comprises a human $β^{A-T87Q}$ globin gene, which is operably linked to a β-globin LCR region that comprises a 860 bp HS2 region (e.g., one having the nucleotide sequence set forth in SEQ ID NO:9), a 1301 bp HS3 region (e.g., one having the nucleotide sequence set forth in SEQ ID NO:5), and a 1065 bp HS4 region (e.g., one having the nucleotide sequence set forth in SEQ ID NO:7).

FIG. 2 shows one exemplary recombinant vector comprising an expression cassette in accordance with one embodiment of the presently disclosed subject matter. FIG. 2 shows a recombinant vector comprising a presently disclosed expression cassette that comprises a human $β^{A-T87Q}$ globin gene, which is operably linked to a β-globin LCR region that comprises a 1.1 kb HS1 region (e.g., one having the nucleotide sequence set forth in SEQ ID NO:2), a 1301 bp HS3 region (e.g., one having the nucleotide sequence set forth in SEQ ID NO:5), and a 1065 bp HS4 region (e.g., one having the nucleotide sequence set forth in SEQ ID NO:6).

FIG. 3 shows one exemplary recombinant vector comprising an expression cassette in accordance with one embodiment of the presently disclosed subject matter. FIG. 3 shows a recombinant vector comprising a presently disclosed expression cassette that comprises a human $\beta^{A-T87Q}$ globin gene, which is operably linked to a β-globin LCR region that comprises a 602 bp HS1 region (e.g., one having the nucleotide sequence set forth in SEQ ID NO:3), a 1301 bp HS3 region (e.g., one having the nucleotide sequence set forth in SEQ ID NO:5), and a 446 bp HS4 region (e.g., one having the nucleotide sequence set forth in SEQ ID NO:8).

FIG. 4 shows one exemplary recombinant vector comprising an expression cassette in accordance with one embodiment of the presently disclosed subject matter. FIG. 4 shows a recombinant vector comprising a presently disclosed expression cassette that comprises a human $\beta^{A-T87Q}$ globin gene, which is operably linked to a β-globin LCR region that comprises a 1301 bp HS3 region (e.g., one having the nucleotide sequence set forth in SEQ ID NO:5), and a 1065 bp HS4 region (e.g., one having the nucleotide sequence set forth in SEQ ID NO:6). The expression cassette shown in FIG. 4 also comprises the following five erythroid-specific enhancers (shown as "EE5" in FIG. 4): one erythroid-specific enhancer having the nucleotide sequence set forth in SEQ ID NO:13, one erythroid-specific enhancer having the nucleotide sequence set forth in SEQ ID NO:14, one erythroid-specific enhancer having the nucleotide sequence set forth in SEQ ID NO:15, one erythroid-specific enhancer having the nucleotide sequence set forth in SEQ ID NO:16, and one erythroid-specific enhancer having the nucleotide sequence set forth in SEQ ID NO:17.

As shown in FIGS. 1-4, each of the expression cassettes comprise an insulator having the nucleotide sequence set forth in SEQ ID NO:1 (i.e., insulator A1). In addition, as shown in FIGS. 1-4, each of the expression cassettes comprise a 879 bp human β-globin 3' enhancer, which is positioned upstream of the human β-globin gene. Furthermore, as shown in FIGS. 1-4, each of the recombinant vectors comprise a Woodchuck hepatitis post-regulatory element (WPRE) and a bovine growth hormone polyadenylation signal in the 3' long terminal repeat (LTR) of the vector (e.g., 3' to the R region in the 3' LTR).

III. VECTORS, NUCLEASES AND CRISPR-CAS SYSTEMS

The presently disclosed subject matter provides vectors and delivery systems (e.g., a non-naturally occurring or engineered nucleases or a CRISPR-Cas system) comprising the above-described expression cassettes. The vectors and delivery systems are suitable delivery vehicles for the stable introduction of globin gene (e.g., human β-globin) into the genome of a broad range of target cells to increase expression of the globin protein (human β-globin protein) in the cell.

In certain embodiments, the vector is a retroviral vector (e.g., gamma retroviral or lentiviral) that is employed for the introduction or transduction of the above-described expression cassette into the genome of a host cell (e.g., a hematopoietic stem cell, an embryonic stem cell, an induced pluripotent stem cell, or a hemogenic endothelium cell). In certain embodiments, the retroviral vector comprises an expression cassette that comprises one of the above-described insulators, e.g., insulator A1. The insulator can be positioned at the 3' or the 5' end of the expression cassette. In one embodiment, the insulator is positioned at the 3' end of the expression cassette. During reverse transcription and vector integration, the insulator positioned at the 3' end is copied into the 5' end of the expression cassette. The resulting topology places copies of the insulator between the genomic regions located at the 5' LTR and the 3' LTR of the integrated virus and enhancer activity from the 5' LTR and internal package promoter, but does not contain the enhancer in the 3' LTR. This topology can decrease genotoxicity, thereby resulting in decreased tumor formation and increased survival of the animals.

In certain embodiments, the recombinant vector further comprises a Woodchuck hepatitis post-regulatory element (WPRE) in the 3' long terminal repeat (LTR) of the vector (e.g., 3' to the R region in the 3' LTR of the vector). In certain embodiments, the recombinant vector further comprises a bovine growth hormone polyadenylation signal in addition to the WPRE in the 3' long terminal repeat (LTR) of the vector (e.g., 3' to the R region in the 3' LTR of the vector). An essential feature of therapeutic globin vectors is to achieve a high titer, sufficient for effective transduction of patient cells. By virtue of their large cargo, comprising a gene, promoter, enhancers and/or LCR elements, globin lentiviral vectors inherently have low titer, complicating their manufacture and limiting their clinical use. This problem is further compounded by the incorporation of additional genomic elements such as an insulator, which further increase the size of the vector. The WPRE can increase the titer of the recombinant vector. Addition of a bovine growth hormone polyadenylation signal to the WPRE can further increase the titer of the recombinant vector. In certain embodiments, the WPRE and the bovine growth hormone polyadenylation signal are not comprised within the expression cassette, and thus, not transferred to the cells transduced with the recombinant vector. The incorporation of these elements for enhancing the production of globin lentiviral vectors is essential to yield higher titers and hence for the clinical usefulness of the vectors described in this application.

In one non-limiting example, a presently disclosed expression cassette can be cloned into a retroviral vector and expression can be driven from its endogenous promoter, from the retroviral long terminal repeat, or from an alternative internal promoter. Combinations of retroviral vector and an appropriate packaging line are also suitable, where the capsid proteins will be functional for infecting human cells. Various amphotropic virus-producing cell lines are known, including, but not limited to, PA12 (Miller, et al. (1985) *Mol. Cell. Biol.* 5:431-437); PA317 (Miller, et al. (1986) *Mol. Cell. Biol.* 6:2895-2902); and CRIP (Danos, et al. (1988) *Proc. Natl. Acad. Sci. USA* 85:6460-6464). Non-amphotropic particles are suitable too, e.g., particles pseudotyped with VSVG, RD114 or GALV envelope and any other known in the art.

Suitable methods of transduction also include direct co-culture of the cells with producer cells, e.g., by the method of Bregni, et al. (1992) *Blood* 80:1418-1422, or culturing with viral supernatant alone or concentrated vector stocks with or without appropriate growth factors and polycations, e.g., by the method of Xu, et al. (1994) *Exp. Hemat.* 22:223-230; and Hughes, et al. (1992) *J. Clin. Invest.* 89:1817.

Transducing viral vectors can be used to express a globin gene (e.g., a human β-globin gene) in a host cell (e.g., hematopoietic stem cells, an embryonic stem cell, or an induced pluripotent stem cell). Preferably, the chosen vector exhibits high efficiency of infection and stable integration and expression (see, e.g., Cayouette et al., Human Gene Therapy (1997); 8:423-430; Kido et al., Current Eye Research (1996); 15:833-844; Bloomer et al., Journal of Virology (1997); 71:6641-6649; Naldini et al., Science (1996); 272:263 267; and Miyoshi et al., Proc. Natl. Acad. Sci. U.S.A. 94:10319, 1997). Other viral vectors that can be used include, for example, adenoviral, lentiviral, and adeno-associated viral vectors, vaccinia virus, a bovine papilloma virus, or a herpes virus, such as Epstein-Barr Virus (also see, for example, the vectors of Miller, *Human Gene Therapy* (1990); 15-14; Friedman, *Science* (1989); 244: 1275-1281; Eglitis et al., *BioTechniques* 6:608-614, 1988; Tolstoshev et al., *Current Opinion in Biotechnology* (1990); 1:55-61; Sharp, *The Lancet* (1991); 337:1277-1278; Cornetta et al., *Nucleic Acid Research and Molecular Biology* (1987) 36:311-322; Anderson, *Science* (1984); 226:401-409; Moen, *Blood Cells* (1991); 17:407-416; Miller et al., *Biotechnology* (1989); 7:980-990; Le Gal La Salle et al., *Science* (1993); 259:988-990; and Johnson, *Chest* (1995); 107:775-83S). Retroviral vectors are particularly well developed and have been used in clinical settings (Rosenberg et al., *N. Engl. J. Med* (1990); 323:370; Anderson et al., U.S. Pat. No. 5,399, 346).

The requirement for efficient delivery and integration make retroviral vectors suitable for transducing a presently disclosed expression cassette. Retroviral vectors can be derived from three genera of the retroviridae: the γ-retroviruses (also known as C-type murine retroviruses or oncoretroviruses), the lentiviruses, and the spumaviruses (also known as foamy viruses). Several reviews detailing molecular approaches for the generation of replication-defective retroviral particles are available (Cornetta et al. (2005); Cockrell & Kafri (2007)). The vector itself, which encodes the therapeutic transgene or cDNA, retains the minimal viral sequences needed to enable packaging in viral particles in a packaging cell line, reverse transcription, and integration. The packaging cell expresses the necessary structural proteins and enzymes that are required to assemble an infectious recombinant particle that contains the vector sequence and the machinery needed for its reverse transcription and integration in the transduced cell.

While the manufacturing aspects of all retroviral vector types follow the same general principles, γ-retroviral, lentiviral and spumaviral vectors differ in some of their intrinsic biological properties. Gamma-retroviruses, including the prototypic murine leukaemia viruses (MLV), effectively infect many cell types but are unable to integrate in cells that do not proceed to S phase soon after infection. In contrast, lentiviruses and their vector derivatives can transduce non-dividing cells (Follenzi & Naldini, 2002; Salmon & Trono, 2002) owing to their ability to translocate to the nucleus and integrate in the absence of cell division (Lewis & Emerman, 1994; Goff, 2001). Another fundamental attribute of lentiviral vectors is their relative genomic stability, as established for globin lentiviral vectors (May et al., 2000), which contrasts with the genomic instability of MLV-based globin vectors (Leboulch et al., 1994; Sadelain et al., 1995). Lentiviral and foamy vectors further provide a greater packaging capacity (Kumar et al., 2001; Rethwilm, 2007). All three vector types have been used successfully for the transduction of cytokineactivated HSCs (Miyoshi et al., 1999; Josephson et al., 2002; Leurs et al., 2003).

These three vector systems differ in their integration patterns. The integration pattern of retroviruses is semi-random and biased towards genes and their vicinity in approximately two-thirds of all integration events (Schroder et al., 2002; Wu et al., 2003; Mitchell et al., 2004; De Palma et al., 2005; Trobridge et al., 2006). There are however subtle and possibly significant differences in their exact distribution. Gamma-retroviruses have a propensity to integrate upstream of transcribed genes, whereas lentiviruses and lentiviral vectors target the entire transcribed gene sequence. Foamy vectors appear to be less prone to intragenic integration (Trobridge et al., 2006). In one embodiment, the vector comprising the expression cassette is a lentivirus vector. The vectors can be derived from human immunodeficiency-1 (HIV-1), human immunodeficiency-2 (HIV-2), simian immunodeficiency virus (SIV), feline immunodeficiency virus (FIV), bovine immunodeficiency virus (BIV), Jembrana Disease Virus (JDV), equine infectious anemia virus (EIAV), caprine arthritis encephalitis virus (CAEV) and the like. In one non-limiting embodiment, the lentiviral vector is an HIV vector. HIV-based constructs are the most efficient at transduction of human cells.

The semi-random pattern of vector integration exposes patients to the risk of insertional oncogenesis when the vector trans-activates a neighboring oncogene. This may result in clonal expansion (Ott et al, 2006; Cavazzana-Calvo et al, 2010), myelodysplasia (Stein et al, 2010) or leukaemia (Hacein-Bey-Abina et al, 2003, 2008; Howe et al, 2008). Targeted gene delivery strategies, utilizing a non-naturally occurring or engineered nuclease (including, but not limited to, Zinc-finger nuclease (ZNFs), meganuclease, transcription activator-like effector nuclease (TALEN)), or a CRISPR-Cas system, can reduce or even eliminate the concern of insertional oncogenesis that is inherent to the use of retroviral vectors.

Eukaryotic cells utilize two distinct DNA repair mechanisms in response to DNA double strand breaks (DSBs): Homologous recombination (HR) and non-homologous end-joining (NHEJ). The activation of the HR repair machinery depends on the cell cycle status, and it is restricted to the S and G2 phases; in contrast, the NHEJ pathway is active throughout the cell cycle. Mechanistically, HR is an error-free DNA repair mechanism, because it requires a homologous template to repair the damaged DNA strand. On the other hand, NHEJ is a template-independent repair mechanism that is imprecise, due to DNA end processing during repair that leads to insertions or deletions at the DNA break site (Moynahan & Jasin, 2010). Because of its homology-based mechanism, HR has been used as a tool to site-specifically engineer the genome of different species. From a therapeutic perspective, HR has been successfully used to repair mutated genes, thus offering a promising approach to cell-mediated treatment of monogenic diseases (Porteus et al, 2006).

Gene targeting by HR requires the use of two homology arms that flank the transgene/target site of interest. Generally, standard plasmid DNAs have been used to deliver 5-10 kb homology arms along with transgenes for positive and negative selection. This method is commonly used to knockout/knockin genes in mouse embryonic stem (mES) cells (Capecchi, 2005; FIG. 2B). In human cells, the use of this approach has allowed gene targeting with efficiencies in the order of $10^{-6}$, which are lower than in mES cells and are not therapeutically practical. HR efficiency can be increased by the introduction of DNA-doubled stranded breaks (DSBs) at the target site using specific rare-cutting endonucleases, resulting in over 1,000-fold increase in correct gene targeting (Jasin, 1996). The discovery of this phenomenon prompted the development of methods to create site-specific DSBs in the genome of different species. Various chimeric enzymes have been designed for this purpose over the last decade, namely zinc-finger nucleases (ZFNs), meganucleases, and transcription activator-like effector nucleases (TALENs).

ZFNs are modular chimeric proteins that contain a ZF-based DNA binding domain (DBD) and a FokI nuclease domain (Porteus & Carroll, 2005). DBD is usually composed of three ZF domains, each with 3-base pair specificity; the FokI nuclease domain provides a DNA nicking activity, which is targeted by two flanking ZFNs. Owing to the modular nature of the DBD, any site in a genome could be targeted in principle. However, as a single ZFN can bind and nick DNA, there is potential for a high number of off-target effects, resulting in the activation of the NHEJ pathway that may either introduce insertions/deletions or integrate the targeting vector in a non-specific manner. Obligate FokI domains that can nick their respective DNA strand only when they form a heterodimer were recently reported (Doyon et al, 2011). The use of such obligate ZFNs can reduce the genotoxic effects of this approach.

Meganucleases (MNs)/homing endonucleases (HEs) are dsDNA nucleases that recognize and cleave large DNA sites (14-40 bp) with low cleavage frequencies in eukaryotic genomes (Paques & Duchateau, 2007). Although this limits the potential target sites, MN-DNA structures have been used as a guide to specifically modify DNA-interacting residues in order to change the MN specificity (Marcaida et al, 2010). I-CreI has been successfully engineered to generate chimeric meganucleases that target the human XPC and RAG1 genes, and they have been shown to stimulate HR activity in mammalian cells with no evident genotoxicity (Redondo et al, 2008; Grizot et al, 2009). The genotoxicity of this approach will need to be compared to that of ZFNs and TALE nucleases.

TALENs are similar ZFN except that the DBD is derived from transcription activator-like effcetors (TALEs), which are virulent factors used by phytopathogenic bacteria (Herbers, 1992). The TALE DBD is modular, and it is composed of 34-residue repeats, and its DNA specificity is determined by the number and order of repeats (Herbers, 1992). Each repeat binds a single nucleotide in the target sequence through only two residues (Boch, 2011). The advantage over ZFN technology is the rapid construction of DBDs.

A number of studies have used these chimeric enzymes to stimulate HR for either gene addition or gene repair at their target site (Paques & Duchateau, 2007; Urnov et al, 2010). Porteus designed a ZFN to a half site sequence from the human HBB that surrounds the sickle cell mutation nucleotide (Porteus, 2006). This ZFN targets the sequence and stimulates HR at a chimeric DNA target when combined with a ZFN targeting the Zif268 binding site. There have been recent advances in targeting genes in cord blood CD34+ cells. Use of non-integrating lentiviruses to deliver ZFNs and the donor DNA in these cells to target the CCR5 gene was reported in Lombardo et al, 2007. Lombardo et al, 2007 showed gene addition at this locus with correct targeting in 80% of the positively selected cells.

The presently disclosed subject matter provides a non-naturally occurring or engineered nuclease comprising a presently disclosed expression cassette, as described above. Suitable nucleases include, but are not limited to, ZFNs, meganucleases, and TALENs. A presently disclosed nuclease comprises a DNA binding domain and a nuclease cleavage domain. The DNA binding domain of the nuclease can be engineered to bind to a sequence of choice, e.g., a predetermined site. An engineered DNA binding domain can have a distinct binding specificity, compared to a naturally occurring nuclease. Engineering methods include, but are not limited to, rational design and various types of selection. Any suitable cleavage domain can be operatively linked to a DNA-binding domain to form a nuclease. For example, Zinc-finger protein (ZFP) DNA-binding domains can be fused to nuclease cleavage domains to create ZFNs-a functional entity that is able to recognize its intended nucleic acid target through its engineered ZFP DNA binding domain and cause the DNA to be cut near the ZFP binding site via the nuclease activity. See, e.g., Kim et al. *Proc Nat'l Acad Sci USA* (1996); 93(3):1156-1160. Likewise, TALE DNA-binding domains can be fused to nuclease cleavage domains to create TALENs. See, e.g., U.S. Publication No. 20110301073.

The cleavage domain can be heterologous to the DNA-binding domain, e.g., a meganuclease DNA-binding domain and cleavage domain from a different nuclease. Heterologous cleavage domains can be obtained from any endonuclease or exonuclease. Exemplary endonucleases from which a cleavage domain can be derived include, but are not limited to, restriction endonucleases and homing endonucleases. See, for example, 2002-2003 Catalog, New England Biolabs, Beverly, Mass.; and Belfort et al. (1997) *Nucleic Acids Res.* 25:3379-3388. Additional enzymes which cleave DNA are known (e.g., S1 Nuclease; mung bean nuclease; pancreatic DNase I; micrococcal nuclease; yeast HO endonuclease; see also Linn et al. (eds.) *Nucleases*, Cold Spring Harbor Laboratory Press, 1993). One or more of these enzymes (or functional regions thereof) can be used as a source of cleavage domains and cleavage half-domains.

Similarly, a cleavage half-domain can be derived from the above-described nuclease that requires dimerization for cleavage activity. In general, two fusion proteins are required for cleavage if the fusion proteins comprise cleavage half-domains. Alternatively, a single protein comprising two cleavage half-domains can be used. The two cleavage half-domains can be derived from the same endonuclease (or functional portions thereof), or each cleavage half-domain can be derived from a different endonuclease (or functional portions thereof).

In certain embodiments, the nuclease comprises an expression cassette that comprises two of the above-described insulators, e.g., two of the insulator having the nucleotide sequence set forth in SEQ ID NO:1. One of the two insulators is positioned at the 3' end of the expression cassette, and the other insulator is positioned at the 5' end of the expression cassette.

The presently disclosed subject matter also provides a non-naturally occurring or engineer CRISPR-Cas system comprising the above-described expression cassette. The CRISPR (Clustered Regularly Interspaced Short Palindromic Repeats)-Cas (CRISPR Associated) system is an engineered nuclease system based on a bacterial system that can be used for genome engineering. It is based on part of the adaptive immune response of many bacteria and archea. When a virus or plasmid invades a bacterium, segments of the invader's DNA are converted into CRISPR RNAs (crRNA) by the "immune" response. The crRNA then associates, through a region of partial complementarity, with another type of RNA called tracrRNA to guide a CRISPR-Cas nuclease to a region homologous to the crRNA in the target DNA called a "proto spacer". The CRISPR-Cas nuclease cleaves the DNA to generate blunt ends at the DSB at sites specified by a 20-nucleotide guide sequence contained within the crRNA transcript. The CRISPR-Cas nuclease requires both the crRNA and the tracrRNA for site specific DNA recognition and cleavage. This system has been engineered such that the crRNA and tracrRNA can be combined into one molecule (the "single guide RNA"); and the crRNA equivalent portion of the single guide RNA can be engineered to guide the CRISPR-Cas nuclease to target any desired sequence (see Jinek et al., *Science* (2012); 337:816-821). Thus, the CRISPR-Cas system can be engineered to create a DSB at a desired target in a genome. In certain embodiments, the CRISPR-Cas system comprises a CRISPR-Cas nuclease and a single-guide RNA. Suitable examples of CRISPR-Cas nucleases include, but are not limited to, Cas1, Cas1B, Cas2, Cas3, Cas4, Cas5, Cash, Cas7, Cas8, Cas9 (also known as Csn1 and Csx12), Cas10, Csy1, Csy2, Csy3, Cse1, Cse2, Csc1, Csc2, Csa5, Csn2. Csm2, Csm3, Csm4, Csm5, Csm6, Cmr1, Cmr3, Cmr4, Cmr5, Cmr6, Csb1, Csb2, Csb3, Csx17, Csx14, Csx10, Csx16, CsaX, Csx3, Csx1, Csx15, Csf1, Csf2, Csf3, Csf4, homologs thereof, or modified versions thereof. These CRISPR-Cas nucleases are known; for example, the amino acid sequence of *S. pyogenes* Cas9 protein may be found in the SwissProt database under accession number Q99ZW2. In some embodiments, the CRISPR-Cas nuclease has DNA cleavage activity, e.g., Cas9. In certain embodiments, the CRISPR-Cas nuclease is Cas9. The CRISPR-Cas nuclease can direct cleavage of one or both strands at the location of a target sequence (e.g., a genomic safe harbor site). Additionally, the CRISPR-Cas nuclease can direct cleavage of one or both strands within about 1, 2, 3, 4, 5, 6, 7, 8, 9, 10, 15, 20, 25, 50, 100, 200, 500, or more base pairs from the first or last nucleotide of a target sequence.

The presently disclosed nucleases and CRISPR-Cas system allow for targeted delivery of the expression cassette. In certain embodiments, a presently disclosed CRISPR-Cas system or the DNA binding domain of a presently disclosed nuclease binds to a genomic safe harbor site. A nuclease or the CRISPR-Cas system generates a double strand break at the genomic safe harbor site. Genomic safe harbor sites are intragenic or extragenic regions of the human genome that are able to accommodate the predictable expression of newly integrated DNA without adverse effects on the host cell or organism. A useful safe harbor must permit sufficient transgene expression to yield desired levels of the vector-encoded protein or non-coding RNA. A genomic safe harbor site also must not predispose cells to malignant transformation nor alter cellular functions. Methods for identifying genomic safe harbor sites are described in Sadelain et al., "Safe Harbours for the integration of new DNA in the human genome," *Nature Reviews* (2012); 12:51-58; Papapetrou et al., "Genomic safe harbors permit high β-globin transgene expression in thalassemia induced pluripotent stem cells" *Nat Biotechnol*. (2011) January; 29(1):73-8, which are incorporated by reference in their entireties. A presently disclosed genomic safe harbor site meets one or more (one, two, three, four, or five) of the following five criteria: (1) distance of at least 50 kb from the 5' end of any gene (e.g., from the 5' end of the gene), (ii) distance of at least 300 kb from any cancer-related gene, (iii) within an open/accessible chromatin structure (measured by DNA cleavage with natural or engineered nucleases), (iv) location outside a gene transcription unit and (v) location outside ultraconserved regions (UCRs), microRNA or long non-coding RNA of the human genome. As the most common insertional oncogenesis event is transactivation of neighboring tumor-promoting genes, the first two criteria exclude the portion of the human genome located near promoters of genes, in particular, cancer-related genes, which are genes functionally implicated in human cancers or the human homologs of genes implicated in cancer in model organisms. Proximity to miRNA genes is one exclusion criterion because miRNAs are implicated in the regulation of many cellular processes, including cell proliferation and differentiation. As vector integration within a transcription unit can disrupt gene function through the loss of function of a tumor suppressor gene or the generation of an aberrantly spliced gene product, the fourth (iv) criterion excludes all sites located inside transcribed genes. UCRs, which are regions that are highly conserved over multiple vertebrates and known to be enriched for enhancers and exons, and long non-coding RNAs, are also excluded. In certain embodiments, the genomic safe harbor site is an extragenic genomic safe harbor site. In certain embodiments, the genomic safe harbor site is located on chromosome 1.

The presently disclosed subject matter also provides polynucleotides encoding the above-described nucleases, vectors comprising the polynucleotides encoding the above-described nucleases, polynucleotides encoding the above-described CRISPR-Cas system, and vectors comprising the polynucleotides encoding the above-described CRISPR-Cas system.

The nucleases and polynucleotides encoding these nucleases, and the CRISPR-Cas system and polynucleotides encoding the CRISPR-Cas system can be delivered in vivo or ex vivo by any suitable means. For example, nucleases and CRISPR-Cas system as described herein can be delivered to a cell (e.g., a hematopoietic stem cell, an embryonic stem cell, an induced pluripotent stem cell, or an hemogenic endothelium cell) by a vector comprising polynucleotides encoding the nuclease or the CRISPR-Cas system. Any vectors can be used including, but not limited to, plasmid vectors, retroviral vectors (e.g., γ-retroviral vectors, lentiviral vectors and foamy viral vectors), adenovirus vectors, poxvirus vectors; herpes virus vectors and adena-associated virus vectors, etc. In one embodiment, the vector comprising a polynucleotide encoding an above-described nuclease or an above-described CRISPR-Cas system is a lentiviral vector. In one particular embodiment, the lentiviral vector is a non-integrating lentiviral vector. Examples of non-integrating lentiviral vector are described in Ory et al. (1996) *Proc. Natl. A cad. Sci. USA* 93:11382-11388; Dull et al., (1998) *J. Viral.* 72:8463-8471; Zuffery et al. (1998) *J. Viral.* 72:9873-9880; Follenzi et al., (2000) *Nature Genetics* 25:217-222; U.S. Patent Publication No 2009/054985.

Additionally, non-viral approaches can also be employed for the expression of a globin gene in cells. For example, a nucleic acid molecule can be introduced into a cell by administering the nucleic acid in the presence of lipofection (Feigner et al., *Proc. Natl. Acad. Sci. U.S.A.* 84:7413, 1987; Ono et al., *Neuroscience Letters* 17:259, 1990; Brigham et al., *Am. J. Med. Sci.* 298:278, 1989; Staubinger et al., *Methods in Enzymology* 101:512, 1983), asialoorosomucoid-polylysine conjugation (Wu et al., Journal of Biological Chemistry 263:14621, 1988; Wu et al., *Journal of Biological Chemistry* 264:16985, 1989), or by micro-injection under surgical conditions (Wolff et al., Science 247:1465, 1990). Other non-viral means for gene transfer include transfection in vitro using calcium phosphate, DEAE dextran, electroporation, and protoplast fusion. Liposomes can also be potentially beneficial for delivery of DNA into a cell. Transplantation of normal genes into the affected tissues of a subject can also be accomplished by transferring a normal nucleic acid into a cultivatable cell type ex vivo (e.g., an autologous or heterologous primary cell or progeny thereof), after which the cell (or its descendants) are injected into a targeted tissue or are injected systemically. Recombinant receptors can also be derived or obtained using transposases. Transient expression may be obtained by RNA electroporation.

IV. CELLS

Genetic modification of cells (e.g., hematopoietic stem cells, embryonic stem cells, induced pluripotent stem cells, and hemogenic endothelium cells) can be accomplished by transducing a substantially homogeneous cell composition with a recombinant DNA or RNA construct (e.g., a vector or a delivery system comprising the above-described expression cassette). The presently disclosed subject matter provides cells transduced with the above-described expression cassettes, cells transduced with the above-described vectors, and cells transduced with the above-described nucleases or with vectors comprising polynucleotides encoding the nucleases, and cell transduced with the above-described CARISPR-Cas system or with vectors comprising polynucleotides encoding the CARISPR-Cas system, which are collectively referred to as "transduced cells". As described above, the vectors, nucleases and CRISPR-Cas system are employed for transduction of the expression cassette to the cells to express a globin gene (e.g., a human β-globin gene). In certain embodiments, the transduced cells are administered to a subject to treat and/or prevent a hematopoietic disease, disorder, or condition. The presently disclosed insulators can enhance the efficiency of the transduction of the expression cassette to cells.

Suitable transduced cells include, but are not limited to, stem cells, progenitor cells, and differentiated cells. As used herein, the term "progenitor" or "progenitor cells" refers to cells that have the capacity to self-renew and to differentiate into more mature cells. Progenitor cells have a reduced potency compared to pluripotent and multipotent stem cells. Many progenitor cells differentiate along a single lineage, but may also have quite extensive proliferative capacity.

In certain embodiments, the transduced cells are stem cells. Stem cells have the ability to differentiate into the appropriate cell types when administered to a particular biological niche, in vivo. A stem cell is an undifferentiated cell capable of (1) long term self-renewal, or the ability to generate at least one identical copy of the original cell, (2) differentiation at the single cell level into multiple, and in some instance only one, specialized cell type and (3) of in vivo functional regeneration of tissues. Stem cells are sub-classified according to their developmental potential as totipotent, pluripotent, multipotent and oligo/unipotent. As used herein, the term "pluripotent" means the ability of a cell to form all lineages of the body or soma (i.e., the embryo proper). For example, embryonic stem cells are a type of pluripotent stem cells that are able to form cells from each of the three germs layers, the ectoderm, the mesoderm, and the endoderm. As used herein, the term "multipotent" refers to the ability of an adult stem cell to form multiple cell types of one lineage. For example, hematopoietic stem cells are capable of forming all cells of the blood cell lineage, e.g., lymphoid and myeloid cells.

In certain embodiments, the transduced cells are embryonic stem cells, bone marrow stem cells, umbilical cord stem cells, placental stem cells, mesenchymal stem cells, neural stem cells, liver stem cells, pancreatic stem cells, cardiac stem cells, kidney stem cells, and/or hematopoietic stem cells. In one embodiment, the transduced cells are hematopoietic stem cells (HSCs). HSCs give rise to committed hematopoietic progenitor cells (HPCs) that are capable of generating the entire repertoire of mature blood cells over the lifetime of an organism. The term "hematopoietic stem cell" or "HSC" refers to multipotent stem cells that give rise to all blood cell types of an organism, including myeloid (e.g., monocytes and macrophages, neutrophils, basophils, eosinophils, erythrocytes, megakaryocytes/platelets, dendritic cells), and lymphoid lineages (e.g., T-cells, B-cells, NK-cells). When transplanted into lethally irradiated animals or humans, hematopoietic stem and progenitor cells can repopulate the erythroid, neutrophil-macrophage, megakaryocyte and lymphoid hematopoietic cell pool.

HSCs can be isolated or collected from bone marrow, umbilical cord blood, or peripheral blood. HSCs can be identified according to certain phenotypic or genotypic markers. For example, HSCs can be identified by their small size, lack of lineage (lin) markers, low staining (side population) with vital dyes such as rhodamine 123 (rhodaminеDULL, also called rholo) or Hoechst 33342, and presence of various antigenic markers on their surface, many of which belong to the cluster of differentiation series (e.g., CD34, CD38, CD90, CD133, CD105, CD45, Ter119, and c-kit, the receptor for stem cell factor). In one embodiment, the transduced cell is a CD34$^+$ HSC.

In one embodiment, the transduced cell is an embryonic stem cell. In another embodiment, the transduced cell is an induced pluripotent stem cell. In yet another embodiment, the transduced cell is a hemogenic endothelium cell.

While HSCs are the natural vehicle for restoring long-term hematopoiesis, their use has some important limitations. The first is their relative scarcity, which can eventually preclude autologous HSC therapy when the harvested cellular product is too small. The second is the difficulty to perform biosafety testing such as integration site analysis and consequently to select cells with chosen integration sites, because adult HSCs cannot be replicated in vitro. The third limitation is that homologous recombination using current technologies is practically impossible thus compromising the advent of gene correction. All of these limitations are ultimately due to the fact that adult HSCs cannot be expanded in vitro without losing their stem cell potency. These limitations explain the critical importance of viral vectors such as gamma-retroviral and lentiviral vectors, which are remarkably quick and efficient in achieving stable gene transfer. This is essential when dealing with HSCs that are only available in limited quantities.

Use of ESs and induced pluripotent stem (iPS) cells for globin gene therapy is disclosed in Moi et al., *Haematol* Mar. 1, 2008; 93(3):325-330. Embryonic stem (ES) cells are amenable to gene targeting and correction, which requires unlimited in vitro cell division without losing multipotency. Chang et al., *Proc Natl Acad Sci USA* 2006; 103:1036-40 provided proof of principle of the feasibility of the homologous recombination approach in mice with sickle cell anemia. Takahashi et al. *Cell* 2006; 126:663-76 reported the successful reprogramming of fibroblasts to an embryonic stem-like state. Cells obtained by this reverse-differentiation process, called induced pluripotent stem (iPS) cells, were produced by exposing embryonic or young adult bulk fibroblast cultures to gamma-retroviral vectors encoding 4 transcription factors, which are physiologically active in the embryonic stem cells, but generally turned off when differentiation progresses. The cultured cells formed colonies similar to ES cell colonies. These findings have been confirmed and extended by others to both mouse and human fibroblasts (Meissner et al., Nat Biotechnol 2007; 25:1177-81; Nakagawa et al., Nat Biotechnol 2007; 26:101-6; Okita et al., Nature 2007; 448:313-7; Park et al., Nature 2007; 451:141-6; Takahashi et al., Nat Protoc 2007; 2:3081-9; Takahashi K et al., Cell 2007; 131:861-72; Wernig et al., Nature 2007; 448:318-24; Yu J et al., Science 2007; 318: 1917-20). Rudolf Jaenisch and co-workers achieved a successful gene therapy in a mouse model of sickle cell disease, using homologous recombination in ES-like iPS cells (Hanna et al., Science 2007; 318:1920-3). The process has so far been mostly applied to fibroblast harvested from a skin biopsy, which are then induced to become iPS by transduction with retroviral vectors that encode four stem cell transcription factors. iPS are amenable to the correction of the SC mutation by standard homologous recombination techniques and can then be differentiated in vitro into unlimited amounts of hematopoietic stem cells. The whole process ends with the autologous transplantation of the corrected HSC into the original mouse donor, which will now be cured of its SC disease. This technique is not only useful for homologous recombination, but can also enhance lentiviral-mediated globin gene transfer for the treatment of β-thalassemia by providing a means to perform detailed integration site analysis and adequate in vitro cell expansion before infusing cells into the recipient.

The cell of the presently disclosed subject matter can be autologous ("self") or non-autologous ("non-self," e.g., allogeneic, syngeneic or xenogeneic). As used herein, "autologous" refers to cells from the same subject. As used herein, "allogeneic" refers to cells of the same species that differ genetically to the cell in comparison. As used herein, "syngeneic" refers to cells of a different subject that are genetically identical to the cell in comparison. As used herein, "xenogeneic" refers to cells of a different species to the cell in comparison. In certain embodiments, the cell is autologous, e.g., a cell transduced with the presently disclosed expression cassette is administered to a subject from whom the cell is collected, e.g., the cell is collected from bone marrow, umbilical cord blood, peripheral blood, and/or adipose tissue of the subject. In certain embodiments, the cell is obtained or collected from bone marrow of a subject.

In certain embodiments, prior to transduction with the expression cassette, the cell is pre-stimulated, e.g., in the presence of one or more cytokines (e.g., IL-3, IL-1α, IL-6, Kit ligand (also known as "Stem Cell Factor (SCF)"), and Flt-3 ligand), and/or one or more glycoproteins (e.g., thrombopoietin and fibronectin). In one non-limiting example, the cell is pre-stimulated in the presence of Flt-3 ligand, SCF, thrombopoietin, interleukin-3, and fibronectin. The cell can be pre-stimulated for about 24 hours or longer, e.g., about 48 hours, or about 36 hours. Subsequently, the cell is transduced with a presently disclosed expression cassette, or a vector or another delivery system comprising such expression cassette. Transduction can be performed on a fresh cell, or on a frozen cell. Genomic DNA of the cell is isolated to determine the vector copy number and analyze the integration site or integrated vector structure, e.g., by South blot analysis and/or by Quantitative PCR. For quantification of globin mRNA (e.g., human β-globin transgene analysis), total RNA is extracted from the cell. Quantitative primer extension assay can be used for quantification of globin mRNA.

V. COMPOSITIONS AND FORMULATIONS

The presently disclosed subject matter provides pharmaceutical compositions comprising a presently disclosed transduced cell as described above and a pharmaceutically acceptable carrier. As used herein, "pharmaceutically acceptable carrier" includes any and all solvents, dispersion media, coatings, antibacterial and antifungal agents, isotonic and absorption delaying agents, and the like that are physiologically compatible, including pharmaceutically acceptable cell culture media. The pharmaceutically acceptable carrier can be suitable for parenteral (e.g., intravenous, intramuscular, subcutaneous, or intraperitoneal), spinal or epidermal administration (e.g., by injection, infusion or implantation). Depending on the route of administration, the active compound, e.g., the transduced cell, may be coated in a material to protect the compound from the action of acids and other natural conditions that may inactivate the compound.

Pharmaceutically acceptable carriers include sterile aqueous solutions or dispersions and sterile powders for the extemporaneous preparation of sterile injectable solutions or dispersion. The use of such media and agents for pharmaceutically active substances is well known in the art. Except insofar as any conventional media or agent is incompatible with the transduced cells, use thereof in the pharmaceutical compositions of the invention is contemplated.

The pharmaceutical compositions of the presently disclosed subject matter can further comprise one or more polypeptides, polynucleotides, vectors comprising the same, transduced cells, etc., as described herein, formulated in pharmaceutically-acceptable or physiologically-acceptable solutions for administration to a cell or an animal, either alone, or in combination with one or more other modalities of therapy. If desired, the pharmaceutical compositions of the presently disclosed subject matter can be administered in combination with other agents, including, but not limited to, cytokines, growth factors, hormones, small molecules or various pharmaceutically-active agents. Any additional agents that do not adversely affect the ability of the composition to deliver the intended gene therapy can be included in the compositions.

In the pharmaceutical compositions of the presently disclosed subject matter, formulation of pharmaceutically-acceptable excipients and carrier solutions is well known to those of ordinary skill in the art, as is the development of suitable dosing and treatment regimens for using the particular compositions described herein in a variety of treatment regimens, including, e.g., oral, parenteral, intravenous, intranasal, and intramuscular administration and formulation.

The pharmaceutical compositions of the presently disclosed subject matter can be delivered parenterally (e.g., intravenously, intramuscularly, or intraperitoneally) as described, for example, in U.S. Pat. Nos. 5,543,158; 5,641, 515 and 5,399,363. Solutions of the active compounds as free base or pharmacologically acceptable salts may be prepared in water suitably mixed with a surfactant, such as hydroxypropylcellulose. Dispersions may also be prepared in glycerol, liquid polyethylene glycols, and mixtures thereof and in oils. Under ordinary conditions of storage and use, these preparations contain a preservative to prevent the growth of microorganisms.

Pharmaceutically acceptable carriers include sterile aqueous solutions or dispersions and sterile powders for the extemporaneous preparation of sterile injectable solutions or dispersion. The use of such media and agents for pharmaceutically active substances is known in the art. Except insofar as any conventional media or agent is incompatible with the active compound, use thereof in the pharmaceutical compositions of the invention is contemplated. Supplementary active compounds can also be incorporated into the compositions.

Therapeutic compositions typically must be sterile and stable under the conditions of manufacture and storage. The composition can be formulated as a solution, microemulsion, liposome, or other ordered structure suitable to high drug concentration. The pharmaceutically acceptable carrier can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. In many cases, it will be preferable to include isotonic agents, for example, sugars, polyalcohols such as mannitol, sorbitol, or sodium chloride in the composition. Prolonged absorption of the injectable compositions can be brought about by including in the composition an agent that delays absorption, for example, monostearate salts and gelatin.

The pharmaceutical compositions of the presently disclosed subject matter can be conveniently provided as sterile liquid preparations, e.g., isotonic aqueous solutions, suspensions, emulsions, dispersions, or viscous compositions, which can be buffered to a selected pH. Liquid preparations are normally easier to prepare than gels, other viscous compositions, and solid compositions. Additionally, liquid compositions are somewhat more convenient to administer, especially by injection. Viscous compositions, on the other hand, can be formulated within the appropriate viscosity range to provide longer contact periods with specific tissues. Liquid or viscous compositions can comprise carriers, which can be a solvent or dispersing medium containing, for example, water, saline, phosphate buffered saline, polyol (for example, glycerol, propylene glycol, liquid polyethylene glycol, and the like) and suitable mixtures thereof.

Sterile injectable solutions can be prepared by incorporating the compositions of the presently disclosed subject matter in the required amount of the appropriate solvent with various amounts of the other ingredients, as desired. Such compositions may be in admixture with a suitable carrier, diluent, or excipient such as sterile water, physiological saline, glucose, dextrose, or the like. The compositions can also be lyophilized. The compositions can contain auxiliary substances such as wetting, dispersing, or emulsifying agents (e.g., methylcellulose), pH buffering agents, gelling or viscosity enhancing additives, preservatives, flavoring agents, colors, and the like, depending upon the route of administration and the preparation desired. Standard texts, such as "REMINGTON'S PHARMACEUTICAL SCIENCE", 17th edition, 1985, incorporated herein by reference, may be consulted to prepare suitable preparations, without undue experimentation.

Various additives which enhance the stability and sterility of the compositions, including antimicrobial preservatives, antioxidants, chelating agents, and buffers, can be added. Prevention of the action of microorganisms can be ensured by various antibacterial and antifungal agents, for example, parabens, chlorobutanol, phenol, sorbic acid, and the like. Prolonged absorption of the injectable pharmaceutical form can be brought about by the use of agents delaying absorption, for example, alum inurn monostearate and gelatin.

The compositions can be isotonic, i.e., they can have the same osmotic pressure as blood and lacrimal fluid. The desired isotonicity of the compositions of the presently disclosed subject matter can be accomplished using sodium chloride, or other pharmaceutically acceptable agents such as dextrose, boric acid, sodium tartrate, propylene glycol or other inorganic or organic solutes. Sodium chloride is preferred particularly for buffers containing sodium ions.

For parenteral administration in an aqueous solution, for example, the solution should be suitably buffered if necessary and the liquid diluent first rendered isotonic with sufficient saline or glucose. Sterile injectable solutions can be prepared by incorporating the active compound in the required amount in an appropriate solvent with one or a combination of ingredients enumerated above, as required, followed by sterilization microfiltration. Generally, dispersions are prepared by incorporating the active compound into a sterile vehicle that contains a basic dispersion medium and the required other ingredients from those enumerated above. In the case of sterile powders for the preparation of sterile injectable solutions, the preferred methods of preparation are vacuum drying and freeze-drying (lyophilization) that yield a powder of the active ingredient plus any additional desired ingredient from a previously sterile-filtered solution thereof.

In certain embodiments, the compositions can be delivered by intranasal sprays, inhalation, and/or other aerosol delivery vehicles. Methods for delivering genes, polynucleotides, and peptide compositions directly to the lungs via nasal aerosol sprays are described, e.g., in U.S. Pat. Nos. 5,756,353 and 5,804,212. Methods of delivering drugs using lysophosphatidyl-glycerol compounds are described, e.g., in U.S. Pat. No. 5,725,871. Transmucosal drug delivery in the form of a polytetrafluoroetheylene support matrix is described, e.g., in U.S. Pat. No. 5,780,045. The compositions of the presently disclosed subject matter can be formulated for delivery either encapsulated in a lipid particle, a liposome, a vesicle, a nanosphere, a nanoparticle or the like. The formulation and use of such delivery vehicles can be carried out using known and conventional techniques. The formulations and compositions of the presently disclosed subject matter can comprise one or more repressors and/or activators comprising a combination of any number of polypeptides, polynucleotides, and small molecules, as described herein, formulated in pharmaceutically-acceptable or physiologically-acceptable solutions (e.g., culture medium) for administration to a cell or an animal, either alone, or in combination with one or more other modalities of therapy.

In certain aspects, the presently disclosed subject matter provides formulations or compositions suitable for the delivery of viral vector systems (i.e., viral-mediated transduction) including, but not limited to, retroviral (e.g., lentiviral) vectors. Exemplary formulations for ex vivo delivery can also include the use of various transfection agents known in the art, such as calcium phosphate, electoporation, heat shock and various liposome formulations (i.e., lipid-mediated transfection). Liposomes are lipid bilayers entrapping a fraction of aqueous fluid. DNA spontaneously associates to the external surface of cationic liposomes (by virtue of its charge) and these liposomes will interact with the cell membrane.

The skilled artisan can readily determine the amount of cells and optional additives, vehicles, and/or carrier in compositions and to be administered in methods of the presently disclosed subject matter. Typically, any additives (in addition to the transduced cell(s) and/or agent(s)) are present in an amount of from about 0.001% to about 50% by weight) solution in phosphate buffered saline, and the active ingredient is present in the order of micrograms to milligrams, such as from about 0.0001 wt % to about 5 wt %, from about 0.0001 wt % to about 1 wt %, from about 0.0001 wt % to about 0.05 wt %, from about 0.001 wt % to about 20 wt %, from about 0.01 wt % to about 10 wt %, or from about 0.05 wt % to about 5 wt %. For any composition to be administered to an animal or human, and for any particular method of administration, toxicity should be determined, such as by determining the lethal dose (LD) and LD50 in a suitable animal model e.g., rodent such as mouse; and, the dosage of the composition(s), concentration of components therein and timing of administering the composition(s), which elicit a suitable response. Such determinations do not require undue experimentation from the knowledge of the skilled artisan, this disclosure and the documents cited herein. And, the time for sequential administrations can be ascertained without undue experimentation.

VI. USES AND METHODS

Vectors and other delivery systems (nucleases and CRISPR-Cas systems) comprising the presently disclosed expression cassette provide improved methods of gene therapy. As used herein, the term "gene therapy" refers to the introduction of a polynucleotide into a cell's genome that restores, corrects, or modifies the gene and/or expression of the gene. In various non-limiting embodiments, a presently disclosed vector or other delivery system (e.g., a nuclease or a CRISPR-Cas system) comprises an expression cassette comprising a globin gene or a functional portion thereof that encodes a globin protein (e.g., human β globin protein), which provides curative, preventative, or ameliorative benefits to a subject diagnosed with or that is suspected of having a disease, disorder, or condition of the hematopoietic system. The vector or other delivery systems (e.g., a nuclease and the CRISPR-Cas system) can infect and transduce the cell in vivo, ex vivo, or in vitro. In ex vivo and in vitro embodiments, the transduced cells can then be administered to a subject in need of therapy. The presently disclosed subject matter contemplates that the vectors and other delivery systems (e.g., nucleases or CRISPR-Cas systems), viral particles, and transduced cells of the presently disclosed subject matter are be used to treat, prevent, and/or ameliorate a disease, disorder, or condition of the hematopoietic system in a subject, e.g., a hemoglobinopathy.

As used herein, the term "hemoglobinopathy" or "hemoglobinopathic condition" includes any disorder involving the presence of an abnormal hemoglobin molecule in the blood. Examples of hemoglobinopathies included, but are not limited to, hemoglobin C disease, hemoglobin sickle cell disease (SCD), sickle cell anemia, and thalassemias. Also included are hemoglobinopathies in which a combination of abnormal hemoglobins are present in the blood (e.g., sickle cell/Hb-C disease).

As used herein, "thalassemia" refers to a hereditary disorder characterized by defective production of hemoglobin. Examples of thalassemias include α- and β-thalassemia. β-thalassemias are caused by a mutation in the beta globin chain, and can occur in a major or minor form. In the major form of β-thalassemia, children are normal at birth, but develop anemia during the first year of life. The mild form of β-thalassemia produces small red blood cells and the thalassemias are caused by deletion of a gene or genes from the globin chain. α-thalassemia typically results from deletions involving the HBA1 and HBA2 genes. Both of these genes encode α-globin, which is a component (subunit) of hemoglobin. There are two copies of the HBA1 gene and two copies of the HBA2 gene in each cellular genome. As a result, there are four alleles that produce α-globin. The different types of a thalassemia result from the loss of some or all of these alleles. Hb Bart syndrome, the most severe form of a thalassemia, results from the loss of all four α-globin alleles. HbH disease is caused by a loss of three of the four [alpha]-globin alleles. In these two conditions, a shortage of [alpha]-globin prevents cells from making normal hemoglobin. Instead, cells produce abnormal forms of hemoglobin called hemoglobin Bart (Hb Bart) or hemoglobin H (HbH). These abnormal hemoglobin molecules cannot effectively carry oxygen to the body's tissues. The substitution of Hb Bart or HbH for normal hemoglobin causes anemia and the other serious health problems associated with a thalassemia.

As used herein, the term "sickle cell disease" refers to a group of autosomal recessive genetic blood disorders, which results from mutations in a globin gene and which is characterized by red blood cells that assume an abnormal, rigid, sickle shape. They are defined by the presence of $\beta^S$-gene coding for a β-globin chain variant in which glutamic acid is substituted by valine at amino acid position 6 of the peptide, and second β-gene that has a mutation that allows for the crystallization of HbS leading to a clinical phenotype. As used herein, the term "sickle cell anemia" refers to a specific form of sickle cell disease in patients who are homozygous for the mutation that causes HbS. Other common forms of sickle cell disease include HbS/β-thalassemia, HbS/HbC and HbS/HbD.

In certain embodiments, gene therapy methods of the presently disclosed subject mater are used to treat, prevent, or ameliorate a hemoglobinopathy that is selected from the group consisting of: hemoglobin C disease, hemoglobin sickle cell disease (SCD), sickle cell anemia, hereditary anemia, thalassemia, β-thalassemia, thalassemia major, thalassemia intermedia, α-thalassemia, and hemoglobin H disease. In one non-limiting embodiment, the hemoglobinopathy is β-thalassemia. In another non-limiting embodiment, the hemoglobinopathy is sickle cell anemia In various non-limiting embodiments, vectors or other delivery systems (e.g., nucleases or CRISPR-Cas systems) comprising a presently disclosed expression cassette are administered by direct injection to a cell, tissue, or organ of a subject in need of gene therapy, in vivo. In various other embodiments, cells are transduced in vitro or ex vivo with vectors or other delivery systems (e.g., nucleases or CRISPR-Cas systems) of the presently disclosed subject matter, and optionally expanded ex vivo. The transduced cells are then administered to a subject in need of gene therapy, e.g., within a pharmaceutical formulation disclosed herein.

The presently disclosed subject matter provides a method of providing a transduced cell to a subject. In various non-limiting embodiments, the method comprises administering (e.g., parenterally) one or more cells (a population of cells) transduced with a presently disclosed expression cassette or a vector or another delivery system (e.g., a nuclease or CRISPR-Cas system) comprising such expression cassette to the subject.

The presently disclosed subject matter provides a method of treating a hemoglobinopathy in a subject. In various non-limiting embodiments, the method comprises administering an effective amount of a presently disclosed transduced cell or a population of the presently disclosed transduced cells (e.g., HSCs, embryonic stem cells, or iPSCs) to the subject.

For treatment, the amount administered is an amount effective in producing the desired effect. An effective amount can be provided in one or a series of administrations. An effective amount can be provided in a bolus or by continuous perfusion. An "effective amount" (or "therapeutically effective amount") is an amount sufficient to affect a beneficial or desired clinical result upon treatment. An effective amount can be administered to a subject in one or more doses. In terms of treatment, an effective amount is an amount that is sufficient to palliate, ameliorate, stabilize, reverse or slow the progression of the disease, or otherwise reduce the pathological consequences of the disease. The effective amount is generally determined by the physician on a case-by-case basis and is within the skill of one in the art. Several factors are typically taken into account when determining an appropriate dosage to achieve an effective amount. These factors include age, sex and weight of the subject, the condition being treated, the severity of the condition and the form and effective concentration of the immunoresponsive cells administered.

In one non-limiting example, following administration of one or more of the presently disclosed transduced cells, peripheral blood of the subject is collected and hemoglobin levels is measured. A therapeutically relevant level of hemoglobin is produced following administration of one or more of the presently disclosed transduced cells. Therapeutically relevant level of hemoglobin is a level of hemoglobin that is sufficient (1) to improve or correct anemia, (2) to restore the ability of the subject to produce red blood cells containing normal hemoglobin, (3) to correct ineffective erythropoiesis in the subject, (4) to correct extra-medullary hematopoiesis (e.g., splenic and hepatic extra-medullary hematopoiesis), and/or (5) to reduce iron accumulation, e.g., in peripheral tissues and organs. Therapeutically relevant level of hemoglobin can be at least about 7 g/dL Hb, at least about 7.5 g/dL Hb, at least about 8 g/dL Hb, at least about 8.5 g/dL Hb, at least about 9 g/dL Hb, at least about 9.5 g/dL Hb, at least about 10 g/dL Hb, at least about 10.5 g/dL Hb, at least about 11 g/dL Hb, at least about 11.5 g/dL Hb, at least about 12 g/dL Hb, at least about 12.5 g/dL Hb, at least about 13 g/dL Hb, at least about 13.5 g/dL Hb, at least about 14 g/dL Hb, at least about 14.5 g/dL Hb, or at least about 15 g/dL Hb. Additionally or alternatively, therapeutically relevant level of hemoglobin can be from about 7 g/dL Hb to about 7.5 g/dL Hb, from about 7.5 g/dL Hb to about 8 g/dL Hb, from about 8 g/dL Hb to about 8.5 g/dL Hb, from about 8.5 g/dL Hb to about 9 g/dL Hb, from about 9 g/dL Hb to about 9.5 g/dL Hb, from about 9.5 g/dL Hb to about 10 g/dL Hb, from about 10 g/dL Hb to about 10.5 g/dL Hb, from about 10.5 g/dL Hb to about 11 g/dL Hb, from about 11 g/dL Hb to about 11.5 g/dL Hb, from about 11.5 g/dL Hb to about 12 g/dL Hb, from about 12 g/dL Hb to about 12.5 g/dL Hb, from about 12.5 g/dL Hb to about 13 g/dL Hb, from about 13 g/dL Hb to about 13.5 g/dL Hb, from about 13.5 g/dL Hb to about 14 g/dL Hb, from about 14 g/dL Hb to about 14.5 g/dL Hb, from about 14.5 g/dL Hb to about 15 g/dL Hb, from about 7 g/dL Hb to about 8 g/dL Hb, from about 8 g/dL Hb to about 9 g/dL Hb, from about 9 g/dL Hb to about 10 g/dL Hb, from about 10 g/dL Hb to about 11 g/dL Hb, from about 11 g/dL Hb to about 12 g/dL Hb, from about 12 g/dL Hb to about 13 g/dL Hb, from about 13 g/dL Hb to about 14 g/dL Hb, from about 14 g/dL Hb to about 15 g/dL Hb, from about 7 g/dL Hb to about 9 g/dL Hb, from about 9 g/dL Hb to about 11 g/dL Hb, from about 11 g/dL Hb to about 13 g/dL Hb, or from about 13 g/dL Hb to about 15 g/dL Hb. In certain embodiments, the therapeutically relevant level of hemoglobin is maintained in the subject for at least about 6 months, for at least about 12 months (or 1 year), for at least about 24 months (or 2 years). In certain embodiments, the therapeutically relevant level of hemoglobin is maintained in the subject for up to about 6 months, for up to about 12 months (or 1 year), for up to about 24 months (or 2 years). In certain embodiments, the therapeutically relevant level of hemoglobin is maintained in the subject for about 6 months, for about 12 months (or 1 year), for about 24 months (or 2 years). In certain embodiments, the therapeutically relevant level of hemoglobin is maintained in the subject for from about 6 months to about 12 months (e.g., from about 6 months to about 8 months, from about 8 months to about 10 months, from about 10 months to about 12 months), from about 12 months to about 18 months (e.g., from about 12 months to about 14 months, from about 14 months to about 16 months, or from about 16 months to about 18 months), or from about 18 months to about 24 months (e.g., from about 18 months to about 20 months, from about 20 months to about 22 months, or from about 22 months to about 24 months).

In certain embodiments, the method comprises administering one or more cells transduced with a recombinant vector comprising a presently disclosed expression cassette as described above. The vector copy number of the recombinant vector in the cells that provide for the therapeutically relevant level of hemoglobin (e.g., 9-10 g/dL) in the subject is from about 0.5 to about 2, from about 0.5 to about 1, or from about 1 to about 2 vector copy number per cell. In certain embodiments, the vector copy number of the presently disclosed vector is about 0.5, about 0.6, about 0.7, about 0.8, about 0.9, about 1.0, about 1.1, about 1.2, about 1.3, about 1.4, about 1.5, about 1.6, about 1.7, about 1.8, about 1.9, or about 2.0 vector copy number per cell.

In certain embodiments, the subject lacks a human leukocyte antigen (HLA)-matched donor. In certain embodiments, the transduced cell is from the same subject. In one embodiment, the transduced cell is from bone marrow of the same subject. Thus, administration of the transduced cells do not incur the risk of graft-versus host disease in the subject. The method does not require immune suppression to prevent graft rejection, e.g., the method does not comprise administering an immunosuppressive agent to the subject.

The present disclosed subject matter also provides a method of increasing the proportion of red blood cells or erythrocytes compared to white blood cells or leukocytes in a subject. In various non-limiting embodiments, the method comprises administering an effective amount of a presently disclosed transduced cell or a population of the presently disclosed transduced cells (e.g., HSCs, embryonic stem cells, or iPSCs) to the subject, wherein the proportion of red blood cell progeny cells of the hematopoietic stem cells are increased compared to white blood cell progeny cells of the hematopoietic stem cells in the subject.

Without wishing to be bound to any particular theory, an important advantage provided by the expression cassette, vectors and other delivery systems (e.g., nucleases and CRISPR-Cas systems), compositions, and methods of the presently disclosed subject is the high efficacy of globin gene therapy that can be achieved by administering populations of cells comprising lower percentages of transduced cells compared to existing methods. This provides important safety advantages associated with reduced chances of deleterious mutation, transformation, or oncogene activation of cellular genes in transduced cells. The transduced cells can be administered as part of a bone marrow or cord blood transplant in an individual that has or has not undergone bone marrow ablative therapy.

One consideration concerning the therapeutic use of the presently disclosed cells transduced with the expression cassette described herein ("transduced cells") is the quantity of cells necessary to achieve an optimal effect. The quantity of transduced cells to be administered will vary for the subject being treated. In one embodiment, from about $1\times10^4$ to about $1\times10^5$ cells/kg, from about $1\times10^5$ to about $1\times10^6$ cells/kg, from about $1\times10^6$ to about $1\times10^7$ cells/kg, from about $1\times10^7$ to about $1\times10^8$ cells/kg, from about $1\times10^8$ to about $1\times10^9$ cells/kg, or from about $1\times10^9$ to about $1\times10^{10}$ cells/kg of the presently disclosed transduced cells are administered to a subject. More effective cells may be administered in even smaller numbers. In some embodiments, at least about $1\times10^8$ cells/kg, at least about $2\times10^8$ cells/kg, at least about $3\times10^8$ cells/kg, at least about $4\times10^8$ cells/kg, or at least about $5\times10^8$ cells/kg of the presently disclosed transduced cells are administered to a subject. The precise determination of what would be considered an effective dose may be based on factors individual to each subject, including their size, age, sex, weight, and condition of the particular subject. Dosages can be readily ascertained by those skilled in the art from this disclosure and the knowledge in the art.

In various embodiments, the expression cassettes, vectors and other delivery systems (nucleases and CRISPR-Cas systems), compositions, and methods of the presently disclosed subject matter offer improved methods of gene therapy using ex vivo gene therapy and autologous transplantation. Transplantation of cells transduced with the expression cassette or into subjects having a hemoglobinopathy results in long-term correction of the disease.

One or more presently disclosed transduced cells can be administered by any methods known in the art, including, but not limited to, parenteral administration (e.g., intramuscular administration, intravenous administration, subcutaneous administration, or intraperitoneal administration), spinal administration, and epidermal administration. In one non-limiting embodiment, one or more transduced cells are delivered to a subject intravenously. One or more presently disclosed transduced cells can be administered by injection, infusion, or implantation. In one non-limiting embodiment, one or more transduced cells are administered by injection. In another non-limiting embodiment, one or more transduced cells are administered by intravenous injection.

The subjects can have an advanced form of disease, in which case the treatment objective can include mitigation or reversal of disease progression, and/or amelioration of side effects. The subjects can have a history of the condition, for which they have already been treated, in which case the therapeutic objective will typically include a decrease or delay in the risk of recurrence.

VII. KITS

The presently disclosed subject matter provides kits for the treatment or prevention of a hemoglobinopathy. In one embodiment, the kit comprises a therapeutic or prophylactic composition containing an effective amount of a cell transduced with the presently disclosed expression cassette in unit dosage form. In one non-limiting embodiment, the kit comprises one or more expression cassettes disclosed herein. In certain embodiments, the kit comprises one or more vectors comprising an expression cassette disclosed herein. In some embodiments, the kit comprises a sterile container, which can be a box, an ampule, a bottle, a vial, a tube, a bag, a pouch, a blister-pack, or other suitable container forms known in the art. Such containers can be made of plastic, glass, laminated paper, metal foil, or other materials suitable for holding medicaments.

If desired, the transduced cell is provided together with instructions for administering the cell to a subject having or at risk of developing a hemoglobinopathy. The instructions will generally include information about the use of the composition for the treatment or prevention of a hemoglobinopathy. In other embodiments, the instructions include at least one of the following: description of the therapeutic agent; dosage schedule and administration for treatment or prevention of a hemoglobinopathy or symptoms thereof; precautions; warnings; indications; counter-indications; overdosage information; adverse reactions; animal pharmacology; clinical studies; and/or references. Alternatively or additionally, the kit can include instructions for transducing a cell with the one or more expression cassettes and/or vectors comprising such expression cassettes. The instructions may be printed directly on the container (when present), or as a label applied to the container, or as a separate sheet, pamphlet, card, or folder supplied in or with the container.

EXAMPLES

The practice of the presently disclosed subject matter employs, unless otherwise indicated, conventional techniques of molecular biology (including recombinant techniques), microbiology, cell biology, biochemistry and immunology, which are well within the purview of the skilled artisan. Such techniques are explained fully in the literature, such as, "Molecular Cloning: A Laboratory Manual", second edition (Sambrook, 1989); "Oligonucleotide Synthesis" (Gait, 1984); "Animal Cell Culture" (Freshney, 1987); "Methods in Enzymology" "Handbook of Experimental Immunology" (Weir, 1996); "Gene Transfer Vectors for Mammalian Cells" (Miller and Calos, 1987); "Current Protocols in Molecular Biology" (Ausubel, 1987); "PCR: The Polymerase Chain Reaction", (Mullis, 1994); "Current Protocols in Immunology" (Coligan, 1991). These techniques are applicable to the production of the polynucleotides and polypeptides of the presently disclosed subject matter, and, as such, may be considered in making and practicing the presently disclosed subject matter. Particularly useful techniques for particular embodiments will be discussed in the sections that follow.

The following examples are put forth so as to provide those of ordinary skill in the art with a complete disclosure and description of how to make and use the expression cassettes, vectors, delivery systems, and therapeutic methods of the presently disclosed subject matter, and are not intended to limit the scope of what the inventors regard as their invention.

Example 1: Discovery of Novel Insulators

The problems created by insertional mutagenesis of viral vectors are widely known (Nienhuis (2013), Baum et al. (2006), Nienhuis et al. (2006)) as is the evidence that the risks of genotoxicity can be reduced by the use of chromatin insulators (Arumugam et al. (2007), Emery (2011), Evans-Galea et al. (2007), Rivella et al. (2000), Emery et al. (2000), Emery et al. (2002), Yannaki et al. (2002), Hino et al. (2004), Ramezani et al. (2003), Ramezani et al. (2008)). Approaches allowing the efficient identification of enhancer blocking insulators in the human genome have been developed. These new insulators are short, on the average 150 bp, and they do not affect adversely the titers of viral vectors and they are several times more powerful than the insulator cHS4. Genomic approaches were used to discover the most powerful enhancer blocker and barrier insulators of the human genome. For gene therapy of the hemoglobinopathies, powerful enhancers are required to achieve therapeutic levels of globin gene expression. Powerful insulators may thus provide one means to protect the genomic environment from the powerful enhancers of the integrating vectors.

Several studies have demonstrated the ability of the cHS4 insulator to reduce position-effect silencing of gammaretroviral vectors (Evans-Galea et al. (2007), Rivella et al. (2000), Emery et al. (2000), Emery et al. (2002), Yannaki et al. (2002), Hino et al. (2004), Ramezani et al. (2006), Yao et al. (2003), Nishino et al. (2006), Aker et al. (2007), Li and Emery (2008)), and lentiviral vectors (Evans-Galea et al. (2007), Ramezani et al. (2003), Puthenveetil et al. (2004), Arumugam et al. (2007), Bank et al. (2005), Aker et al. (2007), Ma et al. (2003), Chang et al. (2005), Pluta et al. (2005)). Those studies that were appropriately designed demonstrated that inclusion of the 1.2 kb version of the cHS4 insulator increased the likelihood and/or consistency of vector transgene expression in at least some settings (Arumugam et al. (2007), Evans-Galea et al. (2007), Emery et al. (2002), Yannaki et al. (2002), Hino et al. (2004), Ramezani et al. (2006), Aker et al. (2007), Li and Emery (2008), Pluta et al. (2005), Jakobsson et al. (2004)). Nevertheless, the degree of protection afforded by the cHS4 insulator is far from complete. In addition, the inclusion of the 1.2 Kb cHS4 can adversely affect vector titers while the smallest cHS4 core has been proven ineffective (Aker et al. (2007), Jakobsson et al. (2004)).

Effects on genotoxicity were tested using an in vivo assay based on quantitation of tumor formation in mice. Vectors insulated by insulator A1 decreased tumor formation induced by random vector integration in hematopoietic chimeras compared to mice that received uninsulated or cHS4-insulated controls.

To assess effects on vector titers, insulator A1 was introduced into the double-copy region of a third-generation lentiviral vector expressing GFP from a constitutive package promoter, and the viral titers and GFP expression were measured. Insulator A1 did not affect adversely vector GFP expression.

Figure 5:
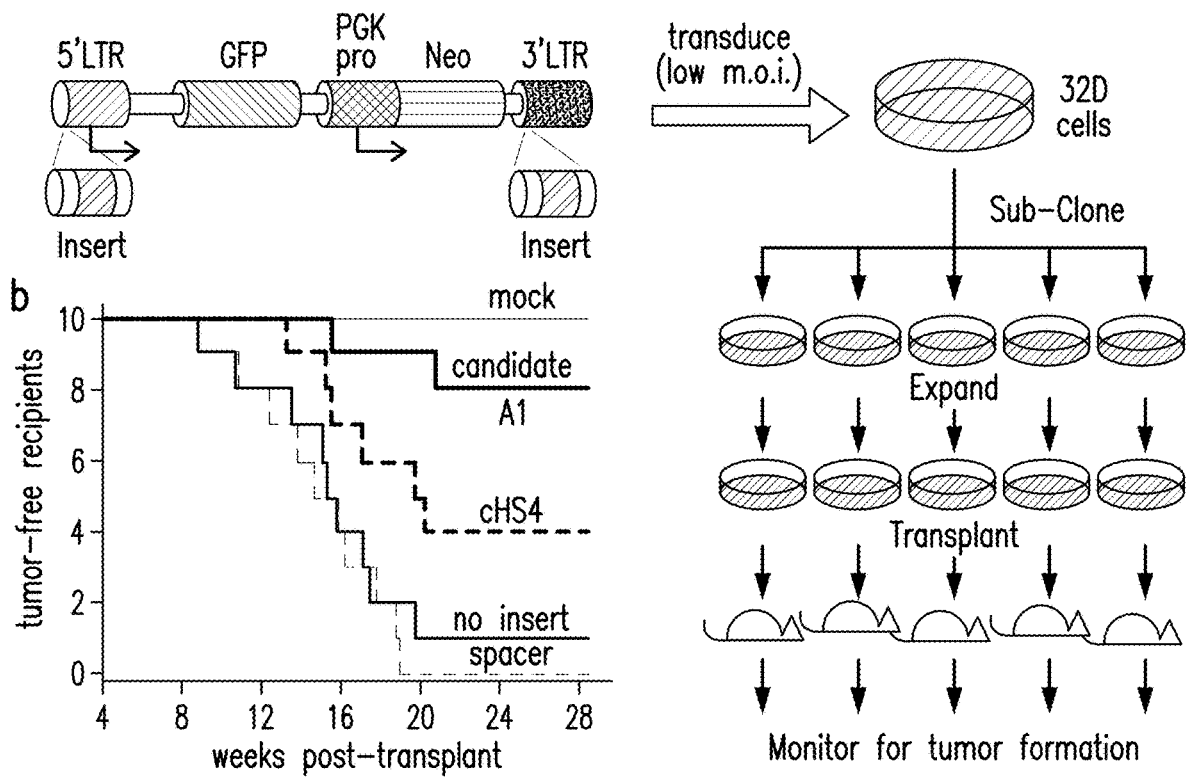
FIGS. 5A-C represent the genotoxicity of insulator A1. (A) demonstrate the gammaretroviral vector genotoxicity assay used. (B) notice the increased survival of mice receiving 32D cells transduced with insulated gammaretroviral vector. Also notice the results obtained with cHS4 and with the uninsulated control. (C) show that insulator A1 decreased the risk of genotoxicity.

In the in vivo genotoxicity assay, a cell line transduced with gammaretroviral vectors produced tumors after transplantation in mice and allowed quantitation of genotoxic effects by measuring rates of tumor free survival. Effects of an insulator on genotoxicity were quantitated by the number of tumors formed in the mice and the rates of tumor free survival. Insulator A1 was inserted in the proximal portion of the 3' LTR, from which it is copied into the 5' LTR during reverse transcription and vector integration. The resulting topology places copies of the insulator between the genomic regions located 5' and 3' of the integrated provirus and enhancer activity from the 5' viral LTR and internal Pgk promoter, but does not contain the enhancer in the 3' LTR. This can decrease genotoxicity thus resulting in decreased tumor formation and increased survival of the animals. Gamma-retroviral reporter vectors flanked with insulator A1 or control regions were used to transduce the growth factor-dependent cell line 32D, and 10 independent sub-pools for each vector were transplanted into syngeneic C3H/HeJ mice. All 10 mice transplanted with mock-transduced cells remained free of 32D cell-derived tumors, while nearly all mice transplanted with 32D cells transduced with vectors containing no inserts or a 790 bp neutral spacer developed tumors within a median of 16 weeks (FIG. 5B). Flanking this vector with the cHS4 insulator delayed the onset of tumor formation by several weeks, and reduced the frequency of animals that developed tumors to 6 of 10. In contrast, only two of 10 animals developed tumors following transplantation with 32D cells transduced with the vector flanked with insulator A1 (FIG. 5B). The frequency of animals with tumors and the number of vector transduction events in the original sub-pools suggested that flanking the vector with insulator A1 reduced the overall rate of tumor formation 12-fold, from 46.9 tumors per $10^5$ provirus to 3.9 tumors per $10^5$ provirus (FIG. 5C). In comparison, the cHS4 insulator reduced the overall rate of tumor formation 2.8-fold (to 16.9 tumors per $10^5$ provirus), while the neutral spacer had no statistically discernable effect on the rate of tumor formation. These results indicate that the discovered enhancer blocking insulators can decrease substantially the risks of insertional mutagenesis and genotoxicity.

Example 2: Characterization of Globin Vectors Comprising at Least One Insulator

A presently disclosed expression cassette (designated as "Expression Cassette 1"; as shown in FIG. 1), which comprises insulator A1, and a human $\beta^A$-globin gene encoding a threonine to glutamine mutation at codon 87 ($\beta^{A-T87Q}$) operably linked to a β-globin LCR region comprising a HS2 region having the nucleotide sequence set forth in SEQ ID NO:9, a HS3 region having the nucleotide sequence set forth in SEQ ID NO:5, and a HS4 region having the nucleotide sequence set forth in SEQ ID NO:7, was generated. The rationale for using the variant β chain ($\beta^A$) is to facilitate the detection of the vector-encoded β-globin gene, distinguishing it from endogenous or transfused beta chains. The glutamine (GLN) residue at position 87 in the γ-globin chain augments the anti-sickling activity of the gamma chain relative to the β chain, while preserving adult oxygen-binding characteristics of the β chain (Nagel et al. (1979)). In Vector 1, a point mutation altering codon 87 ($\beta^{A-T87Q}$, or β87) replaces the normal threonine with glutamine and augments anti-sickling activity of the vector-encoded β chain. This β87 chain has been safely used in a patient with HbE-thalassemia (Cavazzana-Calvo et al. (2010)).

Figure 6:
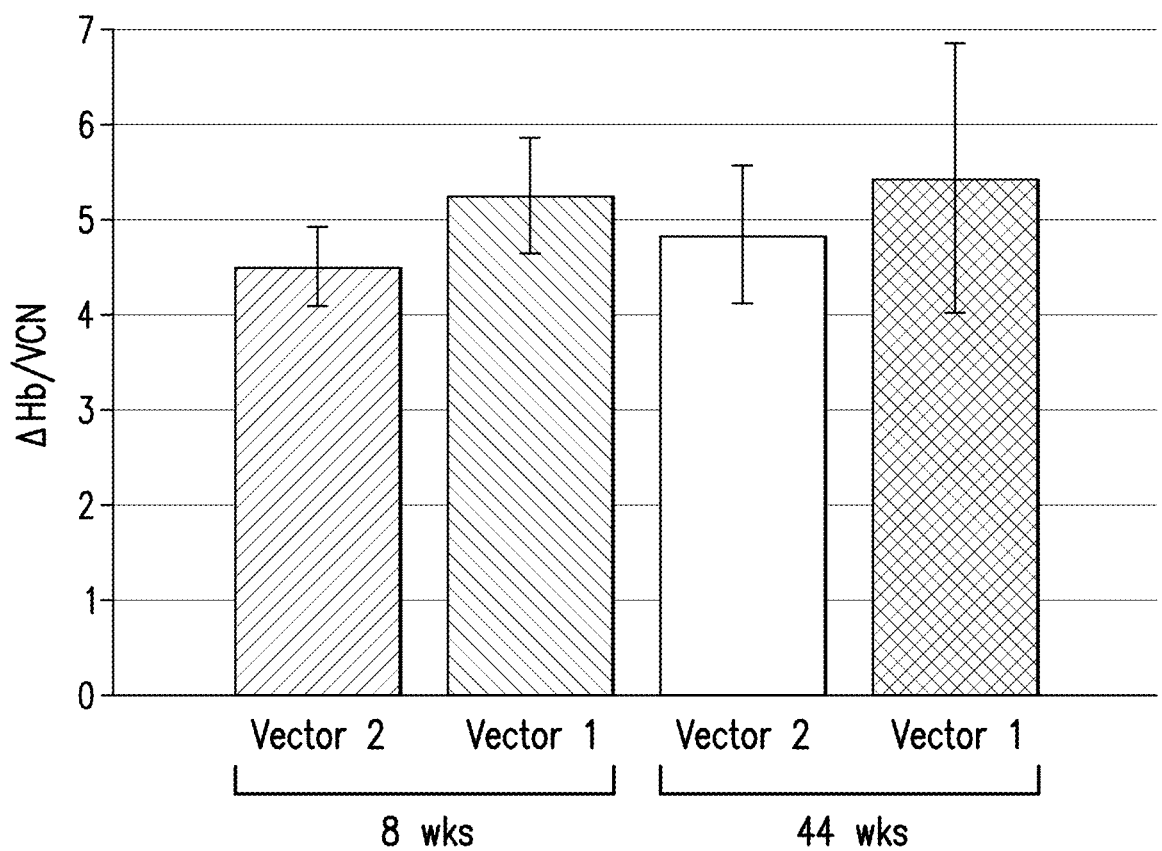
FIG. 6 represents normalized β chain expression in thalassemic $Hbb^{th3/+}$ mice 8 and 44 weeks post-treatment.

Expression cassette 1 was incorporated or introduced to a lentivirus vector (designated as "Vector 1"). Vector 1 was introduced in bone marrow cells of C57BL/6-Hbb th3/+ mice and transplanted to syngeneic lethally irradiated recipients as previously described (May et al. (2000), May et al. (2002), Lisowski et al. (2007)). The vector titer of V1 was comparable to that of a lentivirus vector comprising an expression cassette lacking insulator A1. The β-globin expression of Vector 1 was compared to that of a lentivirus vector (designated as "Vector 2") comprising an expression cassette that lacks an insulator and comprises a wild human β-globin gene operably linked to a β-globin LCR region comprising a HS2 region having the nucleotide sequence set forth in SEQ ID NO:9, a HS3 region having the nucleotide sequence set forth in SEQ ID NO:5, and a HS4 region having the nucleotide sequence set forth in SEQ ID NO:6. In comparison to Vector 2, β-globin expression of Vector 1 normalized to vector copy was equivalent or slightly increased, suggesting an added benefit for in vivo expression provided by the flanking barrier elements, as shown in FIG. 6.

Example 3: Evaluation of Enhancer Activity in Non-Erythroid K562 Cells

Figure 7:
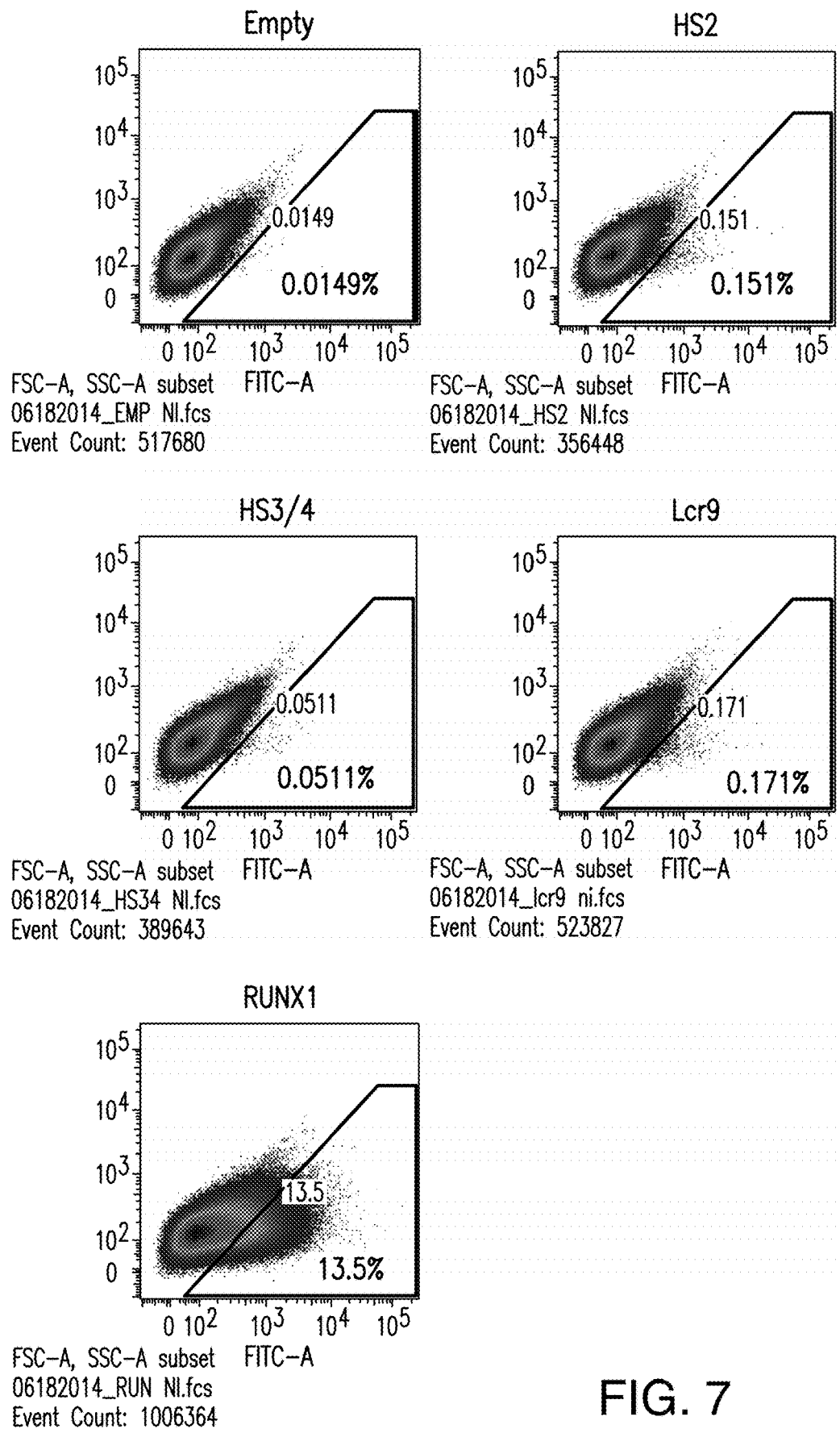
FIG. 7 represents the evaluation of enhancer activity in non-erythroid K562 cells.

The enhancer activity of HS2 was evaluated in Non-erythroid K562 Cells. As shown in FIG. 7, GFP expression in K562 cells transduced with vectors driven by a minimal promoter linked to no enhancer ("Empty", HS2, HS3-4, HS2-3-4 or the runx1 enhancer used as positive control ("RUNX1"). Background expression was on the order or 0.01% ("empty), but increased over 10-fold with HS2-3-4 ("Lcr9", 0.17%). This enhancement was mostly due to HS2

(0.15%) but not HS3-4 (0.05%). All cell lines were comparably transduced (mean vector copy number 2.5). The results support that HS2 but not HS3-HS4 may pose an oncogenic risk in non-erythroid hematopoietic stem and progenitor cells.

Example 4: Novel Erythroid-Specific Enhancers

As shown in FIGS. 8 and 9, five erythroid-specific enhancers were substituted for HS2: ALAS Intron 1, ALAS Intron 8, BLVRB, PPDX, and Spectrin-alpha. The inventors have shown that all these five enhancers are powerful enhancers, and lack enhancer activity in non-erythroid tissues, and do not reduce the vector titer.

Example 5: Increasing Globin Lentiviral Vector Production Through 3' LTR Modifications An essential feature of therapeutic globin vectors is to achieve a high titer, sufficient for effective transduction of patient cells. By virtue of their large cargo, comprising a gene, promoter, enhancers and/or LCR elements, globin lentiviral vectors inherently have low titer, complicating their manufacture and limiting their clinical use. This problem is further compounded by the incorporation of additional genomic elements such as an insulator, which further increase the size of the vector.

Figure 10A:
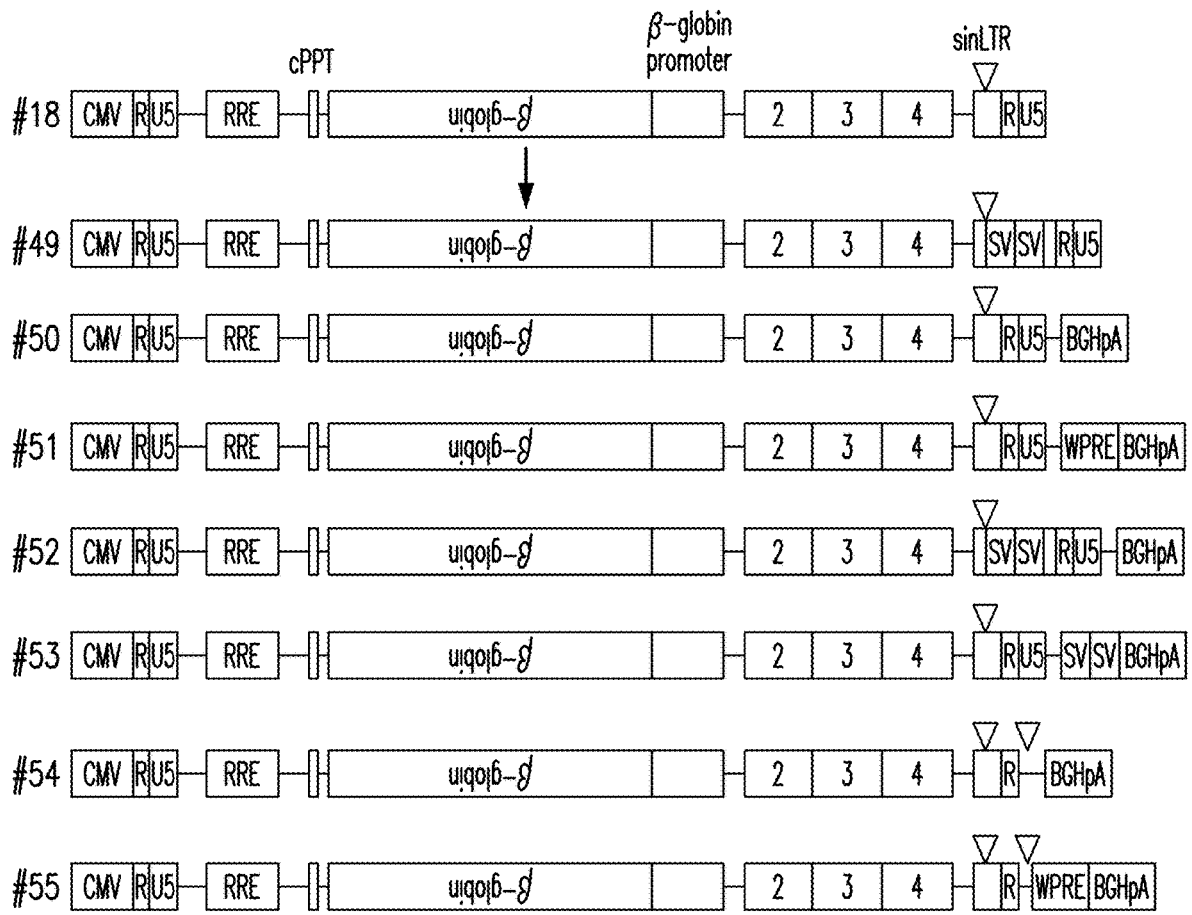
FIGS. 10A-B depict various recombinant vectors comprising the presently disclosed expression cassettes.
Figure 10B:
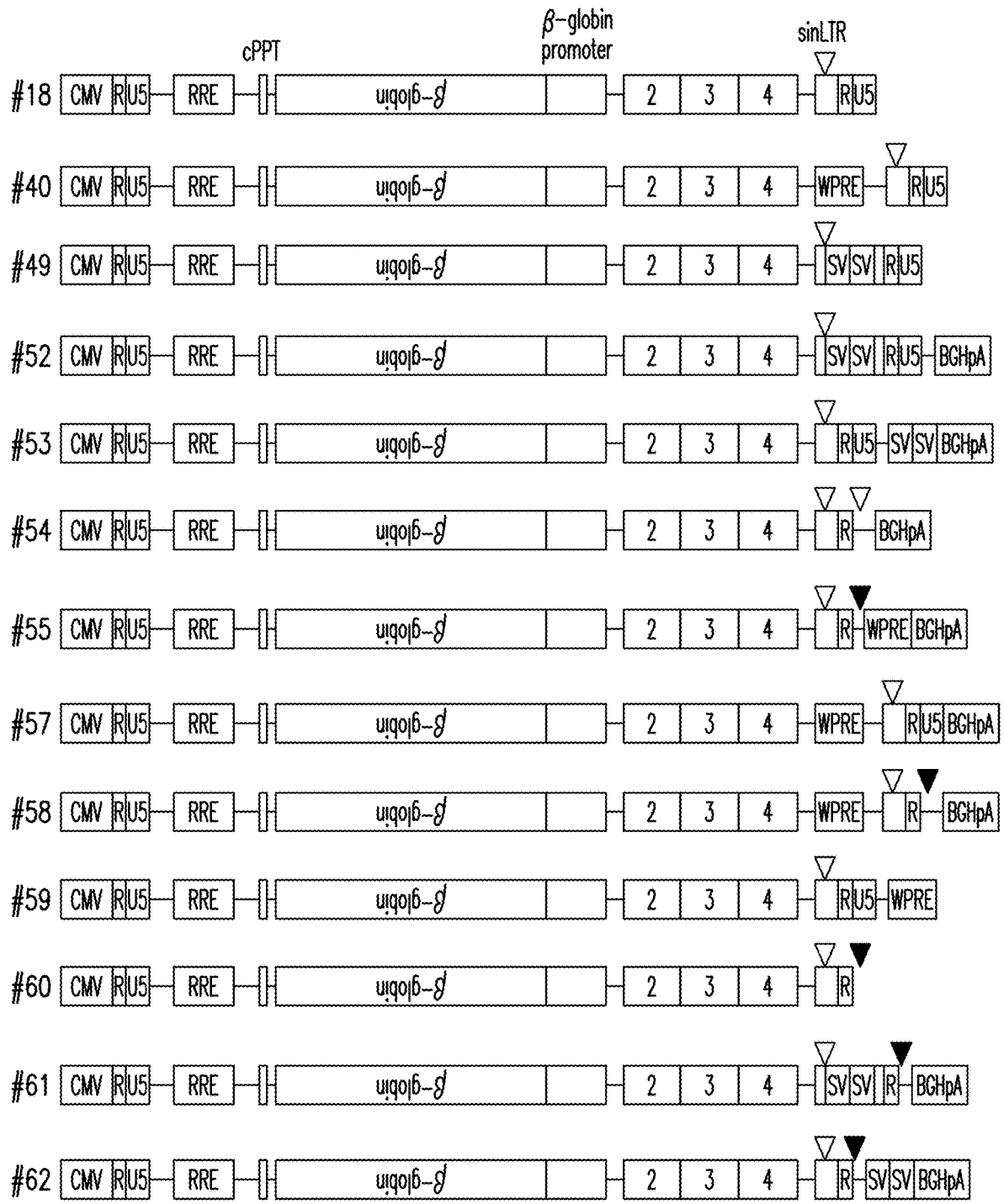

The inventors explored different modifications of the 3' long terminal repeat (LTR) of globin vectors to increase the titer of globin vectors. Over 62 variations were evaluated, numbered 1 through 62, modeled on a lentivirus vector comprising a human β-globin gene operably linked to a β-globin LCR region comprising a HS2 region having the nucleotide sequence set forth in SEQ ID NO:9, a HS3 region having the nucleotide sequence set forth in SEQ ID NO:5, and a HS4 region having the nucleotide sequence set forth in SEQ ID NO:7. In other words, all of Vectors #1 through Vector 62 comprise a β-globin LCR region comprising a HS2 region having the nucleotide sequence set forth in SEQ ID NO:9, a HS3 region having the nucleotide sequence set forth in SEQ ID NO:5, and a HS4 region having the nucleotide sequence set forth in SEQ ID NO:7. Vector #18 served as a baseline, comprising a standard U3 deletion in the 3'LTR. Vector #1 (not depicted) comprised a full, i.e., wild-type LTR, which cannot be used clinically. Modifications to the 3'LTR are depicted in FIGS. 10A and 10B, and their titers shown in FIGS. 11 and 12 (the Y axis shows the vector copy number of vector stocks manufactured and tested under strictly identical conditions). Titrations were measured in triple replicas, performed in parallel by two operators, and repeated in multiple experiments.

Figure 11:
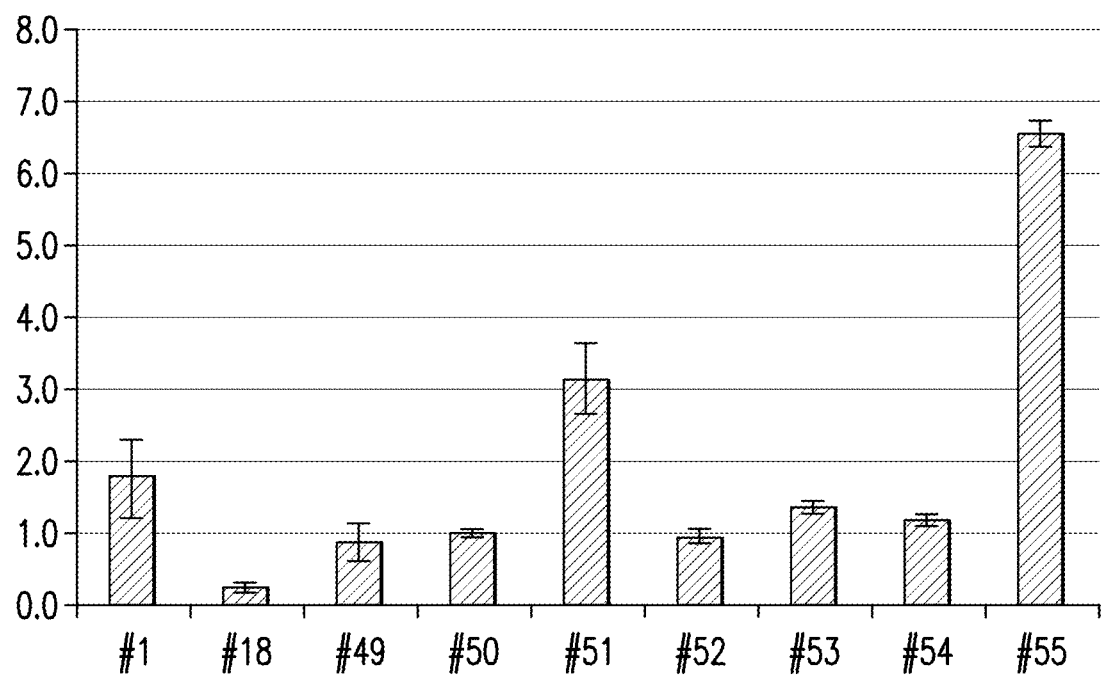
FIG. 11 represents the titer of the recombinant vectors comprising the presently disclosed expression cassettes.
Figure 12:
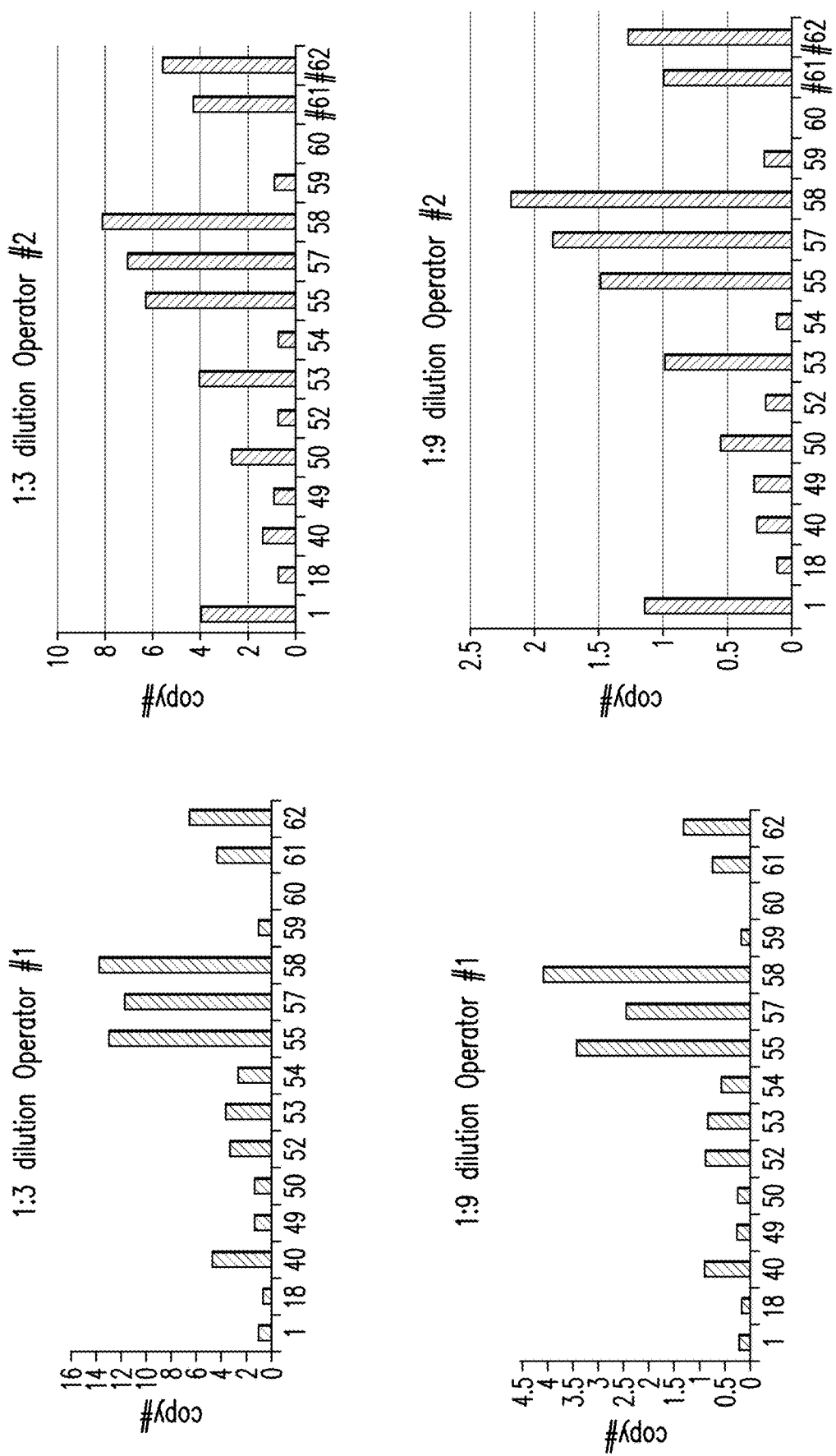
FIG. 12 represents the titer of the recombinant vectors comprising the presently disclosed expression cassettes.

As shown in FIGS. 11 and 12, Vector #55 repeatedly showed a higher titer. This vector comprises a Woodchuck hepatitis post-regulatory element (WPRE) and a bovine growth hormone polyadenylation signal 3' to the R region in the 3' LTR. The WPRE element is therefore not transferred to the transduced cells.

The incorporation of these elements for enhancing the production of globin lentiviral vectors is essential to yield higher titers and hence for the clinical usefulness of the vectors described in this application.

REFERENCES

1. Weatherall, D. J. & Clegg, J. B. The Thalassemia Syndrome. *Blackwell Scientific Oxford* (1981).
2. Stamatoyannopoulos, G., Nienhuis, A. W., Majerus, P. & Varmus, H. The Molecular Basis of Blood Diseaes. WB Saunders, Philadelphia (1994).
3. Weatherall, D. J. Phenotype-genotype relationships in monogenic disease: lessons from the thalassaemias. *Nat Rev Genet* 2, 245-255. (2001).
4. Steinberg, M. H., Forget, B. G., Higgs, D. R. & Nagel, R. L. *Molecular Mechanism of β Thalassemia*; Bernard G. Forget, (Cambridge University Press, Cambridge, UK, 2001).
5. Cooley, T. B. & Lee, P. A series of cases of splenomegaly in children with anemia and peculiar bone changes. *Trans. Am. Pediatr. Soc.* 37, 29 (1925).
6. Giardina, P. J. & Grady, R. W. Chelation therapy in beta-thalassemia: an optimistic update. *Semin Hematol* 38, 360-366. (2001).
7. Giardini, C. & Lucarelli, G. Bone marrow transplantation in the treatment of thalassemia. *Current opinion in hematology* 1, 170-176. (1994).
8. Boulad, F., Giardina, P., Gillio, A., Kernan, N., Small, T., Brochstein, J., Van Syckle, K., George, D., Szabolcs, P. & O'Reilly, R. J. Bone marrow transplantation for homozygous beta-thalassemia. The Memorial Sloan-Kettering Cancer Center experience. *Ann N Y Acad Sci* 850, 498-502. (1998).
9. Lucarelli, G., Clift, R. A., Galimberti, M., Angelucci, E., Giardini, C., Baronciani, D., Polchi, P., Andreani, M., Gaziev, D., Erer, B., Ciaroni, A., D'Adamo, F., Albertini, F. & Muretto, P. Bone marrow transplantation in adult thalassemic patients. *Blood* 93, 1164-1167. (1999).
10. Tisdale, J. & Sadelain, M. Toward gene therapy for disorders of globin synthesis. *Semin Hematol* 38, 382-392 (2001).
11. Pauling, L., Itano, H. A., Singer, S. J. & Wells, I. C. Sickle cell anemia, a molecular disease. *Science* 110, 543-546 (1949).
12. Swank, R. A. & Stamatoyannopoulos, G. Fetal gene reactivation. *Curr Opin Genet Dev* 8, 366-370 (1998).
13. Platt, O. S., Orkin, S. H., Dover, G., Beardsley, G. P., Miller, B. & Nathan, D. G. Hydroxyurea enhances fetal hemoglobin production in sickle cell anemia. *J Clin Invest* 74, 652-656. (1984).
14. Charache, S., Dover, G. J., Moore, R. D., Eckert, S., Ballas, S. K., Koshy, M., Milner, P. F., Orringer, E. P., Phillips, G., Jr., Platt, O. S. & et al. Hydroxyurea: effects on hemoglobin F production in patients with sickle cell anemia. *Blood* 79, 2555-2565. (1992).
15. Atweh, G. F. & Loukopoulos, D. Pharmacological induction of fetal hemoglobin in sickle cell disease and beta-thalassemia. *Semin Hematol* 38, 367-373. (2001).
16. Perrine, S. P., Castaneda, S. A., Boosalis, M. S., White, G. L., Jones, B. M. & Bohacek, R. Induction of fetal globin in beta-thalassemia: Cellular obstacles and molecular progress. *Ann N Y Acad Sci* 1054, 257-265 (2005).
17. Stamatoyannopoulos, G. Prospects for developing a molecular cure for thalassemia. *Hematology* 10 Suppl 1, 255-257 (2005).
18. Vermylen, C., Cornu, G., Ferster, A., Brichard, B., Ninane, J., Ferrant, A., Zenebergh, A., Maes, P., Dhooge, C., Benoit, Y., Beguin, Y., Dresse, M. F. & Sariban, E. Haematopoietic stem cell transplantation for sickle cell anaemia: the first 50 patients transplanted in Belgium. *Bone Marrow Transplant* 22, 1-6 (1998).
19. Luzzatto, L. & Goodfellow, P. Sickle cell anaemia. A simple disease with no cure. *Nature* 337, 17-18 (1989).

20. Sadelain, M. Genetic treatment of the haemoglobinopathies: recombinations and new combinations. *Br J Haematol* 98, 247-253 (1997).
21. Sadelain, M., Boulad, F., Galanello, R., Giardina, P., Locatelli, F., Maggio, A., Rivella, S., Riviere, I. & Tisdale, J. Therapeutic options for patients with severe beta-thalassemia: the need for globin gene therapy. *Hum Gene Ther* 18, 1-9 (2007).
22. Borgna-Pignatti, C., Rugolotto, S., De Stefano, P., Zhao, H., Cappellini, M. D., Del Vecchio, G. C., Romeo, M. A., Forni, G. L., Gamberini, M. R., Ghilardi, R., Piga, A. & Cnaan, A. Survival and complications in patients with thalassemia major treated with transfusion and deferoxamine. *Haematologica* 89, 1187-1193 (2004).
23. Telfer, P. T., Warburton, F., Christou, S., Hadjigavriel, M., Sitarou, M., Kolnagou, A. & Angastiniotis, M. Improved survival in thalassemia major patients on switching from desferrioxamine to combined chelation therapy with desferrioxamine and deferiprone. *Haematologica* 94, 1777-1778 (2009).
24. Ladis, V., Chouliaras, G., Berdoukas, V., Chatziliami, A., Fragodimitri, C., Karabatsos, F., Youssef, J., Kattamis, A. & Karagiorga-Lagana, M. Survival in a large cohort of Greek patients with transfusion-dependent beta thalassaemia and mortality ratios compared to the general population. *European journal of haematology* 86, 332-338 (2011).
25. Mancuso, A., Sciarrino, E., Renda, M. C. & Maggio, A. A prospective study of hepatocellular carcinoma incidence in thalassemia. *Hemoglobin* 30, 119-124 (2006).
26. Persons, D. A. & Tisdale, J. F. Gene therapy for the hemoglobin disorders. *Semin Hematol* 41, 279-286 (2004).
27. Sadelain, M. Recent advances in globin gene transfer for the treatment of beta-thalassemia and sickle cell anemia. *Current opinion in hematology* 13, 142-148 (2006).
28. May, C., Rivella, S., Callegari, J., Heller, G., Gaensler, K. M., Luzzatto, L. & Sadelain, M. Therapeutic haemoglobin synthesis in beta-thalassaemic mice expressing lentivirus-encoded human beta-globin. *Nature* 406, 82-86 (2000).
29. May, C., Rivella, S., Chadburn, A. & Sadelain, M. Successful treatment of murine beta-thalassemia intermedia by transfer of the human beta-globin gene. *Blood* 99, 1902-1908 (2002).
30. Rivella, S., May, C., Chadburn, A., Riviere, I. & Sadelain, M. A novel murine model of Cooley anemia and its rescue by lentiviral-mediated human beta-globin gene transfer. *Blood* 101, 2932-2939 (2003).
31. Sadelain, M., Boulad, F., Lisowki, L., Moi, P. & Riviere, I. Stem cell engineering for the treatment of severe hemoglobinopathies. *Curr Mol Med* 8, 690-697 (2008).
32. Bank, A., Dorazio, R. & Leboulch, P. A phase I/II clinical trial of beta-globin gene therapy for beta-thalassemia. *Ann N Y Acad Sci* 1054, 308-316 (2005).
33. Cavazzana-Calvo, M., Payen, E., Negre, O., Wang, G., Hehir, K., Fusil, F., Down, J., Denaro, M., Brady, T., Westerman, K., Cavallesco, R., Gillet-Legrand, B., Caccavelli, L., Sgarra, R., Maouche-Chretien, L., Bernaudin, F., Girot, R., Dorazio, R., Mulder, G. J., Polack, A., Bank, A., Soulier, J., Larghero, J., Kabbara, N., Dalle, B., Gourmel, B., Socie, G., Chretien, S., Cartier, N., Aubourg, P., Fischer, A., Cornetta, K., Galacteros, F., Beuzard, Y., Gluckman, E., Bushman, F., Hacein-Bey-Abina, S. & Leboulch, P. Transfusion independence and HMGA2 activation after gene therapy of human beta-thalassaemia. *Nature* 467, 318-322 (2010).
34. Braun, C. J., Bortug, K., Paruzynski, A., Witzel, M., Schwarzer, A., Rothe, M., Modlich, U., Beier, R., Gohring, G., Steinemann, D., Fronza, R., Ball, C. R., Haemmerle, R., Naundorf, S., Kuhlcke, K., Rose, M., Fraser, C., Mathias, L., Ferrari, R., Abboud, M. R., Al-Herz, W., Kondratenko, I., Marodi, L., Glimm, H., Schlegelberger, B., Schambach, A., Albert, M. H., Schmidt, M., von Kalle, C. & Klein, C. Gene therapy for Wiskott-Aldrich syndrome—long-term efficacy and genotoxicity. *Sci Transl Med* 6, 227ra233 (2014).
35. Chang, A. H. & Sadelain, M. The genetic engineering of hematopoietic stem cells: the rise of lentiviral vectors, the conundrum of the ltr, and the promise of lineage-restricted vectors. *Mol Ther* 15, 445-456 (2007).
36. Pawliuk, R., Westerman, K. A., Fabry, M. E., Payen, E., Tighe, R., Bouhassira, E. E., Acharya, S. A., Ellis, J., London, I. M., Eaves, C. J., Humphries, R. K., Beuzard, Y., Nagel, R. L. & Leboulch, P. Correction of sickle cell disease in transgenic mouse models by gene therapy. *Science* 294, 2368-2371 (2001).
37. Emery, D. W., Chen, H., Li, Q. & Stamatoyannopoulos, G. Development of a condensed locus control region cassette and testing in retrovirus vectors for A gamma-globin. *Blood Cells Mol Dis* 24, 322-339 (1998).
38. Miccio, A., Cesari, R., Lotti, F., Rossi, C., Sanvito, F., Ponzoni, M., Routledge, S. J., Chow, C. M., Antoniou, M. N. & Ferrari, G. In vivo selection of genetically modified erythroblastic progenitors leads to long-term correction of beta-thalassemia. *Proc Natl Acad Sci USA* 105, 10547-10552 (2008).
39. Sadelain, M., Wang, C. H., Antoniou, M., Grosveld, F. & Mulligan, R. C. Generation of a high-titer retroviral vector capable of expressing high levels of the human beta-globin gene. Proc Natl Acad Sci USA 92, 6728-6732 (1995).
40. Samakoglu, S., Lisowski, L., Budak-Alpdogan, T., Usachenko, Y., Acuto, S., Di Marzo, R., Maggio, A., Zhu, P., Tisdale, J. F., Riviere, I. & Sadelain, M. A genetic strategy to treat sickle cell anemia by coregulating globin transgene expression and RNA interference. *Nat Biotechnol* 24, 89-94 (2006).
41. Pestina, T. I., Hargrove, P. W., Jay, D., Gray, J. T., Boyd, K. M. & Persons, D. A. Correction of murine sickle cell disease using gamma-globin lentiviral vectors to mediate high-level expression of fetal hemoglobin. *Mol Ther* 17, 245-252 (2009).
42. Hanawa, H., Yamamoto, M., Zhao, H., Shimada, T. & Persons, D. A. Optimized lentiviral vector design improves titer and transgene expression of vectors containing the chicken beta-globin locus HS4 insulator element. *Mol Ther* 17, 667-674 (2009).
43. Arumugam, P. I., Scholes, J., Perelman, N., Xia, P., Yee, J. K. & Malik, P. Improved human beta-globin expression from self-inactivating lentiviral vectors carrying the chicken hypersensitive site-4 (cHS4) insulator element. *Mol Ther* 15, 1863-1871 (2007).
44. Fraser, P., Pruzina, S., Antoniou, M. & Grosveld, F. Each hypersensitive site of the human beta-globin locus control region confers a different developmental pattern of expression on the globin genes. *Genes & development* 7, 106-113 (1993).
45. Navas, P. A., Peterson, K. R., Li, Q., Skarpidi, E., Rohde, A., Shaw, S. E., Clegg, C. H., Asano, H. & Stamatoyannopoulos, G. Developmental specificity of the interaction between the locus control region and embryonic or fetal globin genes in transgenic mice with an HS3 core deletion. *Molecular and cellular biology* 18, 4188-4196 (1998).
46. Li, Q. & Stamatoyannopoulos, G. Hypersensitive site 5 of the human beta locus control region functions as a chromatin insulator. *Blood* 84, 1399-1401 (1994).
47. Li, Q., Zhang, M., Han, H., Rohde, A. & Stamatoyannopoulos, G. Evidence that DNase I hypersensitive site 5 of the human beta-globin locus control region functions as a chromosomal insulator in transgenic mice. *Nucleic Acids Res* 30, 2484-2491 (2002).
48. Puthenveetil, G., Scholes, J., Carbonell, D., Qureshi, N., Xia, P., Zeng, L., Li, S., Yu, Y., Hiti, A. L., Yee, J. K. & Malik, P. Successful correction of the human beta-thalassemia major phenotype using a lentiviral vector. *Blood* 104, 3445-3453 (2004).
49. Wilber, A., Nienhuis, A. W. & Persons, D. A. Transcriptional regulation of fetal to adult hemoglobin switching: new therapeutic opportunities. *Blood* 117, 3945-3953 (2011).
50. Arumugam, P. I., Higashimoto, T., Urbinati, F., Modlich, U., Nestheide, S., Xia, P., Fox, C., Corsinotti, A., Baum, C. & Malik, P. Genotoxic potential of lineage-specific lentivirus vectors carrying the beta-globin locus control region. *Mol Ther* 17, 1929-1937 (2009).
51. Chang, K. H., Fang, X., Wang, H., Huang, A., Cao, H., Yang, Y., Bonig, H., Stamatoyannopoulos, J. A. & Papayannopoulou, T. Epigenetic modifications and chromosome conformations of the beta globin locus throughout development. *Stem cell reviews* 9, 397-407 (2013).
52. Papayannopoulou, T., Priestley, G. V., Rohde, A., Peterson, K. R. & Nakamoto, B. Hemopoietic lineage commitment decisions: in vivo evidence from a transgenic mouse model harboring micro LCR-betapro-LacZ as a transgene. *Blood* 95, 1274-1282 (2000).
53. Nienhuis, A. W. Development of gene therapy for blood disorders: an update. *Blood* 122, 1556-1564 (2013).
54. Baum, C., Kustikova, O., Modlich, U., Li, Z. & Fehse, B. Mutagenesis and oncogenesis by chromosomal insertion of gene transfer vectors. *Hum Gene Ther* 17, 253-263 (2006).
55. Nienhuis, A. W., Dunbar, C. E. & Sorrentino, B. P. Genotoxicity of retroviral integration in hematopoietic cells. *Mol Ther* 13, 1031-1049 (2006).
56. Emery, D. W. The use of chromatin insulators to improve the expression and safety of integrating gene transfer vectors. *Hum Gene Ther* 22, 761-774 (2011).
57. Evans-Galea, M. V., Wielgosz, M. M., Hanawa, H., Srivastava, D. K. & Nienhuis, A. W. Suppression of clonal dominance in cultured human lymphoid cells by addition of the cHS4 insulator to a lentiviral vector. *Mol Ther* 15, 801-809 (2007).
58. Rivella, S., Callegari, J. A., May, C., Tan, C. W. & Sadelain, M. The cHS4 insulator increases the probability of retroviral expression at random chromosomal integration sites. *J Virol* 74, 4679-4687 (2000).
59. Emery, D. W., Yannaki, E., Tubb, J. & Stamatoyannopoulos, G. A chromatin insulator protects retrovirus vectors from chromosomal position effects. *Proc Natl Acad Sci USA* 97, 9150-9155 (2000).
60. Emery, D. W., Yannaki, E., Tubb, J., Nishino, T., Li, Q. & Stamatoyannopoulos, G. Development of virus vectors for gene therapy of beta chain hemoglobinopathies: flanking with a chromatin insulator reduces gamma-globin gene silencing in vivo. *Blood* 100, 2012-2019 (2002).
61. Yannaki, E., Tubb, J., Aker, M., Stamatoyannopoulos, G. & Emery, D. W. Topological constraints governing the use of the chicken HS4 chromatin insulator in oncoretrovirus vectors. *Mol Ther* 5, 589-598 (2002).
62. Hino, S., Fan, J., Taguwa, S., Akasaka, K. & Matsuoka, M. Sea urchin insulator protects lentiviral vector from silencing by maintaining active chromatin structure. *Gene Ther* 11, 819-828 (2004).
63. Ramezani, A., Hawley, T. S. & Hawley, R. G. Performance- and safety-enhanced lentiviral vectors containing the human interferon-beta scaffold attachment region and the chicken beta-globin insulator. *Blood* 101, 4717-4724 (2003).
64. Ramezani, A., Hawley, T. S. & Hawley, R. G. Combinatorial incorporation of enhancer-blocking components of the chicken beta-globin 5'HS4 and human T-cell receptor alpha/delta BEAD-1 insulators in self-inactivating retroviral vectors reduces their genotoxic potential. *Stem Cells* 26, 3257-3266 (2008).
65. Yannaki, E., Emery, D. W. & Stamatoyannopoulos, G. Gene therapy for beta-thalassaemia: the continuing challenge. *Expert reviews in molecular medicine* 12, e31 (2010).
66. Persons, D. A. The challenge of obtaining therapeutic levels of genetically modified hematopoietic stem cells in beta-thalassemia patients. *Ann N Y Acad Sci* 1202, 69-74 (2010).
67. Perumbeti, A. & Malik, P. Therapy for beta-globinopathies: a brief review and determinants for successful and safe correction. *Ann N Y Acad Sci* 1202, 36-44 (2010).
68. Johnson, K. D., Grass, J. A., Park, C., Im, H., Choi, K. & Bresnick, E. H. Highly restricted localization of RNA polymerase II within a locus control region of a tissue-specific chromatin domain. *Molecular and cellular biology* 23, 6484-6493 (2003).
69. Vieira, K. F., Levings, P. P., Hill, M. A., Crusselle, Kang, S. H., Engel, J. D. & Bungert, J. Recruitment of transcription complexes to the beta-globin gene locus in vivo and in vitro. *J Biol Chem* 279, 50350-50357 (2004).
70. Levings, P. P., Zhou, Z., Vieira, K. F., Crusselle-Davis, V. J. & Bungert, J. Recruitment of transcription complexes to the beta-globin locus control region and transcription of hypersensitive site 3 prior to erythroid differentiation of murine embryonic stem cells. *The FEBS journal* 273, 746-755 (2006).
71. Felsenfeld, G. & Groudine, M. Controlling the double helix. *Nature* 421, 448-453 (2003).
72. Felsenfeld, G. Chromatin as an essential part of the transcriptional mechanism. *Nature* 355, 219-224 (1992).
73. Brownell, J. E. & Allis, C. D. Special HATs for special occasions: linking histone acetylation to chromatin assembly and gene activation. *Curr Opin Genet Dev* 6, 176-184 (1996).
74. Kingston, R. E. & Narlikar, G. J. ATP-dependent remodeling and acetylation as regulators of chromatin fluidity. *Genes & development* 13, 2339-2352 (1999).
75. Tsukiyama, T. & Wu, C. Chromatin remodeling and transcription. *Curr Opin Genet Dev* 7, 182-191 (1997).
76. Wolffe, A. P., Wong, J. & Pruss, D. Activators and repressors: making use of chromatin to regulate transcription. *Genes to cells: devoted to molecular & cellular mechanisms* 2, 291-302 (1997).
77. Kadonaga, J. T. Eukaryotic transcription: an interlaced network of transcription factors and chromatin-modifying machines. *Cell* 92, 307-313 (1998).
78. Struhl, K. Histone acetylation and transcriptional regulatory mechanisms. *Genes & development* 12, 599-606 (1998).

79. Gross, D. S. & Garrard, W. T. Nuclease hypersensitive sites in chromatin. *Annual review of biochemistry* 57, 159-197 (1988).
80. Elgin, S. C. Anatomy of hypersensitive sites. *Nature* 309, 213-214 (1984).
81. Wu, C. The 5' ends of *Drosophila* heat shock genes in chromatin are hypersensitive to DNase I. *Nature* 286, 854-860 (1980).
82. Felsenfeld, G., Boyes, J., Chung, J., Clark, D. & Studitsky, V. Chromatin structure and gene expression. *Proc Natl Acad Sci USA* 93, 9384-9388 (1996).
83. Burgess-Beusse, B., Farrell, C., Gaszner, M., Litt, M., Mutskov, V., Recillas-Targa, F., Simpson, M., West, A. & Felsenfeld, G. The insulation of genes from external enhancers and silencing chromatin. *Proc Natl Acad Sci USA* 99 Suppl 4, 16433-16437 (2002).
84. Elgin, S. C. DNAase I-hypersensitive sites of chromatin. *Cell* 27, 413-415 (1981).
85. McGhee, J. D., Wood, W. I., Dolan, M., Engel, J. D. & Felsenfeld, G. A 200 base pair region at the 5' end of the chicken adult beta-globin gene is accessible to nuclease digestion. *Cell* 27, 45-55 (1981).
86. Lowrey, C. H., Bodine, D. M. & Nienhuis, A. W. Mechanism of DNase I hypersensitive site formation within the human globin locus control region. *Proc Natl Acad Sci USA* 89, 1143-1147 (1992).
87. Adams, C. C. & Workman, J. L. Binding of disparate transcriptional activators to nucleosomal DNA is inherently cooperative. *Molecular and cellular biology* 15, 1405-1421 (1995).
88. McArthur, M., Gerum, S. & Stamatoyannopoulos, G. Quantification of DNaseI-sensitivity by real-time PCR: quantitative analysis of DNaseI-hypersensitivity of the mouse beta-globin LCR. *J Mol Biol* 313, 27-34 (2001).
89. Dorschner, M. O., Hawrylycz, M., Humbert, R., Wallace, J. C., Shafer, A., Kawamoto, J., Mack, J., Hall, R., Goldy, J., Sabo, P. J., Kohli, A., Li, Q., McArthur, M. & Stamatoyannopoulos, J. A. High-throughput localization of functional elements by quantitative chromatin profiling. *Nat Methods* 1, 219-225 (2004).
90. Sabo, P. J., Kuehn, M. S., Thurman, R., Johnson, B. E., Johnson, E. M., Cao, H., Yu, M., Rosenzweig, E., Goldy, J., Haydock, A., Weaver, M., Shafer, A., Lee, K., Neri, F., Humbert, R., Singer, M. A., Richmond, T. A., Dorschner, M. O., McArthur, M., Hawrylycz, M., Green, R. D., Navas, P. A., Noble, W. S. & Stamatoyannopoulos, J. A. Genome-scale mapping of DNase I sensitivity in vivo using tiling DNA microarrays. *Nat Methods* 3, 511-518 (2006).
91. Sabo, P. J., Hawrylycz, M., Wallace, J. C., Humbert, R., Yu, M., Shafer, A., Kawamoto, J., Hall, R., Mack, J., Dorschner, M. O., McArthur, M. & Stamatoyannopoulos, J. A. Discovery of functional noncoding elements by digital analysis of chromatin structure. *Proc Natl Acad Sci USA* 101, 16837-16842 (2004).
92. Sabo, P. J., Humbert, R., Hawrylycz, M., Wallace, J. C., Dorschner, M. O., McArthur, M. & Stamatoyannopoulos, J. A. Genome-wide identification of DNaseI hypersensitive sites using active chromatin sequence libraries. *Proc Natl Acad Sci USA* 101, 4537-4542 (2004).
93. Thurman, R. E., Rynes, E., Humbert, R., Vierstra, J., Maurano, M. T., Haugen, E., Sheffield, N. C., Stergachis, A. B., Wang, H., Vernot, B., Garg, K., John, S., Sandstrom, R., Bates, D., Boatman, L., Canfield, T. K., Diegel, M., Dunn, D., Ebersol, A. K., Frum, T., Giste, E., Johnson, A. K., Johnson, E. M., Kutyavin, T., Lajoie, B., Lee, B. K., Lee, K., London, D., Lotakis, D., Neph, S., Neri, F., Nguyen, E. D., Qu, H., Reynolds, A. P., Roach, V., Safi, A., Sanchez, M. E., Sanyal, A., Shafer, A., Simon, J. M., Song, L., Vong, S., Weaver, M., Yan, Y., Zhang, Z., Zhang, Z., Lenhard, B., Tewari, M., Dorschner, M. O., Hansen, R. S., Navas, P. A., Stamatoyannopoulos, G., Iyer, V. R., Lieb, J. D., Sunyaev, S. R., Akey, J. M., Sabo, P. J., Kaul, R., Furey, T. S., Dekker, J., Crawford, G. E. & Stamatoyannopoulos, J. A. The accessible chromatin landscape of the human genome. *Nature* 489, 75-82 (2012).
94. Stergachis, A. B., Neph, S., Reynolds, A., Humbert, R., Miller, B., Paige, S. L., Vernot, B., Cheng, J. B., Thurman, R. E., Sandstrom, R., Haugen, E., Heimfeld, S., Murry, C. E., Akey, J. M. & Stamatoyannopoulos, J. A. Developmental fate and cellular maturity encoded in human regulatory DNA landscapes. *Cell* 154, 888-903 (2013).
95. Neph, S., Stergachis, A. B., Reynolds, A., Sandstrom, R., Borenstein, E. & Stamatoyannopoulos, J. A. Circuitry and dynamics of human transcription factor regulatory networks. *Cell* 150, 1274-1286 (2012).
96. Maurano, M. T., Humbert, R., Rynes, E., Thurman, R. E., Haugen, E., Wang, H., Reynolds, A. P., Sandstrom, R., Qu, H., Brody, J., Shafer, A., Neri, F., Lee, K., Kutyavin, T., Stehling-Sun, S., Johnson, A. K., Canfield, T. K., Giste, E., Diegel, M., Bates, D., Hansen, R. S., Neph, S., Sabo, P. J., Heimfeld, S., Raubitschek, A., Ziegler, S., Cotsapas, C., Sotoodehnia, N., Glass, I., Sunyaev, S. R., Kaul, R. & Stamatoyannopoulos, J. A. Systematic localization of common disease-associated variation in regulatory DNA. *Science* 337, 1190-1195 (2012).
97. Stergachis, A. B., Haugen, E., Shafer, A., Fu, W., Vernot, B., Reynolds, A., Raubitschek, A., Ziegler, S., LeProust, E. M., Akey, J. M. & Stamatoyannopoulos, J. A. Exonic transcription factor binding directs codon choice and affects protein evolution. *Science* 342, 1367-1372 (2013).
98. Neph, S., Vierstra, J., Stergachis, A. B., Reynolds, A. P., Haugen, E., Vernot, B., Thurman, R. E., John, S., Sandstrom, R., Johnson, A. K., Maurano, M. T., Humbert, R., Rynes, E., Wang, H., Vong, S., Lee, K., Bates, D., Diegel, M., Roach, V., Dunn, D., Neri, J., Schafer, A., Hansen, R. S., Kutyavin, T., Giste, E., Weaver, M., Canfield, T., Sabo, P., Zhang, M., Balasundaram, G., Byron, R., MacCoss, M. J., Akey, J. M., Bender, M. A., Groudine, M., Kaul, R. & Stamatoyannopoulos, J. A. An expansive human regulatory lexicon encoded in transcription factor footprints. *Nature* 489, 83-90 (2012).
99. Ramezani, A., Hawley, T. S. & Hawley, R. G. Stable gammaretroviral vector expression during embryonic stem cell-derived in vitro hematopoietic development. *Mol Ther* 14, 245-254 (2006).
100. Recillas-Targa, F., Pikaart, M. J., Burgess-Beusse, B., Bell, A. C., Litt, M. D., West, A. G., Gaszner, M. & Felsenfeld, G. Position-effect protection and enhancer blocking by the chicken beta-globin insulator are separable activities. *Proc Natl Acad Sci USA* 99, 6883-6888 (2002).
101. Gaszner, M. & Felsenfeld, G. Insulators: exploiting transcriptional and epigenetic mechanisms. *Nat Rev Genet* 7, 703-713 (2006).
102. Wallace, J. A. & Felsenfeld, G. We gather together: insulators and genome organization. *Curr Opin Genet Dev* 17, 400-407 (2007).
103. Chung, J. H., Bell, A. C. & Felsenfeld, G. Characterization of the chicken beta-globin insulator. *Proc Natl Acad Sci USA* 94, 575-580 (1997).
104. Bell, A. C., West, A. G. & Felsenfeld, G. The protein CTCF is required for the enhancer blocking activity of vertebrate insulators. *Cell* 98, 387-396 (1999).

105. Ryu, B. Y., Persons, D. A., Evans-Galea, M. V., Gray, J. T. & Nienhuis, A. W. A chromatin insulator blocks interactions between globin regulatory elements and cellular promoters in erythroid cells. *Blood Cells Mol Dis* 39, 221-228 (2007).
106. Ryu, B. Y., Evans-Galea, M. V., Gray, J. T., Bodine, D. M., Persons, D. A. & Nienhuis, A. W. An experimental system for the evaluation of retroviral vector design to diminish the risk for proto-oncogene activation. *Blood* 111, 1866-1875 (2008).
107. Yao, S., Osborne, C. S., Bharadwaj, R. R., Pasceri, P., Sukonnik, T., Pannell, D., Recillas-Targa, F., West, A. G. & Ellis, J. Retrovirus silencer blocking by the cHS4 insulator is CTCF independent. *Nucleic Acids Res* 31, 5317-5323 (2003).
108. Nishino, T., Tubb, J. & Emery, D. W. Partial correction of murine beta-thalassemia with a gammaretrovirus vector for human gamma-globin. *Blood Cells Mol Dis* 37, 1-7 (2006).
109. Aker, M., Tubb, J., Groth, A. C., Bukovsky, A. A., Bell, A. C., Felsenfeld, G., Kiem, H. P., Stamatoyannopoulos, G. & Emery, D. W. Extended core sequences from the cHS4 insulator are necessary for protecting retroviral vectors from silencing position effects. *Hum Gene Ther* 18, 333-343 (2007).
110. Li, C. L. & Emery, D. W. The cHS4 chromatin insulator reduces gammaretroviral vector silencing by epigenetic modifications of integrated provirus. *Gene Ther* 15, 49-53 (2008).
111. Ma, Y., Ramezani, A., Lewis, R., Hawley, R. G. & Thomson, J. A. High-level sustained transgene expression in human embryonic stem cells using lentiviral vectors. *Stem Cells* 21, 111-117 (2003).
112. Chang, L. J., Liu, X. & He, J. Lentiviral siRNAs targeting multiple highly conserved RNA sequences of human immunodeficiency virus type 1. *Gene Ther* 12, 1133-1144 (2005).
113. Pluta, K., Luce, M. J., Bao, L., Agha-Mohammadi, S. & Reiser, J. Tight control of transgene expression by lentivirus vectors containing second-generation tetracycline-responsive promoters. *J Gene Med* 7, 803-817 (2005).
114. Jakobsson, J., Rosenqvist, N., Thompson, L., Barraud, P. & Lundberg, C. Dynamics of transgene expression in a neural stem cell line transduced with lentiviral vectors incorporating the cHS4 insulator. *Experimental cell research* 298, 611-623 (2004).
115. Leboulch, P., Huang, G. M., Humphries, R. K., Oh, Y. H., Eaves, C. J., Tuan, D. Y. & London, I. M. Mutagenesis of retroviral vectors transducing human beta-globin gene and beta-globin locus control region derivatives results in stable transmission of an active transcriptional structure. *EMBO J* 13, 3065-3076 (1994).
116. Kim, T. H., Abdullaev, Z. K., Smith, A. D., Ching, K. A., Loukinov, D. I., Green, R. D., Zhang, M. Q., Lobanenkov, V. V. & Ren, B. Analysis of the vertebrate insulator protein CTCF-binding sites in the human genome. *Cell* 128, 1231-1245 (2007).
117. Yusufzai, T. M. & Felsenfeld, G. The 5'-HS4 chicken beta-globin insulator is a CTCF-dependent nuclear matrix-associated element. *Proc Natl Acad Sci USA* 101, 8620-8624 (2004).
118. Phillips, J. E. & Corces, V. G. CTCF: master weaver of the genome. *Cell* 137, 1194-1211 (2009).
119. Giles, K. E., Gowher, H., Ghirlando, R., Jin, C. & Felsenfeld, G. Chromatin boundaries, insulators, and long-range interactions in the nucleus. *Cold Spring Harbor symposia on quantitative biology* 75, 79-85 (2010).
120. Barski, A., Cuddapah, S., Cui, K., Roh, T. Y., Schones, D. E., Wang, Z., Wei, G., Chepelev, I. & Zhao, K. High-resolution profiling of histone methylations in the human genome. *Cell* 129, 823-837 (2007).
121. Wang, H., Maurano, M. T., Qu, H., Varley, K. E., Gertz, J., Pauli, F., Lee, K., Canfield, T., Weaver, M., Sandstrom, R., Thurman, R. E., Kaul, R., Myers, R. M. & Stamatoyannopoulos, J. A. Widespread plasticity in CTCF occupancy linked to DNA methylation. *Genome research* 22, 1680-1688 (2012).
122. Schmidt, D., Schwalie, P. C., Wilson, M. D., Ballester, B., Goncalves, A., Kutter, C., Brown, G. D., Marshall, A., Flicek, P. & Odom, D. T. Waves of retrotransposon expansion remodel genome organization and CTCF binding in multiple mammalian lineages. *Cell* 148, 335-348 (2012).
123. Renda, M., Baglivo, I., Burgess-Beusse, B., Esposito, S., Fattorusso, R., Felsenfeld, G. & Pedone, P. V. Critical DNA binding interactions of the insulator protein CTCF: a small number of zinc fingers mediate strong binding, and a single finger-DNA interaction controls binding at imprinted loci. *J Biol Chem* 282, 33336-33345 (2007).
124. Dickson, J., Gowher, H., Strogantsev, R., Gaszner, M., Hair, A., Felsenfeld, G. & West, A. G. VEZF1 elements mediate protection from DNA methylation. *PLoS Genet* 6, e1000804 (2010).
125. Li, C. L., Xiong, D., Stamatoyannopoulos, G. & Emery, D. W. Genomic and functional assays demonstrate reduced gammaretroviral vector genotoxicity associated with use of the cHS4 chromatin insulator. *Mol Ther* 17, 716-724 (2009).
126. Lisowski, L. & Sadelain, M. Locus control region elements HS1 and HS4 enhance the therapeutic efficacy of globin gene transfer in beta-thalassemic mice. *Blood* 110, 4175-4178 (2007).
127. Nagel, R. L., Bookchin, R. M., Johnson, J., Labie, D., Wajcman, H., Isaac-Sodeye, W. A., Honig, G. R., Schiliro, G., Crookston, J. H. & Matsutomo, K. Structural bases of the inhibitory effects of hemoglobin F and hemoglobin A2 on the polymerization of hemoglobin S. *Proc Natl Acad Sci USA* 76, 670-672 (1979).
128. Sadelain et al., *Proc. Nat'l Acad. Sci.* (USA) (1995); 92:6728-6732.
129. Armstrong, J. A., Emerson, B. M., 1996. NFE2 disrupts chromatin structure at human fl-globin locus control region hypersensitive site 2 in vitro. *Mol. Cell. Biol.* 16, 5634-5644.
130. Caterina, J. J., Ciavatta, D. J., Donze, D., Behringer, R. R., Townes, T. M., 1994. Multiple elements in human fl-globin locus control region 5' HS2 are involved in enhancer activity and position-independent transgene expression. *Nucleic Acids Res.* 22, 1006 1011.
131. Moi, P., Kan, Y. W., 1990. Synergistic enhancement of globin gene expression by activator protein-1-like proteins. *Proc. Natl. Acad, Sci. USA* 87, 9000-9004.
132. Ney, P., Sorrentino, B., McDonagh, K., Nienhuis, A., 1990. Tandem AP-1-binding sites within the human /j-globin dominant control region function as an inducible enhancer in erythroid cells. *Genes Dev.* 4, 993 1006.
133. Shivdasani, R. A., Rosenblatt, M. F., Zucker-Franklin, D., Jackson, C. W., Hunt, P., Saris, C. J. M., Orkin, S. H., 1995. Transcription factor NF-E2 is required for platelet formation independent of the actions of thrombopoietin/MGDF in megakaryocyte development. *Cell* 81, 695-704.

134. Talbot, D., Grosveld, F., 1991. The 5'HS2 of the globin locus control region enhances transcription through the interaction of a multimeric complex binding at two functionally distinct NF-E2 binding sites. *EMBO J.* 10, 1391-1398.
135. Hardison et al., *Gene* (1997); 205:73-94.
136. Elnitski et al., *The Journal of Biological Chemistry* (1997); 272(1):369-378; Horak et al., *PNAS* (2002); 99(5):2924-2929.
137. Shimotsuma et al., *Journal of Biological Chemistry* (2010); 285(19): 14495-14503.

From the foregoing description, it will be apparent that variations and modifications may be made to the presently disclosed subject matter described herein to adopt it to various usages and conditions. Such embodiments are also within the scope of the following claims.

All patents and publications and sequences referred to by accession or reference number mentioned in this specification are herein incorporated by reference to the same extent as if each independent patent and publication and sequence was specifically and individually indicated to be incorporated by reference.

What is claimed is:

1. A viral vector comprising an expression cassette comprising an insulator that comprises the nucleotide sequence set forth in SEQ ID NO:1, SEQ ID NO: 24, or SEQ ID NO: 25, and a globin gene operably linked to a β-globin locus control region (LCR) region.

2. The viral vector of claim 1, wherein the β-globin LCR region does not comprise a HS1 region.

3. The viral vector of claim 2, wherein the β-globin LCR region does not comprise a core sequence of the HS1.

4. The viral vector of claim 3, wherein the core sequence of the HS1 consists of the nucleotide sequence set forth in SEQ ID NO:22 or SEQ ID NO: 23.

5. The viral vector of claim 2, wherein the HS1 region sustains the HS1 function.

6. The viral vector of claim 2, wherein the β-globin LCR region comprises a HS3 region and a HS4 region.

7. The viral vector of claim 6, wherein the HS3 region is positioned between the globin gene and the HS4 region.

8. The viral vector of claim 2, wherein the β-globin LCR region comprises a HS3 region consisting of the nucleotide sequence set forth in SEQ ID NO:5 and a HS4 region consisting of the nucleotide sequence set forth in SEQ ID NO:6, and the (β-globin LCR region does not comprise a HS2 region.

9. The viral vector of claim 1, wherein the β-globin LCR region does not comprise a Dnase I hypersensitive site-2 (HS2) region.

10. The viral vector of claim 9, wherein the β-globin LCR region does not comprise a core sequence of HS2.

11. The viral vector of claim 10, wherein the core sequence of HS2-consists of the nucleotide sequence set forth in SEQ ID NO:20 or SEQ ID NO: 21.

12. The viral vector of claim 9, wherein the β-globin LCR region comprises a HS1 region consisting of the nucleotide sequence set forth in SEQ ID NO:2, a HS3 region consisting of the nucleotide sequence set forth in SEQ ID NO:5, and a HS4 region consisting of the nucleotide sequence set forth in SEQ ID NO:6.

13. The viral vector of claim 9, wherein the β-globin LCR region comprises a HS1 region consisting of the nucleotide sequence set forth in SEQ ID NO:3, a HS3 region consisting of the nucleotide sequence set forth in SEQ ID NO:5, and a HS4 region consisting of the nucleotide sequence set forth in SEQ ID NO:8.

14. The viral vector of claim 9, wherein the β-globin LCR region comprises a HS1 region consisting of the nucleotide sequence set forth in SEQ ID NO:4, a HS3 region consisting of the nucleotide sequence set forth in SEQ ID NO:5, and a HS4 region consisting of the nucleotide sequence set forth in SEQ ID NO:8.

15. The viral vector of claim 1, wherein the β-globin LCR region does not comprise a HS2 region that sustains the enhancer activity of HS2.

16. The viral vector of claim 1, wherein the β-globin LCR region comprises a Dnase I hypersensitive site-1 (HS1) region, a Dnase I hypersensitive site-3 (HS3) region, and a Dnase I hypersensitive site-4 (HS4) region.

17. The viral vector of claim 16, wherein the HS3 region is positioned between the HS1 region and the HS4 region.

18. The viral vector of claim 16, wherein the HS1 region is about 1.1 kb in length.

19. The viral vector of claim 18, wherein the HS1 region consists of the nucleotide sequence set forth in SEQ ID NO:2.

20. The viral vector of claim 16, wherein the HS1 region is about 600 bp in length.

21. The viral vector of claim 20, wherein the HS1 region consists of the nucleotide sequence set forth in SEQ ID NO:3.

22. The viral vector of claim 16, wherein the HS1 region is about 490 bp in length.

23. The viral vector of claim 22, wherein the HS1 region consists of the nucleotide sequence set forth in SEQ ID NO:4.

24. The viral vector of claim 16, wherein the HS3 region is about 1300 bp in length.

25. The viral vector of claim 24, wherein the HS3 region consists of the nucleotide sequence set forth in SEQ ID NO:5.

26. The viral vector of claim 16, wherein the HS4 region is about 1.1 kb in length.

27. The viral vector of claim 26, wherein the HS4 region consists of the nucleotide sequence set forth in SEQ ID NO:6.

28. The viral vector of claim 26, wherein the HS4 region consists of the nucleotide sequence set forth in SEQ ID NO:7.

29. The viral vector of claim 16, wherein the HS4 region is about 450 bp in length.

30. The viral vector of claim 29, wherein the HS4 region consists of the nucleotide sequence set forth in SEQ ID NO:8.

31. The viral vector of claim 1, wherein the β-globin LCR region comprises a HS2 region, a HS3 region, and a HS4 region.

32. The viral vector of claim 31, wherein the HS2 region is about 860 bp in length.

33. The viral vector of claim 32, wherein the HS2 region consists of the nucleotide sequence set forth in SEQ ID NO:9.

34. The viral vector of claim 31, wherein the HS3 region is about 1300 bp in length.

35. The viral vector of claim 34, wherein the HS3 region consists of the nucleotide sequence set forth in SEQ ID NO:5.

36. The viral vector of claim 31, wherein the HS4 region is about 1.1 kb in length.

37. The viral vector of claim 36, wherein the HS4 region consists of the nucleotide sequence set forth in SEQ ID NO:7.

38. The viral vector of claim 31, wherein the HS2 region consists of the nucleotide sequence set forth in SEQ ID NO:9, the HS3 region consists of the nucleotide sequence set forth in SEQ ID NO:5, and the HS4 region consists of the nucleotide sequence set forth in SEQ ID NO:7.

39. The viral vector of claim 31, wherein the β-globin LCR region further comprises a HS1 region.

40. The viral vector of claim 1, further comprising a β-globin promoter.

41. The viral vector of claim 40, wherein the β-globin promoter is positioned between the globin gene and the β-globin LCR region.

42. The viral vector of claim 40, wherein the β-globin promoter is a human β-globin promoter that is about 613 bp in length.

43. The viral vector of claim 42, wherein the human β-globin promoter consists of the nucleotide sequence set forth in SEQ ID NO:10.

44. The viral vector of claim 40, wherein the β-globin promoter is a human β-globin promoter that is about 265 bp in length.

45. The viral vector of claim 44, wherein the human β-globin promoter consists of the nucleotide sequence set forth in SEQ ID NO:11.

46. The viral vector of claim 1, wherein the globin gene is selected from the group consisting of β-globin gene, γ-globin gene, and δ-globin gene.

47. The viral vector of claim 46, wherein the globin gene is human β-globin gene.

48. The viral vector of claim 47, wherein the human β-globin gene is selected from the group consisting of a wild-type human β-globin gene, a human β-globin gene comprising one or more deletions of intron sequences, and a mutated human β-globin gene encoding at least one anti-sickling amino acid residue.

49. The viral vector of claim 48, wherein the human β-globin gene is human $β^A$-globin gene encoding a threonine to glutamine mutation at codon 87 ($β^{A-T87Q}$).

50. The viral vector of claim 1, wherein the expression cassette consists of one of the insulator or two of the insulators.

51. The viral vector of claim 1, further comprising a human β-globin 3' enhancer.

52. The viral vector of claim 51, wherein the human β-globin 3' enhancer is positioned in the upstream of the globin gene.

53. The viral vector of claim 51, wherein the human β-globin 3' enhancer is about 879 bp in length.

54. The viral vector of claim 53, wherein the human β-globin 3' enhancer consists of the nucleotide sequence set forth in SEQ ID NO:12.

55. The viral vector of claim 1, further comprising one or both of a Woodchuck hepatitis post-regulatory element (WPRE) and a bovine growth hormone polyadenylation signal in the 3' long terminal repeat (LTR) of the vector.

56. The viral vector of claim 1, wherein the viral vector is a retroviral vector.

57. The viral vector of claim 56, wherein the retroviral vector is a lentiviral vector.

58. An in vitro cell transduced with the viral vector of claim 1.

59. The cell of claim 58, wherein the hematopoietic stem cell is a $CD34^+$ hematopoietic stem cell.

60. A pharmaceutical composition comprising an effective amount of the cell of claim 58 and a pharmaceutically acceptable carrier.

61. A kit for treating a hemoglobinopathy comprising the cell of claim 58.

\* \* \* \* \*

SEQUENCE LISTING

```
<160> NUMBER OF SEQ ID NOS: 26

<210> SEQ ID NO 1
<211> LENGTH: 305
<212> TYPE: DNA
<213> ORGANISM: Homo sapiens

<400> SEQUENCE: 1
tccttccttt ctaaatgacg agagagacag aagaattctt caaggttagt gtgtccagca    60
tgcaaccttt ccttcctgga tgagcatccc tggagtagga gagccagcct gcctcctgcg   120
ctggcacaga gcccggttcc ctagacaact gcctctccaa atctgatgtc cagcgccacc   180
tggtgtccac atcaagcaga cacaattaat agtcaacctg ttcaggaaaa ctgtgagggg   240
gaaaaaaaag aaagaggatt tatgaaggga aaagaaagtt tagaggatat gccacgattg   300
gctag                                                              305

<210> SEQ ID NO 2
<211> LENGTH: 1074
<212> TYPE: DNA
<213> ORGANISM: Homo sapiens

<400> SEQUENCE: 2
aagtaaactt ccacaaccgc aagcttattg aggctaaggc atctgtgaag gaaagaaaca    60
tctcctctaa accactatgc tgctagagcc tcttttctgt actcaagcct cattcagaca   120
ctagtgtcac cagtctcctc atatacctat tgtattttct tcttcttgct ggtttagtca   180
tgttttctgg gagcttaggg gcttatttta ttttgttttg ttttctaatc aacagagatg   240
ggcaaaccca ttatttttt ctttagactt gggatggtga tagctgggca gcgtcagaaa   300
ctgtgtgtgg atatagataa gagctcggac tatgctgagc tgtgatgagg gagggaccta   360
gccaaaggca gtgagagtca gaatgctcct gctattgcct tctcagtccc cacgcttggt   420
ttctacacaa gtagatacat agaaaaggct ataggttagt gtttgagagt cctgcatgag   480
ttagttgctc agaaatgccc gataaatatg ttatgtgtgt ttatgtatat atatgttta   540 tatatatata tgtgtgtgtg tgtgtgtgtg tgtgttgtgt ttacaaatat gtgattatca   600
tcaaaacgtg agggctaaag tgaccagata acttgcaggt cctaggatac caggaaaata   660
aattacattc caaaaattta actgagactt taaaaaaaaa aaaaaaaaaa aaaaaaaac   720 cagtgatcca tggacacagg gagggggaaca tcacacactg gggcctgttg ggggtggggg   780 gctagggaa ggatagcatt aggagaaata cctaatgtag atgacgggtt gatgggtgca   840
gcaaaccacc atggcacatg taccccagaa cttaaagcat attaaaaaaa cagtgatcat   900
aaaagaagct caaatttaac tataagagac ggaatggctc ccacaattct taactataat   960
cttacagaat attctcattg aatagaagta tgcttatcat tagagatttg gacagccagg  1020
```
aaagcacaga aaaaaaaaaa aggagctctg ttgccttata gcctagaggt gttt        1074

<210> SEQ ID NO 3
<211> LENGTH: 602
<212> TYPE: DNA
<213> ORGANISM: Homo sapiens

<400> SEQUENCE: 3

| | |
|---|---|
| ggcatctgtg aaggaaagaa acatctcctc taaaccacta tgctgctaga gcctcttttc | 60 |
| tgtactcaag cctcattcag acactagtgt caccagtctc ctcatatacc tattgtattt | 120 |
| tcttcttctt gctggtttag tcatgttttc tgggagctta ggggcttatt ttattttgtt | 180 |
| ttgttttcta atcaacagag atgggcaaac ccattatttt tttctttaga cttgggatgg | 240 |
| tgatagctgg gcagcgtcag aaactgtgtg tggatataga taagagctcg gactatgctg | 300 |
| agctgtgatg agggagggac ctagccaaag gcagtgagag tcagaatgct cctgctattg | 360 |
| ccttctcagt ccccacgctt ggtttctaca caagtagata catagaaaag gctataggtt | 420 |
| agtgtttgag agtcctgcat gagttagttg ctcagaaatg cccgataaat atgttatgtg | 480 |
| tgtttatgta tatatatgtt ttatatatat atatgtgtgt gtgtgtgtgt gtgtgtgttg | 540 |
| tgtttacaaa tatgtgatta tcatcaaaac gtgagggcta aagtgaccag ataacttgca | 600 |
| gg | 602 |

<210> SEQ ID NO 4
<211> LENGTH: 489
<212> TYPE: DNA
<213> ORGANISM: Homo sapiens

<400> SEQUENCE: 4

| | |
|---|---|
| ggcatctgtg aaggaaagaa acatctcctc taaaccacta tgctgctaga gcctcttttc | 60 |
| tgtactcaag cctcattcag acactagtgt caccagtctc ctcatatacc tattgtattt | 120 |
| tcttcttctt gctggtttag tcatgttttc tgggagctta ggggcttatt ttattttgtt | 180 |
| ttgttttcta atcaacagag atgggcaaac ccattatttt tttctttaga cttgggatgg | 240 |
| tgatagctgg gcagcgtcag aaactgtgtg tggatataga taagagctcg gactatgctg | 300 |
| agctgtgatg agggagggac ctagccaaag gcagtgagag tcagaatgct cctgctattg | 360 |
| ccttctcagt ccccacgctt ggtttctaca caagtagata catagaaaag gctataggtt | 420 |
| agtgtttgag agtcctgcat gagttagttg ctcagaaatg cccgataaat atgttatgtg | 480 |
| tgtttatgt | 489 |

<210> SEQ ID NO 5
<211> LENGTH: 1301
<212> TYPE: DNA
<213> ORGANISM: Homo sapiens

<400> SEQUENCE: 5

| | |
|---|---|
| aagctttcat taaaaaaagt ctaaccagct gcattcgact ttgactgcag cagctggtta | 60 |
| gaaggttcta ctggaggagg gtcccagccc attgctaaat taacatcagg ctctgagact | 120 |
| ggcagtatat ctctaacagt ggttgatgct atcttctgga acttgcctgc tacattgaga | 180 |
| ccactgaccc atacatagga agcccatagc tctgtcctga actgttaggc cactggtcca | 240 |
| gagagtgtgc atctcctttg atcctcataa taacccctatg agatagacac aattattact | 300 |
| cttactttat agatgatgat cctgaaaaca taggagtcaa ggcacttgcc cctagctggg | 360 |
| ggtatagggg agcagtccca tgtagtagta gaatgaaaaa tgctgctatg ctgtgcctcc | 420 |

```
cccacctttc ccatgtctgc cctctactca tggtctatct ctcctggctc ctgggagtca      480
tggactccac ccagcaccac caacctgacc taaccaccta tctgagcctg ccagcctata      540
acccatctgg gccctgatag ctggtggcca gccctgaccc caccccaccc tccctggaac      600
ctctgataga cacatctggc acaccagctc gcaaagtcac cgtgagggtc ttgtgtttgc      660
tgagtcaaaa ttccttgaaa tccaagtcct tagagactcc tgctcccaaa tttacagtca      720
tagacttctt catggctgtc tcctttatcc acagaatgat tcctttgctt cattgcccca      780
tccatctgat cctcctcatc agtgcagcac agggcccatg agcagtagct gcagagtctc      840
acataggtct ggcactgcct ctgacatgtc cgaccttagg caaatgcttg actcttctga      900
gctcagtctt gtcatggcaa aataaagata ataatagtgt ttttttatgg agttagcgtg      960
aggatggaaa acaatagcaa aattgattag actataaaag gtctcaacaa atagtagtag     1020 atttttatcat ccattaatcc ttccctctcc tctcttactc atcccatcac gtatgcctct    1080
taattttccc ttacctataa taagagttat tcctcttatt atattcttct tatagtgatt    1140
ctggatatta agtgggaat gaggggcagg ccactaacga agaagatgtt tctcaaagaa      1200
gccattctcc ccacatagat catctcagca gggttcagga agataaagga ggatcaaggt     1260
cgaaggtagg aactaaggaa gaacactggg caagtggatc c                        1301

<210> SEQ ID NO 6
<211> LENGTH: 1065
<212> TYPE: DNA
<213> ORGANISM: Homo sapiens

<400> SEQUENCE: 6
tgagcccctt ttcctctaac tgaaagaagg aaaaaaaaaa tggaacccaa atatattctac      60 atagttccca tgtcacagcc agggctgggc agtctcctgt tatttctttt aaaataaata     120
tatcatttaa atgcataaat aagcaaaccc tgctcgggaa tgggagggag agtctctgga     180
gtccacccct tctcggccct ggctctgcag atagtgctat caaagccctg acagagccct     240
gcccattgct gggccttgga gtgagtcagc ctagtagaga ggcagggcaa gccatctcat     300
agctgctgag tgggagagag aaaagggctc attgtctata aactcaggtc atggctattc     360
ttattctcac actaagaaaa agaatgagat gtctacatat accctgcgtc ccctcttgtg     420
tactggggcc cccaagagct ctctaaaagt gatggcaaag tcattgcgct agatgccatc     480
ccatctatta taaacctgca tttgtctcca cacaccagtc atggacaata accctcctcc     540
caggtccacg tgcttgtctt tgtataatac tcaagtaatt tcggaaaatg tattctttca     600
atcttgttct gttattcctg tttcaatggc ttagtagaaa aagtacatac ttgttttccc     660
ataaattgac aatagacaat ttcacatcaa tgtctatatg ggtcgttgtg tttgctgtgt     720
ttgcaaaaac tcacaataac tttatattgt tactactcta agaaagttac aacatggtga     780
atacaagaga aagctattac aagtccagaa aataaaagtt atcatcttga ggcctcagct     840
ttctaggaat aatatcaata ttacaaaatt taatctaaca attatgaaca gcaatgagat     900
aatatgtaca aagtacccag acctatgtgg tagagcatca aggaagcgca ttgcggagca     960
gttttttgtt tgtttgtttt tgtattctgt ttcgtgaggc aaggtttcac tctgctgtcc    1020
aggctggagt gcagtggcaa gatcatgtct cactgcagcc ttgac                    1065

<210> SEQ ID NO 7
<211> LENGTH: 1065
<212> TYPE: DNA
```

<213> ORGANISM: Homo sapiens

<400> SEQUENCE: 7

| | | |
|---|---|---|
| tgagcccctt ttcctctaac tgaaagaagg aaaaaaaaaa tggaacccaa aatattctac | 60 | |
| atagtttcca tgtcacagcc agggctgggc agtctcctgt tatttctttt aaaataaata | 120 | |
| tatcattaaa tgcataaata agcaaaccct gctcgggaat gggagggaga gtctctggag | 180 | |
| tccaccccctt ctcggccctg gctctgcaga tagtgctatc aaagccctga cagagccctg | 240 | |
| cccattgctg ggccttggag tgagtcagcc tagtagagag gcagggcaag ccatctcata | 300 | |
| gctgctgagt gggagagaga aaagggctca ttgtctataa actcaggtca tggctattct | 360 | |
| tattctcaca ctaagaaaaa gaatgagatg tctacatata ccctgcgtcc cctcttgtgt | 420 | |
| actgggccc ccaagagctc tctaaaagtg atggcaaagt cattgcgcta gatgccatcc | 480 | |
| catctattat aaacctgcat ttgtctccac acaccagtca tggacaataa ccctcctccc | 540 | |
| aggtccacgt gcttgtcttt gtataatact caagtaattt cggaaaatgt attctttcaa | 600 | |
| tcttgttctg ttattcctgt ttcaatggct tagtagaaaa agtacatact tgttttccca | 660 | |
| taaattgaca atagacaatt tcacatcaat gtctatatgg gtcgttgtgt ttgctgtgtt | 720 | |
| tgcaaaaact cacaataact ttatattgtt actactctaa gaaagttaca acatggtgaa | 780 | |
| tacaagagaa agctattaca agtccagaaa ataaagtta tcatcttgag gcctcagctt | 840 | |
| tctaggaata atatcaatat tacaaaatta atctaacaat tatgaacagc aatgagataa | 900 | |
| tatgtacaaa gtacccagac ctatgtggta gagcatcaag gaagcgcatt gcggagcagt | 960 | |
| ttttttgtttg tttgttttg tattctgttt cgtgaggcaa ggtttcactc tgctgtccag | 1020 | |
| gctggagtgc agtggcaaga tcatgtctca ctgcagcctt gacac | 1065 | |

<210> SEQ ID NO 8
<211> LENGTH: 446
<212> TYPE: DNA
<213> ORGANISM: Homo sapiens

<400> SEQUENCE: 8

| | | |
|---|---|---|
| tggaacccaa aatattctac atagtttcca tgtcacagcc agggctgggc agtctcctgt | 60 | |
| tatttctttt aaaataaata tatcatttaa atgcataaat aagcaaaccc tgctcgggaa | 120 | |
| tgggagggag agtctctgga gtccaccccct tctcggccct ggctctgcag atagtgctat | 180 | |
| caaagccctg acagagccct gcccattgct gggccttgga gtgagtcagc ctagtagaga | 240 | |
| ggcagggcaa gccatctcat agctgctgag tgggagagag aaaagggctc attgtctata | 300 | |
| aactcaggtc atggctattc ttattctcac actaagaaaa agaatgagat gtctacatat | 360 | |
| accctgcgtc cctcttgtg tactggggtc cccaagagct ctctaaaagt gatggcaaag | 420 | |
| tcattgcgct agatgccatc ccatct | 446 | |

<210> SEQ ID NO 9
<211> LENGTH: 860
<212> TYPE: DNA
<213> ORGANISM: Homo sapiens

<400> SEQUENCE: 9

| | | |
|---|---|---|
| gtatatgtgt atatatatat atatatattc aggaaataat atattctaga atatgtcaca | 60 | |
| ttctgtctca ggcatccatt ttctttatga tgccgtttga ggtggagttt tagtcaggtg | 120 | |
| gtcagcttct cctttttttt gccatctgcc ctgtaagcat cctgctgggg acccagatag | 180 | |
| gagtcatcac tctaggctga gaacatctgg gcacacaccc taagcctcag catgactcat | 240 | |

```
catgactcag cattgctgtg cttgagccag aaggtttgct tagaaggtta cacagaacca     300
gaaggcgggg gtggggcact gaccccgaca ggggcctggc cagaactgct catgcttgga     360
ctatgggagg tcactaatgg agacacacag aaatgtaaca ggaactaagg aaaaactgaa     420
gcttatttaa tcagagatga gatgctggaa gggatagagg gagctgagct tgtaaaaagt     480
atagtaatca ttcagcaaat ggttttgaag cacctgctgg atgctaaaca ctattttcag     540
tgcttgaatc ataaataaga ataaaacatg tatcttattc cccacaagag tccaagtaaa     600
aaataacagt taattataat gtgctctgtc ccccaggctg gagtgcagtg gcacgatctc     660
agctcactgc aacctccgcc tcccgggttc aagcaattct cctgcctcag ccaccctaat     720
agctgggatt acaggtgcac accaccatgc caggctaatt tttgtacttt tgtagaggc     780 agggtatcac catgttgtcc aagatggtct tgaactcctg agctccaagc agtccaccca     840
cctcagcctc ccaaagtgct                                                860
```

```
<210> SEQ ID NO 10
<211> LENGTH: 613
<212> TYPE: DNA
<213> ORGANISM: Homo sapiens

<400> SEQUENCE: 10
aagcaataga tggctctgcc ctgacttttta tgcccagccc tggctcctgc cctccctgct      60
cctgggagta gattggccaa ccctagggtg tggctccaca gggtgaggtc taagtgatga     120
cagccgtacc tgtccttggc tcttctggca ctggcttagg agttggactt caaaccctca     180
gccctccctc taagatatat ctcttggccc cataccatca gtacaaattg ctactaaaaa     240
catcctcctt tgcaagtgta tttacgtaat atttggaatc acagcttggt aagcatattg     300
aagatcgttt tcccaatttt cttattacac aaataagaaa ttgatgcact aaaagtggaa     360
gagttttgtc taccataatt cagctttggg atatgtagat ggatctcttc ctgcgtctcc     420
agaatatgca aaatacttac aggacagaat ggatgaaaac tctacctcag ttctaagcat     480
atcttctcct tatttggatt aaaaccttct ggtaagaaaa gaaaaaaaat atatatatat     540
atgtgtatat atacacacat acatatacat atatatgcat tcatttgttg ttgttttttct     600 taatttgctc atg                                                        613
```

```
<210> SEQ ID NO 11
<211> LENGTH: 265
<212> TYPE: DNA
<213> ORGANISM: Homo sapiens

<400> SEQUENCE: 11
aagcaataga tggctctgcc ctgacttttta tgcccagccc tggctcctgc cctccctgct      60
cctgggagta gattggccaa ccctagggtg tggctccaca gggtgaggtc taagtgatga     120
cagccgtacc tgtccttggc tcttctggca ctggcttagg agttggactt caaaccctca     180
gccctccctc taagatatat ctcttggccc cataccatca gtacaaattg ctactaaaaa     240
catcctcctt tgcaagtgta tttac                                           265
```

```
<210> SEQ ID NO 12
<211> LENGTH: 879
<212> TYPE: DNA
<213> ORGANISM: Homo sapiens

<400> SEQUENCE: 12
```

| | |
|---|---|
| taggtattga ataagaaaaa tgaagttaag gtggttgatg gtaacactat gctaataact | 60 |
| gcagagccag aagcaccata agggacatga taagggagcc agcagacctc tgatctcttc | 120 |
| ctgaatgcta atcttaaaca tcctgaggaa gaatgggact tccatttggg gtgggcctat | 180 |
| gatagggtaa taagacagta gtgaatatca agctacaaaa agccccctttt caaattcttc | 240 |
| tcagtcctaa cttttcatac taagcccagt ccttccaaag cagactgtga aagagtgata | 300 |
| gttccgggag actagcactg cagattccgg gtcactgtga gtgggggagg cagggaagaa | 360 |
| gggctcacag gacagtcaaa ccatgccccc tgttttttcct tcttcaagta gacctctata | 420 |
| agacaacaga gacaactaag gctgagtggc caggcgagga gaaaccatct cgccgtaaaa | 480 |
| catggaagga acacttcagg ggaaaggtgg tatctctaag caagagaact gagtggagtc | 540 |
| aaggctgaga gatgcaggat aagcaaatgg gtagtgaaaa gacattcatg aggacagcta | 600 |
| aaacaataag taatgtaaaa tacagcatag caaaacttta acctccaaat caagcctcta | 660 |
| cttgaatcct tttctgaggg atgaataagg cataggcatc aggggctgtt gccaatgtgc | 720 |
| attagctgtt tgcagcctca ccttctttca tggagtttaa gatatagtgt attttcccaa | 780 |
| ggtttgaact agctcttcat ttcttatgt tttaaatgca ctgacctccc acattccctt | 840 |
| tttagtaaaa tattcagaaa taatttaaat acatcattg | 879 |

```
<210> SEQ ID NO 13
<211> LENGTH: 152
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 13
```

| | |
|---|---|
| tctcccacgc cctggtctca gcttggggag tggtcagacc ccaatggcga taaactctgg | 60 |
| caactttatc tgtgcactgc aggctcagcc ccaacagctt tagctttcac aagcaggcag | 120 |
| gggaagggaa acacatatct ccagatatga gg | 152 |

```
<210> SEQ ID NO 14
<211> LENGTH: 157
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 14
```

| | |
|---|---|
| ctaaacccct ccccacccct agccccaagc ttcatcttag ctccactcct gaccctatcc | 60 |
| agctaaaggt ccccacccag ctcctgccta tctagtcatt gcatatggca agacttgaaa | 120 |
| gtcctatctc aaagcagcag aattatcagc tacgact | 157 |

```
<210> SEQ ID NO 15
<211> LENGTH: 141
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 15
```

| | |
|---|---|
| ccatccccca gcactccctg cccccacagc ccagacttga ccaactccca gctccgcctg | 60 |
| ggacttccag atatggggcc ccacccttgc aggccttggg gacgctgaag atattgacta | 120 |

| | |
|---|---|
| tctgcgtgcc ggaaaagggt g | 141 |

<210> SEQ ID NO 16
<211> LENGTH: 171
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 16

| | |
|---|---|
| aaaggctggg ggtgggagta gcggatttga agcacttgtt ggcctacaga ggtgtggcaa | 60 |
| gcagagcacc tcagaactca ggcgtactgc ccgccgcccg agccctgcga gggccgatag | 120 |
| cgagggtgtg gcccttatct gcacccagca gagcgccggc ggggtacggt c | 171 |

<210> SEQ ID NO 17
<211> LENGTH: 195
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 17

| | |
|---|---|
| cagttgcctc agctgagtat gtcttctaaa gataatgtcg attgtgtatg gctgatggga | 60 |
| ttctaggacc aagcaagagg ttttttttt tccccccacat acttaacgtt tctatatttc | 120 |
| tatttgaatt cgactggaca gttccatttg aattatttct ctctctctct ctctctgaca | 180 |
| cattttatct tgcca | 195 |

<210> SEQ ID NO 18
<211> LENGTH: 14
<212> TYPE: DNA
<213> ORGANISM: Homo sapiens

<400> SEQUENCE: 18

| | |
|---|---|
| caccaggtgg cgct | 14 |

<210> SEQ ID NO 19
<211> LENGTH: 81706
<212> TYPE: DNA
<213> ORGANISM: Homo sapiens

<400> SEQUENCE: 19

| | |
|---|---|
| ggatcctcac atgagttcag tatataattg taacagaata aaaaatcaat tatgtattca | 60 |
| agttgctagt gtcttaagag gttcacattt ttatctaact gattatcaca aaaatacttc | 120 |
| gagttacttt tcattataat tcctgactac acatgaagag actgacacgt aggtgcctta | 180 |
| cttaggtagg ttaagtaatt tatccaaaac cacacaatgt agaacctaag ctgattcggc | 240 |
| catagaaaca caatatgtgg tataaatgag acagagggat ttctctcctt cctatgctgt | 300 |
| cagatgaata ctgagataga atatttagtt catctatcac acattaaacg ggactttaca | 360 |
| tttctgtctg ttgaagattt gggtgtgggg ataactcaag gtatcatatc caagggatgg | 420 |
| atgaaggcag gtgactctaa cagaaaggga aaggatgttg gcaaggctat gttcatgaaa | 480 |
| gtatatgtaa aatccacatt aagcttcttt ctgcatgcat tggcaatgtt tatgaataat | 540 |
| gtgtatgtaa aagtgtgctg tatattcaaa agtgtttcat gtgcctaggg gtgtcaaata | 600 |
| ctttgagttt gtaagtatat acttctctgt aatgtgtctg aatatctcta tttacttgat | 660 |
| tctcaataag taggtatcat agtgaacatc tgacaaatgt ttgaggaaca atttagtgtt | 720 |

```
tacctattca ccaaaattta ttaaatgcct aatctgtatc agatatacaa ttatctggcg    780
aaatctgtaa ttcctaattt aaacagctgt gtagcctaat tagggataaa ggcatgcaaa    840
cccataattt gtgtaggttg aaatgagcta tagaaaaatg cagtatattt atcagaagtc    900
tttagggtca tgaaaggaa tggtcaactg acactgccag ggactcatat gtaagagata     960
actaatgtga agtgacttta aaggagaaat tagcagaagt tttctttcca tgtctcctca   1020
tcatgttaca ataacggaag agattaaaac aacaaataca tttagacagc aatgtttatc   1080
ctggttagat gttttaatct aaatctatct tggagtgtta aaatgcattt gctcacctac   1140
tttaaaatat aaatgaaggt aggaacctgt agatacaaaa agttggagaa aaaagacaa    1200 taaagatgac aaaaatctat taatccttga tagaaaatga aagagataa aacactggtt    1260 tacataaaga aaataagatg gatagatagc agatccttat aaaagtgata atttgagaaa   1320
aaaaatactc catattctga gtttcttcac ataaaataat acaaatctgc tgtggtaagt   1380
tacaaagaga tagatttttt atcattatat aaaagatatt ttaaacagag ttatacaaca   1440
aaggaacaga ctatgtcata tattctcact tatcactata aacatctcag aaaaatctgc   1500
aaaatcattt catagcattt taaatagtta ggaataatgt agaaaactga aacagttcta   1560
agtttcccac aaacttagag tctcaaatgt tgcattacct aacttacctg caaatatttt   1620
atacaaattt gcacatgcta ctctagtcaa aaatatatgt acattatggg tattttctgt   1680
gtgtaacttg gttctagttg cttctttcag aaatagcctc tattttgat ttacctgata    1740 aaatcacatt cctctccaaa gccttctaaa tacttccaga ctaactactt tttagtacat   1800
ctaagaagaa aagagttttg tctcttatcc acctctgagt caaaaagcag catgtccatc   1860
aattggtaca tagttcccac agccccactt agctctggat tggagttcta cttggcattg   1920
tttgcaacta catggacgta aaatgcatgg attctcttga aaaaatgttt ctgccatgat   1980
gttctctgaa agagactaac cttccctcgc tttgcagaga aagactcgtg taatccttga   2040
caatgtcatc tcatctattt attcccatgt ctacccatat gtgaccttca tgtctttgct   2100
ctaagcccct acatcctcaa tctacacact aggatagtat aaaagtaata gtaataatag   2160
tagtaatagt aataacaata caatgattat ggcttatact atacacaaga cactgttgat   2220 atatttttc atttagtatt cacagtaact ctgtgcctca agtactattg taatacccttt   2280 taagaggagg aaactgaggc acagggccct aaagtaatat tccaagatga agtggctact   2340
aactgacaga gggcataatt caactcatga tatttggctc tagaatacat gctctgaatc   2400
attatacaat aataattcat gaggaaacat tttttaaagc ctaagttatt tgctctgaaa   2460
taagacataa tttggggtga gaaagcttag attccatgaa gtattacagc atttggtagt   2520 cttttttgcac tccaggtctt attttactg cttaaacata ataaacata tggttcagta    2580 tgcctttgat tttacaataa tattcctgtt attttttggaa gcacagggtg tgggataatg   2640
ctaattacta gtgattagta ttgagaggtg acagcgtgct ggcagtcctc acagccctcg   2700
ctcgctcttg gcgcctcctc tgcctgggct cccacattgg tggcacttga ggagcccttc   2760
agccggccgc tgcactgtgg gagccctttt ctgggctggc caaggccaga gccggctccc   2820
tcagcttgcc aggaggtgtg gagggacaga cgcgggcagg aaccgggctg tgcgccgtgc   2880
ttgagggagt tccgggtggg catgggctcc gaggacccg cactcggagc cgccagccgg    2940
ccccaccggc cgcgggcagt gaggggctta gcacctgggc cagcagctgc tgtgctcaat   3000
tcctcgccgg gccttagctg ccttcctgcg gggcagggct cgggacctgc agcgcgccat   3060
```

```
gcctgagcct ccccaccttc atgggctcct gtgcggcccg agcctcgccg acgagcgccg    3120 cccccctgctc cagggcaccc agtcccatcg accacccaag ggctgaagag tgcgggcgca    3180
cggcagggga ctggcaggca gctcccctg cagcccaggt gcgggatcca ctgggtgaag      3240
ccggctaggc tcctgagttt gctggggatg cgaagaaccc ttatgtctag ataagggatt    3300
gtaaatacac caattggcac tctgtatcta gctcaaggtt tgtaaacaca ccaatcagca    3360
ccctgtgtct agctcagggt tgtgaatgc accaatcaac actctatcta gctactctgg     3420
tggggccttg gagaaccttt atgtctagct cagggattgt aaatacacca atcggcagtc    3480
tgtatctagc tcaaggtttg taaacacacc aatcagcacc ctgtgtctag ctcagggttt    3540
gtgaatgcac caatcaacac tctgtatcta gctactctgg tggggacgtg gagaaccttt    3600
atgtctagct cagggattgt aaatacacca ctcggcagtc tgtatctagc tcaaggtttg    3660
taaacacacc aatcagcacc ctgtgtctag ctcagggttt gtgaatgcac caatcaacac    3720
tctgtatcta gctactctgg tggggacttg gagaaccttt gtgtggacac tctgtatcta    3780
gctaatctgg tggggacgtg gagaaccttt gtgtctagct catggattgt aaatgcacca    3840
atcagtgccc tgtcaaaaca gaccactggg ctctaccaat cagcaggatg tgggtggggc    3900
cagataagag aataaaagca ggctgcccga gccagcagtg gcaacccgct cgggtccoct    3960 tccacactgt ggaagctttg ttctttcgct ctttgcaata aatcttgctg ctgctcactg    4020
tttgggtcta cactgccttt atgagctgta acgctcaccg cgaaggtctg cagcttcact    4080
cttgaagcca gcgagaccac gaacccaccg ggaggaacga acaactccag aggcgccgcc    4140
ttaagagctg aacgttcac tgtgaaggtc tgcagcttca ctcctgagcc agcgagacca     4200
cgaacccatc agaaggaaga actccgaac acatccaaac atcagaacga acaaactcca    4260
cacacgcagc ctttaagaac tgtaacactc accacgaggg tccccggctt cattcttgaa    4320
gtcagtgaaa ccaagaaccc accaattccg gacacagtat gtcagaaaca atatgagtca    4380
ctaaatcaat atacttctca acaatttcca acagcccttg caattaactt ggccatgtga    4440
ctggttgtga ctaaaataat gtggagataa taatgtgtta ctccctaagg cagagtgccc    4500
ttctatcatt ctctttccct tcctctatgt ggcagaaagt aaaagattct gaaatgataa    4560
agtcaatcac aggaaggcac ctggactcct ggcccactgc ttggaggaga gcactcagga    4620
ccatgaacat ctgactgtga cgtagcaata aagaaaccca cgtttcatat gaaactgctt    4680
aaaattaatg gcacaagtca tgttttgat gttgcacatt tgtctttatt tgtggcttgt     4740
tttgcttcca catcaatcca ctcaaggcct acattctgct ataatgcaat ttcaagttct    4800
ttacaggccg agaaaaatga atctgaattc ctgacctcca aaagtgatca agatattttt    4860
agttcaggct ccaaaatttt ctcattttca taggttttcc tcgattgatc attattcatg    4920
atttgcaagg aatcattcaa tgttttctaa atctattact gcatcctgac acatatgaca    4980
ttttaactat gttccagatt tttgaatgaa gagtgtaaat tttaaatgtt ttccaccacaa    5040 aaaataagta tgtgaagtgg tggatttgtt aattagcctt atttaaccat ttaatattgt    5100
acacgtacac caaagcatca tgttgtaccc catgaataca cacaattatt atttgtcaat    5160
ttaaaatgaa ataataaaaa ataacaaagg cattagcctc tgcattgcct ttaccggtca    5220
tcctcacggt gactaacgca aaaaacgttc tatttcatcc ttacaaacat ccctatcttt    5280
gatgcctctt tgtctagatc tctatcccct cctgttttct ctacgttatt tatatgggta    5340
tcatcaccat cctggacaac atcaggacag atatccctca ccaagccaat gttcctctct    5400
atgttggctc aaatgtccct gaactttcct ttcaccaccc tttccacagt caaaaggata    5460
```

```
ttgtagttta atgcctcaga gttcagcttt taagcttctg acaaattatt cttcctcttt    5520
aggttctcct ttatggaatc ttctgtactg atggccatgt cctttaacta ctatgtagat    5580
atctgctact acctgtatta tgcctctacc tttattagca gagttatctg tactgttggc    5640
atgacaatca tttgttaata tgacttgcct ttccttttc tgctattctt gatcaaatgg     5700
ctcctctttc ttgctcctct catttctcct gccttcactt ggacgtgctt cacgtagtct    5760
gtgcttatga ctgattaaa aattgatatg gacttatcct aatgttgttc gtcataatat     5820
gggttttatg gtccattatt atttcctatg cattgatctg gagaaggctt caatcctttt    5880
actctttgtg gaaaatatct gtaaaccttc tggttcactc tgctatagca atttcagttt    5940
aggctagtaa gcatgaggat gcctccttct ctgattttc ccacagtctg ttggtcacag     6000
aataacctga gtgattactg atgaaagagt gagaatgtta ttgatagtca caatgacaaa    6060
aaacaaacaa ctacagtcaa aatgtttctc tttttattag tggattatat ttcctgacct    6120
atatctggca ggactcttta gagggtagc tgaagctgct gttatgacca ctagagggaa     6180
gaagatacct gtggagctaa tggtccaaga tggtggagcc ccaagcaagg aagttgttaa    6240
ggagcccttt tgattgaagg tgggtgcccc caccttacag ggacaggaca tctggatact    6300
cctcccagtt tctccagttt ccctttttcc taatatatct cctgataaaa tgtctatact    6360
cacttcccca tttctaataa taaagcaaag gctagttagt aagacatcac cttgcatttt    6420
gaaaatgcca tagactttca aaattatttc atacatcggt cttcttat ttcaagagtc      6480 cagaaatggc aacattacct ttgattcaat gtaatggaaa gagctctttc aagagacaga    6540
gaaaagaata atttaatttc tttcccacac cctccttccc tgtctcttac cctatcttcc    6600
ttccttctac cctccccatt tctctctctc atttctcaga agtatatttt gaaaggattc    6660
atagcagaca gctaaggctg gttttttcta agtgaagaag tgatattgag aaggtagggt    6720
tgcatgagcc ctttcagttt tttagtttat atacatctgt attgttagaa tgttttataa    6780
tataaataaa attatttctc agttatatac tagctatgta acctgtggat atttccttaa    6840
gtattacaag ctatacttaa ctcacttgga aaactcaaat aaatacctgc ttcatagtta    6900
ttaataagga ttaagtgaga taatgcccat aagattccta ttaataacag ataaatacat    6960
acacacacac acacattgaa aggattctta ctttgtgcta ggaactataa taagttcatt    7020
gatgcattat atcattaagt tctaatttca acactagaag gcaggtatta tctaaatttc    7080
atactggata cctccaaact cataaagata attaaattgc cttttgtcat atatttattc    7140
aaaagggtaa actcaaacta tggcttgtct aattttatat atcaccctac tgaacatgac    7200
cctattgtga tattttataa aattattctc aagttattat gaggatgttg aaagacagag    7260
aggatggggt gctatgcccc aaatcagcct cacaattaag ctaagcagct aagagtcttg    7320
cagggtagtg tagggaccac agggttaagg gggcagtaga attatactcc cactttagtt    7380
tcatttcaaa caatccatac acacacagcc ctgagcactt acaaattata ctacgctcta    7440
tactttttgt ttaaatgtat aaataagtgg atgaaagaat agatagatag atagacagat    7500
agatgataga tagaataaat gcttgccttc atagctgtct ccctaccttg ttcaaaatgt    7560
tcctgtccag accaaagtac cttgccttca cttaagtaat caattcctag gttatattct    7620
gatgtcaaag gaagtcaaaa gatgtgaaaa acaatttctg acccacaact catgctttgt    7680
agatgactag atcaaaaaat ttcagccata tcttaacagt gagtgaacag gaaatctcct    7740
cttttcccta catctgagat cccagcttct aagaccttca attctcactc ttgatgcaac    7800
```

```
agaccttgga agcatacagg agagctgaac ttggtcaaca aaggagaaaa gtttgttggc    7860
ctccaaaggc acagctcaaa cttttcaagc cttctctaat cttaaaggta aacaagggtc    7920
tcatttcttt gagaacttca gggaaaatag acaaggactt gcctggtgct tttggtaggg    7980
gagcttgcac tttcccccct tctggaggaa atatttatcc ccaggtagtt ccctttttgc    8040
accagtggtt ctttgaagag acttccacct gggaacagtt aaacagcaac tacagggcct    8100
tgaactgcac actttcagtc cggtcctcac agttgaaaag acctaagctt gtgcctgatt    8160
taagcctttt tggtcataaa acattgaatt ctaatctccc tctcaaccct acagtcaccc    8220
atttggtata ttaaagatgt gttgtctact gtctagtatc cctcaagtag tgtcaggaat    8280
tagtcattta aatagtctgc aagccaggag tggtggctca tgtctgtaat tccagcactt    8340
gagaggtaga agtgggagga ctgcttgagc tcaagagttt gatattatcc tggacaacat    8400
agcaagacct cgtctctact taaaaaaaaa aaaaaatta gccaggcatg tgatgtacac    8460
ctgtagtccc agctactcag gaggccgaaa tgggaggatc ccttgagctc aggaggtcaa    8520
ggctgcagtg agacatgatc ttgccactgc actccagcct ggacagcaga gtgaaacctt    8580
gcctcacgaa acagaataca aaacaaaca aacaaaaaac tgctccgcaa tgcgcttcct    8640
tgatgctcta ccacataggt ctgggtactt tgtacacatt atctcattgc tgttcataat    8700
tgttagatta attttgtaat attgatatta ttcctagaaa gctgaggcct caagatgata    8760
acttttattt tctggacttg taatagcttt ctcttgtatt caccatgttg taactttctt    8820
agagtagtaa caatataaag ttattgtgag ttttgcaaa cacagcaaac acaacgaccc    8880
atatagacat tgatgtgaaa ttgtctattg tcaatttatg ggaaaacaag tatgtacttt    8940
ttctactaag ccattgaaac aggaataaca gaacaagatt gaaagaatac attttccgaa    9000
attacttgag tattatacaa agacaagcac gtggacctgg gaggagggtt attgtccatg    9060
actggtgtgt ggagacaaat gcaggtttat aatagatggg atggcatcta gcgcaatgac    9120
tttgccatca ctttagaga gctcttgggg accccagtac acaagagggg acgcagggta    9180
tatgtagaca tctcattctt tttcttagtg tgagaataag aatagccatg acctgagttt    9240
atagacaatg agccctttc tctctcccac tcagcagcta tgagatggct tgccctgcct    9300
ctctactagg ctgactcact ccaaggccca gcaatgggca gggctctgtc agggctttga    9360
tagcactatc tgcagagcca gggccgagaa ggggtggact ccagagactc ccctcccat    9420 tcccgagcag ggtttgctta tttatgcatt taaatgatat atttatttta aaagaaataa    9480
caggagactg cccagccctg gctgtgacat ggaaactatg tagaatattt tgggttccat    9540
ttttttttcc ttctttcagt tagaggaaaa ggggctcact gcacatacac tagacagaaa    9600
gtcaggagct ttgaatccaa gcctgatcat ttccatgtca tactgagaaa gtccccaccc    9660
ttctctgagc ctcagtttct cttttataa gtaggagtct ggagtaaatg atttccaatg    9720
gctctcattt caatacaaaa tttccgttta ttaaatgcat gagcttctgt tactccaaga    9780
ctgagaagga aattgaacct gagactcatt gactggcaag atgtccccag aggctctcat    9840
tcagcaataa aattctcacc ttcacccagg cccactgagt gtcagatttg catgcactag    9900
ttcacgtgtg taaaaaggag gatgcttctt tcctttgtat tctcacatac ctttaggaaa    9960
gaacttagca ccccttcccac acagccatcc caataactca tttcagtgac tcaacccttg    10020
actttataaa agtcttgggc agtatagagc agagattaag agtacagatg ctggagccag    10080
accacctgag tgattagtga ctcagttct cttagtagtt gtatgactca gtttcttcat    10140
ctgtaaaatg gagggttttt taattagttt gttttgaga aagggtctca ctctgtcacc    10200
```

```
caaatgggag tgtagtggca aaatctcggc tcactgcaac ttgcacttcc caggctcaag   10260
cggtcctccc acctcaacat cctgagtagc tggaaccaca ggtacacacc accatacctc   10320 gctaatttt tgtattttg gtagagatgg ggtttcacat gttacacagg atggtctcag     10380
actccggagc tcaagcaatc tgcccacctc agccttccaa agtgctggga ttataagcat   10440
gattacagga gttttaacag gctcataaga ttgttctgca gcccgagtga gttaatacat   10500
gcaaagagtt taaagcagtg acttataaat gctaactact ctagaaatgt ttgctagtat   10560 ttttttgttta actgcaatca ttcttgctgc aggtgaaaac tagtgttctg tactttatgc   10620
ccattcatct ttaactgtaa taataaaaat aactgacatt tattgaaggc tatcagagac   10680
tgtaattagt gctttgcata attaatcata tttaatactc ttggattctt tcaggtagat   10740
actattatta tccccatttt actacagtta aaaaaactac ctctcaactt gctcaagcat   10800
acactctcac acacacaaac ataaactact agcaaatagt agaattgaga tttggtccta   10860
attatgtctt tgctcactat ccaataaata tttattgaca tgtacttctt ggcagtctgt   10920
atgctggatg ctggggatac aaagatgttt aaatttaagc tccagtctct gcttccaaag   10980
gcctcccagg ccaagttatc cattcagaaa gcatttttta ctctttgcat tccactgttt   11040
ttcctaagtg actaaaaaat tacactttat tcgtctgtgt cctgctctgg gatgatagtc   11100
tgactttcct aacctgagcc taacatccct gacatcagga aagactacac catgtggaga   11160
aggggtggtg gttttgattg ctgctgtctt cagttagatg gttaactttg tgaagttgaa   11220
aactgtggct ctctggttga ctgttagagt tctggcactt gtcactatgc ctattattta   11280
acaaatgcat gaatgcttca gaatatggga atattatctt ctggaatagg gaatcaagtt   11340
atattatgta acccaggatt agaagattct tctgtgtgta agaatttcat aaacattaag   11400
ctgtctagca aaagcaaggg cttggaaaat ctgtgagctc ctcaccatat agaaagcttt   11460
taacccatca ttgaataaat ccctataggg gatttctacc ctgagcaaaa ggctggtctt   11520
gattaattcc caaactcata tagctctgag aaagtctatg ctgttaacgt tttcttgtct   11580
gctaccccat catatgcaca acaataaatg caggcctagg catgactgaa ggctctctca   11640
taattcttgg ttgcatgaat cagattatca acagaaatgt tgagacaaac tatggggaag   11700
cagggtatga aagagctctg aatgaaatgg aaaccgcaat gcttcctgcc cattcagggc   11760
tccagcatgt agaaatctgg ggcttttgtga agactggctt aaaatcagaa gccccattgg   11820
ataagagtag ggaagaacct agagcctacg ctgagcaggt ttccttcatg tgacagggag   11880
cctcctgccc cgaacttcca gggatcctct cttaagtgtt tcctgctgga atctcctcac   11940
ttctatctgg aaatggtttc tccacagtcc agccctggc tagttgaaag agttacccat    12000
gcagaggccc tcctagcatc cagagactag tgcttagatt cctactttca gcgttggaca   12060
acctggatcc acttgcccag tgttcttcct tagttcctac cttcgacctt gatcctcctt   12120
tatcttcctg aaccctgctg agatgatcta tgtggggaga atggcttctt tgagaaacat   12180
cttcttcgtt agtggcctgc ccctcattcc cactttaata tccagaatca ctataagaag   12240
aatataataa gaggaataac tcttattata ggtaagggaa aattaagagg catacgtgat   12300
gggatgagta agagaggaga gggaaggatt aatggacgat aaaatctact actatttgtt   12360
gagacctttt atagtctaat caattttgct attgttttcc atcctcacgc taactccata   12420
aaaaaacact attattatct ttattttgcc atgacaagac tgagctcaga agagtcaagc   12480
atttgcctaa ggtcggacat gtcagaggca gtgccagacc tatgtgagac tctgcagcta   12540
```

```
ctgctcatgg gccctgtgct gcactgatga ggaggatcag atggatgggg caatgaagca    12600
aaggaatcat tctgtggata aaggagacag ccatgaagaa gtctatgact gtaaatttgg    12660
gagcaggagt ctctaaggac ttggatttca aggaattttg actcagcaaa cacaagaccc    12720
tcacggtgac tttgcgagct ggtgtgccag atgtgtctat cagaggttcc agggagggtg    12780
gggtggggtc agggctggcc accagctatc agggcccaga tgggttatag gctggcaggc    12840
tcagataggt ggttaggtca ggttggtggt gctgggtgga gtccatgact cccaggagcc    12900
aggagagata gaccatgagt agagggcaga catgggaaag gtgggggagg cacagcatag    12960
cagcattttt cattctacta ctacatggga ctgctcccct ataccccag ctaggggcaa     13020 gtgccttgac tcctatgttt tcaggatcat catctataaa gtaagagtaa taattgtgtc    13080
tatctcatag ggttattatg aggatcaaag gagatgcaca ctctctggac cagtggccta    13140
acagttcagg acagagctat gggcttccta tgtatgggtc agtggtctca atgtagcagg    13200
caagttccag aagatagcat caaccactgt tagagatata ctgccagtct cagagcctga    13260
tgttaattta gcaatgggct gggaccctcc tccagtagaa ccttctaacc agctgctgca    13320
gtcaaagtcg aatgcagctg gttagacttt ttttaatgaa agcttagctt tcattaaaga    13380
ttaagctcct aagcagggca cagatgaaat tgtctaacag caactttgcc atctaaaaaa    13440
atctgacttc actggaaaca tggaagccca aggttctgaa catgagaaat ttttaggaat    13500
ctgcacagga gttgagaggg aaacaagatg gtgaagggac tagaaccac atgagagaca     13560 cgaggaaata gtgtagattt aggctggagg taaatgaaag agaagtggga attaatactt    13620
actgaaatct ttctatatgt caggtgccat tttatgatat ttaataatct cattacatat    13680
ggtaattctg tgagatatgt attattgaac atactataat taatactaat gataagtaac    13740
acctcttgag tacttagtat atgctagaat caaatttaag tttatcatat gaggccgggc    13800
acggtggctc atatatggga ttacatgcct gtaatcccag cactttggga ggccaaggca    13860
attggatcac ctgaggtcag gagttccaga ccagcctggc caacatggtg aaaccccttc    13920
tctactaaaa aatacaaaaa atcagccagg tgtggtggca cgcgtctata atcccagcta    13980
ctcaggaggc tgaggcagga gaatcacttg aacccaggag gtggaggttg cagtgagcta    14040
agattgcacc actgcactcc agcctaggcg acagagtgag actccatctc aaaaaaaaaa    14100
aaagaagttt attatatgaa ttaacttagt tttactcaca ccaatactca gaagtagatt    14160
attacctcat ttattgatga ggagcccaat gtacttgtag tgtagatcaa cttattgaaa    14220
gcacaagcta ataagtagac aattagtaat tagaagtcag atggtctgag ctctcctact    14280
gtctacatta catgagctct tattaactgg ggactcgaaa atcaaagaca tgaaataatt    14340
tgtccaagct tacagaacca ccaagtagta aggctaggat gtagacccag ttctgctacc    14400
tctgaagaca gtgttttttc cacagcaaaa cacaaactca gatattgtgg atgcgagaaa    14460
ttagaagtag atattcctgc cctgtggccc ttgcttctta cttttacttc ttgtcgattg    14520
gaagttgtgg tccaagccac agttgcagac catacttcct caaccataat tgcatttctt    14580
caggaaagtt tgagggagaa aaaggtaaag aaaaatttag aaacaacttc agaataaaga    14640
gattttctct tgggttacag agattgtcat atgacaaatt ataagcagac acttgagaaa    14700
actgaaggcc catgcctgcc caaattaccc tttgaccct tggtcaagct gcaactttgg     14760
ttaaagggag tgtttatgtg ttatagtgtt catttactct tctggtctaa cccattggct    14820
ccgtcttcat cctgcagtga cctcagtgcc tcagaaacat acatatgttt gtctagttta    14880
agtttgtgtg aaattctaac tagcgtcaag aactgagggc cctaaactat gctaggaata    14940
```

```
gtgctgtggt gctgtgatag gtacacaaga aatgagaaga aactgcagat tctctgcatc   15000 tcccttttgcc gggtctgaca acaaagtttc cccaaatttt accaatgcaa gccatttctc   15060
catatgctaa ctactttaaa atcatttggg gcttcacatt gtctttctca tctgtaaaaa   15120
gaatggaaga actcattcct acagaactcc ctatgtcttc cctgatgggc tagagttcct   15180
ctttctcaaa aattagccat tattgtattt ccttctaagc caaagctcag aggtcttgta   15240
ttgcccagtg acatgcacac tggtcaaaag taggctaagt agaagggtac tttcacagga   15300
acagagagca aaagaggtgg gtgaatgaga gggtaagtga gaaaagacaa atgagaagtt   15360
acaacatgat ggcttgttgt ctaaatatct cctagggaat tattgtgaga ggtctgaata   15420
gtgttgtaaa ataagctgaa tctgctgcca acattaacag tcaagaaata cctccgaata   15480
actgtacctc caattattct ttaaggtagc atgcaactgt aatagttgca tgtatatatt   15540
tatcataata ctgtaacaga aaacacttac tgaatatata ctgtgtccct agttctttac   15600
acaataaact aatctcatcc tcataattct attagctaat acatattatc atcctatatt   15660
tcagagactt caagaagtta agcaacttgc tcaagatcat ctaagaagta ggtggtattt   15720
ctgggctcat ttggcccctc ctaatctctc atggcaacat ggctgcctaa agtgttgatt   15780
gccttaattc atcagggatg ggctcatact cactgcagac cttaactggc atcctctttt   15840
cttatgtgat ctgcctgacc ctagtagact tatgaaattt ctgatgagaa aggagagagg   15900
agaaaggcag agctgactgt gatgagtgat gaaggtgcct tctcatctgg gtaccagtgg   15960
ggcctctaag actaagtcac tctgtctcac tgtgtcttag ccagttcctt acagcttgcc   16020
ctgatgggag atagagaatg ggtatcctcc aacaaaaaaa taaattttca tttctcaagg   16080
tccaacttat gttttcttaa tttttaaaaa aatcttgacc attctccact ctctaaaata   16140
atccacagtg agagaaacat tcttttcccc catcccataa atacctctat taaatatgga   16200
aaatctgggc atggtgtctc acacctgtaa tcccagcact tgggaggct gaggtgggtg   16260 gactgcttgg agctcaggag ttcaagacca tcttggacaa catggtgata ccctgcctct   16320
acaaaaagta caaaaattag cctggcatgg tggtgtgcac ctgtaatccc agctattagg   16380
gtggctgagg caggagaatt gcttgaaccc gggaggcgga ggttgcagtg agctgagatc   16440
gtgccactgc actccagcct ggggacaga gcacattata attaactgtt attttttact   16500
tggactcttg tggggaataa gatacatgtt ttattcttat ttatgattca agcactgaaa   16560
atagtgttta gcatccagca ggtgcttcaa aaccatttgc tgaatgatta ctatacttt   16620 tacaagctca gctccctcta tcccttccag catcctcatc tctgattaaa taagcttcag   16680 ttttcctta gttcctgtta catttctgtg tgtctccatt agtgacctcc catagtccaa   16740
gcatgagcag ttctggccag gccctgtcg gggtcagtgc cccaccccg ccttctggtt   16800 ctgtgtaacc ttctaagcaa accttctggc tcaagcacag caatgctgag tcatgatgag   16860
tcatgctgag gcttagggtg tgtgcccaga tgttctcagc ctagagtgat gactcctatc   16920
tgggtcccca gcaggatgct tacagggcag atggcaaaaa aaggagaag ctgaccacct   16980 gactaaaact ccacctcaaa cggcatcata aagaaaatgg atgcctgaga cagaatgtga   17040
catattctag aatatattat ttcctgaata tatatatata tatacacata tacgtatata   17100
tatatatata tatatatttg ttgttatcaa ttgccataga atgattagtt attgtgaatc   17160
aaatatttat cttgcaggtg gcctctatac ctagaagcgg cagaatcagg ctttattaat   17220
acatgtgtat agattttttag gatctataca catgtattaa tatgaaacaa ggatatggaa   17280
```

```
gaggaaggca tgaaaacagg aaaagaaaac aaaccttgtt tgccatttta aggcacccct    17340
ggacagctag gtggcaaaag gcctgtgctg ttagaggaca catgctcaca tacgggtca     17400 gatctgactt ggggtgctac tgggaagctc tcatcttaag gatacatctc aggccagtct    17460
tggtgcatta ggaagatgta ggcaactctg atcctgagag gaaagaaaca ttcctccagg    17520
agagctaaaa gggttcacct gtgtgggtaa ctgtgaagga ctacaagagg atgaaaaaca    17580
atgacagaca gacataatgc ttgtgggaga aaaacagga ggtcaagggg atagagaagg     17640
cttccagaag aatggctttg aagctggctt ctgtaggagt tcacagtggc aaagatgttt    17700
cagaaatgtg acatgactta aggaactata caaaaggaa caaatttaag gagaggcaga    17760
taaattagtt caacagacat gcaaggaatt ttcagatgaa tgttatgtct ccactgagct    17820
tcttgaggtt agcagctgtg agggttttgc aggcccagga cccattacag gacctcacgt    17880
atacttgaca ctgtttttttg tattcatttg tgaatgaatg acctcttgtc agtctactcg    17940
gtttcgctgt gaatgaatga tgtcttgtca gcctacttgg tttcgctaag agcacagaga    18000
gaagatttag tgatgctatg taaaaacttc cttttttggtt caagtgtatg tttgtgatag    18060
aaatgaagac aggctacatg atgcatatct aacataaaca caaacattaa gaaaggaaat    18120
caacctgaag agtattata cagataacaa atacagaga gtgagttaaa tgtgtaataa      18180
ctgtggcaca ggctggaata tgagccattt aaatcacaaa ttaattagaa aaaaaacagt     18240
ggggaaaaaa ttccatggat gggtctagaa agactagcat tgttttaggt tgagtggcag    18300 tgttaaagg gtgatatcag actaaacttg aaatatgtgg ctaaataact agaatactct     18360 ttatttttttc gtatcatgaa tagcagatat agcttgatgg ccccatgctt ggtttaacat    18420
ccttgctgtt cctgacatga aatccttaat ttttgacaaa ggggctattc attttcattt    18480
tatattgggc ctagaaatta tgtagatggt cctgaggaaa agtttatagc ttgtctattt    18540
ctctctctaa catagttgtc agcacaatgc ctaggctata ggaagtactc aaagcttgtt    18600
aaattgaatt ctatccttct tattcaattc tacacatgga ggaaaaactc atcagggatg    18660
gaggcacgcc tctaaggaag gcaggtgtgg ctctgcagtg tgattgggta cttgcaggac    18720
gaagggtggg gtgggagtgg ctaaccttcc attcctagtg cagaggtcac agcctaaaca    18780
tcaaattcct tgaggtgcgg tggctcactc ctgtaatcac agcagtttgg gacgccaagg    18840
tgggcagatc acttgaggtc aggagttgga caccagccca gccaacatag tgaaacctgg    18900
tctctgctta aaaatataaa aattagctgg acgtggtgac gggagcctgt aatccaacta    18960
cttgggaggc tgaggcagga gaatcgcttg aaccggggag gtggagtttg cactgagcag    19020
agatcatgcc attgcactcc agcctccaga gcgagactct gtctaaagaa aaacgaaaac    19080
aaacaaacaa acaaacaaac aaaacccatc aaattccctg accgaacaga attctgtctg    19140
attgttctct gacttatcta ccattttccc tccttaaaga aactgtgaac ttccttcagc    19200
tagaggggcc tggctcagaa gcctctggtc agcatccaag aaatacttga tgtcactttg    19260
gctaaaggta tgatgtgtag acaagctcca gagatggttt ctcatttcca tatccaccca    19320
cccagctttc caatttttaaa gccaattctg aggtagagac tgtgatgaac aaacaccttg    19380
acaaaattca acccaaagac tcactttgcc tagcttcaaa atccttactc tgacatatac    19440
tcacagccag aaattagcat gcactagagt gtgcatgagt gcaacacaca cacacaccaa    19500
ttccatattc tctgtcagaa aatcctgttg gttttttcgtg aaaggatgtt ttcagaggct    19560 gacccccttgc cttcacctcc aatgctacca ctctggtcta agtcactgtc accaccacct    19620
aaattatagc tgttgactca taacaatctt cctgcttcta ccactgcccc actacaattt    19680
```

```
cttcccaata tactatccaa attagtctttt tcaaaatgta agtcatatat ggtcacctct    19740
ttgttcaaag tcttctgata gtttcctata tcatttataa taaaaccaaa tccttacaat    19800
tctctacaat agttgttcat gcatatatta tgtttattac agatacatat atatagctct    19860
catataaata aatatatata tttatgtgta tgtgtgtaga gtgttttttc ttacaactct    19920
atgatgtagg tattattagt gtcccaaatt ttataattta ggacttctat gatctcatct    19980
tttattctcc ccttcaccga atctcatcct acattggcct tattgatatt ccttgaaaat    20040
tctaagcatc ttacatcttt agggtattta catttgccat tccctatgcc ctaaatattt    20100
aatcatagtt tcatataaat gggttcctca tcatctatgg gtactctctc aggtgttaac    20160
tttatagtga ggactttcct gccatactac ttaaagtagc gatacccttt caccctgtcc    20220
taatcacact ctggccttca tttcagtttt ttttttttct ccatagcacc taatctcatt    20280
ggtatataac atgtttcatt tgcttattta atgtcaagct ctttccacta tcaagtccat    20340
gaaaacagga actttattcc tctattctgt ttttgtgctg tattcttagc aattttacaa    20400
ttttgaatga atgaatgagc agtcaaacac atatacaact ataattaaaa ggatgtatgc    20460
tgacacatcc actgctatgc acacacaaag aaatcagtgg agtagagctg gaagtgctaa    20520
gcctgcatag agctagttag ccctccgcag gcagagcctt gatgggatta ctgagttcta    20580
gaattggact catttgtttt gtaggctgag atttgctctt gaaaacttgt tctgaccaaa    20640
ataaaaggct caaagatga atatcgaaac cagggtgttt tttacactgg aatttataac    20700
tagagcactc atgtttatgt aagcaattaa ttgtttcatc agtcaggtaa agtaaagaa    20760 aaactgtgcc aaggcaggta gcctaatgca atatgccact aaagtaaaca ttatttcata    20820
ggtgtcagat atggcttatt catccatctt catgggaagg atggccttgg cctggacatc    20880
agtgttatgt gaggttcaaa acacctctag gctataaggc aacagagctc cttttttttt    20940
tttctgtgct ttcctggctg tccaaatctc taatgataag catacttcta ttcaatgaga    21000
atattctgta agattatagt taagaattgt gggagccatt ccgtctctta tagttaaatt    21060
tgagcttctt ttatgatcac tgttttttta atatgcttta agttctgggg tacatgtgcc    21120
atggtggttt gctgcaccca tcaacccgtc atctacatta ggtatttctc ctaatgctat    21180
ccttccccta gccccccacc cccaacaggc cccagtgtgt gatgttcccc tccctgtgtc    21240
catggatcac tggttttttt ttgtttttt tttttttta aagtctcagt taaattttg    21300 gaatgtaatt tattttcctg gtatcctagg acttgcaagt tatctggtca ctttagccct    21360
cacgttttga tgataatcac atatttgtaa acacaacaca cacacacaca cacacacaca    21420
tatatatata tataaaacat atatatacat aaacacacat aacatattta tcgggcattt    21480
ctgagcaact aatcatgcag gactctcaaa cactaaccta tagccttttc tatgtatcta    21540
cttgtgtaga aaccaagcgt gggggactgag aaggcaatag caggagcatt ctgactctca    21600
ctgcctttag ctaggcccct ccctcatcac agctcagcat agtcctgagc tcttatctat    21660
atccacacac agtttctgac gctgcccagc tatcaccatc ccaagtctaa agaaaaaaat    21720
aatgggtttg cccatctctg ttgattagaa aacaaaacaa aataaaataa gcccctaagc    21780
tcccagaaaa catgactaaa ccagcaagaa gaagaaaata caataggtat atgaggagac    21840
tggtgacact agtgtctgaa tgaggcttga gtacagaaaa gaggctctag cagcatagtg    21900
gtttagagga gatgtttctt tccttcacag atgcccttagc ctcaataagc ttgcggttgt    21960
ggaagtttac tttcagaaca aactcctgtg gggctagaat tattgatggc taaaagaagc    22020
```

```
ccgggggagg gaaaaatcat tcagcatcct caccgttagt gacacaaaac agaggggggcc   22080 tggttttcca tatttcctca tgatggatga tctcgttaat gaaggtggtc tgacgagatc   22140
attgcttctt ccatttaagc cttgctcact tgccaatcct cagttttaac cttctccaga   22200
gaaatacaca tttttattc aggaaacata ctatgttata gtttcaatac taaataatca   22260
aagtactgaa gatagcatgc ataggcaaga aaaagtcctt agctttatgt tgctgttgtt   22320
tcagaattta aaaagatca ccaagtcaag gacttctcag ttctagcact agaggtggaa   22380
tcttagcata taatcagagg ttttttcaaaa tttctagaca taagattcaa agccctgcac   22440
ttaaaatagt ctcatttgaa ttaactcttt atataaattg aaagcacatt ctgaactact   22500
tcagagtatt gttttatttc tatgttctta gttcataaat acattaggca atgcaattta   22560
attaaaaaaa cccaagaatt tcttagaatt ttaatcatga aaataaatga aggcatcttt   22620
acttactcaa ggtcccaaaa ggtcaaagaa accaggaaag taaagctata tttcagcgga   22680
aaatgggata tttatgagtt ttctaagttg acagactcaa gttttaaccT tcagtgccca   22740
tcatgtagga aagtgtggca taactggctg attctggctt tctactcctt tttcccatta   22800
aagatccctc ctgcttaatt aacattcaca gtaactctg gttgtacttt aggcacagtg   22860
gctcccgagg tcagtcacac aataggatgt ctgtgctcca agttgccaga gagagagatt   22920
actcttgaga atgagcctca gccctggctc aaactcacct gcaaacttcg tgagagatga   22980
ggcagaggta cactacgaaa gcaacagtta gaagctaaat gatgagaaca catggactca   23040
tagagggaaa caacgcatac tggggcctat cagagggtgg agggtgagag aaggagagga   23100
tcaggaaaaa tcactaatgg atgctaagcg taatacctga gtgatgagat catctataca   23160
acaaaccccc ttgacattca tttatctatg taacaaacct gcacatcctg tacatgtacc   23220
cctgaactta aaataaaagt tgaaaacaag aaagcaacag tttgaacact tgttatggtc   23280
tattctctca ttctttacaa ttacactaga aaatagccac aggcttcctg caaggcagcc   23340
acagaattta tgacttgtga tatccaagtc attcctggat aatgcaaaat ctaacacaaa   23400
atctagtaga atcatttgct tacatctatt tttgttctga gaatatagat ttagatacat   23460
aatggaagca gaataattta aaatctggct aatttagaat cctaagcagc tcttttccta   23520
tcagtggttt acaagccttg tttatatttt tcctatttta aaaataaaaa taaagtaagt   23580
tatttgtggt aaagaatatt cattaaagta tttatttctt agataatacc atgaaaaaca   23640
ttcagtgaag tgaagggcct actttactta acaagaatct aatttatata attttttcata   23700 ctaatagcat ctaagaacag tacaatattt gactcttcag gttaaacata tgtcataaat   23760
tagccagaaa gatttaagaa aatattggat gtttccttgt ttaaattagg catcttacag   23820
tttttagaat cctgcataga acttaagaaa ttacaaatgc taaagcaaac ccaaacaggc   23880
aggaattaat cttcatcgaa tttgggtgtt tctttctaaa agtcctttat acttaaatgt   23940
cttaagacat acatagattt tattttacta attttaatta tatagacaat aaatgaatat   24000
tcttactgat tactttttct gactgtctaa tctttctgat ctatcctgga tggccataac   24060
acttatctct ctgaactttg ggcttttaat ataggaaaga aaagcaataa tccatttttc   24120
atggtatctc atatgataaa caaataaaat gcttaaaaat gagcaggtga agcaatttat   24180
cttgaaccaa caagcatcga agcaataatg agactgcccg cagcctacct gacttctgag   24240
tcaggattta taagccttgt tactgagaca caaacctggg cctttcaatg ctataacctt   24300
tcttgaagct cctccctacc accctttagcc ataaggaaac atggaatggg tcagatccct   24360
ggatgcaagc caggtctgga accataggca gtaaggagag aagaaaatgt gggctctgca   24420
```

```
actggctccg agggagcagg agaggatcaa ccccatactc tgaatctaag agaagactgg    24480
tgtccatact ctgaatggga agaatgatgg gattacccat agggcttgtt ttagggagaa    24540
acctgttctc caaactcttg gccttgagat acctggtcct tattccttgg actttggcaa    24600
tgtctgaccc tcacattcaa gttctgagga agggccactg ccttcatact gtggatctgt    24660
agcaaattcc ccctgaaaac ccagagctgt atcttaattg gttaaaaaaa attatattat    24720
ctcaacgact gttcttctct gagtagccaa gctcagcttg gttcaagcta caagcagctg    24780
agctgctttt tgtctagtca ttgttctttt atttcagtgg atcaaatacg ttctttccaa    24840
acctaggatc ttgtcttcct aggctatata ttttgtccca ggaagtctta atctggggtc    24900
cacagaacac tagggggctg gtgaagttta tagaaaaaaa atctgtattt ttacttacat    24960
gtaactgaaa tttagcattt tcttctactt tgaatgcaaa ggacaaacta gaatgacatc    25020
atcagtacct attgcatagt tataaagaga aaccacagat attttcatac tacaccatag    25080
gtattgcaga tcttttttgtt tttgttttg tttgagatgg agtttcgctc ttattgccca    25140
ggctggagtg cagtggcatg atttcggctc actgcaacct ccccttcctg cattcaagca    25200
attctcctgc cttggcctcc tgagtagctg gggattacag gcacctgcca ccatgccagt    25260 ctaattttg tatttttagt agagatgggg tttcgccatg ttggccaggc tggtcttgaa    25320
ctcctgacct cagatgatct gcccgccttg gcctcctgaa gtgctgggat tataggtgtg    25380
agccaccacg cctggcccat tgcagatatt tttaattcac atttatctgc atcactactt    25440
ggatcttaag gtagctgtag acccaatcct agatctaatg ctttcataaa gaagcaaata    25500
taataaatac tataccacaa atgtaatgtt tgatgtctga taatgatatt tcagtgtaat    25560
taaacttagc actcctatgt atattatttg atgcaataaa aacatatttt tttagcactt    25620
acagtctgcc aaactggcct gtgacacaaa aaaagtttag gaattcctgg ttttgtctgt    25680
gttagccaat ggttagaata tatgctcaga aagataccat tggttaatag ctaaaagaaa    25740
atggagtaga aattcagtgg cctggaataa taacaatttg ggcagtcatt aagtcaggtg    25800
aagacttctg gaatcatggg agaaaagcaa gggagacatt cttacttgcc acaagtgttt    25860
tttttttttt ttttttttat cacaaacata agaaaatata ataaataaca aagtcaggtt    25920
atagaagaga gaaacgctct tagtaaactt ggaatatgga atccccaaag gcacttgact    25980
tgggagacag gagccatact gctaagtgaa aaagacgaag aacctctagg gcctgaacat    26040
acaggaaatt gtaggaacag aaattcctag atctggtggg gcaaggggag ccataggaga    26100
aagaaatggt agaaatggat ggagacggag gcagaggtgg gcagatcatg aggtcaagag    26160
atcgagacca tcctggcaaa catggtgaaa tcccgtctct actaaaaata aaaaaattag    26220
ctgggcatgg tggcatgcgc ctgtagtccc agctgctcgg gaggctgagg caggagaatc    26280
gtttgaaccc aggaggcgaa ggttgcagtg agctgagata gtgccattgc actccagtct    26340
ggcaacagag tgagactccg tctcaaaaaa aaaaaaaaa gaaagaaaga aagaaaaag    26400 aaaaaagaaa aaataaatgg atgtagaaca agccagaagg aggaactggg ctgggcaat    26460 gagattatgg tgatgtaagg gactttata gaattaacaa tgctggaatt tgtggaactc    26520
tgcttctatt attccccaa tcattacttc tgtcacattg atagttaaat aatttctgtg    26580
aatttattcc ttgattctaa aatatgagga taatgacaat ggtattataa gggcagatta    26640
agtgatatag catgagcaat attccttcagg cacatggatc gaattgaata cactgtaaat    26700
cccaacttcc agtttcagct ctaccaagta aagagctagc aagtcatcaa aatggggaca    26760
```

```
tacagaaaaa aaaaaggaca ctagaggaat aatatacct gactcctagc ctgattaata    26820
tatcgattca ctttttctc tgtttgatga caaattctgg ctttaaataa ttttaggatt    26880
ttaggcttct cagctccctt cccagtgaga agtataagca ggacagacag gcaagcaaga   26940
agagagcccc aggcaatact cacaaagtag ccaatgtccc ctgtggtcat agagaaatga   27000
aaagagagag gattctctgg aagcactgga tgtaatcttt tctgtctgtc ctctctaggg   27060
aatcacccca aggtactgta ctttgggatt aaggctttag tcccactgtg gactacttgc   27120
tattctgttc agtttctaga aggaactatg tacggttttt gtctccctag agaaactaag   27180
gtacagaagt tttgtttaca atgcactcct taagagagct agaactgggt gagattctgt   27240
tttaacagct ttatttctt ttccttggcc ctgttttgt cactgtcacc acctttaagg     27300
caaatgttaa atgcgctttg gctgaaactt tttttcctat tttgagattt gctcctttat   27360
atgaggcttt cttggaaaag gagaatggga gagatggata tcattttgga agatgatgaa   27420
gagggtaaaa aagggggacaa atggaaattt gtgttgcaga tagatgagga gccaacaaaa  27480
aagagcctca ggatccagca cacattatca caaacttagt gtccatccat cactgctgac   27540
cctctccgga cctgactcca ccctgagg acacaggtca gccttgacca atgactttta     27600
agtaccatgg agaacagggg gccagaactt cggcagtaaa gaataaaagg ccagacagag   27660
aggcagcagc acatatctgc ttccgacaca gctgcaatca ctagcaagct ctcaggcctg   27720
gcatcatggt gcattttact gctgaggaga aggctgccgt cactagcctg tggagcaaga   27780
tgaatgtgga agaggctgga ggtgaagcct tgggcaggta agcattggtt ctcaatgcat   27840
gggaatgaag ggtgaatatt accctagcaa gttgattggg aaagtcctca agatttttg    27900
catctctaat tttgtatctg atatggtgtc atttcataga ctcctcgttg tttaccctg    27960
gacccagaga ttttttgaca gctttggaaa cctgtcgtct ccctctgcca tcctgggcaa   28020
ccccaaggtc aaggcccatg gcaagaaggt gctgacttcc tttggagatg ctattaaaaa   28080
catgacaac ctcaagcccg cctttgctaa gctgagtgag ctgcactgtg acaagctgca    28140
tgtggatcct gagaacttca aggtgagttc aggtgctggt gatgtgattt tttggcttta   28200
tattttgaca ttaattgaag ctcataatct tattggaaag accaacaaag atctcagaaa   28260
tcatgggtcg agcttgatgt tagaacagca gacttctagt gagcataacc aaaacttaca   28320
tgattcagaa ctagtgacag taaggacta ctaacagcct gaattggctt aacttttcag    28380
gaaatcttgc cagaacttga tgtgtttatc ccagagaatt gtattataga attgtagact   28440
tgtgaaagaa gaatgaaatt tggcttttgg tagatgaaag tccattcaa ggaaatagaa    28500
atgccttatt ttatgtgggt catgataatt gaggtttaga aagagatttt tgcaaaaaaa   28560
ataaaagatt tgctcaaaga aaataagac acattttcta aaatatgtta aatttccccat   28620
cagtattgtg accaagtgaa ggcttgtttc cgaatttgtt ggggattta aactcccgct    28680
gagaactctt gcagcactca cattctacat ttacaaaaat tagacaattg cttaaagaaa   28740
aacagggaga gagggaaccc aataatactg gtaaatggg gaagggggtg agggtgtagg    28800
taggtagaat gttgaatgta gggctcatag aataaaattg aacctaagct catctgaatt   28860
ttttgggtgg gcacaaacct tggaacagtt tgaggtcagg gttgtctagg aatgtaggta   28920
taaagccgtt tttgtttgtt tgtttgtttt ttcatcaagt tgttttcgga aacttctact   28980
caacatgcct gtgtgttatt ttgtcttttg cctaacagct cctgggtaac gtgatggtga   29040
ttattctggc tactcacttt ggcaaggagt tcacccctga agtgcaggct gcctggcaga   29100
agctggtgtc tgctgtcgcc attgccctgg cccataagta ccactgagtt ctcttccagt   29160
```

```
ttgcaggtgt tcctgtgacc ctgacaccct ccttctgcac atggggactg ggcttggcct    29220
tgagagaaag ccttctgttt aataaagtac attttcttca gtaatcaaaa attgcaattt    29280
tatcttctcc atcttttact cttgtgttaa aaggaaaaag tgttcatggg ctgagggatg    29340
gagagaaaca taggaagaac caagagcttc cttaagaaat gtatggggc ttgtaaaatt     29400 aatgtggatg ttatgggaga attccaggat tccaaggagg atgatatgat ggagaaaaat    29460
ctttatcggg gtgggaaaat ggttaattaa gtggacagag actcctaggc agttttact     29520 gcaccgggga aagaaggagc tgttagtggt acctgagaaa gcagatttgt ggtacatgtc    29580
acttttcatt aaaaacaaaa acaaaacaaa acaaaacttc atagatatcc aagatatagg    29640
ctagaattac tattttaatt tactcttatt tacattttga agtagctagc ttgtcacatg    29700
ttttatgaaa ttgatttgga gataagatga gtgtgtatca acaatagcct gctctttcca    29760
tgaaggattc cattatttca tgggttagct gaagctaaga cacatgatat cattgtgcat    29820
tatcttctga tagaatgtaa catgcactaa aataaagtta gagttaggac ctgagtggga    29880
aagtttttgg agagtgtgat gaagactttc cgtgggagat agaatactaa taaaggctta    29940
aattctaaaa ccagcaagct agggcttcgt gacttgcatg aaactggctc tctggaagta    30000
gaagggagag taagacatac gtagaggact aggaaagacc agatagtaca gggcctggct    30060
acaaaaatac aagcttttac tatgctattg caatactaaa cgataagcat taggatgtta    30120
agtgactcag gaaataagat tttgggaaaa agtaatctgc ttatgtgcac aaaatggatt    30180
caagtttgca gataaaataa aatatggatg atgattcaag gggacagata caatggttca    30240
aacccaagag gagcagtgag tctgtggaat ttgaaggatg acaaaggtg gggtgagaaa     30300 gacatagtat tcgactgact gtgggagatg agaaggaaga aggaggtgat aaatgactga    30360
aagctcccag actggtgaag ataacaggag gaaaccatgc actgacctgg tgactctcat    30420
gtgtgaaggg tagagggata ttaacagatt tactttttag gaagtgctag attggtcagg    30480
gagttttgac cttcaggtct tgtgtctttc atatcaagga acctttgcat tttccaagtt    30540
agagtgccat atttttggcaa atataacttt attagtaatt ttatagtgct ctcacattga    30600
tcagactttt tcctgtgaat tacttttgaa tttggctgta tatatccaga atatgggaga    30660
gagacaaata attattgtag ttgcaggcta tcaacaatac tggtctctct gagccttata    30720
acctttcaat atgcccataa acagagtaaa caggattat tcatggcact aaatattttc      30780
acctagtcag tcaacaaatg ggagcaatgt gcatttttg atacatattt ttatatattt      30840
atggggtaca tgtgatactt acatgcctag aacatgtgat gattaagtct agatatttag    30900
gatatccatt gctttgagca tttatcattt ctatgtattg agaaaatttc aaatcctcat    30960
ttctagccat tttgaaatat ataataaata gtaattaact atagtcaccc tactcaaata   31020
tcaaacatta tggcttaatc cttctatcca actgtgtttg tacctattaa ccaacatctc    31080
ttaaatcccc tcccatacac actcacactt ttttccagcct ctgataacta tcattctact  31140
ctctaccacc atgagaccca cttttttagc tcccacagat gaataaaaac atgtgatatt    31200
tgactttctg tatctggctt atttattat ctatctcttt ggcataccaa gagtttgttt     31260
ttgttctgct tcagggcttt caattaacat aatgacctct ggttccatcc atgttgctac    31320
aaatgacaag atttcattct ttttcatggc aaaatagtac tgtgcaaaaa tacaattttt    31380
taatccgttc atctgttgat agacacttag gttgatccca aaccttaact attgtgaata    31440
gtgcttcaat aaacatgagt gtaatgtgtc cattggatat actgatttcc tttcttttgg    31500
```

```
ataaataacc actagtgaga ttgctggatt gtatgatagt tctgttttta gtttactgag    31560
aaatcttcat actgttttcc ataatggttg tactatttta cattcccacc aacagtgtgt    31620
aagaaagagt tcccttttct ccatatcctc acaaggatct gttattttt  gtcttttttg    31680
ttaatagccg ttttaactag agtaagtaga tatctcattg tagttttgat ttgcatttcc    31740
ctgatcatta gtgatgttga gaattttttc atatgtttgt tggtcatttg tatatctttt    31800
tctgagaatt gtctgttcat gtccttagcc tactttttat tgggattgtt tgttattttc    31860
ttgataatct atttgtgttc attttagagc ctggatatta ttcttttgtc agatgtatag    31920
attgtgaaga ttttctccca ctctgtgggt tgtctgttta ttctgcagac tcttcctttt    31980
gccatgcaaa agctctttag tttaatttag tcccagatat tttctttgtt tttatgtatt    32040
tgcatttgtg ttcttggtca tgaaatcctt tcctaagcca atgtgtagaa gggtttttcc    32100
gatgttattt tctagaattg ttacagtttc agggcttaga tttaagtcct tgatccatct    32160
tgagttgatt tttgtataag gtgagagatg aagatccagt ttcattctcc tacatgtagc    32220
ttgccagcta tccccgcacc atttgttgaa tagggtgccc ttccccact  ttatgttttt    32280
gtttgctttg tcaaagatca gttggatgta agtatttgag tttatttctg ggttctctat    32340
tctgttccat tggtcgatgt gcctattgt  acaccagcat catgctgttt tggtgactat    32400
ggccttattg tatagtttga aatgaggtaa tgtaatgcct tcagatttgt tcttttttt     32460
agacttgctt gtttattggg ctcttttttg gttccataag aatttaggga ttgttttttc    32520
tagttctgtg aagactaatg gtggtatttt gatgggaatt gcaatgaatt tgtaggttgc    32580
ttctggcatt atggccattt tcacaatatt gattctaccc atctatgaga atggcatgtg    32640
tttccatttg tttgtgtctt atatgattac tttcagccgt gttttgtagt tttccttgta    32700
gatgtctttc acctccttgg ttaggtatat attcctaagt ttttgttttg tttgtttttg    32760
tttttttgcag ctattgtaaa aggggttgag ttcttgatt  tattctcagc ttggtcattg    32820
ctggtatgta agaaagcaac tcattggtgt acgttaattt tgtatccaga aactttgctg    32880
aattatttta tcagttctag ggggttttgg aggagtcttt agagttttct acatacacaa    32940
tcatatcatc agcaaacagt gacagtttga cttctctttt aacaatttgg atgtgcttta    33000
cttgtttctc ttgtctgatt gctcttgcta ggacttccag taatatgtta aagagaagtg    33060
gtgagagtgg gtatccttgt ctcattccag ttttcagaca gaatgctttt aacttttcc    33120
cattcaatat aatgttggct gtgtgtttac catagctggc ttttattaca ttgaggtatg    33180
tcctttgtaa accgattttg ctgagttta  gtcataaagt gatgttgaat tttgttgaat    33240
gcagttctg  tggctattga gataatcaca tgattttgt  ttccaattct ctttatgttg    33300
tgtatcacac ttattgactt gcgtatgtta aaccatccgt gcatccctcg catgaaaccc    33360
acttgatcat gggttttgat atgctgtcgg atgctattag ctagtatttt gtcaaggatg    33420
ttggcatcta tgttcatcag ggatattgat ctgtagtgtt ttttttttt  ggttatgttc    33480
tttcccagtt ttggtattaa ggtgatactg gcttcataga atgatttagg gaggattctc    33540
tctttctcta tcttgtagaa tactgtcaat aggattggta tcaattcttc tttgaatgtc    33600
tggtagaatt cagctgtgaa tctatctggt cctggacttt ttgttgttg  gtaaattttt    33660
attatcattt cagtcttgct gcttattact ggtctgttca gggtatctaa ttcttcctga    33720
cttaagctag agccctgtat cttttccagga attcgaacgt ctcctttagg ttttctagtt    33780
tatgcatgta aaggtgttca tagtagccctt gaataatctt ttgtatttct gtggtatcag    33840
taatagtatc tcctgttttg tttctaattg agtttatttg cacttctctc ctctttttctt   33900
```

```
ggttaatctt gctaatggtc tatcagtttt atttatcttt tcaaagaacc agcttttat    33960 ttcatttagc ttttgtattt ttttgcagtt gttttaattt catttagttc tcctcttatc    34020
ttagttattc cctttctttt gctgggtttt ggttctgttt gttttttgttt ctctagtttc   34080 ttgtggtgtg accttatatt gtctgtctgt cctctttcag actctttgac atcgacattt    34140
agggctgtga actttccttt tagcaccatc tttgctgtat cctagaggtt ttgataggtt    34200
gtgtcactat tgtcggtcag ttcaagtaat tttgttgttc ttattatact ttaagttctg    34260
ggatacatgt gcagaatgtg caggtttgtt acataggtat agatgtgcca tggtggtttg    34320
ctgcacccat caacctgtca tctacattag gtatttcttt taatgttatc cctctcctaa    34380 cccctcacc ccccgacagg ccctggtgtg tgatgttccc ctccctgtgt ccatgtgttc     34440
tcattgttca actcccactt atgagtgaga acgtgtggtg tttggtttct ctgttcctgt    34500
gttagtttgc tcagaatgat ggtttccacc ttcatccatg tccctgcaaa gacatgaact    34560 catcatttt atggctgcat agtattccat ggtgtatatg tgccacattt tctttatcca    34620
ttatatcgct gatggccatt tgggttggtt ccaagtcttt gctattgtga atagtgccac    34680
aataaacata cgtgtgcacg tgtctttata gtagaatgat ttctaattct ttgggtatat    34740
acccagtaat gggattgctg ggtcaaacag tatttctggt tctagatcct tgaggaatcg    34800
ccacactgtc ttccacaatg gttgaactaa tttacacacc catcaacagt gtaaaatttt    34860
tcctattctt ccacatcctc tccagcacct tttgtttcct gacttttaa taattgccat     34920 tctaactggc atgagatggt atctcattgt ggttttgatt tgcatttctc taatgaccag    34980
tgatgatgag cttcttttca tgtgtttctt ggccacataa atgacttctt tagagaagca    35040
tctgttcata tccttttgtcc acttttgat ggggtcgtta ggttttttct tgtaaatttg     35100
ttgaagttct ttgtagattt tggatgttag ccctttgtca gatggataga ttgcaaaaat    35160
tttctcccat tctgtaggtt gcctgttcac tctgatgata gtcttttgct gtgcagaagc    35220 tcttagttt aattagatcc catatgtcaa ttttggcctt tgttgtcatt gcttttgatg     35280
ttttagtcgt gaattttgc ccatgcctat gtcctgaatg gtattgccta ggttatcttc      35340 taggatttt atggttttag gttgcacatt taagtcttta atccaccttg agttaatttt     35400
tgtataaggt gtaaggaagg ggtacagttt cagttttatg catattgcta gccagttttt    35460
ccagcaccat ttattaaata gggaattctt tctccattgc ttttgtgatg tttgtcaaag    35520
atcagatggt cgtagatgtg tggcattatt tctgaggctt ctgttctgtt ccactggtct    35580
atatatctgt tttggtacca gtaccatgct gttttttgtta ctgtagcctt gtagtatagt    35640
ttgaagtcag gtagcatcat gcctccagct ttgttctttt tgtttaggat tgtcttggct    35700
atatgggctc ttttttgatt ccatatgaca tttaaagtag ttttttctaa ttctttgaaa    35760
aaagtcagtg gtagcttgat ggggatagca ttgaatctat aaattacttt gggcagtatg    35820
gccattttaa agatattgat tcttctctatc tatgagcatg gaatgttttt ccatttgttt    35880
gtgtcctctc ttatttcctt gagcagtgag tggtttgtag ctctccttga agaggttctt    35940
cacatccctt agaagttgta tttctaggta ttttatttta ttctctttgc agcaattgtg    36000
aatgggagtt caccccatgat ttggctctct gcttgtctat tattggtgta taggaacgct    36060
tgtgatttct gcacactgat tttgtatctt gagactttgc tgaagctgtt tatcagctta    36120
agattttggg ctgagatgac agggtcttct aaatatacaa tcatgtcatc tgcaaacaga    36180
gacaatttga cttcctctct tcctatttga atatgcttta tttctttctc ttgcctgatt    36240
```

```
gtcctggcga gaacttccaa tactatgttg agtaagagtg gcgagagggc atccttgtct    36300
tgtgccggtt ttcaaagcaa atgattttta aatttccatc ttgatttcat tgttgaccca    36360
atgatcattc aggagcaggt tatttaattt ccctgtattt gcatggtttt gaaggttcct    36420
tttgtagttg atttccaatt ttattctact gtggtctgag agagtgcttg atataatttc    36480
aatttttaaa aatttattga ggcttgtttt gtggcatatc atatggccta tcttggagaa    36540
agttccatgt gctgatgaat agaatgtgta ttctgcagtt gttgggtaga atgtcctgta    36600
aatatctgtt aagtccattt gttctttaaa tccattgttt ctttgtagac tgtcttgatg    36660
acctgcctag tgcagtcagt ggagtattga agtcccccac tattattatg ttgctgtcta    36720
gtctagtagt aattgtttta taaatttggg atctccagta ttagatgcat atatattaag    36780
aattgtaata ttctcccatt ggacaagggc ttttatcatt atatgatgtc cctctttgtc    36840
ttttttaact gctgtttctt taaagtttgt tttgtctgac ataagaatag ctgctttggc    36900
tcgcttttgg tgtccatttg tgtggaatgt cattttccac cccttttacct taagtttatg    36960 tgagtcctta tgtgttaggt gagtctcctg aaggcggcag ataactggtt ggtgaattct    37020
tattcattct gcaattctgt atctttaag tggagcattt agtccattta cattcaacat    37080
cagtattgag gtgtgaggta ctattccatt cttcgtggta tttgttgcct gtgtatcttt    37140
ttatctgtat ttttgttgta tatgtcctat gggatttatg ctttaaagag gttctgtttt    37200
gatgtgcttc cagggtttat ttcaagattt agagctcctt ttatcagttc ttgtagtgtt    37260
ggcttggtag tgccgaattc tctcagcatt tgttttttctg aaaaacactg tgtattttct    37320
tcatttgtga agcttagttt cactggatat aaaattcttg gctgataatt gtttgtttta    37380
agaaggctga agataggggcc atattcactt ctagctttta cggtttctgc tgagaaatct    37440
gctgttaatc tgataggttt tctttcatag gttacctggt agtttcacct cacagctctt    37500
aagattctct ttgtctttag ataactttgg atactctgat gacaatgtac ctaggcaatg    37560 atattttgc aatgaatttc ccaggtgttt attgagcttc ttgtatttgg atatctaggt    37620
ctctagcaag gtgggggaag ttttccttga ttatttccct ggataagttt tccaaacttt    37680
tagatttctc ttcttctctca ggaatgctga ttattcttag gtttgattgt ttaacataat    37740
cccagatttc ttggaggctt tgttcatatt ttcttattct ttttttctttg tctttgttgg    37800 attgggttaa ttcaaaaaact ttgtcttcaa gctctgaatt tcttctgctt ggattctatt    37860
gctgagactt tctagagcat tttgcatttc tataagtgca tccattcatc cattgttttcc    37920 tgaagttttg aatgtttttt atttatgcta tctctttaac tgaagatttc tcccctcatt    37980
tcttgtatca tattttttggt ttttttaaaa ttggacttca ccttcctcgg atgcctcctt    38040
gattagctta ataactgacc ttctgaatta tttttcaggt aaatcaggga tttcttcttg    38100
gtttggatgc attgctggtg agctagtatg atttttttggg gggtgttaaa gaaccttgtt    38160
tttcatatta ccagagttag ttttctggtt ccttctcact tgggtaggct ctgtcagagg    38220
gaaagtctag gcctcaaggc tgagactttt gtcccatgag gtgttccctt gatgtagcac    38280 agtcccccctt ttcctaggcg tggggcttcc tgagagccga actgtagtga ttgttatctc    38340
tcttctggat ctagccaccc atcaggtcta ccagactcca ggctggtact ggggtttgtc    38400
tgcacagagt cttgtgacgt gaaccatctg tgggtctctc agccatagat acaaccacct    38460
gctccaatgg aggtggcaga ggatgaaatg gactctgtga gggtccttac ttttggttgt    38520
tcaatgcact atttttgtgc tggttggcct cctgccagga ggtggcactt tctagaaagc    38580
atcagcagag gcagtcaggt ggtggtggct gggggggctg gggcacccta gaactcccaa    38640
```

```
gaatatatgc cctttgtctt cagctaccag ggtgagtaag gaaggaccat caggtggggg    38700
caggactagt cgtgtctgag ctcagagtct ccttgggcag gtctttctgt ggctactgtg    38760
ggaggatggg ggtgtagttt ccaggtcaat ggatttatgt tcctaggaca attatggctg    38820
cctctgctgt gtcatgcagg tcatcaggaa agtgggggaa agcaagcagt cacgtgactt    38880
gcccagctcc catgcaactc aaaaggttgg tctcacttcc agcgtgcacc ctcccccgca    38940
acagcaccga atctgtttcc atgcagtcag tgagcaaggc tgagaacttg ccccaggcta    39000
ccagctgcga aaccaagtag ggctgtccta cttccctgcc agtggagtct gcacaccaaa    39060
ttcatgtccc cccaccaacc cccccactgc ccagcccta  gatctggcca ggtggagatt    39120 ttcttttttcc tgtcatcttt tcccagttcc tctggcagcc ctcccaaatg acccctgtga    39180
ggcaaggcag aaatggcttc ctaggggacc cagagagccc acagggcttt tcccgctgct    39240
tcctctaccc ctgtattttg cttggccctc taaattgact cagctccagg taaggtcaga    39300
atcttctcct gtggtctaga tcttcaggtt ccccagtgag gatgtgtgtt tgggggtaga    39360 cggtcccccct tttccacttc cacagtttgg gcactcacaa atttggggt  gtttcccggg    39420 tcctgcagga gcaatctgct tctttcagag ggtgtgtgcg ttctctcagc tttcttgatt    39480
tatttctgca ggtggttctg caaaaaaaat tcctgatggg agacttcaca tgctgctctg    39540
tgcatccgag tgggagctgc aatgtacttc tgctgcctcc catctgccat caccctctaa    39600
tttgtcggta atatgcattt ttaatcaatc ttttttttctc tctctctctt tttcttctcc    39660
cccaaaacta tactgccctt tgatatcaag gaatcaagga cgtgatgttg aggggtgggc    39720
agtggataca ctctttaccc cttagggagc tatatctaga tttagatatt gccaattcaa    39780
gataacttaa ttgaaagcaa attcataatg aatacacaca cacacacaca catctgcatg    39840
acaagatttt taatagttga aagaataact aataattgtc cacaggcaat aagggctttt    39900
taagcaaaac agttgtgata aacaggtcat tcttagaata gtaatccagc caatagtaca    39960
ggttgcttag agattatgtc attaccagag ttaaaattct ataatggctt ctcactccct    40020
accactgagg acaagtttat gtccttaggt ttatgcttcc ctgaaacaat accacctgct    40080
attctccact ttacatatca acggcactgg ttctttatct aactctctgg cacagcagga    40140
gtttgttttc ttctgcttca gagctttgaa tttactattt cagcttctaa actttatttg    40200
gcaatgcctt cccatggcag attccttctg tcattttgcc tctgttcgaa tactttctcc    40260
ttaatttcat tcttagttaa taatatctga aattattttg ttgtttaact taattattaa    40320
ttttatgtat gttctaccta gattataatc ttcagaggaa agttttattc tctgacttat    40380
ttaacttaaa tgcccactac tttaaaaatt atgacattta tttaacagat atttgctgaa    40440
caaatgtttg aaaatacatg ggaagaatg  cttgaaaaca cttgaaattg cttgtgtaaa    40500
gaaacagttt tatcagttag gatttaatca atgtcagaag caatgatata ggaaaaatcg    40560
aggaataaga cagttatgga taaggagaaa tcaacaaact cttaaaagat attgcctcaa    40620
aagcataaga ggaaataagg gtttatacat gacttttaga acactgcctt ggttttttgga   40680 taaatgggga agttgtttga aaacaggagg gatcctagat attccttagt ctgaggagga    40740
gcaattaaga ttcacttgtt tagaggctgg gagtggtggc tcacgcctgt aatcccagaa    40800
ttttgggagg ccaaggcagg cagatcacct gaggtcaaga gttcaagacc aacctggcca    40860
acatggtgaa atcccatctc tacaaaaata caaaaattag acaggcatga tggcaagtgc    40920
ctgtaatccc agctacttgg gaggctgagg aaggagaatt gcttgaacct ggaaggcagg    40980
```

```
agttgcagtg agccgagatc ataccactgc actccagcct gggtgacaga acaagactct    41040
gtctcaaaaa aaaaaagag agattcaaaa gattcacttg tttaggcctt agcgggctta    41100
gacaccagtc tctgacacat tcttaaaggt caggctctac aaatggaacc caaccagact    41160
ctcagatatg gccaaagatc tatacacacc catctcacag atccctatc ttaaagagac    41220 cctaatttgg gttcacctca gtctctataa tctgtaccag cataccaata aaaatctttc    41280
tcacccatcc ttagattgag agaagtcact tattattatg tgagtaactg gaagatactg    41340
ataagttgac aaatcttttt ctttcctttc ttattcaact tttattttaa cttccaaaga    41400
acaagtgcaa tatgtgcagc tttgttgcgc aggtcaacat gtatctttct ggtcttttag    41460
ccgcctaaca ctttgagcag atataagcct tacacaggat tatgaagtct gaaaggattc    41520
caccaatatt attataattc ctatcaacct gataggttag gggaaggtag agctctcctc    41580
caataagcca gatttccaga gtttctgacg tcataatcta ccaaggtcat ggatcgagtt    41640
cagagaaaaa acaaaagcaa aaccaaacct accaaaaaat aaaaatccca agaaaaaat     41700 aaagaaaaaa acagcatgaa tacttcctgc catgttaagt ggccaatatg tcagaaacag    41760
cactgagtta cagataaaga tgtctaaact acagtgacat cccagctgtc acagtgtgtg    41820
gactattagt caataaaaca gtccctgcct cttaagagtt gttttccatg caaatacatg    41880
tcttatgtct tagaataaga ttccctaaga agtgaaccta gcatttatac aagataatta    41940
attctaatcc atagtatctg gtaaagagca ttctaccatc atctttaccg agcatagaag    42000
agctacacca aaaccctggg tcatcagcca gcacatacac ttatccagtg ataaatacac    42060
atcatcgggt gcctacatac ataccctgaat ataaaaaaaa tacttttgct gagatgaaac    42120
aggcgtgatt tatttcaaat aggtacggat aagtagatat tgaagtaagg attcagtctt    42180
atattatatt acataacatt aatctattcc tgcactgaaa ctgttgcttt ataggatttt    42240
tcactacact aatgagaact taagagataa tggcctaaaa ccacagagag tatattcaaa    42300
gataagtata gcacttctta tttggaaacc aatgcttact aaatgagact aagacgtgtc    42360
ccatcaaaaa tcctggaccct atgcctaaaa cacatttcac aatccctgaa cttttcaaaa    42420
attggtacat gctttaactt taaactacag gcctcactgg agctacagac aagaaggtga    42480
aaaacggctg acaaaagaag tcctggtatc ttctatggtg ggagaagaaa actagctaaa    42540
gggaagaata aattagagaa aaattggaat gactgaatcg gaacaaggca aaggctataa    42600
aaaaaattaa gcagcagtat cctcttgggg gcccttccc cacactatct caatgcaaat    42660
atctgtctga aacggtccct ggctaaactc cacccatggg ttggccagcc ttgccttgac    42720
caatagcctt gacaaggcaa acttgaccaa tagtcttaga gtatccagtg aggccagggg    42780
ccggcggctg gctagggatg aagaataaaa ggaagcaccc ttcagcagtt ccacacactc    42840
gcttctggaa cgtctgaggt tatcaataag ctcctagtcc agacgccatg ggtcatttca    42900
cagaggagga caaggctact atcacaagcc tgtggggcaa ggtgaatgtg gaagatgctg    42960
gaggagaaac cctgggaagg taggctctgg tgaccaggac aagggaggga aggaaggacc    43020
ctgtgcctgg caaaagtcca ggtcgcttct caggatttgt ggcaccttct gactgtcaaa    43080
ctgttcttgt caatctcaca ggctcctggt tgtctaccca tggacccaga ggttctttga    43140
cagctttggc aacctgtcct ctgcctctgc catcatgggc aaccccaaag tcaaggcaca    43200
tggcaagaag gtgctgactt ccttgggaga tgccataaag cacctggatg atctcaaggg    43260 caccttgcc cagctgagtg aactgcactg tgacaagctg catgtggatc ctgagaactt    43320
caaggtgagt ccaggagatg tttcagcact gttgcctta gtctcgaggc aacttagaca    43380
```

```
actgagtatt gatctgagca cagcagggtg tgagctgttt gaagatactg gggttgggag   43440
tgaagaaact gcagaggact aactgggctg agacccagtg gcaatgtttt agggcctaag   43500
gagtgcctct gaaaatctag atggacaact ttgactttga gaaaagagag gtggaaatga   43560
ggaaaatgac ttttctttat tagatttcgg tagaaagaac tttcaccttt ccctattttt   43620
tgttattcgt tttaaaacat ctatctggag gcaggacaag tatggtcatt aaaaagatgc   43680
aggcagaagg catatattgg ctcagtcaaa gtggggaact ttggtggcca aacatacatt   43740
gctaaggcta ttcctatatc agctggacac atataaaatg ctgctaatgc ttcattacaa   43800
acttatatcc tttaattcca gatgggggca aagtatgtcc aggggtgagg aacaattgaa   43860
acatttgggc tggagtagat tttgaaagtc agctctgtgt gtgtgtgtgt gtgtgtgcgc   43920
gcgtgtgttt gtgtgtgtgt gagagcgtgt gtttcttttta acgttttcag cctacagcat   43980
acagggttca tggtggcaag aagataacaa gatttaaatt atggccagtg actagtgctg   44040
caagaagaac aactacctgc atttaatggg aaagcaaaat ctcaggcttt gagggaagtt   44100
aacataggct tgattctggg tggaagcttg gtgtgtagtt atctggaggc caggctggag   44160
ctctcagctc actatgggtt catctttatt gtctcctttc atctcaacag ctcctgggaa   44220
atgtgctggt gaccgttttg gcaatccatt tcggcaaaga attcacccct gaggtgcagg   44280
cttcctggca gaagatggtg actggagtgg ccagtgccct gtcctccaga taccactgag   44340
ctcactgccc atgatgcaga gctttcaagg ataggcttta ttctgcaagc aatcaaataa   44400
taaatctatt ctgctaagag atcacacatg gttgtcttca gttcttttt tatgtctttt   44460 taaatatatg agccacaaag ggttttatgt tgagggatgt gtttatgtgt atttatacat   44520
ggctatgtgt gtttgtgtca tgtgcacact ccacactttt ttgtttacgt tagatgtggg   44580
ttttgatgag caaataaaag aactaggcaa taaagaaact tgtacatggg agttctgcaa   44640
gtgggagtaa aaggtgcagg agaaatctgg ttggaagaaa gacctctata ggacaggact   44700
cctcagaaac agatgttttg gaagagatgg ggaaaggttc agtgaagggg gctgaacccc   44760
cttccctgga ttgcagcaca gcagcgagga aggggctcaa cgaagaaaaa gtgttccaag   44820 cttaggaag tcaaggttta ggcagggata gccattctat tttattaggg gcaatactat   44880
ttccaacggc atctggcttt tctcagccct tgtgaggctc tacagggagg ttgaggtgtt   44940
agagatcaga gcaggaaaca ggtttttctt tccacggtaa ctacaatgaa gtgatcctta   45000
ctttactaag gaacttttca ttttaagtgt tgacgcatgc ctaaagaggt gaaattaatc   45060
ccataccctt aagtctacag actggtcaca gcatttcaag gaggagacct cattgtaagc   45120
ttctagggag gtggggactt aggtgaagga aatgagccag cagaagctca caagtcagca   45180
tcagcgtgtc atgtctcagc agcagaacag cacggtcaga tgaaaatata gtgtgaagaa   45240
tttgtataac attaattgag aaggcagatt cactggagtt cttatataat tgaaagttaa   45300
tgcacgttaa taagcaagag tttagtttaa tgtgatggtg ttatgaactt aacgcttgtg   45360
tctccagaaa attcacatgc tgaatcccca actcccaatt ggctccattt gtggggagg    45420 ctttggaaaa gtaatcaggt ttagaggagc tcatgagagc agatccccat catagaatta   45480
ttttcctcat cagaagcaga gagattagcc atttctcttc cttctggtga ggacacagtg   45540
ggaagtcagc cacctgcaac ccaggaagag agccctgacc aggaaccagc agaaaagtga   45600
gaaaaaatcc tgttgttgaa gtcacccagt ctatgctatt ttgttatagc accttgcact   45660
aagtaaggca gatgaagaaa gagaaaaaaa taagcttcgg tgttcagtgg attagaaacc   45720
```

```
atgtttatct caggtttaca aatctccact tgtcctctgt gtttcagaat aaaataccaa  45780
ctctactact ctcatctgta agatgcaaat agtaagcctg agcccttctg tctaactttg  45840
aattctattt tttcttcaac gtactttagg cttgtaatgt gtttatatac agtgaaatgt  45900
caagttcttt ctttatattt cttctttct tttttttcct cagcctcaga gttttccaca   45960
tgcccttcct actttcagga acttctttct ccaaacgtct tctgcctggc tccatcaaat  46020
cataaaggac ccacttcaaa tgccatcact cactaccatt tcacaattcg cactttcttt  46080
ctttgtcctt ttttttttta gtaaaacaag tttataaaaa attgaaggaa taaatgaatg  46140
gctacttcat aggcagagta gacgcaaggg ctactggttg ccgattttta ttgttatttt  46200
tcaatagtat gctaaacaag gggtagatta tttatgctgc ccattttag accataaaag   46260
ataacttcct gatgttgcca tggcatttt ttccttttaa ttttatttca tttcatttta   46320
atttcgaagg tacatgtgca ggatgtgcag gcttgttaca tgggtaaatg tgtgtctttc  46380
tggccttta gccatctgta tcaatgagca gatataagct ttacacagga tcatgaagga   46440
tgaaagaatt tcaccaatat tataataatt tcaatcaacc tgatagctta ggggataaac  46500
taatttgaag atacagcttg cctccgataa gccagaattc cagagcttct ggcattataa  46560
tctagcaagg ttagagatca tggatcactt tcagagaaaa acaaaaacaa actaaccaaa  46620
agcaaaacag aaccaaaaaa ccaccataaa tacttcctac cctgttaatg gtccaatatg  46680
tcagaaacag cactgtgtta gaaataaagc tgtctaaagt acactaatat tcgagttata  46740
atagtgtgtg gactattagt caataaaaac aacccttgcc tctttagagt tgttttccat  46800
gtacacgcac atcttatgtc ttagagtaag attccctgag aagtgaacct agcatttata  46860
caagataatt aattctaatc cacagtacct gccaaagaac attctaccat catctttact  46920
gagcatagaa gagctacgcc aaaaccctgg gtcatcagcc agcacacaca cttatccagt  46980
ggtaaataca catcatctgg tgtatacata catacctgaa tatggaatca atattttc    47040
taagatgaaa cagtcatgat ttatttcaaa taggtacgga taagtagata ttgaggtaag  47100
cattaggtct tatattatgt aacactaatc tattactgcg ctgaaactgt ggctttatag  47160
aaattgtttt cactgcacta ttgagaaatt aagagataat ggcaaaagtc acaaagagta  47220
tattcaaaaa gaagtatagc acttttcct tagaaaccac tgctaactga aagagactaa   47280
gatttgtccc gtcaaaaatc ctggacctat gcctaaaaca catttcacaa tccctgaact  47340
tttcaaaaat tggtacatgc tttagcttta aactacaggc ctcactggag ctagagacaa  47400
gaaggtaaaa aacggctgac aaaagaagtc ctggtatcct ctatgatggg agaaggaaac  47460
tagctaaagg gaagaataaa ttagagaaaa actggaatga ctgaatcgga acaaggcaaa  47520
ggctataaaa aaaattagca gtatcctctt gggggcccct tccccacact atctcaatgc  47580
aaatatctgt ctgaaacggt ccctggctaa actccaccca tgggttggcc agccttgcct  47640
tgaccaatag ccttgacaag gcaaacttga ccaatagtct tagagtatcc agtgaggcca  47700
ggggccggcg gctggctagg gatgaagaat aaaaggaagc acccttcagc agttccacac  47760
actcgcttct ggaacgtctg aggttatcaa taagctccta gtccagacgc catgggtcat  47820
ttcacagagg aggacaaggc tactatcaca agcctgtggg gcaaggtgaa tgtggaagat  47880
gctggaggag aaaccctggg aaggtaggct ctggtgacca ggacaaggga gggaaggaag  47940
gaccctgtgc ctggcaaaag tccaggtcgc ttctcaggat ttgtggcacc ttctgactgt  48000
caaactgttc ttgtcaatct cacaggctcc tggttgtcta cccatggacc cagaggttct  48060
ttgacagctt tggcaacctg tcctctgcct ctgccatcat gggcaacccc aaagtcaagg  48120
```

```
cacatggcaa gaaggtgctg acttccttgg gagatgccac aaagcacctg gatgatctca   48180
agggcacctt tgcccagctg agtgaactgc actgtgacaa gctgcatgtg gatcctgaga   48240
acttcaaggt gagtccagga gatgtttcag ccctgttgcc tttagtctcg aggcaactta   48300
gacaacggag tattgatctg agcacagcag ggtgtgagct gttttgaagat actggggttg   48360
ggggtgaaga aactgcagag gactaactgg gctgagaccc agtggtaatg ttttagggcc   48420
taaggagtgc ctctaaaaat ctagatggac aattttgact ttgagaaaag agaggtggaa   48480
atgaggaaaa tgacttttct ttattagatt ccagtagaaa gaactttcat cttccctca    48540
ttttgttgt tttaaaacat ctatctggag gcaggacaag tatggtcgtt aaaaagatgc    48600
aggcagaagg catatattgg ctcagtcaaa gtggggaact ttggtggcca aacatacatt   48660
gctaaggcta ttcctatatc agctggacac atataaaatg ctgctaatgc ttcattacaa   48720
acttatatcc tttaattcca gatggggggca aagtatgtcc aggggtgagg aacaattgaa   48780
acatttgggc tggagtagat tttgaaagtc agctctgtgt gtgtgtgtgt gtgtgcgcgc   48840
gcgcgtgtgt gtgtgtgtgt cagcgtgtgt ttcttttaac gtcttcagcc tacaacatac   48900
agggttcatg gtggcaagaa gatagcaaga tttaaattat ggccagtgac tagtgcttga   48960
aggggaacaa ctacctgcat ttaatgggaa ggcaaaatct caggctttga gggaagttaa   49020
cataggcttg attctgggtg gaagcttggt gtgtagttat ctggaggcca ggctggagct   49080
ctcagctcac tatgggttca tctttattgt ctcctttcat ctcaacagct cctgggaaat   49140
gtgctggtga ccgttttggc aatccatttc ggcaaagaat tcacccctga ggtgcaggct   49200
tcctggcaga agatggtgac tgcagtggcc agtgccctgt cctccagata ccactgagct   49260
cactgcccat gattcagagc tttcaaggat aggcttatt ctgcaagcaa tacaaataat    49320
aaatctattc tgctgagaga tcacacatga ttttcttcag ctctttttt tacatctttt    49380
taaatatatg agccacaaag ggttatatt gagggaagtg tgtatgtgta tttctgcatg    49440
cctgtttgtg tttgtggtgt gtgcatgctc ctcatttatt tttatatgag atgtgcattt   49500
tgatgagcaa ataaaagcag taaagacact tgtacacggg agttctgcaa gtgggagtaa   49560
atggtgtagg agaaatccgg tgggaagaaa gacctctata ggacaggact tctcagaaac   49620
agatgttttg gaagagatgg gaaaaggttc agtgaagacc tgggggctgg attgattgca   49680
gctgagtagc aaggatggtt cttaaggaag ggaaagtgtt ccaagcttta ggaattcaag   49740
gtttagtcag gtgtagcaat tctatttat taggaggaat actatttcta atggcactta   49800
gcttttcaca gcccttgtgg atgcctaaga aagtgaaatt aatcccatgc cctcaagtgt   49860
gcagattggt cacagcattt caagggagag acctcattgt aagactctgg gggaggtggg   49920
gacttaggtg taagaaatga atcagcagag gctcacaagt cagcatgagc atgttatgtc   49980
tgagaaacag accagcactg tgagatcaaa atgtagtggg aagaatttgt acaacattaa   50040
ttggaaggct tacttaatgg aatttttgta tagttggatg ttagtgcatc tctataagta   50100
agagtttaat atgatggtgt tacggaccta atgtttgtgt ctcctcaaaa ttcacatgct   50160
gaatccccaa ctcccaactg accttatctg tgggggaggc ttttgaaaag taattaggtt   50220
tagatgagct cataagagca gatccccatc ataaaattat tttccttatc agaagcagag   50280
agacaagcca tttctctttc ctcccggtga ggacacagtg agaagtccgc catctgcaat   50340
ccaggaagag aaccctgacc acgagtcagc cttcagaaat gtgagaaaaa actctgttgt   50400
tgaagccacc cagtctttg tattttgtta tagcaccttg cactgagtaa ggcagatgaa    50460
```

-continued

```
gaaggagaaa aaaataagct tgggttttga gtggactaca gaccatgttt atctcaggtt   50520
tgcaaagctc ccctcgtccc ctatgtttca gtataaaata cctactctac tactctcatc   50580
tataagaccc aaataataag cctgcgccct tctctctaac tttgatttct cctatttta   50640
cttcaacatg ctttactcta gccttgtaat gtctttacat acagtgaaat gtaaagttct   50700
ttattctttt tttctttctt tctttttct cctcagcctc agaatttggc acatgccctt   50760
ccttctttca ggaacttctc caacatctct gcctggctcc atcatatcat aaaggtccca   50820
cttcaaatgc agtcactacc gtttcagaat atgcactttc tttctttttt gttttttgtt   50880
tttttttaagt caaagcaaat ttcttgagag agtaaagaaa taaacgaatg actactgcat   50940
aggcagagca gccccgaggg ccgctggttg ttccttttat ggttatttct tgatgatatg   51000
ttaaacaagt tttggattat ttatgccttc tcttttagg ccatatagg taactttctg    51060
acattgccat ggcattttc ttttaattta atttactgtt accttaaatt caggggtaca    51120
cgtacaggat atgcaggttt gttttatagg taaaagtgtg ccatggtttt aatgggtttt   51180
tttttcttg taaagttgtt taagtttctt gtttactctg atattaggc ctttgtcaga     51240
agaatagatt ggaaaatctt tttcccattc tgtagattgt ctttcgctct gatggtagtt   51300
tcttttgctg agcaggagct ctttagttta attagattcc attggtcaat ttttgctttt   51360
gctgcaattg cttttcacgc tttcatcatg aaatctgtgc ccgtgtttat atcatgaata   51420
gtattgcctt gatttttc taggctttt atagttggg gttttcatt taagtctcta       51480
atccatctgg agttaatttt ggataaggta taaggaagga gtccagtttc attttcagc    51540
atatggctag ccagttctcc cccatcattt attaaattga aaatcctttc cccattgctt   51600
gcttttgtca ggtttctaaa agaccagatg gttgtaggta caatatgcag tttcttcaag   51660
tcatataata ccatctgaaa tctcttatta attcatttct tttagtatgt atgctggtct   51720
cctctgctca ctatagtgag ggcaccatta gccagagaat ctgtctgtct agttcatgta   51780
agattctcag aattaagaaa aatggatggc atatgaatga aacttcatgg atgacatatg   51840
gaatctaata tgtatttgtt gaattaatgc ataagatgca acagagagaa gttgacaact   51900
gcaatgataa cctggtattg atgatataag agtctataga tcacagtaga agcaataatc   51960
atggaaaaca attggaaatg gggaacagcc acaaacaaga aagaatcaat acttccagga   52020
aagtgactgc aggtcacttt tcctggagcg ggtgagagaa aagtggaagt tagcagtaac   52080
tgctgaattc ctggttggct gatggaaaga tggggcagct gttcactggt acgcagggtt   52140
ttagatgtat gtacctaagg atatgaggta tggcaatgaa cagaaattct tttgggaatg   52200
agttttaggg ccattaaagg acatgacctg aagtttcctc tgaggccagt ccccacaact   52260
caatataaat gtgtttcctg catatagtca aagttgccac ttcttttct tcatatcatc    52320
gatctctgct cttaaagata atcttggttt tgcctcaaac tgtttgtcac tacaaacttt   52380
ccccatgttc ctaagtaaaa caggtaactg cctctcaact atatcaagta gactaaaata   52440
ttgtgtctct aatatcagaa attcagcttt aatatattgg gtttaactct ttgaaattta   52500
gagtctcctt gaaatacaca tgggggtgat ttcctaaact ttatttcttg taaggattta   52560
tctcaggggt aacacacaaa ccagcatcct gaacctctaa gtatgaggac agtaagcctt   52620
aagaatataa aataaactgt tcttctctct gccggtggaa gtgtgccctg tctattcctg   52680
aaattgcttg tttgagacgc atgagacgtg cagcacatga gacacgtgca gcagcctgtg   52740
gaatattgtc agtgaagaat gtctttgcct gattagatat aaagacaagt taaacacagc   52800
attagactat agatcaagcc tgtgccagac acaaatgacc taatgcccag cacgggccac   52860
```

```
ggaatctcct atcctcttgc ttgaacagag cagcacactt ctcccccaac actattagat   52920
gttctggcat aattttgtag atatgtagga tttgacatgg actattgttc aatgattcag   52980
aggaaatctc ctttgttcag ataagtacac tgactactaa atggattaaa aaacacagta   53040
ataaaaccca gttttcccct tacttcccta gtttgtttct tattctgctt tcttccaagt   53100
tgatgctgga tagaggtgtt tatttctatt ctaaaagtg atgaaattgg ccgggcgcgg    53160
tggctcacac ctgtaatccc agcactttgg gaggctgagg tgggcggatc acgaggtcag   53220
gagatcaaga ccatcctggc taacatggtg aaaccccatc tctactaaaa atacaaaaaa   53280
ttagccagac acagtggcgg gtgcctgtag tcccagctac tcgggaggct gaggcaggag   53340
aatggcgtga acctgggagg cagagcttgc ggtgagcaga gatcgcgcca ctgcacactc   53400
cagcctgggt gacaaagcga gactccatct caaaaaaaaa aaaaaaaaaa agaaaaagaa   53460
agaaagaaag aaaaaaaaac tgatgaaatt gtgtattcaa tgtagtctca agagaattga   53520
aaaccaagaa aggctgtggc ttcttccaca taaagcctgg atgaataaca ggataacacg   53580
ttgttacatt gtcacaactc ctgatccagg aattgatggc taagatattc gtaattctta   53640
tccttttcag ttgtaactta ttcctatttg tcagcattca ggttattagc ggctgctggc   53700
gaagtccttg agaaataaac tgcacactgg atggtggggg tagtgtagga aaatggaggg   53760
gaaggaagta aagtttcaaa ttaagcctga acagcaaagt tcccctgaga aggccacctg   53820
gattctatca gaaactcgaa tgtccatctt gcaaaacttc cttgcccaaa ccccacccct   53880
ggagtcacaa cccaccccttg accaatagat tcattttact gagggaggca aagggctggt   53940
caatagattc atttcactgg gagaggcaaa gggctggggg ccagagagga gaagtaaaaa   54000
gccacacatg aagcagcaat gcaggcatgc ttctggctca tctgtgatca ccaggaaact   54060
cccagatctg acactgtagt gcatttcact gctgacaaga aggctgctgc caccagcctg   54120
tgaagcaagg ttaaggtgag aaggctggag gtgagattct gggcaggtag gtactggaag   54180
ccgggacaag gtgcagaaag gcagaaagtg tttctgaaag agggattagc ccgttgtctt   54240
acatagtctg actttgcacc tgctctgtga ttatgactat cccacagtct cctggttgtc   54300
tacccatgga cctagaggta ctttgaaagt tttggatatc tgggctctga ctgtgcaata   54360
atgggcaacc ccaaagtcaa ggcacatggc aagaaggtgc tgatctcctt cggaaaagct   54420
gttatgctca cggatgacct caaaggcacc tttgctacac tgagtgacct gcactgtaac   54480
aagctgcacg tggaccctga aacttcctg gtgagtagta agtacactca cgctttcttc    54540 tttacccttta gatatttgca ctatgggtac ttttgaaagc agaggtggct ttctcttgtg   54600
ttatgagtca gctatgggat atgatatttc agcagtggga ttttgagagt tatgttgctg   54660
taaataacat aactaaaatt tggtagagca aggactatga ataatggaag gccacttacc   54720
atttgatagc tctgaaaaac acatcttata aaaaattctg gccaaaatca aactgagtgt   54780
ttttggatga gggaacagaa gttgagatag agaaaataac atctttcctt tggtcagcga   54840 aatttttctat aaaaattaat agtcactttt ctgcatagtc ctggaggtta gaaaaagatc   54900
aactgaacaa agtagtggga agctgttaaa aagaggattg tttccctccg aatgatgatg   54960
gtatactttt gtacgcatgg tacaggattc tttgttatga gtgtttggga aaattgtatg   55020
tatgtatgta tgtatgtatg tgatgactgg ggacttatcc tatccattac tgttccttga   55080
agtactatta tcctactttt taaaaggacg aagtctctaa aaaaaaaatg aaacaatcac   55140
aatatgttgg ggtagtgagt tggcatagca agtaagagaa ggataggaca caatgggagg   55200
```

```
tgcagggctg ccagtcatat tgaagctgat atctagccca taatggtgag agttgctcaa    55260
actctggtga aaaaggatgt aagtgttata tctatttact gcaagtccag cttgaggcct    55320
tctattcact atgtaccatt ttctttttta tcttcactcc ctccccagct cttaggcaac    55380
gtgatattga ttgttttggc aacccacttc agcgaggatt ttaccctaca gatacaggct    55440
tcttggcagt aactaacaaa tgctgtggtt aatgctgtag cccacaagac cactgagttc    55500
cctgtccact atgtttgtac ctatggtcca ctatgtttgt acctatgtcc caaaatctca    55560
tctcctttag atgggggagg ttggggagaa gagcagtatc ctgcctgctg attcagttcc    55620
tgcatgataa aaatagaata aagaaatatg ctctctaaga aatatcattg tactcttttt    55680
ctgtctttat attttaccct gattcagcca aaaggacgca ctatttctga tggaaatgag    55740
aatgttggag aatgggagtt taaggacaga gaagatactt tcttgcaatc ctgcaagaaa    55800
agagagaact cgtgggtgga tttagtgggg tagttactcc taggaagggg aaatcgtctc    55860
tagaataaga caatgttttt acagaaaggg aggtcaatgg aggtactctt tggaggtgta    55920
agaggattgt tggtagtgtg tagaggtatg ttaggactca aattagaagt tctgtatagg    55980
ctattatttg tatgaaactc aggatatagc tcatttggtg actgcagttc acttctactt    56040
attttaaaca acatatttttt tattatttat aatgaagtgg ggatggggct tcctagagac    56100
caatcaaggg ccaaaccttg aactttctct taacgtcttc aatggtatta atagagaatt    56160
atctctaagg catgtgaact ggctgtcttg gttttcatct gtacttcatc tgctacctct    56220
gtgacctgaa acatatttat aattccatta agctgtgcat atgatagatt tatcatatgt    56280
attttcctta aaggattttt gtaagaacta attgaattga tacctgtaaa gtctttatca    56340
cactacccaa taaataataa atctcttttgt tcagctctct gtttctataa atatgtacaa    56400
gttttattgt tttagtggt agtgatttta ttctcttttct atatatatac acacacatgt    56460
gtgcattcat aaatatatac aattttttatg aataaaaaat tattagcaat caatattgaa    56520
aaccactgat ttttgtttat gtgagcaaac agcagattaa aaggctgaga tttaggaaac    56580
agcacgttaa gtcaagttga tagaggagaa tatggacatt taaaagaggc aggatgatat    56640
aaaattaggg aaactggatg cagagaccag atgaagtaag aaaaatagct atcgttttga    56700
gcaaaaatca ctgaagtttc ttgcatatga gagtgacata ataaataggg aaacgtagaa    56760
aattgattca catgtatata tatatataga actgattaga caaagtctaa cttgggtata    56820
gtcagaggag cttgctgtaa ttatattgag gtgatggata aagaactgaa gttgatggaa    56880
acaatgaagt taagaaaaaa aatcgagtaa gagaccattg tggcagtgat tgcacagaac    56940
tggaaaacat tgtgaaacag agagtcagag atgacagcta aaatccctgt ctgtgaatga    57000
aaagaaggaa atttattgac agaacagcaa atgcctacaa gccccctgtt tggatctggc    57060
aatgaacgta gccattctgt ggcaatcact tcaaactcct gtacccaaga cccttaggaa    57120
gtatgtagca ccctcaaacc taaaacctca agaaagagg ttttagaaga tataatcccc    57180
tttcttctcc agtttcatta atcccaaaac ctctttctca aagtatttcc tctatgtgtc    57240
cacccccaaag agctcaccctc accatatctc ttgagtggga gcacatagat aggcggtgct    57300
accatctaac agcttctgaa attcctttgt catattttg agtccccact aataacccac    57360
aaagcagaat aaataccagt tgctcatgta caataatcac tcaactgctg tcttgtagca    57420
tacattaatt aagcacattc tttgaataat tactgtgtcc aaacaatcac actttaaaat    57480
ctcacacttg tgctatccct tgcccttctg aatgtcactc tgtattttaa atgaagagat    57540
gagggttgaa tttcctgtgt tacttattgt tcatttctcg atgaggagtt ttcacattca    57600
```

```
cctttagtgg aaaacacata agtacacatc ttacaggaaa aatataccaa actgacatgt    57660
agcatgaatg cttgtgcatg tagtcatata aaatcttgta gcaatgtaaa cattctctga    57720
tatacacata cagatgtgtc tatatgtcta cacaatttct tatgctccat gaacaaacat    57780
tccatgcaca cataagaaca cacactgtta cagatgcata cttgagtgca ttgacaaaat    57840
taccccagtc aatctagaga atttggattt ctgcatttga ctctgttagc tttgtacatg    57900
ctgttcattt actctgggtg atgtcttcc ctcattttgc cttgtctatc ttgtactcat     57960
actttaagtc ctaacttata tgttatctca actaagaagc tattttttt taatttaac     58020 tgggcttaaa gccctgtcta taaactctgc tacaattatg ggctcttct tataatattt    58080 agtgttttc ctactaatgt acttaatctg ctcattgtat attcctacca ctaaatttta    58140
acctctttta tggtagagac attgtcttgt aaactcttat ttccctagta tttggagatg    58200 aaaaaaaga ttaaattatc caaaattaga tctctcttt ctacattatg agtattacac      58260
tatccataga gaagtttgtt tgagacctaa actgaggaac ctttggttct aaaatgacta    58320
tgtgatatct tagtatttat aggtcatgag gttccttcct ctgcctctgc tatagtttga    58380
ttagtcaaca agcatgtgtc atgcatttat tcacatcaga atttcataca ctaataagac    58440
atagtatcag aagtcagttt attagttata tcagttaggg tccatcaagg aaaggacaaa    58500
ccattatcag ttactcaacc tagaattaaa tacagctctt aatagttaat tatccttgta    58560
ttggaagagc taaatatca aataaaggac agtgcagaaa tctagatgtt agtaacatca     58620
gaaaccctct tccgccatta ggcctagaag ggcagaagga gaaatgtttt ataccaccag    58680
agtccagaac cagagcccat aaccagaggt ccactggatt cagtgagcta gtgggtgctc    58740
cttggagaga gccagaactg tctaatgggg gcatcaaagt atcagccata aaaaaccata    58800
aaaaagactg tctgctgtag gagatccgtt cagagagaga gagagaccag aaataatctt    58860
gcttatgctt tccctcagcc agtgtttacc attgcagaat gtacatgcga ctgaaagggt    58920
gaggaaacct gggaaatgtc agttcctcaa atacagagaa cactgaggga aggatgagaa    58980
ataaatgtga aagcagacat gaatggtaat tgacagaagg aaactaggat gtgtccagta    59040
aatgaataat tacagtgtgc agtgattatt gcaatgatta atgtattgat aagataatat    59100
gaaaacacag aattcaaaca gcagtgaact gagattagaa ttgtggagag cactggcatt    59160
taagaatgtc acacttagaa tgtgtctcta ggcattgttc tgtgcatata tcatctcaat    59220
attcattatc tgaaaattat gaattaggta caaagctcaa ataatttatt ttttcaggtt    59280
agcaagaact ttttttttt ttttctgaga tagagcattg ctatggttgc ccaggctgga    59340
gtgcaatggc atgatccagg ctcactgcaa catctgcctc ccaggttcaa gcgattctcc    59400
tgcctcagcc tcccaagtag ctggcactac aggcatgtgc caccaccatg cctggctaat    59460
tttctatttt tagtagatag ggggtttcac catgttggtc aggctgatct cgaactccta    59520
acatcaggtg atccaccctc ctcggcctct gaaagtgctg ggatcacagg cgtgagccac    59580
cacacccagc caagaatgtg aattttgtag aaggatataa cccatatttc tctgacccta    59640
gagtccttag tatacctccc ataccatgtg gctcatcctc cttacataca tttcccatct    59700
ttcaccctac cttttccttt ttgtttcagc ttttcactgt gtcaaaatct agaaccttat    59760
ctcctacctg ctctgaaacc aacagcaagt tgacttccat tctaacccac attggcatta    59820
cactaattaa aatcgatact gagttctaaa atcatcgggg attttgggga ctatgtctta    59880
cttcatactt ccttgagatt tcacattaaa tgttggtgtt cattaaaggt ccttcattta    59940
```

```
actttgtatt catcacactc ttggattcac agttatatct aaactcttaa atacagcctg    60000
tataatccca attcccaact ctgatttcta acctctgacc tccaacctca gtgccaaacc    60060
catatatcaa acaatgtact gggcttattt atatagatgt cctataggca cctcagactc    60120
agcatgggta tttcacttgt tatactaaaa ctgtttctct tccagtgttt tccattttag    60180
tcattagata gctacttgcc cattcaccaa ggtcacagat taaaatcatt tccctacctc    60240
taatcaacag ttcgattctg cttcaatttg tccctatcta ttaatcacca ctcttactgc    60300
ccagtcaggt cctcattgtt tcctgaacaa gagtagatgc tattctttcc acttttagac    60360
cttatcctgg ctggatgcgg tggctcaggc ttgtaaaccc agcactttgg gaggccaagg    60420
caggcagatc acttgaggtc aggagttcaa gaccagcctg accaacatgg tgaaaccccca   60480 tctctactaa aaatacaaaa tcagccgggc gtgtggtgca tgcctgcagt cccagctatt    60540
caggtggctg aggcaggaga attgcttgaa cccaggaggc agaggttgcg gtgagcctag    60600
attgcaccat tgcactctag cttgggcaat agggatgaaa ctccatctca gaagagaaaa    60660
gaaaaaaaga cctattctg ttatacaaat cctctcaatg caatccatat agaataaaca    60720
tgtaaccaga tctcccaatg tgtaaaatca tttcaggtag aacagaatta aagtgaaaag    60780 ccaagtctt ggaattaaca gacaaagatc aaataacagt cctcatggcc ttaagaattt    60840
acctaacatt tttttagaa tcaattttct tatatatgaa ttggaaacat aattcctccc    60900
tcacaaacac attctaagat tttaaggaga tattgatgaa gtacatcatc tgtcattttt    60960
aacaggtagt ggtagtgatt cacacagcac attatgatct gttcttgtat gttctgttcc    61020
attctgtatt cttgacctgg ttgtattctt tctgagctcc agatccacat atctaagtac    61080 atcttttgc attttacaag agtgcataca atacaatgta tccaagactg tatttctgat    61140
tttatcgtac cactaaactc acaaatgtgg ccctattctt gtgttcacga ctgacatcac    61200
cgtcatggtc caagtctgat aatagaaatg gcattgtcac tttcttccct actgcaacag    61260
aagcccagct atttgtctcc catttttctct acttctaaaa tacatttctt cactaagtga    61320
gaataatctt ttaaagacac aaatcaaacc atgccaccac ctttcttgaa ttattcaata    61380
tctttcgttg gcttccaggt tacagaaaaa taacttgtaa caaagtttaa aggtcattca    61440
tggctcctct ctaccctatt ttataacatt tccccttgtg atcagaatct caggcacatc    61500
atccatcttt ctatatacaa ataaagtcat atagtttgaa ctcacctctg gttactttta    61560
atcaaccaaa tgctgtaaaa tgcatttgta tcgctacgtg ttaagcagta gttgattctt    61620
ttcatttctg tgtaatattc tattctttga ctataccgta atttatcaat tctactgttg    61680
gtaagcattt aagtggctac cggtttgagg tttttatgat tattgctgtc ataagcattt    61740
ctatacatgt ctttggatac acacatgcat gtgtttctga atatctaaaa atgtaattgc    61800
taggtaatag acttatcaag catccagcat ttgtggatac tattaaaggt tttccaaagg    61860
ggttatacta ttgtacagtg tcaccaacag agtttgagtt tctattgatc catatccacca   61920 ccaaaatttg aactgtcagt cttatctctt ctcttgtctc ttttttcctc ttttttttcc    61980
ttcccttccc ctctcttcgt ttcttttctc tcctcttctc ttctttcctc tcttcccttc    62040
cctttctctt tctcttccct atcccttctc ctctcctctc cctcctttt ttctcctctc    62100 ctctccatta tttatttttc cttcttctcc tccatcccct ccatcctctc tcttccctc    62160 ttccttcctt cctttctcca tttcttcctc ctctttcctt caatccttcc ttttggatat    62220
gctcatgggt gtgtatttgt ctgccattgt ggcattattg gaattcagaa aagagtgaaa    62280
aactactggg atcttcattc ctgggtctaa ttccacattt tttttttaaga acacatctgt    62340
```

```
aaaaatgttc tgtactagca tattcccagg aacttcgtta aatttaatct ggctgaatat   62400
ggtaaatcta cttttcactt tgcattcttt ctttagtcat accataattt taaacattca   62460
aaatatttgt atataatatt tgattttatc tgtcattaaa atgttaacct taaaattcat   62520
gtttccagaa cctatttcaa taactggtaa ataaacacta ttcatttttt aaatattctt   62580
ttaatggata tttatttcaa tataataaaa aattagagtt ttattatagg aagaatttac   62640
caaaagaagg aggaagcaag caagtttaaa ctgcagcaat agatttgtcc attccaacct   62700
ctcaaaattc ccttggagac aaaaatctct agaggcaaag aagaacttta tattgagtca   62760
acttgttaaa acatctgctt ttagataagt tttcttagta taaagtgaca gaaacaaata   62820
agttaaactc taagatacat tccactatat tagcctaaaa cacttctgca aaaatgaaac   62880
taggaggata ttttagaaaa caactgctga aagagatgcg gtggggagat atgtagagga   62940
gaacagggtt tctgagtcaa gacacacatg acagaacagc caatctcagg gcaagttaag   63000
ggaatagtgg aatgaaggtt catttttcat tctcacaaac taatgaaacc ctgcttatct   63060
taaaccaacc tgctcactgg agcagggagg acaggaccag cataaaaggc agggcagagt   63120
cgactgttgc ttacactttc ttctgacata acagtgttca ctagcaacct caaacagaca   63180
ccatggtgca tctgactcct gaggagaaga ctgctgtcaa tgccctgtgg ggcaaagtga   63240
acgtggatgc agttggtggt gaggccctgg gcaggttggt atcaaggtta taagagaggc   63300
tcaaggaggc aaatggaaac tgggcatgtg tagacagaga agactcttgg gtttctgata   63360
ggcactgact ctctgtccct tgggctgttt tcctaccctc agattactgg tggtctaccc   63420
ttggacccag aggttctttg agtcctttgg ggatctgtcc tctcctgatg ctgttatggg   63480
caaccctaag gtgaaggctc atggcaagaa ggtgctaggt gcctttagtg atggcctggc   63540
tcacctggac aacctcaagg gcacttttc tcagctgagt gagctgcact gtgacaagct   63600
gcacgtggat cctgagaact caggtgag tccaggagat gcttcacttt tctctttta   63660 cttttctaatc ttacattttg gttcttttac ctacctgctc ttctcccaca ttttttgtcat   63720 tttactatat tttatcattt aatgcttcta aaattttgtt aattttttat ttaaatattc   63780 tgcattttt ccttcctcac aatcttgcta tttttaaatta tttaatatcc tgtctttctc   63840
tcccaacccc ctcccttcat ttttccttct ctaacaacaa ctcaaattat gcataccagc   63900
tctcacctgc taattctgca cttagaataa tccttttgtc tctccacatg ggtatgggag   63960
aggctccaac tcaaagatga gaggcataga atactgtttt agaggctata aatcattta   64020 caataaggaa taattggaat tttataaatt ctgtagtaaa tggaatgaa aggaaagtga   64080 atatttgatt atgaaagact aggcagttac actggaggtg gggcagaagt cgttgctagg   64140
agacagccca tcatcacact gattaatcaa ttaatttgta tctattaatc tgtttatagt   64200
aattaatttg tatatgctat atacacatac aaaattaaaa ctaatttgga attaatttgt   64260
atatagtatt atacagcata tatagcatat atgtacatat atagactaca tgctagttaa   64320
gtacatagag gatgtgtgtg tatagatata tgttatatgt atgcattcat atatgtactt   64380
atttatgctg atgggaataa cctggggatc agttttgtct aagatttggg cagaaaaaaa   64440
tgggtgttgg ctcagtttct cagaagccag tcttatttc tctgttaacc atatgcatgt   64500
atctgcctac ctcttctccg cagctcttgg gcaatgtgct ggtgtgtgtg ctggcccgca   64560
actttggcaa ggaattcacc ccacaaatgc aggctgccta tcagaaggtg gtggctggtg   64620
tggctaatgc cctggctcac aagtaccatt gagatcctgg actgtttcct gataaccata   64680
```

```
agaagaccct atttccctag attctatttt ctgaacttgg gaacacaatg cctacttcaa    64740
gggtatggct tctgcctaat aaagaatgtt cagctcaact tcctgattaa tttcacttat    64800 ttcattttt tgtccaggtg tgtaagaagg ttcctgaggc tctacagata gggagcactt    64860
gtttatttta caaagagtac atgggaaaag agaaaagcaa gggaaccgta caaggcatta    64920
atgggtgaca cttctacctc caaagagcag aaattatcaa gaactcttga tacaaagata    64980
atactggcac tgcagaggtt ctagggaaga cctcaaccct aagacatagc ctcaagggta    65040
atgctacgat taaactccaa caattactga gaaaataatg tgctcaatta aaggcataat    65100
gattactcaa gacaatgtta tgttgtcttt cttcctcctt cctttgcctg cacattgtag    65160
cccataatac tataccccat caagtgttcc tgctccaaga aatagcttcc tcctcttact    65220
tgccccagaa catctctgta aagaatttcc tcttatcttc ccatatttca gtcaagattc    65280
attgctcacg tattacttgt gacctctctt gaccccagcc acaataaact tctctatact    65340
acccaaaaaa tctttccaaa ccctccccca caccattttt tatattttta tattttctt     65400 atttattca tgcacacaca cacactccgt gctttataag caattctgcc tattctctac    65460
cttcttacat gcctactgtg cctcatatta aattcatcaa tgggcagaaa gaaaatattt    65520
attcaagaaa acagtgaatg aatgaacgaa tgagtaaatg agtaaatgaa ggaatgatta    65580
ttccttgctt tagaacttct ggaattagag gacaatatta ataataccat cgcacagtgt    65640
ttctttgttg ttaatgctac aacatacaaa gaggaagcat gcagtaaaca accgaacagt    65700
tatttccttt ctgatcatag gagtaatatt ttttttccttg agcaccattt ttgccatagg    65760
taaaattaga aggattttta gaactttctc agttgtatac attttaaaaa atctgtatta    65820
tatgcatgtt gattaatttt aaacttactt gaatacctaa acagaatctg ttgtttcctt    65880
gtgtttgaaa gtgctttcac agtaactctg tctgtactgc cagaatatac tgacaatgtg    65940
ttatagttaa ctgttttgat cacaacattt tgaattgact ggcagcagaa gctctttat     66000 atccatgtgt tttccttaag tcattataca tagtaggcac tgagaactct ttatatctga    66060
ataagatatt taggaaccac tggtttacat atcagaagca gagctactca gggcattttg    66120
gggaagatca ctttcacatt cctgagcata gggaagttct cataagagta agatattaaa    66180
aggagatact tgtgtggtat tcgaaagaca gtaagagaga ttgtagacct tatgatcttg    66240
atagggaaaa caaactacat tcctttctcc aaaagtcaaa aaaaaagagc aaatatagct    66300 tactataacct tctattccta caccattaga agtagtcagt gagtctaggc aagatgttgg    66360
ccctaaaaat ccaaatacca gagaattcat gagaacatca cctggatggg acatgtgccg    66420
agcacacaca attactatat gctaggcatt gctatcttca tattgaagat gaggaggtca    66480
agagatgaaa aaagacttgg caccttgttg ttatattaaa attatttgtt agagtagagc    66540
ttttgtaaga gtctaggagt gtgggagcta aatgatgata cacatggaca caaaaaatag    66600
atcaacagac acccaggcct acttgagggt tgagggtggg aagagggaga cgatgaaaaa    66660
gaacctattg ggtattaagt tcatcactga gtgatgaaat aatctgtaca tcaagaccca    66720
gtgatatgca atttacctat ataacttgta catgtacccc caaatttaaa atgaaagtta    66780
aaacaaagta taggaatgga attaattcct caagatttgg ctttaatttt atttgataat    66840
ttatcaaatg gttgttttc ttttctcact atggcgttgc tttataaact atgttcagta    66900
tgtctgaatg aaagggtgtg tgtgtgtgtg aaagagaggg agagaggaag ggaagagagg    66960
acgtaataat gtgaatttga gttcatgaaa attttttcaat aaaataattt aatgtcagga    67020
gaattaagcc taatagtctc ctaaatcatc catctcttga gcttcagagc agtcctctga    67080
```

```
attaatgcct acatgtttgt aaagggtgtt cagactgaag ccaagattct acctctaaag   67140
agatgcaatc tcaaatttat ctgaagactg tacctctgct ctccataaat tgacaccatg   67200
gcccacttaa tgaggttaaa aaaaagctaa ttctgaatga aaatctgagc ccagtggagg   67260
aaatattaat gaacaaggtg cagactgaaa tataaatttt tctgtaataa ttatgcatat   67320
actttagcaa agttctgtct atgttgactt tattgctttt tggtaagaaa tacaactttt   67380
taaagtgaac taaactatcc tatttccaaa ctattttgtg tgtgtgcggt ttgtttctat   67440
gggttctggt tttcttggag cattttatt tcattttaat taattaattc tgagagctgc    67500
tgagttgtgt ttactgagag attgtgtatc tgcgagagaa gtctgtagca agtagctaga   67560
ctgtgcttga cctaggaaca tatacagtag attgctaaaa tgtctcactt ggggaatttt   67620
agactaaaca gtagagcatg tataaaaata ctctagtcaa gtgctgcttt tgaaacaaat   67680
gataaaacca cactcccata gatgagtgtc atgattttca tggaggaagt taatattcat   67740
cctctaagta tacccagact agggccattc tgatataaaa cattaggact taagaaagat   67800
taatagactg gagtaaagga aatggacctc tgtctctctc gctgtctctt ttttgaggac   67860
ttgtgtgtgt gtgtgtgtgt gtgtgtgtgt gtgtgttgtg gtcagtgggg ctggaataaa   67920
agtagaatag acctgcacct gctgtggcat ccattcacag agtagaagca agctcacaat   67980
agtgaagatg tcagtaagct tgaatagttt ttcaggaact ttgaatgctg atttagattt   68040
gaaactgagg ctctgaccat aaccaaattt gcactattta ttgcttcttg aaacttattt   68100
gcctggtatg cctgggcttt tgatggtctt agtatagctt gcagccttgt ccctgcaggg   68160
tattatgggt aatagaaaga aaagtctgcg ttacactcta gtcacactaa gtaactacca   68220
ttggaaaagc aaccctgcc ttgaagccag gatgatggta tctgcagcag ttgccaacac    68280
aagagaagga tccatagttc atcatttaaa aaagaaaaca aaatagaaaa aggaaaacta   68340
tttctgagca taagaagttg tagggtaagt ctttaagaag gtgacaattt ctgccaatca   68400
ggatttcaaa gctcttgctt tgacaatttt ggtctttcag aatactataa atataaccta   68460
tattataatt tcataaagtc tgtgcatttt ctttgaccca ggatatttgc aaaagacata   68520
ttcaaacttc cgcagaacac tttatttcac atatacatgc ctcttatatc agggatgtga   68580
aacagggtct tgaaaactgt ctaaatctaa aacaatgcta atgcaggttt aaatttaata   68640
aaataaaatc caaatctaa cagccaagtc aaatctgcat gttttaacat ttaaatatt     68700
ttaaagacgt ctttttcccag gattcaacat gtgaaatctt ttctcaggga tacacgtgtg   68760
cctagatcct cattgcttta gttttttaca gaggaatgaa tataaaaaga aaatacttaa   68820
attttatccc tcttacctct ataatcatac ataggcataa ttttttaacc taggctccag   68880
atagccatag aagaaccaaa cactttctgc gtgtgtgaga ataatcagag tgagattttt   68940
tcacaagtac ctgatgaggg ttgagacagg tagaaaaagt gagagatctc tatttattta   69000
gcaataatag agaaagcatt taagagaata aagcaatgga aataagaaat ttgtaaattt   69060
ccttctgata actagaaata gaggatccag tttcttttgg ttaacctaaa ttttatttca   69120
ttttattgtt ttattttatt ttattttatt ttattttgtg taatcgtagt ttcagagtgt   69180
tagagctgaa aggaagaagt aggagaaaca tgcaaagtaa aagtataaca ctttccttac   69240
taaaccgaca tgggtttcca ggtaggggca ggattcagga tgactgacag ggcccttagg   69300
gaacactgag accctacgct gacctcataa atgcttgcta cctttgctgt tttaattaca   69360
tcttttaata gcaggaagca gaactctgca cttcaaaagt ttttcctcac ctgaggagtt   69420
```

```
aatttagtac aagggaaaaa agtacagggg gatgggagaa aggcgatcac gttgggaagc   69480
tatagagaaa gaagagtaaa ttttagtaaa ggaggtttaa acaaacaaaa tataaagaga   69540
aataggaact tgaatcaagg aaatgatttt aaaacgcagt attcttagtg gactagagga   69600
aaaaaataat ctgagccaag tagaagacct tttcccctcc tacccctact ttctaagtca   69660
cagaggcttt tgttccccc agacactctt gcagattagt ccaggcagaa acagttagat    69720
gtccccagtt aacctcctat ttgacaccac tgattacccc attgatagtc acactttggg   69780
ttgtaagtga cttttttattt atttgtattt ttgactgcat taagaggtct ctagtttttt   69840
atctcttgtt tcccaaaacc taataagtaa ctaatgcaca gagcacattg atttgtattt   69900
attctatttt tagacataat ttattagcat gcatgagcaa attaagaaaa acaacaacaa   69960
atgaatgcat atatatgtat atgtatgtgt gtatatatac acacatatat atatatattt   70020
tttcttttct taccagaagg ttttaatcca aataaggaga agatatgctt agaaccgagg   70080
tagagttttc atccattctg tcctgtaagt attttgcata ttctggagac gcaggaagag   70140
atccatctac atatcccaaa gctgaattat ggtagacaaa actcttccac ttttagtgca   70200
tcaacttctt atttgtgtaa taagaaaatt gggaaaacga tcttcaatat gcttaccaag   70260
ctgtgattcc aaatattacg taaatacact tgcaaaggag gatgttttta gtagcaattt   70320
gtactgatgg tatggggcca agagatatat cttagaggga gggctgaggg tttgaagtcc   70380
aactcctaag ccagtgccag aagagccaag gacaggtacg gctgtcatca cttagacctc   70440
accctgtgga gccacaccct agggttggcc aatctactcc caggagcagg gagggcagga   70500
gccagggctg ggcataaaag tcagggcaga gccatctatt gcttacattt gcttctgaca   70560
caactgtgtt cactagcaac ctcaaacaga caccatggtg catctgactc ctgaggagaa   70620
gtctgccgtt actgccctgt ggggcaaggt gaacgtggat gaagttggtg gtgaggccct   70680
gggcaggttg gtatcaaggt tacaagacag gtttaaggag accaatagaa actgggcatg   70740
tggagacaga gaagactctt gggtttctga taggcactga ctctctctgc ctattggtct   70800
attttcccac ccttaggctg ctggtggtct acccttggac ccagaggttc tttgagtcct   70860
ttggggatct gtccactcct gatgctgtta tgggcaaccc taaggtgaag gctcatggca   70920
agaaagtgct cggtgccttt agtgatggcc tggctcacct ggacaacctc aagggcacct   70980
ttgccacact gagtgagctg cactgtgaca agctgcacgt ggatcctgag aacttcaggg   71040
tgagtctatg gacgcttga tgttttcttt ccccttcttt tctatggtta agttcatgtc    71100
ataggaaggg gataagtaac agggtacagt ttagaatggg aaacagacga atgattgcat   71160
cagtgtggaa gtctcaggat cgttttagtt tcttttatttt gctgttcata acaattgttt   71220
tcttttgttt aattcttgct ttctttttt ttcttctccg caatttttac tattatactt    71280
aatgccttaa cattgtgtat aacaaaagga aatatctctg agatacatta agtaacttaa   71340
aaaaaaactt tacacagtct gcctagtaca ttactatttg gaatatatgt gtgcttattt   71400
gcatattcat aatctcccta ctttattttc tttttatttttt aattgataca taatcattat  71460
acatatttat gggttaaagt gtaatgtttt aatatgtgta cacatattga ccaaatcagg   71520
gtaattttgc atttgtaatt ttaaaaaatg ctttcttctt ttaatatact ttttttgttta   71580 tcttatttct aatactttcc ctaatctctt tctttcaggg caataatgat acaatgtatc   71640
atgcctcttt gcaccattct aaagaataac agtgataatt ctgggttaa ggcaatagca    71700 atatctctgc atataaatat ttctgcatat aaattgtaac tgatgtaaga ggtttcatat   71760
tgctaatagc agctacaatc cagctaccat tctgctttta ttttatggtt gggataaggc   71820
```

```
tggattattc tgagtccaag ctaggcccTt ttgctaatca tgttcatacc tcttatcttc  71880
ctcccacagc tcctgggcaa cgtgctggtc tgtgtgctgg cccatcactt tggcaaagaa  71940
ttcaccccac cagtgcaggc tgcctatcag aaagtggtgg ctggtgtggc taatgccctg  72000
gcccacaagt atcactaagc tcgctttctt gctgtccaat ttctattaaa ggttcctttg  72060
ttccctaagt ccaactacta aactggggga tattatgaag ggccttgagc atctggattc  72120
tgcctaataa aaaacattta ttttcattgc aatgatgtat ttaaattatt tctgaatatt  72180
ttactaaaaa gggaatgtgg gaggtcagtg catttaaaac ataaagaaat gaagagctag  72240
ttcaaacctt gggaaaatac actatatctt aaactccatg aaagaaggtg aggctgcaaa  72300
cagctaatgc acattggcaa cagcccctga tgcatatgcc ttattcatcc ctcagaaaag  72360
gattcaagta gaggcttgat ttggaggtta aagttttgct atgctgtatt ttacattact  72420
tattgtttta gctgtcctca tgaatgtctt ttcactaccc atttgcttat cctgcatctc  72480
tcagccttga ctccactcag ttctcttgct tagagatacc acctttcccc tgaagtgttc  72540
cttccatgtt ttacggcgag atggtttctc ctcgcctggc cactcagcct tagttgtctc  72600
tgttgtctta tagaggtcta cttgaagaag gaaaaacagg ggtcatggtt tgactgtcct  72660
gtgagccctt cttccctgcc tcccccactc acagtgaccc ggaatctgca gtgctagtct  72720
cccggaacta tcactctttc acagtctgct ttggaaggac tgggcttagt atgaaaagtt  72780
aggactgaga agaatttgaa aggcggcttt ttgtagcttg atattcacta ctgtcttatt  72840
accctgtcat aggcccaccc caaatggaag tcccattctt cctcaggatg tttaagatta  72900
gcattcagga agagatcaga ggtctgctgg ctcccttatc atgtccctta tggtgcttct  72960
ggctctgcag ttattagcat agtgttacca tcaaccacct taacttcatt tttcttattc  73020
aatacctagg taggtagatg ctagattctg gaaataaaat atgagtctca agtggtcctt  73080
gtcctctctc ccagtcaaat tctgaatcta gttggcaaga ttctgaaatc aaggcatata  73140
atcagtaata agtgatgata gaagggtata tagaagaatt ttattatatg agagggtgaa  73200
accctcaaaa tgaaatgaaa tcagacccct gtcttacacc ataaacaaaa ataaatttga  73260
atgggttaaa gaattaaact aagacctaaa accataaaaa ttttaaaga aatcaaaaga  73320
agaaaattct aatattcacg ttgcagccgt tttttgaatt tgatatgaga agcaaaggca  73380
acaaaggaa aaataaagaa gtgaggctac atcaaactaa aaaatttcca cacaaaaaac  73440
aaaacaatga acaaatgaaa ggtgaaccat gaaatggcat atttgcaaac caaatatttc  73500
ttaaatattt tggttaatat ccaaaatata taagaaacac agatgattca ataacaaaca  73560
aaaaattaaa aataggaaaa taaaaaaatt aaaagaaga aaatcctgcc atttatggca  73620
gaattgatga acctggagga tgtaaaacta agaaaaataa gcctgacaca aaaagacaaa  73680
tactacacaa ccttgctcat atgtgaaaca taaaaaagtc actctcatgg aaacagacag  73740
tagaggtatg gttccaggg gttgggggtg ggagaatcag gaaactatta ctcaaagggt  73800
ataaaatttc agttatgtgg gatgaataaa ttctagatat ctaatgtaca gcatcgtgac  73860
tgtagttaat tgtactgtaa gtatatttaa aatttgcaaa gagagtagat ttttttttt  73920
ttttagatgg agttttgctc ttgttgtcca ggctggagtg caatgcaag atcttggctc  73980
actgcaacct ccgcctcctg ggttcaagca aatctcctgc ctcagcctcc cgagtagctg  74040
ggattacagg catgcgacac catgcccagc taatttgta tttttagtag agacggggtt  74100
tctccatgtt ggtcaggctg atccgcctgc ctcggccacc caagggctg ggattacagg  74160
```

```
cgtgagccac cgggcctggc cgagagtaga tcttaaaagc atttaccaca agaaaaaggt    74220
aactatgtga gataatgggt atgttaatta gcttgattgt ggtaatcatt tcacaaggta    74280
tacatatatt aaaacatcat gttgtacacc ttaaatatat acaattttta tttgtgaatg    74340
atacctcaat aaagttgaag aataataaaa aagaatagac atcacatgaa ttaaaaaact    74400
aaaaaataaa aaaatgcatc ttgatgatta gaattgcatt cttgattttt cagatacaaa    74460
tatccatttg actgtttact cttttccaaa acaatacaat aaattttagc actttatctt    74520
cattttcccc ttcccaatct ataattatat atatatatat tttagatatt ttgtatagtt    74580
ttactcccta gattttctag tgttattatt aaatagtgaa gaaatgttta cacttatgta    74640
caaaatgttt tgcatgcttt tcttcatttc taacattctc tctaagttta ttctattttt    74700
ttctgattat ccttaatatt atctctttct gctggaaata cattgttact tttggtttat    74760
ctaaaaatgg cttcattttc ttcattctaa aatcatgtta aattaatacc actcatgtgt    74820
aagtaagata gtggaataaa tagaaatcca aaaactaaat ctcactaaaa tataataatg    74880
tgatatataa aaatatagct tttaaattta gcttggaaat aaaaaacaaa cagtaattga    74940
acaactatac tttttgaaaa gagtaaagtg aaatgcttaa ctgcatatac cacaatcgat    75000
tacacaatta ggtgtgaagg taaaattcag tcacgaaaaa actagaataa aaatatggga    75060
agacatgtat ataatcttag agataacact gttatttaat tatcaaccca aagtagaaac    75120
tatcaaggga gaaataaatt cagtcaacaa taaaagcatt taagaagtta ttctaggctg    75180
ggagcggtgg ctcacacctg caattgcagc actttgggag gcctagacag gcggatcacg    75240
acgtcaggag ttcaagatca gcctggccaa catagtgaaa cctcatcgct actaaaaata    75300
taaaaactta gcctggcgtg gtggcaggca tgtgtaatcc cagcaatttg ggaggctgag    75360
gcaggagaat cgcttgatcc tgggaggcag aggttgcagt gagccaagat tgtgccactg    75420
cattccagcc caggtgacag catgagactc cgtcacaaaa aaaaagaaa aaaaaagggg    75480 ggggggagc ggtggagcca agatgaccga ataggaacag ctccagtcta tagctcccat    75540
cgtgagtgac gcagaagacg ggtgatttct gcatttccaa ctgaggtacc aggttcatct    75600
cacagggaag tgccaggcag tgggtgcagg acagtaggtg cagtgcactg tgcatgagcc    75660
aaagcagggc gaggcatcac ctcacccggg aagcacaagg ggtcagggaa ttcccttcc    75720 tagtcaaaga aaagggtgac agatggcacc tggaaaatcg ggtcactccc gccctaatac    75780
tgcgctcttc caacaagctt aacaaatggc acaccaggag attatatccc atgcctggct    75840
cagagggtcc tacgcccatg gagcctcgct cattgctagc acagcagtct gaggtcaaac    75900
tgcaaggtgg cagtgaggct gggggagggg tgcccaccat tgtccaggct tgagcaggta    75960
aacaaagccg cctggaagct cgaactgggt ggagcccacc acagctcaag gaggcctgcc    76020
tgcctctgta ggctccacct ctaggggcag ggcacagaca aacaaagac aacaagaacc    76080 tctgcagact taaatgtccc tgtctgacag ctttgaagag agtagtggtt ctcccagcac    76140
atagcttcag atctgagaac aggcagactg cctcctcaag tgggtccctg accccccgagt    76200 agcctaactg ggaggcatcc cccagtaggg gcagactgac acctcacatg gctggtactc    76260
ctctaagaca aaacttccag aggaatgatc aggcagcagc atttgcggtt caccaatatc    76320
cactgttctg cagccaccgc tgttgatacc caggaaaaca gcttctggag tggacctcca    76380
gtaaactcca acagacctgc agctgagggt cctgactgtt agaaggaaaa ctaacaaaca    76440
gaaaggacat ccacaccaaa aacccatctg tacatcgcca tcatcaaaga ccaaaggtag    76500
ataaaaccat aaagatgggg aaaaagcaga gcagaaaaac tggacactct aaaaatgaga    76560
```

```
gtgcctctcc tcctccaaag taacgcagct cctcaccagc aatggaacaa agctgggcag   76620
agaatgactt tgacgagttg agagaggaag gcttcagaag atcaaactac tccaagctaa   76680
aggaggaagt tcgaacaaac ggcaagaag taaaaaactt tgaaaaaaaa ttagatgaat   76740
ggataactag aataaccaat gcacagaagt ccttaaagga cctgatggag ctgaaaacca   76800
aggcaggaga actacgtgac aaatacacaa gcctcagtaa ccgatgagat caactggaag   76860
aaagggtatc aatgacgaaa gatgaaatga atgaaatgaa gcatgaagag aagtttagag   76920 aaaaagaat aaaagaaac gaacaaagcc tccaagaaat atgggactat gtgaaaagac   76980
caaatctaca tctaattggt gtagctgaaa gtgatgggga gaatggaacc aagttggaaa   77040
acactctgca ggatattatc caggagaact tccccaatct agcaaggcaa gcccaaattc   77100
acattcagga aatacagaga acgccacaaa gatactccta gagaaaagca actccaagac   77160
acataactgt cagattcacc aaagttgaaa tgaaggaaaa aatgttaagg gcagccagag   77220
agaaaggtcg ggttacccac aaagggaagc ccatcagact aacagctgat ctatcggcag   77280
aaactctaca agccagaaga aagtgggggc caatattcaa cattgttaaa gaaaagaatt   77340
ttcaacccag aatttcatat ccagccaaac taagcttcat aagtgaagga gaataaaat   77400 cctttacaga caagcaaatg ctgagagatt ttgtcaccac caggcctgcc ctacaagagc   77460
tcctgaagga agcactaaac atggaaagga acaactagta tcagccactg caaaaacatg   77520
ccaaattgta aagaccatca aggctaggaa gaaactgcat caacgagcaa ataaccagc   77580 taacatcata atgacaggat caaattcata cataacaata ctcaccttaa atgtaaatag   77640
gctaaatgct ccaattaaaa gacacagact ggcaaattgg ataaggagtc aagacccatc   77700
tgtgttctgt attcaggaaa cccatctcac gtgcagagac acacataggc tcgaaataaa   77760
aggatggagg aatatctacc aagcaaatgg aaaacaaaaa aaggcagggg ttgcaatcct   77820
agtctctgat aaaacagatt ttaaaccaac aaagatcaaa agagacaaag aaggccatta   77880
cataatggca aagggatcta ttcaagaaga agaactaact atactaaata tatatgcacc   77940
caatacagga gcacccagat tcataaaaca agtcctgagt gacctacaaa gagacttaga   78000
tgcccacaca ataataatgg gagactttaa caccccactg tcaacattag acagatcaac   78060
gagacagaaa gttaacaagg atatccagga attggactca gctctgcacc aagcagacct   78120
aatagacatc tacagaactc tccaccccaa atcaacagaa tatacattct tttcagcacc   78180
acaccacacc tattccaaaa ctgaccacat agttggaagt aaagctctcc tcagcaaatg   78240
taaaagaaca gaaactataa caaactgtct ctcagaccac agtgcaatca aactagaact   78300
caggattaag aaactcactc aaaaccactc agctacatgg aaactgaaca gcctgctcct   78360
gaatgactac tgggtacata acaaaatgaa ggcagaaata aagatgttct ttgaaaccaa   78420
cgagaacaaa gacacaacac accagaatct ctgagacaca ttcaaagcag tgtgtagagg   78480
gaaatttata gcactaaatg cccacaaggg aaagcaggaa agatctaaaa ttgacaccct   78540
aacatcacaa ttaaaaaact agagaagcag gagcaaacac attcaaaagc taacagaaga   78600
caagaaataa ctaagatcag agcagaagtg aaggacatag agacacaaaa aaacccttca   78660
aaaaaatcaa tgaatccaga agctgttttt ttgaaaagat caacaaaatt gatagactgc   78720
tagcaagact aataaagaag aaaagagaga agaatcaaat agacgcaata aaaaatgaca   78780
cggggtatca ccactgatcc cacagaaata caaactaccg tcagagaata ctataaacac   78840
ctctacgcaa ataaactaga aaatctagaa gaaatggata aattcctcga cacatacact   78900
```

```
ctgccaagac taaaccagga agaagttgta tctctgaata gaccaataac aggctctgaa  78960
attgaggcaa taattaatag cttatcaacc aaaaaaagtc cgggaccagt aggattcata  79020
gccgaattct accagaggta caaggaggag ctggtaccat tccttctgaa actattccaa  79080
tcaatagaaa aagagggaat cctccctaac tcattttatg aggccagcat catcctgata  79140
ccaaagcctg acagagacac aacaaaaaaa gagaatgtta caccaatatc cttgatgaac  79200
attgatgcaa aaatcctcaa taaaatactg gcaaactgat ccaccatgat caagtgggct  79260
tcatccctgc catgcaaggc tggttcaaca tacgaaaatc aataaacata tccagcata  79320
taaacagaac caaagacaca aaccatatga ttatctcaat agatgcagaa aaggcctttg  79380
acaaaattca acaacgcttc atgctaaaaa ctctcaataa attaggtatt gatgggacat  79440
atctcaaaat aataagagct atctatgaca aacccacagc caatatcata ctgagtggac  79500
aaaaactgga agcattccct ttgaaaactg gcacaaggca gggatgccct ctctcaccac  79560
tcctattcaa catagtgttg taagttctgg ccagggcaat caggcaggag aaggaaataa  79620
agggcattca attaggaaaa gaggaagtga aattgtccct gtttgcagat gacatgattg  79680
tatatctaga aaaccccatt gtctcagccc aaaatctcct taagctgata agcaacttca  79740
gcaaagtctc aggatataaa atcagtgtgc aaaaatcaca agtattccta tgcaccaata  79800
acagacaaac agagagccaa atcatgagtg aactcccatt cacaattgct tcaaagagaa  79860
taaaatacct aggaatccaa cttacaaggg atgtgaagga cctcttcaag gagaactaca  79920
aaccactgct caatgaaata aaagaggata caaacaaatg gaagaacatt ccatgctcat  79980
gggtaggaag aatcaatatc gtgaaaatgg tcatactgcc caaggtaatt tatagattca  80040
atgccatccc catcaagcta ccaatgactt tcttcacaga actggaaaaa actactttaa  80100
agttcatatg gaaccaaaaa agagcccaca tcaccaaggc aatcctaagc caaaagaaca  80160
aagctggagg catcacgcta cctgacttca aactatacta caatgctacg gtaaccaaaa  80220
cagcatggta ctggtaccaa aacagagatc tagaccaatg gaacagaaca gagccctcag  80280
aaataatgcc gcatatctac aactatctga tctttgacaa acctgagaga aacaagcaat  80340
ggggaaagga ttccctattt aataaatggt gctgggaaaa ctggctagcc atatgtagaa  80400
agctgaaact ggatcccttc cttacacctt atacaaaaat taattcaaga tggattaaag  80460
acttacatgt tagacctaaa accataaaaa ccctagaaaa aacctaggc aataccattc  80520
aggacatagg catgggcaag gacttcatgt ctaaacacc aaaagcaatg gcaacaaaag  80580
acaaaatgga caaacgggat ctaattaaac taaagagctt ctgcacagct aaagaaacta  80640
ccatcagagt gaacaggcaa cctacaaaat gggagaaaat ttttgcaatc tactcatctg  80700
acaaagggct aatatccaga atctacaatg aactcaaaca aatttacaag aaaaaacaaa  80760
caaccccatc aaaaagtggg caaggatat gaacagacac ttcgcaaaag aagacattta  80820
tgtaatcaaa aaacacatga aaaatgctc atcatcacta gccatcagag aaatgcaaat  80880
caaaaccaca atgagatacc atctcacacc agttagaatg gcgatcatta aaaagtcagg  80940
aaacaacagg tgctggagag gatgtggaga acaggaaca acttttacac tgttggtggg  81000
actgtaaact agttcaacca ttgcggaagt cagtgtggca attcctcagg aatctagaac  81060
tagaaatacc atttgaccca gccatcccat tactgggtac atacccaaag gattataaat  81120
catgctgcta taaagacaca tgcacacgta tgtttattgc agcactattc acaatagcaa  81180
agacttggaa ccaaccccaaa tgtccaacaa cgatagactg gattaagaaa atgtggcaca  81240
tatacaccat ggaatactat gcagccataa aaaatgatga gttcatgtcc tttgtaggga  81300
```

```
catggatgaa gctggaaact atcattctca gcaaactatc acaaggagaa taaaccaaac    81360
accgcatgtt ctcactcata ggtgggaatt gaacaatgag aacacatgga cacatgaaga    81420
ggaacatcac actctgggga ctgttatggg gtgggggggca ggggcaggga tagcactagg    81480
agatatacct aatgctaaat gacgagttaa tgggtgcagc acaccaacat ggcacatgta    81540
tacatatata acaaacctgc atgttgtgca catgtaccct aaaacttgaa gtataataat    81600 aaaaaaagt tatcctatta aaactgatct cacacatccg tagagccatt atcaagtctt    81660
tctctttgaa atagacagaa atttagtgtt ttctcagtca gttaac    81706

<210> SEQ ID NO 20
<211> LENGTH: 388
<212> TYPE: DNA
<213> ORGANISM: Homo sapiens

<400> SEQUENCE: 20
taagcttcag ttttttcctta gttcctgtta catttctgtg tgtctccatt agtgacctcc    60
catagtccaa gcatgagcag ttctggccag gcccctgtcg gggtcagtgc cccacccccg    120
ccttctggtt ctgtgtaacc ttctaagcaa accttctggc tcaagcacag caatgctgag    180
tcatgatgag tcatgctgag gcttagggtg tgtgcccaga tgttctcagc ctagagtgat    240
gactcctatc tgggtcccca gcaggatgct tacagggcag atggcaaaaa aaaggagaag    300
ctgaccacct gactaaaact ccacctcaaa cggcatcata agaaaatgg atgcctgaga    360 cagaatgtga catattctag aatatatt    388

<210> SEQ ID NO 21
<211> LENGTH: 387
<212> TYPE: DNA
<213> ORGANISM: Homo sapiens

<400> SEQUENCE: 21
taagcttcag ttttttcctta gttcctgtta catttctgtg tgtctccatt agtgacctcc    60
catagtccaa gcatgagcag ttctggccag gcccctgtcg gggtcagtgc cccacccccg    120
ccttctggtt ctgtgtaacc ttctaagcaa accttctggc tcaagcacag caatgctgag    180
tcatgatgag tcatgctgag gctagggtgt gtgcccagat gttctcagcc tagagtgatg    240
actcctatct gggtccccag caggatgctt acagggcaga tggcaaaaaa aaggagaagc    300
tgaccacctg actaaaactc cacctcaaac ggcatcataa agaaatgga tgcctgagac    360 agaatgtgac atattctaga atatatt    387

<210> SEQ ID NO 22
<211> LENGTH: 286
<212> TYPE: DNA
<213> ORGANISM: Homo sapiens

<400> SEQUENCE: 22
ctgagcaact aactcatgca ggactctcaa acactaacct atagccttt ctatgtatct    60 acttgtgtag aaaccaagcg tggggactga gaaggcaata gcaggagcat tctgactctc    120
actgcctttg gctaggtccc tccctcatca cagctcagca tagtccgagc tcttatctat    180
atccacacac agtttctgac gctgcccagc tatcaccatc ccaagtctaa agaaaaaat    240 aatgggtttg cccatctctg ttgattagaa aacaaaacaa aataaa    286

<210> SEQ ID NO 23
```

<211> LENGTH: 286
<212> TYPE: DNA
<213> ORGANISM: Homo sapiens

<400> SEQUENCE: 23

```
ctgagcaact aatcatgcag gactctcaaa cactaaccta tagccttttc tatgtatcta    60
cttgtgtaga aaccaagcgt ggggactgag aaggcaatag caggagcatt ctgactctca   120
ctgcctttag ctaggcccct ccctcatcac agctcagcat agtcctgagc tcttatctat   180
atccacacac agtttctgac gctgcccagc tatcaccatc ccaagtctaa agaaaaaaat   240
aatgggtttg cccatctctg ttgattagaa aacaaaacaa aataaa                  286
```

<210> SEQ ID NO 24
<211> LENGTH: 301
<212> TYPE: DNA
<213> ORGANISM: Homo sapiens

<400> SEQUENCE: 24

```
ccaatcgtgg catatcctct aaactttctt ttcccttcat aaatcctctt tctttttttt    60
cccccctcaca gttttcctga acaggttgac tattaattgt gtctgcttga tgtggacacc  120
aggtggcgct ggacatcaga tttggagagg cagttgtcta gggaaccggg ctctgtgcca   180
gcgcaggagg caggctggct ctcctattcc agggatgctc atccaggaag gaaaggttgc   240
atgctggaca cactaacctt gaagaattct tctgtctctc tcgtcattta gaaggaagg    300
a                                                                   301
```

<210> SEQ ID NO 25
<211> LENGTH: 305
<212> TYPE: DNA
<213> ORGANISM: Homo sapiens

<400> SEQUENCE: 25

```
ctagccaatc gtggcatatc ctctaaactt tcttttccct tcataaatcc tctttctttt    60
ttttcccccct cacagttttc tgaacaggt tgactattaa ttgtgtctgc ttgatgtgga   120
caccaggtgg cgctggacat cagatttgga gaggcagttg tctagggaac cgggctctgt   180
gccagcgcag gaggcaggct ggctctccta ctccagggat gctcatccag gaaggaaagg   240
ttgcatgctg gacacactaa ccttgaagaa ttcttctgtc tctctcgtca tttagaaagg   300
aagga                                                               305
```

<210> SEQ ID NO 26
<211> LENGTH: 896
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 26

```
ctcgagttaa ttaatctccc acgccctggt ctcagcttgg ggagtggtca gaccccaatg    60
gcgataaaact ctggcaactt tatctgtgca ctgcaggctc agccccaaca gctttagctt   120
tcacaagcag gcaggggaag ggaaacacat atctccagat atgaggttaa ttaacctgca   180
ggctaaaccc ctcccccacc ctagccccaa gcttcatctt agctccactc ctgaccctat   240
ccagctaaag gtcccaccc agctcctgcc tatctagtca ttgcatatgg caagacttga   300
aagtcctatc tcaaagcagc agaattatca gctacgactc ctgcaggtta taaccatccc   360
```

-continued

```
ccagcactcc ctgcccccac agcccagact tgaccaactc ccagctccgc ctgggacttc    420
cagatatggg gccccaccct tgcaggcctt ggggacgctg aagatattga ctatctgcgt    480
gccggaaaag ggtgttataa accggtaaag gctgggggtg ggagtagcgg atttgaagca    540
cttgttggcc tacagaggtg tggcaagcag agcacctcag aactcaggcg tactgcccgc    600
cgcccgagcc ctgcgagggc cgatagcgag ggtgtggccc ttatctgcac ccagcagagc    660
gccggcgggg tacggtcacc ggtcccgggc agttgcctca gctgagtatg tcttctaaag    720
ataatgtcga ttgtgtatgg ctgatgggat tctaggacca agcaagaggt ttttttttt     780 cccccacata cttaacgttt ctatatttct atttgaattc gactggacag ttccatttga    840
attatttctc tctctctctc tctctgacac attttatctt gccacccggg ctcgag        896
```